(12) United States Patent
Ng et al.

(10) Patent No.: US 8,293,769 B2
(45) Date of Patent: Oct. 23, 2012

(54) CSF-1R INHIBITORS, COMPOSITIONS, AND METHODS OF USE

(75) Inventors: Simon C. Ng, Walnut Creek, CA (US);
Keith B. Pfister, San Ramon, CA (US);
Martin Sendzik, San Mateo, CA (US);
James Sutton, Pleasanton, CA (US);
Allan S. Wagman, Belmont, CA (US);
Marion Wiesmann, Bottmingen (CH)

(73) Assignee: Novartis AG, Basel (CH)

( * ) Notice: Subject to any disclaimer, the term of this patent is extended or adjusted under 35 U.S.C. 154(b) by 239 days.

(21) Appl. No.: 12/451,326

(22) PCT Filed: May 20, 2008

(86) PCT No.: PCT/US2008/006475
§ 371 (c)(1),
(2), (4) Date: Jan. 21, 2010

(87) PCT Pub. No.: WO2008/144062
PCT Pub. Date: Nov. 27, 2008

(65) Prior Publication Data
US 2010/0130490 A1    May 27, 2010

(51) Int. Cl.
| | |
|---|---|
| *A61K 31/5377* | (2006.01) |
| *A61K 31/519* | (2006.01) |
| *A61K 31/506* | (2006.01) |
| *A61K 31/501* | (2006.01) |
| *A61K 31/497* | (2006.01) |
| *A61K 31/4745* | (2006.01) |
| *A61K 31/4545* | (2006.01) |
| *A61K 31/454* | (2006.01) |
| *A61K 31/444* | (2006.01) |
| *A61K 31/4439* | (2006.01) |
| *C07D 495/04* | (2006.01) |
| *C07D 487/04* | (2006.01) |
| *C07D 417/12* | (2006.01) |
| *C07D 417/14* | (2006.01) |
| *C07D 413/12* | (2006.01) |
| *C07D 413/14* | (2006.01) |

(52) U.S. Cl. ..... 514/338; 514/272; 514/273; 514/266.2; 514/233.8; 514/260.1; 514/262.1; 514/255.05; 514/300; 514/254.02; 514/252.06; 514/252.11; 514/367; 544/123; 544/124; 544/120; 544/238; 544/262; 544/278; 544/321; 544/319; 544/354; 544/357; 546/113; 546/194; 546/256; 546/270.1; 546/161

(58) Field of Classification Search ................. 514/338; 546/270.1
See application file for complete search history.

(56) References Cited

U.S. PATENT DOCUMENTS
2004/0209892 A1* 10/2004 Di Pietro et al. ......... 514/252.12

FOREIGN PATENT DOCUMENTS
| | | |
|---|---|---|
| EP | 1 674 466 A1 | 6/2006 |
| WO | WO 03/082272 A1 | 10/2003 |
| WO | WO 2005/037273 A1 | 4/2005 |
| WO | WO 2005/073224 A2 | 8/2005 |
| WO | WO 2005073224 A2 * | 8/2005 |
| WO | WO 2007/121484 A2 | 4/2007 |

OTHER PUBLICATIONS

Patani et al. Chem. Rev. 1996, 96, 3147-3176.*

* cited by examiner

*Primary Examiner* — Joseph Kosack
*Assistant Examiner* — Matthew Coughlin
(74) *Attorney, Agent, or Firm* — Michael G. Smith

(57) ABSTRACT

Benzoxazole and benzothiazole compounds and their oxides, esters, prodrugs, solvates, and pharmaceutically acceptable salts thereof are disclosed. Compositions of the compounds, either alone or in combination with at least one additional therapeutic agent, with a pharmaceutically acceptable carrier, and uses of the compounds, either alone or in combination with at least one additional therapeutic agent are also disclosed. The embodiments are useful for inhibiting cellular proliferation, inhibiting the growth and/or metathesis of tumors, treating or preventing cancer, treating or preventing degenerating bone diseases such as rheumatoid arthritis, and/or inhibiting molecules such as CSF 1R.

39 Claims, No Drawings

CSF-1R INHIBITORS, COMPOSITIONS, AND METHODS OF USE

BACKGROUND OF THE INVENTION

1. Field of the Invention

The present invention relates to 6-O-substituted benzoxazole and benzothiazole CSF-1R inhibitory compounds, their oxides, esters, prodrugs, solvates, or pharmaceutically acceptable salts thereof. This invention also relates to compositions of the compounds together with pharmaceutically acceptable carriers. In another aspect, this invention relates to uses of the compounds, either alone or in combination with at least one additional therapeutic agent, in the prophylaxis or treatment of cancer.

2. State of the Art

CSF-1R is the receptor for M-CSF (macrophage colony stimulating factor, also called CSF-1) and mediates the biological effects of this cytokine (Sherr 1985). The cloning of the colony stimulating factor-1 receptor (also called c-fms) was described for the first time in Roussel et al., Nature 325:549-552 (1987). In that publication, it was shown that CSF-1R had transforming potential dependent on changes in the C-terminal tail of the protein including the loss of the inhibitory tyrosine 969 phosphorylation which binds Cbl and thereby regulates receptor down regulation (Lee 1999).

CSF-1R is a single chain, transmembrane receptor tyrosine kinase (RTK) and a member of the family of immunoglobulin (Ig) motif containing RTKs characterized by repeated Ig domains in the extracellular portion of the receptor. The intracellular protein tyrosine kinase domain is interrupted by a unique insert domain that is also present in the other related RTK class III family members that include the platelet derived growth factor receptors (PDGFR), stem cell growth factor receptor (c-Kit) and fms-like cytokine receptor (FLT3). In spite of the structural homology among this family of growth factor receptors, they have distinct tissue-specific functions. CSF-1R is mainly expressed on cells of the monocytic lineage and in the female reproductive tract and placenta. In addition expression of CSF-1R has been reported in Langerhans cells in skin, a subset of smooth muscle cells (Inaba 1992), B cells (Baker 1993) and microglia (Sawada 1990).

The main biological effects of CSF-1R signaling are the differentiation, proliferation, migration, and survival of the precursor macrophages and osteoclasts from the monocytic lineage. Activation of CSF-1R is mediated by its only ligand, M-CSF. Binding of M-CSF to CSF-1R induces the formation of homodimers and activation of the kinase by tyrosine phosphorylation (Stanley 1997). Further signaling is mediated by the p85 subunit of PI3K and Grb2 connecting to the PI3K/AKT and Ras/MAPK pathways, respectively. These two important signaling pathways can regulate proliferation, survival and apoptosis. Other signaling molecules that bind the phosphorylated intracellular domain of CSF-1R include STAT1, STAT3, PLCγ, and Cbl (Bourette 2000).

CSF-1R signaling has a physiological role in immune responses, in bone remodeling and in the reproductive system. The knockout animals for either M-CSF-1 (op/op mouse; Pollard 1996) or CSF-1R (Dai 2002) have been shown to have osteopetrotic, hematopoietic, tissue macrophage, and reproductive phenotypes consistent with a role for CSF-1R in the respective cell types.

The recent success of Herceptin® and Avastin® has underscored the importance in developing therapeutics targeting a specific biological target. These drugs can minimize adverse events, have greater predictability, give physicians greater flexibility in their treatments, and provide researchers with a better understanding of a particular target. Additionally, targeted therapy may allow treatment of multiple indications affected by the same signaling pathway with fewer and potentially easier to manage toxicities. (BioCentury, V. 14(10) February, 2006) Inhibition of an individual kinase, such as CSF-1R, which is integrated within a pathway associated with cancer or other diseases, can effectively modulate downstream kinases as well, thereby affecting the entire pathway. However, the active sites of 491 human protein kinase domains are highly conserved, which makes the design of selective inhibitors a formidable challenge (Cohen 2005). Accordingly, there is a need for selective kinase inhibitors, such as selective CSF-1R inhibitors.

SUMMARY OF THE INVENTION

A continuing need exists for compounds that inhibit cellular proliferation, inhibit the growth of tumors, treat cancer, modulate cell cycle arrest, and/or specifically inhibit molecules such as CSF-1R, and for pharmaceutical formulations and medicaments that contain such compounds. A need also exists for selective CSF-1R inhibitory compounds. A need also exists for methods of administering such compounds, pharmaceutical formulations, and medicaments to patients or subjects in need thereof.

In some embodiments, the present invention is directed to compounds having Formula (I) or oxides, esters, prodrugs, pharmaceutically acceptable salts, or solvates thereof and the related compositions and methods of use thereof

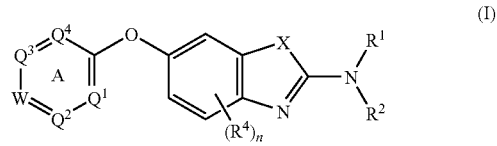

wherein:

X is O, S or S(O);

A is a six-member ring where W is C—$R^3$ or N, each of $Q^1$, $Q^2$, $Q^3$ and $Q^4$ is independently C—$R^3$ or N, provided that at least one of $Q^1$, $Q^2$, $Q^3$ and $Q^4$ is N and at most three of $Q^1$, $Q^2$, $Q^3$, $Q^4$ and W are N;

$R^1$ and $R^2$ are independently hydrogen, alkyl, substituted alkyl, cycloalkyl, substituted cycloalkyl, cycloalkenyl, substituted cycloalkenyl, aryl, substituted aryl, heterocyclyl, substituted heterocyclyl, heteroaryl, substituted heteroaryl, or $R^1$ and $R^2$ are taken together to form a group selected from heterocyclyl, substituted heterocyclyl, heteroaryl, and substituted heteroaryl; provided that $R^1$ and $R^2$ are not both H;

when X is O, one of $R^1$ or $R^2$ is optionally C(O)$R^{1a}$ wherein $R^{1a}$ is selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, substituted hydrazino, heteroaryl, substituted heteroaryl, heterocyclic, substituted heterocyclic, amino, substituted amino, alkoxy, and substituted alkoxy;

each $R^3$ is independently hydrogen or $R^{3a}$, where each $R^{3a}$ is independently selected from the group consisting of halo, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclic, substituted heterocyclic, amino, substituted amino, acyl, acylamino, alkoxy, substituted alkoxy, carboxyl, carboxyl ester, substituted sulfonyl, aminosulfonyl, and aminocarbonyl; or two $R^{3a}$ groups on two adjoining carbon atoms are taken together with the carbon atoms bound thereto to form a group selected from aryl, substituted aryl, heterocyclic, substituted heterocyclic, heteroaryl, or substituted heteroaryl;

each $R^4$ is independently alkyl, substituted alkyl, alkoxy, substituted alkoxy, amino, substituted amino, or halo; and n is 0, 1, or 2.

These and other embodiments of the invention are further described in the Detailed Description that follows.

DETAILED DESCRIPTION

Throughout this application, the text refers to various embodiments relating to compounds, compositions, and methods. The various embodiments described are meant to provide a variety illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

Definitions

Unless specifically defined otherwise, the terms used herein are defined below.

"Alkyl" refers to monovalent saturated aliphatic hydrocarbyl groups having from 1 to 10 carbon atoms and preferably 1 to 6 carbon atoms. "$C_{x-y}$alkyl" refers to alkyl groups having from x to y carbons. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, spirocycloalkylidene, $SO_3H$, substituted sulfonyl, sulfonyloxy, thioacyl, thiocyanate, thiol, alkylthio, and substituted alkylthio, wherein said substituents are defined herein.

"Alkylidene" or "alkylene" refers to divalent saturated aliphatic hydrocarbyl groups having from 1 to 10 carbon atoms and preferably 1 to 6 carbon atoms. "$C_{x-y}$alkylene" refers to alkylene groups having from x to y carbons. The alkylidene and alkylene groups include branched and straight chain hydrocarbyl groups.

"Substituted alkylidene" or "substituted alkylene" refers to an alkylidene group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, oxo, thione, spirocycloalkylidene, $SO_3H$, substituted sulfonyl, sulfonyloxy, thioacyl, thiocyanate, thiol, alkylthio, and substituted alkylthio, wherein said substituents are defined herein.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, substituted hydrazino-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, substituted hydrazino, heteroaryl, substituted heteroaryl, heterocyclic and substituted heterocyclic are as defined herein. Acyl includes the "acetyl" group $CH_3C(O)$—.

"Acylamino" refers to the groups —$NR^{20}$C(O)alkyl, —$NR^{20}$C(O)substituted alkyl, —$NR^{20}$C(O)cycloalkyl, —$NR^{20}$C(O)substituted cycloalkyl, —$NR^{20}$C(O)cycloalkenyl, —$NR^{20}$C(O)substituted cycloalkenyl, —$NR^{20}$C(O)alkenyl, —$NR^{20}$C(O)substituted alkenyl, —$NR^{20}$C(O)alkynyl, —$NR^{20}$C(O)substituted alkynyl, —$NR^{20}$C(O)aryl, —$NR^{20}$C(O)substituted aryl, —$NR^{20}$C(O)heteroaryl, —$NR^{20}$C(O)substituted heteroaryl, —$NR^{20}$C(O)heterocyclic, and —$NR^{20}$C(O)substituted heterocyclic wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Amino" refers to the group —NH$_2$.

"Substituted amino" refers to the group —NR$^{21}$R$^{22}$ where R$^{21}$ and R$^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic and wherein R$^{21}$ and R$^{22}$ are optionally joined, together with the nitrogen bound thereto to form a heterocyclic or substituted heterocyclic group, provided that R$^{21}$ and R$^{22}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein. When R$^{21}$ is hydrogen and R$^{22}$ is alkyl, the substituted amino group is sometimes referred to herein as alkylamino. When R$^{21}$ and R$^{22}$ are alkyl, the substituted amino group is sometimes referred to herein as dialkylamino. When referring to a monosubstituted amino, it is meant that either R$^{21}$ or R$^{22}$ is hydrogen but not both. When referring to a disubstituted amino, it is meant that neither R$^{21}$ nor R$^{22}$ are hydrogen.

"Hydroxyamino" refers to the group —NHOH.

"Alkoxyamino" refers to the group —NHO-alkyl wherein alkyl is defined herein.

"Aminocarbonyl" refers to the group —C(O)NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, substituted heterocyclyl, hydroxy, alkoxy, substituted alkoxy, amino, substituted amino, and acylamino, and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —NR$^{20}$C(O)NR$^{23}$R$^{24}$ where R$^{20}$ is hydrogen or alkyl and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NR$^{20}$C(S)NR$^{23}$R$^{24}$ where R$^{20}$ is hydrogen or alkyl and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO$_2$NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO$_2$NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylamino" refers to the group —NR$^{20}$—SO$_2$NR$^{23}$R$^{24}$ where R$^{20}$ is hydrogen or alkyl and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Amidino" refers to the group —C(=NR$^{25}$)NR$^{23}$R$^{24}$ where R$^{25}$, R$^{23}$, and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiocyanate, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkenyl" refers to alkenyl groups having from 2 to 6 carbon atoms and preferably 2 to 4 carbon atoms and having at least 1 and preferably from 1 to 2 sites of vinyl unsaturation (>C=C<). Such groups are exemplified, for example, by vinyl, allyl, and but-3-en-yl.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy or thiol substitution is not attached to a vinyl (unsaturated) carbon atom.

"Alkynyl" refers to hydrocarbyl groups having from 2 to 6 carbon atoms and preferably 2 to 3 carbon atoms and having at least 1 and preferably from 1 to 2 sites of acetylenic unsaturation (—CC—).

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy or thiol substitution is not attached to an acetylenic carbon atom.

"Azido" refers to the group —$N_3$.

"Hydrazino" refers to the group —$NHNH_2$.

"Substituted hydrazino" refers to the group —$NR^{26}NR^{27}R^{28}$ where $R^{26}$, $R^{27}$, and $R^{28}$ are independently selected from the group consisting of hydrogen, alkyl, substituted alkyl, alkenyl, substituted alkenyl, alkynyl, substituted alkynyl, aryl, substituted aryl, carboxyl ester, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cylcoalkyl, —$SO_2$-cycloalkenyl, —$SO_2$-substituted cycloalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein $R^{27}$ and $R^{28}$ are optionally joined, together with the nitrogen bound thereto to form a heterocyclic or substituted heterocyclic group, provided that $R^{27}$ and $R^{28}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Cyano" or "carbonitrile" refers to the group —CN.

"Cyanate" refers to the group —OCN.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"(Carboxyl ester)amino" refers to the group —$NR^{20}$—C(O)O-alkyl, —$NR^{20}$—C(O)O-substituted alkyl, —$NR^{20}$—C(O)O-alkenyl, —$NR^{20}$—C(O)O-substituted alkenyl, —$NR^{20}$—C(O)O-alkynyl, —$NR^{20}$—C(O)O-substituted alkynyl, —$NR^{20}$—C(O)O-aryl, —$NR^{20}$—C(O)O-substituted aryl, —$NR^{20}$—C(O)O-cycloalkyl, —$NR^{20}$—C(O)O-substituted cycloalkyl, —$NR^{20}$—C(O)O-cycloalkenyl, —$NR^{20}$—C(O)O-substituted cycloalkenyl, —$NR^{20}$—C(O)O-heteroaryl, —$NR^{20}$—C(O)O-substituted heteroaryl, —$NR^{20}$—C(O)O-heterocyclic, and —$NR^{20}$—C(O)O-substituted heterocyclic wherein $R^{20}$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Cycloalkyl" refers to cyclic alkyl groups of from 3 to 10 carbon atoms having single or multiple cyclic rings including fused, bridged, and Spiro ring systems. In fused ring systems, one or more the rings can be cycloalkyl, heterocyclic, aryl, or heteroaryl provided that the point of attachment is through the cycloalkyl ring. Examples of suitable cycloalkyl groups include, for instance, adamantyl, cyclopropyl, cyclobutyl, cyclopentyl, and cyclooctyl. "$C_{x-y}$cycloalkyl" refers to cycloalkyl groups having x to y carbons.

"Cycloalkenyl" refers to non-aromatic cyclic alkyl groups of from 4 to 10 carbon atoms having single or multiple cyclic rings and having at least one >C=C< ring unsaturation and preferably from 1 to 2 sites of >C=C< ring unsaturation. "$C_{x-y}$cycloalkenyl" refers to cycloalkenyl groups having x to y carbons.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiocyanate, thiol, alkylthio, and substituted alkylthio, wherein said substituents are defined herein.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)$NH_2$.

"Substituted guanidino" refers to —$NR^{29}$C(=$NR^{29}$)N($R^{29}$)$_2$ where each $R^{29}$ is independently selected from the group consisting of hydrogen, alkyl, substituted alkyl, aryl, substituted aryl, heteroaryl, substituted heteroaryl, heterocyclyl, and substituted heterocyclyl and two $R^{29}$ groups attached to a common guanidino nitrogen atom are optionally joined together with the nitrogen bound thereto to form a heterocyclic or substituted heterocyclic group, provided that at least one $R^{29}$ is not hydrogen, and wherein said substituents are as defined herein.

"Halo" or "halogen" refers to fluoro, chloro, bromo and iodo.

"Haloalkyl" refers to substitution of alkyl groups with 1 to 5 or preferably 1 to 3 halo groups.

"Haloalkoxy" refers to substitution of alkoxy groups with 1 to 5 or preferably 1 to 3 halo groups.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated, partially saturated, or unsaturated group (but not aromatic) having a single ring or multiple condensed rings, including fused bridged and spirocycyl ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O).

"Oxide" refers to products resulting from the oxidation of one or more heteroatoms. Examples include N-oxides, sulfoxides, and sulfones.

"Spirocyclyl" refers to divalent cyclic groups from 3 to 10 carbon atoms having a cycloalkyl or heterocyclyl ring with a Spiro union (the union formed by a single atom which is the only common member of the rings) as exemplified by the following structure:

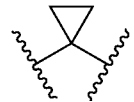

"Spirocycloalkyl" or "spirocycloalkylidene" refers to divalent cyclic groups having a cycloalkyl ring with a spiro union, as described for spirocyclyl.

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SR

"Alkylthio" refers to the group —S-alkyl wherein alkyl is as defined herein.

"Substituted alkylthio" refers to the group —S-(substituted alkyl) wherein substituted alkyl is as defined herein.

"Thiocarbonyl" refers to the divalent group —C(S)— which is equivalent to —C(=S)—.

"Thione" refers to the atom (=S).

"Thiocyanate" refers to the group —SCN.

"Compound" and "compounds" as used herein refers to a compound encompassed by the generic formulae disclosed herein, any subgenus of those generic formulae, and any specific compounds within the generic and subgeneric formulae, including the oxide, ester, prodrug, pharmaceutically acceptable salt, or solvate thereof. The term further includes the stereoisomers and tautomers of the compound or compounds.

"Solvate" or "solvates" of a compound refer to those compounds, where compounds is as defined above, that are bound to a stoichiometric or non-stoichiometric amount of a solvent. Solvates includes solvates of the oxide, ester, prodrug, or pharmaceutically acceptable salt of the disclosed generic and subgeneric formulae. Preferred solvents are volatile, non-toxic, and/or acceptable for administration to humans in trace amounts. Suitable solvates include water.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N-moeity such as pyrazoles, imidazoles, benzimidazoles, triazoles, and tetrazoles.

"Prodrug" refers to any derivative of a compound of the embodiments that is capable of directly or indirectly providing a compound of the embodiments or an active metabolite or residue thereof when administered to a subject. Particularly favored derivatives and prodrugs are those that increase the bioavailability of the compounds of the embodiments when such compounds are administered to a subject (e.g., by allowing an orally administered compound to be more readily absorbed into the blood) or which enhance delivery of the parent compound to a biological compartment (e.g., the brain or lymphatic system) relative to the parent species. Prodrugs include ester forms of the compounds of the invention. Examples of ester prodrugs include formate, acetate, propionate, butyrate, acrylate, and ethylsuccinate derivatives. An general overview of prodrugs is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Pharmaceutically acceptable salt of a compound refers to pharmaceutically acceptable salts including salts of the oxide, ester, or prodrug of the disclosed generic and subgeneric formulae.

"Patient" refers to mammals and includes humans and non-human mammals.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Reference to "selective" inhibition, refers to a compound, composition, or chemotype that preferentially inhibits a particular target or class of targets. Reference to "selective inhibition of CSF-1R" indicates the preferential inhibition of CSF-1R and optionally like kinase receptors such as PDGFR. In some embodiments, selective inhibition of CSF-1R refers to preferential inhibition of CSF-1R over Raf kinase. "Selective," "targeted," "specific," or "preferential" inhibition is not intended to mean complete absence of inhibitory activity with respect to all other kinases or receptors.

"CSF-1R inhibitor" refers to a compound that can inhibit CSF-1R. Preferably, a CSF-1R inhibitor is selective of CSF-1R over other targets. In an embodiment, a CSF-1R inhibitor has selective inhibition of CSF-1R over Raf kinase. In another embodiment, such selective inhibition refers to at least a 2:1 binding preference of a compound of this invention to CSF-1R relative to Raf kinase. In still other embodiments the binding preference is at least 5:1. In yet other embodiments the binding preference is at least 10:1.

Unless indicated otherwise, the nomenclature of substituents that are not explicitly defined herein are arrived at by naming the terminal portion of the functionality followed by the adjacent functionality toward the point of attachment. For example, the substituent "arylalkyloxycabonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

In some embodiments, the present invention provides compounds of Formula (I):

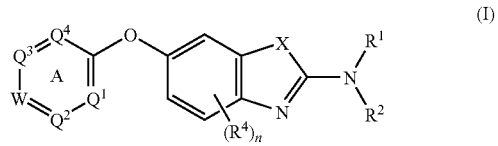

or an oxide, ester, prodrug, pharmaceutically acceptable salt, or solvate thereof, wherein:

X is O, S or S(O);

A is a six-member ring where W is C—$R^3$ or N, each of $Q^1$, $Q^2$, $Q^3$ and $Q^4$ is independently C—$R^3$ or N, provided that at least one of $Q^1$, $Q^2$, $Q^3$ and $Q^4$ is N and at most three of $Q^1$, $Q^2$, $Q^3$, $Q^4$ and W are N;

$R^1$ and $R^2$ are independently hydrogen, alkyl, substituted alkyl, cycloalkyl, substituted cycloalkyl, cycloalkenyl, substituted cycloalkenyl, aryl, substituted aryl, heterocyclyl, substituted heterocyclyl, heteroaryl, substituted heteroaryl, or $R^1$ and $R^2$ are taken together to form a group selected from heterocyclyl, substituted heterocyclyl, heteroaryl, and substituted heteroaryl; provided that $R^1$ and $R^2$ are not both H;

when X is O, one of $R^1$ or $R^2$ is optionally $C(O)R^{1a}$ wherein $R^{1a}$ is selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, substituted hydrazino, heteroaryl, substituted heteroaryl, heterocyclic, substituted heterocyclic, amino, substituted amino, alkoxy, and substituted alkoxy;

each $R^3$ is independently hydrogen or $R^{3a}$, where each $R^{3a}$ is independently selected from the group consisting of halo, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclic, substituted heterocyclic, amino, substituted amino, acyl, acylamino, alkoxy, substituted alkoxy, carboxyl, carboxyl ester, substituted sulfonyl, aminosulfonyl, and aminocarbonyl; or two $R^{3a}$ groups on two adjoining carbon atoms are taken together with the carbon atoms bound thereto to form a group selected from aryl, substituted aryl, heterocyclic, substituted heterocyclic, heteroaryl, or substituted heteroaryl;

each $R^4$ is independently alkyl, substituted alkyl, alkoxy, substituted alkoxy, amino, substituted amino, or halo; and
n is 0, 1, or 2.

In some embodiments, the invention provides a compound of Formula (II):

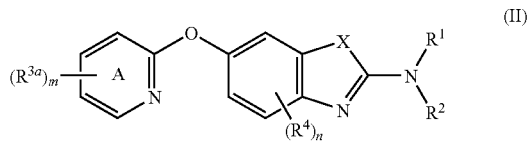

(II)

or an oxide, ester, prodrug, pharmaceutically acceptable salt, or solvate thereof,
wherein:
X is O, S or S(O);
$R^1$ and $R^2$ are independently hydrogen, alkyl, substituted alkyl, cycloalkyl, substituted cycloalkyl, cycloalkenyl, substituted cycloalkenyl, aryl, substituted aryl, heterocyclyl, substituted heterocyclyl, heteroaryl, substituted heteroaryl, or $R^1$ and $R^2$ are taken together to form a group selected from heterocyclyl, substituted heterocyclyl, heteroaryl, and substituted heteroaryl; provided that $R^1$ and $R^2$ are not both H;

when X is O, one of $R^1$ or $R^2$ is optionally $C(O)R^{1a}$ wherein $R^{1a}$ is selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, substituted hydrazino, heteroaryl, substituted heteroaryl, heterocyclic, substituted heterocyclic, amino, substituted amino, alkoxy, and substituted alkoxy;

each $R^{3a}$ is independently selected from the group consisting of halo, nitro, hydroxyamino, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclic, substituted heterocyclic, amino, substituted amino, acyl, acylamino, alkoxy, substituted alkoxy, carboxyl, carboxyl ester, substituted sulfonyl, aminosulfonyl, and aminocarbonyl; or two $R^{3a}$ groups on two adjoining carbon atoms are taken together with the carbon atoms bound thereto to form a group selected from aryl, substituted aryl, heterocyclic, substituted heterocyclic, heteroaryl, or substituted heteroaryl;

each $R^4$ is independently alkyl, substituted alkyl, alkoxy, substituted alkoxy, amino, substituted amino, or halo;
m is 0, 1, 2, or 3, and
n is 0, 1, or 2.

In some embodiments, the invention provides a compound of Formula (III):

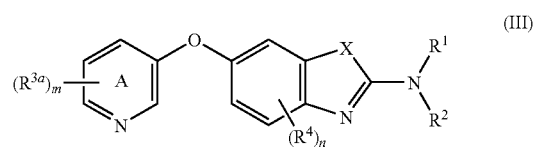

(III)

or an oxide, ester, prodrug, pharmaceutically acceptable salt, or solvate thereof,
wherein:
X is O, S or S(O);
$R^1$ and $R^2$ are independently hydrogen, alkyl, substituted alkyl, cycloalkyl, substituted cycloalkyl, cycloalkenyl, substituted cycloalkenyl, aryl, substituted aryl, heterocyclyl, substituted heterocyclyl, heteroaryl, substituted heteroaryl, or $R^1$ and $R^2$ are taken together to form a group selected from heterocyclyl, substituted heterocyclyl, heteroaryl, and substituted heteroaryl; provided that $R^1$ and $R^2$ are not both H;

when X is O, one of $R^1$ or $R^2$ is optionally $C(O)R^{1a}$ wherein $R^{1a}$ is selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, substituted hydrazino, heteroaryl, substituted heteroaryl, heterocyclic, substituted heterocyclic, amino, substituted amino, alkoxy, and substituted alkoxy;

each $R^{3a}$ is independently selected from the group consisting of halo, nitro, hydroxyamino, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclic, substituted heterocyclic, amino, substituted amino, acyl, acylamino, alkoxy, substituted alkoxy, carboxyl, carboxyl ester, substituted sulfonyl, aminosulfonyl, and aminocarbonyl; or two $R^{3a}$ groups on two adjoining carbon atoms are taken together with the carbon atoms bound thereto to form a group selected from aryl, substituted aryl, heterocyclic, substituted heterocyclic, heteroaryl, or substituted heteroaryl;

each $R^4$ is independently alkyl, substituted alkyl, alkoxy, substituted alkoxy, amino, substituted amino, or halo;
m is 0, 1, 2, or 3, and
n is 0, 1, or 2.

In some embodiments, the invention provides a compound of Formula (IV):

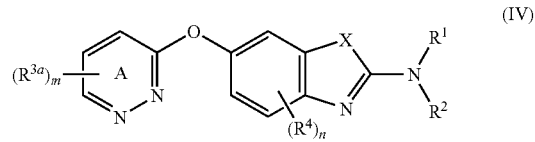

(IV)

or an oxide, ester, prodrug, pharmaceutically acceptable salt, or solvate thereof, wherein:

X is O, S or S(O);

$R^1$ and $R^2$ are independently hydrogen, alkyl, substituted alkyl, cycloalkyl, substituted cycloalkyl, cycloalkenyl, substituted cycloalkenyl, aryl, substituted aryl, heterocyclyl, substituted heterocyclyl, heteroaryl, substituted heteroaryl, or $R^1$ and $R^2$ are taken together to form a group selected from heterocyclyl, substituted heterocyclyl, heteroaryl, and substituted heteroaryl; provided that $R^1$ and $R^2$ are not both H;

when X is O, one of $R^1$ or $R^2$ is optionally $C(O)R^{1a}$ wherein $R^{1a}$ is selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, substituted hydrazino, heteroaryl, substituted heteroaryl, heterocyclic, substituted heterocyclic, amino, substituted amino, alkoxy, and substituted alkoxy;

each $R^{3a}$ is independently selected from the group consisting of hydrogen, halo, nitro, hydroxyamino, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclic, substituted heterocyclic, amino, substituted amino, acyl, acylamino, alkoxy, substituted alkoxy, carboxyl, carboxyl ester, substituted sulfonyl, aminosulfonyl, and aminocarbonyl; or two $R^{3a}$ groups on two adjoining carbon atoms are taken together with the carbon atoms bound thereto to form a group selected from aryl, substituted aryl, heterocyclic, substituted heterocyclic, heteroaryl, or substituted heteroaryl;

each $R^4$ is independently alkyl, substituted alkyl, alkoxy, substituted alkoxy, amino, substituted amino, or halo;

m is 0, 1, 2, or 3, and n is 0, 1, or 2.

In some embodiments, the invention provides a compound of Formula (V):

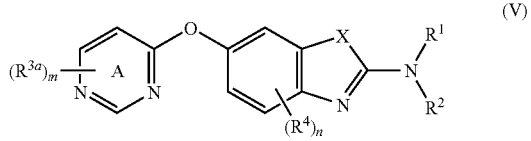

(V)

or an oxide, ester, prodrug, pharmaceutically acceptable salt, or solvate thereof, wherein:

X is O, S or S(O);

$R^1$ and $R^2$ are independently hydrogen, alkyl, substituted alkyl, cycloalkyl, substituted cycloalkyl, cycloalkenyl, substituted cycloalkenyl, aryl, substituted aryl, heterocyclyl, substituted heterocyclyl, heteroaryl, substituted heteroaryl, or $R^1$ and $R^2$ are taken together to form a group selected from heterocyclyl, substituted heterocyclyl, heteroaryl, and substituted heteroaryl; provided that $R^1$ and $R^2$ are not both H;

when X is O, one of $R^1$ or $R^2$ is optionally $C(O)R^{1a}$ wherein $R^{1a}$ is selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, substituted hydrazino, heteroaryl, substituted heteroaryl, heterocyclic, substituted heterocyclic, amino, substituted amino, alkoxy, and substituted alkoxy;

each $R^{3a}$ is independently selected from the group consisting of hydrogen, halo, nitro, hydroxyamino, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclic, substituted heterocyclic, amino, substituted amino, acyl, acylamino, alkoxy, substituted alkoxy, carboxyl, carboxyl ester, substituted sulfonyl, aminosulfonyl, and aminocarbonyl; or two $R^{3a}$ groups on two adjoining carbon atoms are taken together with the carbon atoms bound thereto to form a group selected from aryl, substituted aryl, heterocyclic, substituted heterocyclic, heteroaryl, or substituted heteroaryl;

each $R^4$ is independently alkyl, substituted alkyl, alkoxy, substituted alkoxy, amino, substituted amino, or halo;

m is 0, 1, 2, or 3, and n is 0, 1, or 2.

In some embodiments, the invention provides a compound of Formula (VI):

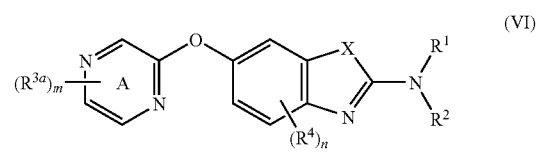

(VI)

or an oxide, ester, prodrug, pharmaceutically acceptable salt, or solvate thereof, wherein:

X is O, S or S(O);

$R^1$ and $R^2$ are independently hydrogen, alkyl, substituted alkyl, cycloalkyl, substituted cycloalkyl, cycloalkenyl, substituted cycloalkenyl, aryl, substituted aryl, heterocyclyl, substituted heterocyclyl, heteroaryl, substituted heteroaryl, or $R^1$ and $R^2$ are taken together to form a group selected from heterocyclyl, substituted heterocyclyl, heteroaryl, and substituted heteroaryl; provided that $R^1$ and $R^2$ are not both H;

when X is O, one of $R^1$ or $R^2$ is optionally $C(O)R^{1a}$ wherein $R^{1a}$ is selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, substituted hydrazino, heteroaryl, substituted heteroaryl, heterocyclic, substituted heterocyclic, amino, substituted amino, alkoxy, and substituted alkoxy;

each $R^{3a}$ is hydrogen or $R^{3a}$, where each $R^{3a}$ is independently selected from the group consisting of halo, nitro, hydroxyamino, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclic, substituted heterocyclic, amino, substituted amino, acyl, acylamino, alkoxy, substituted alkoxy, carboxyl, carboxyl ester, substituted sulfonyl, aminosulfonyl, and aminocarbonyl; or two $R^{3a}$ groups on two adjoining carbon atoms are taken together with the carbon atoms bound thereto to form a group selected from aryl, substituted aryl, heterocyclic, substituted heterocyclic, heteroaryl, or substituted heteroaryl;

each $R^4$ is independently alkyl, substituted alkyl, alkoxy, substituted alkoxy, amino, substituted amino, or halo;

m is 0, 1, 2, or 3, and n is 0, 1, or 2.

In some embodiments, the invention provides a compound of Formula (VII):

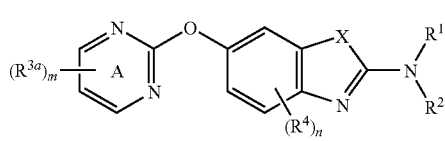

or an oxide, ester, prodrug, pharmaceutically acceptable salt, or solvate thereof,
wherein:
X is O, S or S(O);
$R^1$ and $R^2$ are independently hydrogen, alkyl, substituted alkyl, cycloalkyl, substituted cycloalkyl, cycloalkenyl, substituted cycloalkenyl, aryl, substituted aryl, heterocyclyl, substituted heterocyclyl, heteroaryl, substituted heteroaryl, or $R^1$ and $R^2$ are taken together to form a group selected from heterocyclyl, substituted heterocyclyl, heteroaryl, and substituted heteroaryl; provided that $R^1$ and $R^2$ are not both H;
when X is O, one of $R^1$ or $R^2$ is optionally $C(O)R^{1a}$ wherein $R^{1a}$ is selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, substituted hydrazino, heteroaryl, substituted heteroaryl, heterocyclic, substituted heterocyclic, amino, substituted amino, alkoxy, and substituted alkoxy;
each $R^{3a}$ is independently selected from the group consisting of halo, nitro, hydroxyamino, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclic, substituted heterocyclic, amino, substituted amino, acyl, acylamino, alkoxy, substituted alkoxy, carboxyl, carboxyl ester, substituted sulfonyl, aminosulfonyl, and aminocarbonyl; or two $R^{3a}$ groups on two adjoining carbon atoms are taken together with the carbon atoms bound thereto to form a group selected from aryl, substituted aryl, heterocyclic, substituted heterocyclic, heteroaryl, or substituted heteroaryl;
each $R^4$ is independently alkyl, substituted alkyl, alkoxy, substituted alkoxy, amino, substituted amino, or halo;
m is 0, 1, 2, or 3, and
n is 0, 1, or 2.

Various embodiments relating to a compound of Formula (I)-(VII) or an oxide, ester, prodrug, pharmaceutically acceptable salt, or solvate thereof are given below. These embodiments when referring to different substituents or variables can be combined with each other or with any other embodiments described in this application. In some aspects, provided are compounds of Formula (I)-(VII) having one or more of the following features.

In some embodiments, the compound is a salt.
In some embodiments, X is S.
In some embodiments, X is O.
In some embodiments, X is S(O).
In some embodiments, the oxide is an oxide wherein X is $S(O)_2$.
In some embodiments, $R^2$ is hydrogen or methyl.
In some embodiments, $R^1$ is alkyl substituted with 0, 1, 2, or 3 substituents independently selected from halo, hydroxy, haloalkyl, alkoxy, haloalkoxy, aryloxy, aminocarbonyl, carboxyl ester, carboxyl, and substituted sulfonyl.

In some embodiments, $R^1$ is -L-$R^{1b}$ wherein L is a covalent bond, alkylene, or substituted alkylene, and $R^{1b}$ is selected from cycloalkyl, substituted cycloalkyl, cycloalkenyl, substituted cycloalkenyl, aryl, substituted aryl, heterocyclyl, substituted heterocyclic, heteroaryl, and substituted heteroaryl.

In some embodiments, L is a covalent bond.
In some embodiments, L is alkylene substituted with 0, 1, 2, or 3 substituents independently selected from alkyl, substituted alkyl, hydroxy, alkoxy, haloalkoxy, aminocarbonyl, carboxyl ester, and carboxyl.
In some embodiments, L is methylene optionally substituted with a substituent selected from the group consisting of alkyl, substituted alkyl, hydroxy, alkoxy, haloalkoxy, aminocarbonyl, carboxyl ester, and carboxyl.
In some embodiments, L is —$CH_2$— or —$CH(CH_3)$—.
In some embodiments, $R^{1b}$ is selected from phenyl, furan-2-yl, furan-3-yl, tetrahydropyran-2-yl, tetrahydropyran-3-yl, tetrahydropyran-4-yl, cyclopropyl, cyclobutyl, cyclopentyl, cyclohexyl, cycloheptyl, cyclooctyl, cyclohexenyl, pyridin-2-yl, pyridin-3-yl, pyridin-4-yl, 2,3-dihydrobenzofuran, 2,3-dihydrobenzo[b][1,4]dioxine, 3,4-dihydro-2H-benzo[b][1,4]dioxepine, pyrazinyl, pyrrolidinyl, piperidinyl, piperidinone, pyrrolidinone, pyridin-2(1H)-one, morpholino, napthyl, bicyclo[3.1.1]heptane, bicyclo[2.2.1]heptane, 1,2,3,4-tetrahydronaphthalene, 2,3-dihydro-1H-indene, and azepan-2-one, wherein each $R^{1b}$ is substituted or unsubstituted.

In some embodiments, $R^{1b}$ is

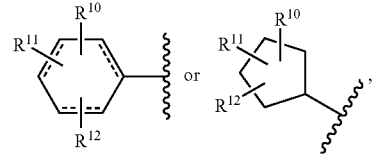

wherein the dashed lines are saturated bonds or unsaturated bonds; and
$R^{10}$, $R^{11}$, and $R^{12}$ are independently selected from the group consisting of hydrogen, halo, hydroxy, alkyl, substituted alkyl, alkoxy, substituted alkoxy, amino, substituted amino, cycloalkyl, substituted cycloalkyl, heterocyclyl, substituted heterocyclyl, aryl, substituted aryl, heteroaryl, and substituted heteroaryl; or $R^{11}$ is taken together with $R^{12}$ to form a group selected from the group consisting of aryl, substituted aryl, heterocyclyl, substituted heterocyclyl, heteroaryl, and substituted heteroaryl.

In some embodiments, $R^{1b}$ is

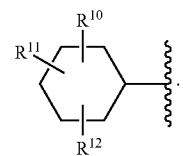

In some embodiments, $R^{10}$, $R^{11}$, and $R^{12}$ are independently selected from the group consisting of hydrogen, halo, hydroxyl, alkyl, substituted alkyl, and alkoxy.
In some embodiments, at least one of $R^{10}$, $R^{11}$, and $R^{12}$ is hydroxy.
In some embodiments, $R^{11}$ is taken together with $R^{12}$ to form aryl or substituted aryl.

In some embodiments, $R^{1b}$ is

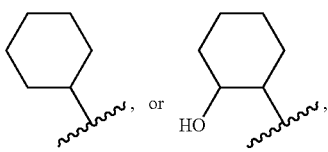

In some embodiments, $R^{1b}$ is

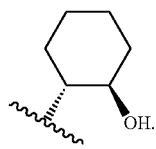

In some embodiments, $R^{1b}$ is

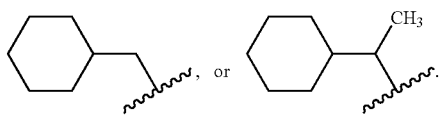

In some embodiments, $R^{1b}$ is

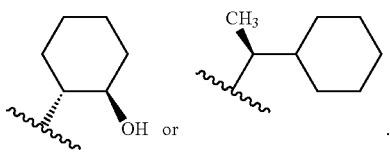

In some embodiments, each $R^{3a}$ is independently selected from the group consisting of halo, nitro, hydroxyamino, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclic, substituted heterocyclic, amino, substituted amino, acyl, acylamino, alkoxy, substituted alkoxy, carboxyl, carboxyl ester, substituted sulfonyl, aminosulfonyl, and aminocarbonyl.

In some embodiments, each $R^{3a}$ group is selected from the group consisting of F, Cl, Br, —NHOH, —NO$_2$, —CN, amino, $C_{1-3}$alkyl, $C_{3-7}$cycloalkyl, $C_{3-7}$cycloalkenyl, pyrrolidinyl, piperidinyl, piperidinone, pyrrolidinone, pyridin-2(1H)-one, morpholino, thiamorpholino, phenyl, pyrrolyl, pyrazolyl, imidazolyl, isoxazolyl, isothiazolyl, furyl, thienyl, furanyl, pyridinyl, pyrazinyl, pyrimidinyl, pyridazinyl, napthyl, and pyrrolo[2,3-b]pyridinyl, wherein said amino, $C_{1-3}$alkyl, $C_{3-7}$cycloalkyl, $C_{3-7}$cycloalkenyl, pyrrolidinyl, piperidinyl, piperidinone, pyrrolidinone, pyridin-2(1H)-one, morpholino, thiamorpholino, phenyl, pyrrolyl, pyrazolyl, imidazolyl, isoxazolyl, isothiazolyl, furyl, thienyl, furanyl, pyridinyl, pyrazinyl, pyrimidinyl, pyridazinyl, napthyl, or pyrrolo[2,3-b]pyridinyl is substituted with 0, 1, 2, or 3 substituents independently selected from the group consisting of halo, hydroxy, haloalkyl, alkoxy, haloalkoxy, aryloxy, acylamino, amino, aminocarbonyl, carbonitrile, carboxyl ester, carboxyl, substituted sulfonyl, alkyl, substituted alkyl, heterocyclic, and substituted heterocyclic.

In some embodiments, each $R^{3a}$ group is independently selected from the group consisting of F, Cl, Br, —NH$_2$, —NHOH, —NO$_2$, —CN, —CF$_3$,

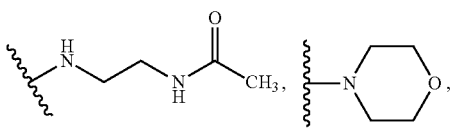

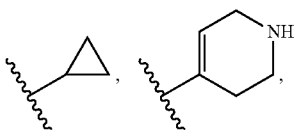

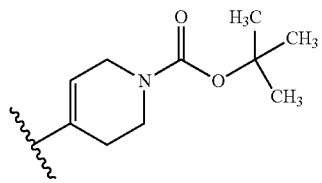

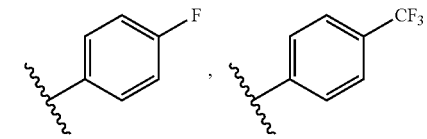

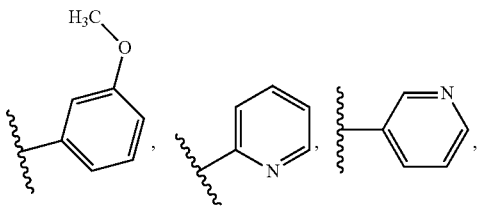

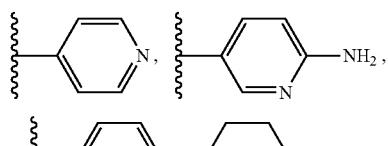

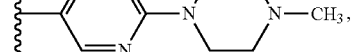
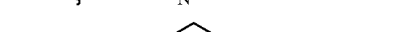

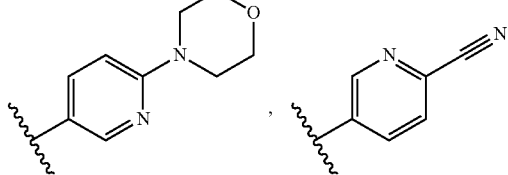

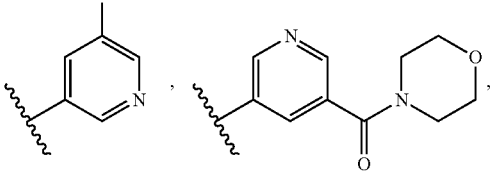

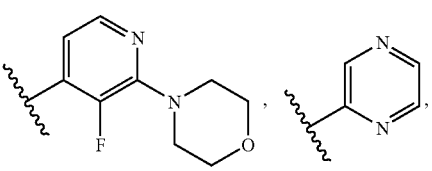

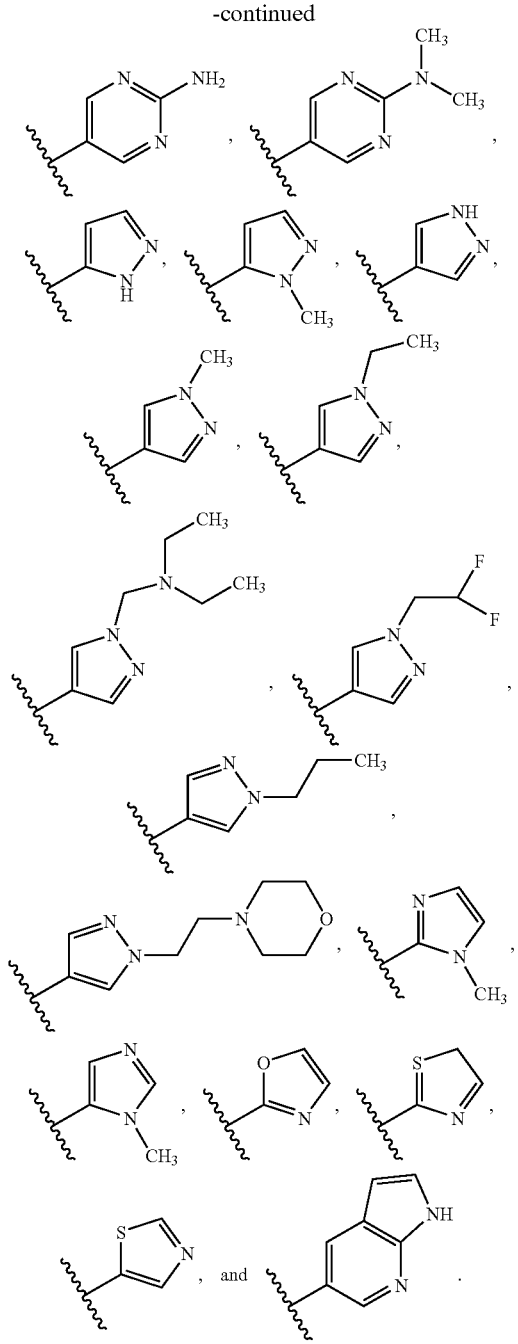

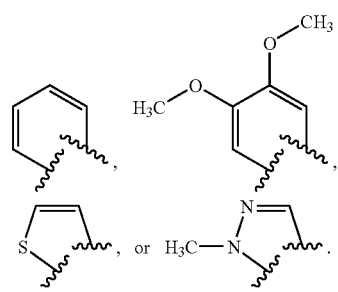

In some embodiments, ring A is

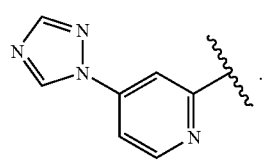

In some embodiments, ring A is selected from the group consisting of

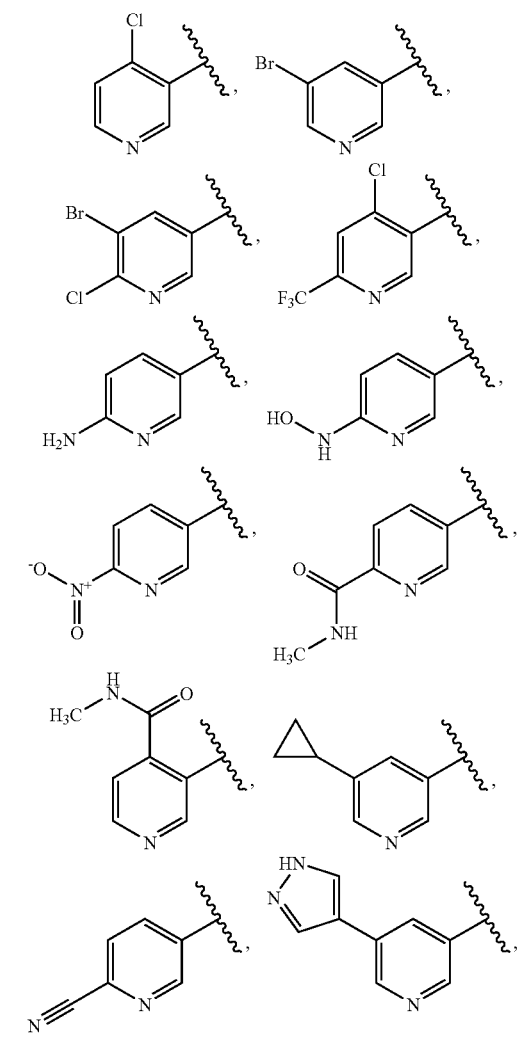

In some embodiments, two R³ᵃ groups on two adjoining carbon atoms are taken together with the carbon atoms bound thereto to form a group selected from aryl, substituted aryl, heterocyclic, substituted heterocyclic, heteroaryl, and substituted heteroaryl.

In some embodiments, two R³ᵃ groups on two adjoining carbon atoms are taken together with the carbon atoms bound thereto to form a benzene, thiophene, or pyrazole ring, wherein said benzene, thiophene, or pyrazole ring is substituted with 0, 1, 2, or 3 substituents independently selected from halo, hydroxy, alkyl, alkoxy.

In some embodiments, two R³ᵃ groups on two adjoining carbon atoms are taken together with the carbon atoms bound thereto to form

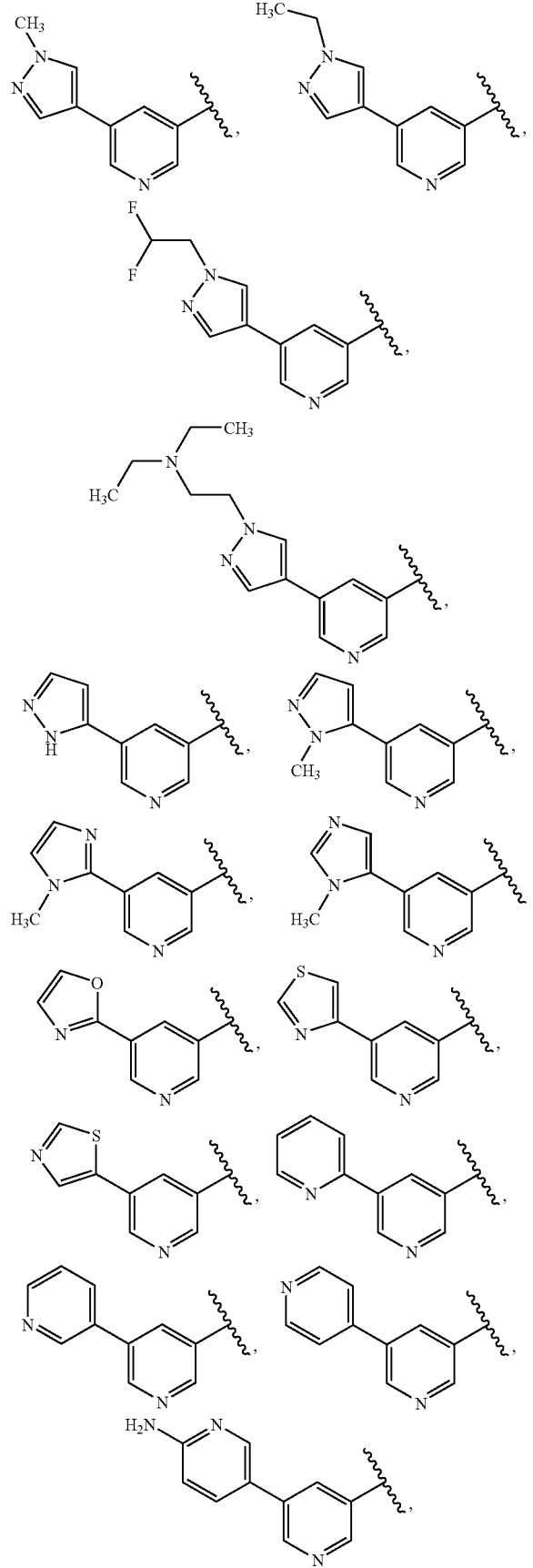
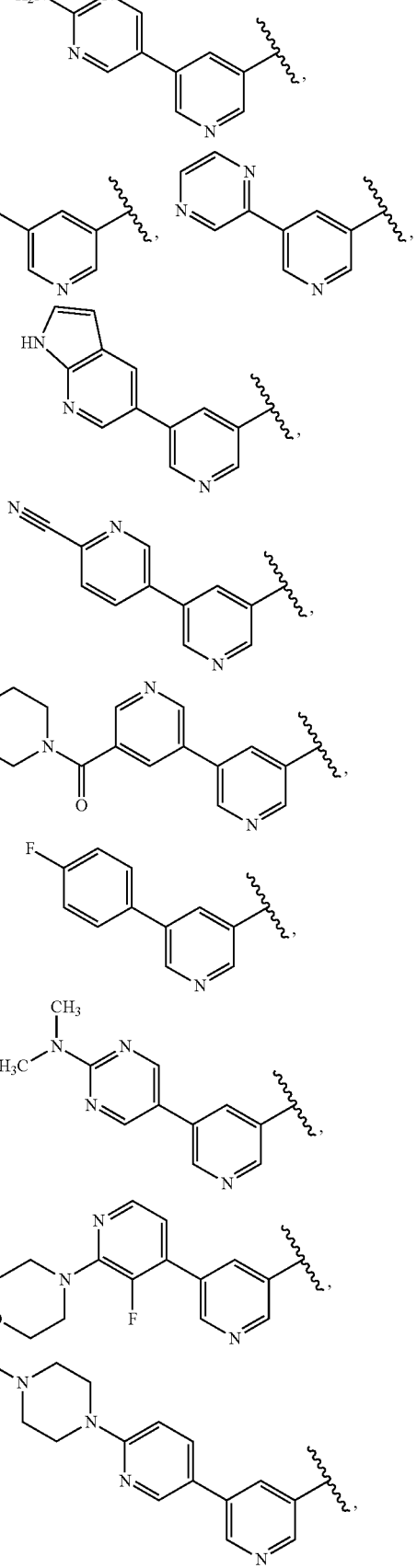

-continued
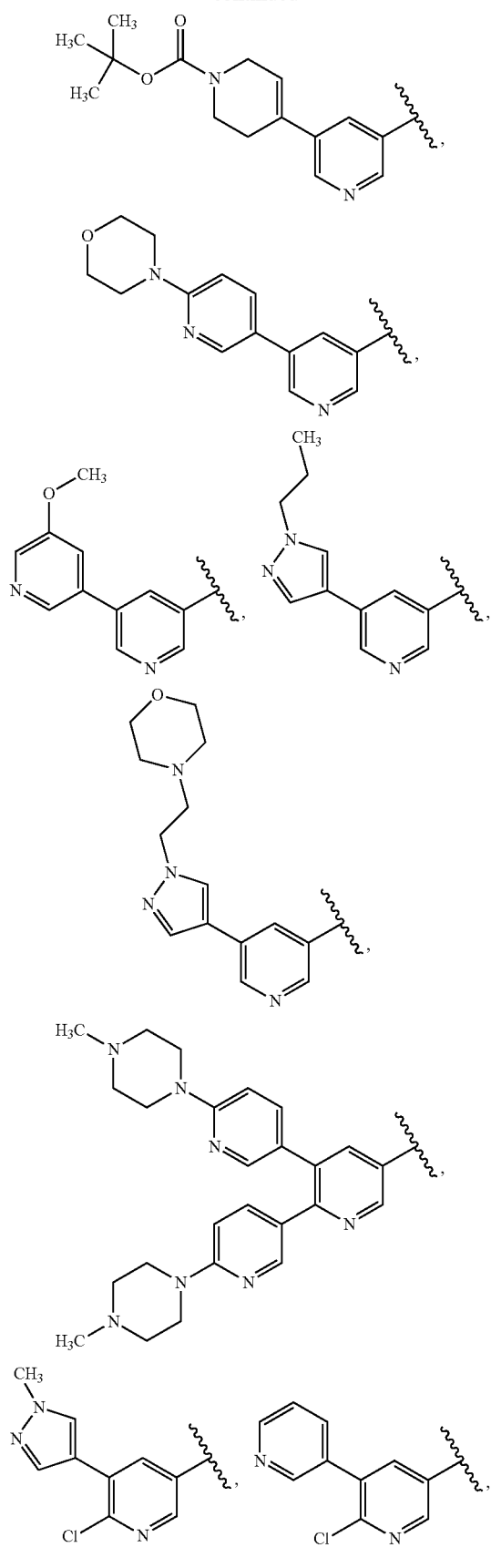
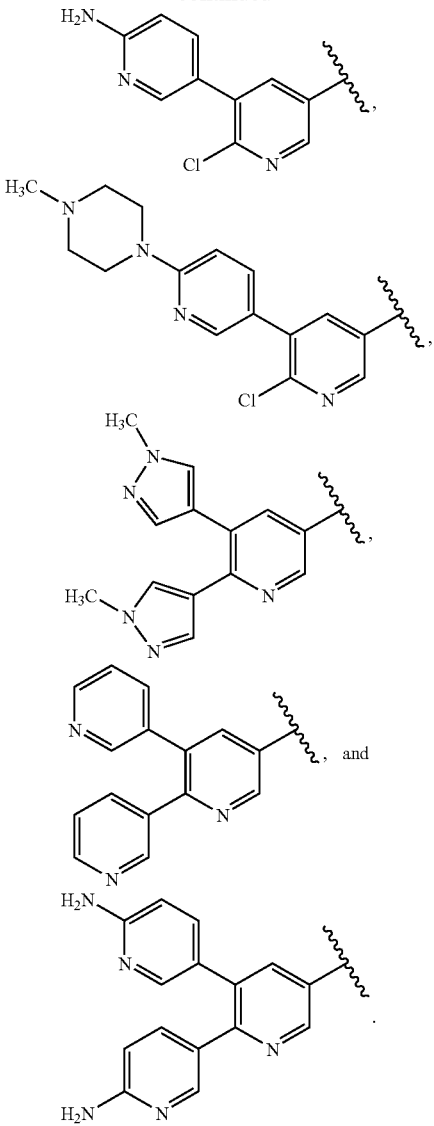
In some embodiments, ring A is
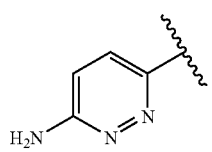
In some embodiments, ring A is selected from the group consisting of
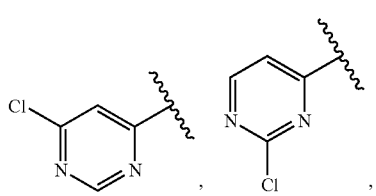

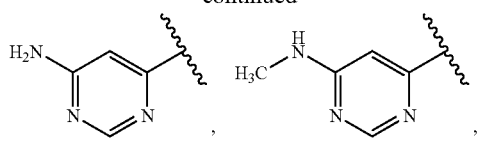
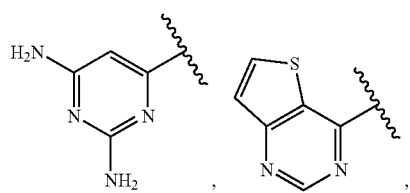
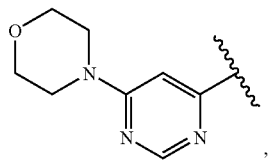
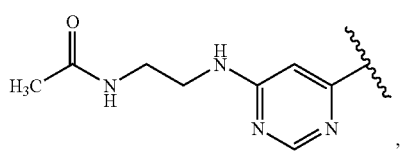
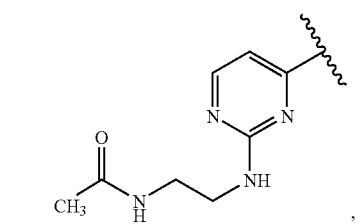
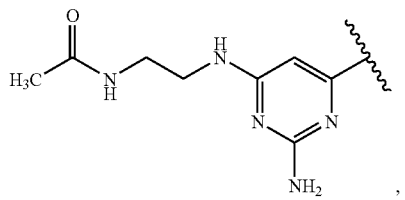
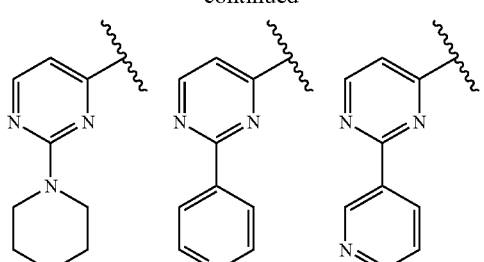
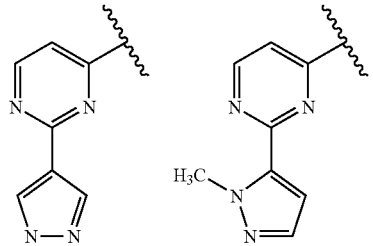
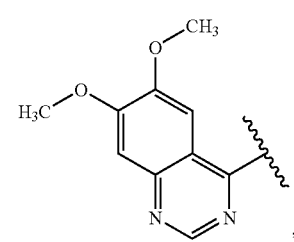
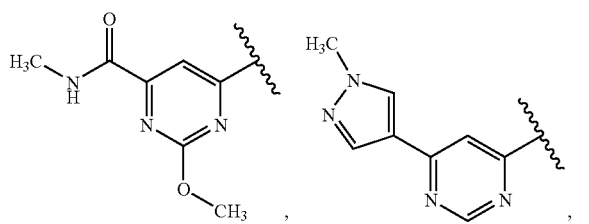
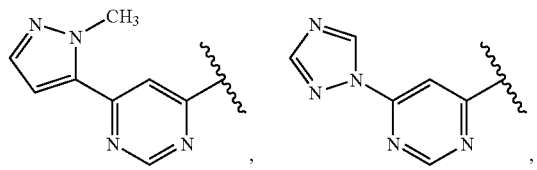
In some embodiments, ring A is selected from the group consisting of
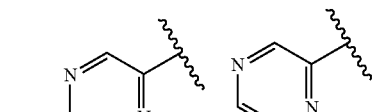
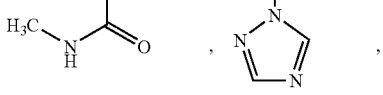
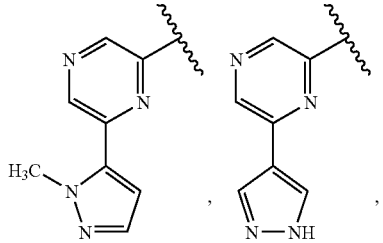

31
-continued

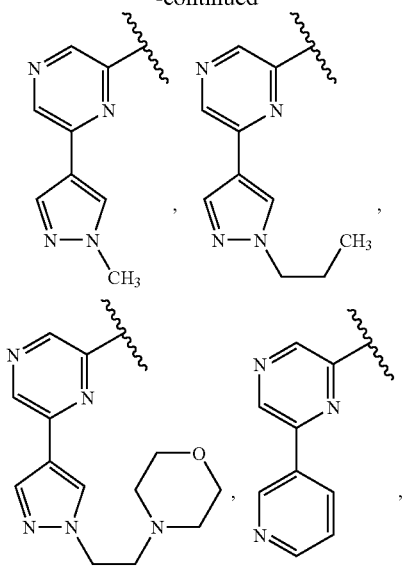

32
-continued

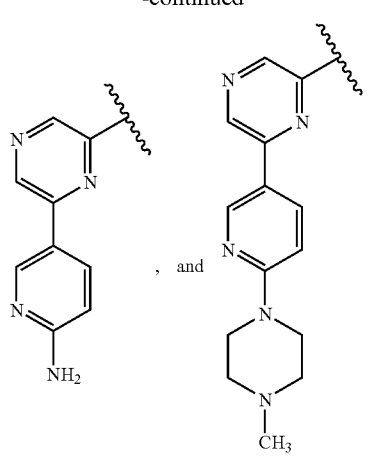

, and .

In some embodiments, a compound selected from Table 1 or an oxide, ester, prodrug, pharmaceutically acceptable salt, or solvate thereof is provided.

TABLE 1

| Cmpd # | Structure | Name |
|---|---|---|
| 1 | 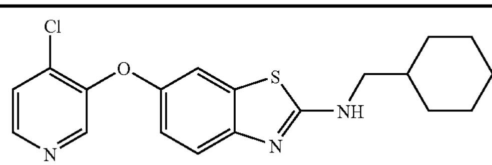 | 6-(4-chloropyridin-3-yloxy)-N-(cyclohexylmethyl)benzo[d]thiazol-2-amine |
| 2 | 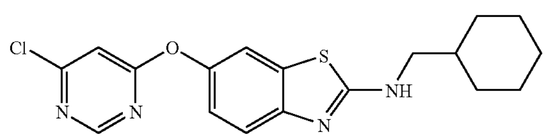 | 6-(6-chloropyrimidin-4-yloxy)-N-(cyclohexylmethyl)benzo[d]thiazol-2-amine |
| 3 | 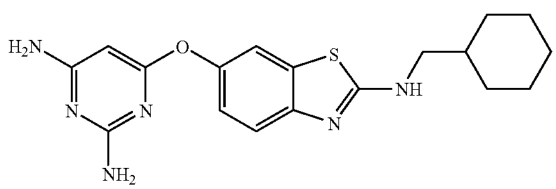 | 6-(2-(cyclohexylmethylamino)benzo[d]thiazol-6-yloxy)pyrimidine-2,4-diamine |
| 4 | 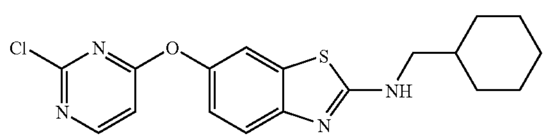 | 6-(2-chloropyrimidin-4-yloxy)-N-(cyclohexylmethyl)benzo[d]thiazol-2-amine |
| 5 | 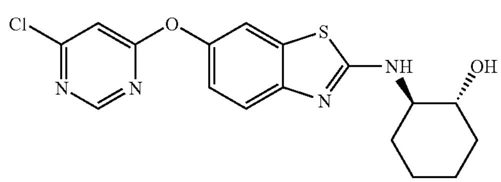 | (1R,2R)-2-(6-(6-chloropyrimidin-4-yloxy)benzo[d]thiazol-2-ylamino)cyclohexanol |
| 6 | 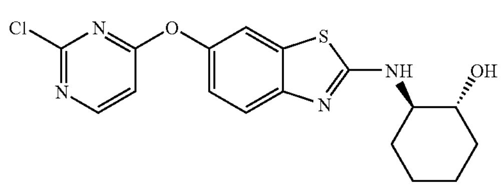 | (1R,2R)-2-(6-(2-chloropyrimidin-4-yloxy)benzo[d]thiazol-2-ylamino)cyclohexanol |

TABLE 1-continued

| Cmpd # | Structure | Name |
|---|---|---|
| 7 | 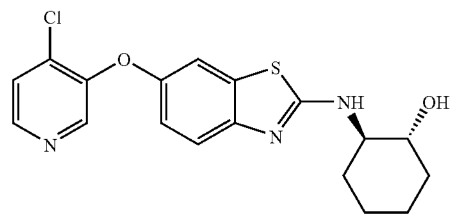 | (1R,2R)-2-(6-(4-chloropyridin-3-yloxy)benzo[d]thiazol-2-ylamino)cyclohexanol |
| 8 | 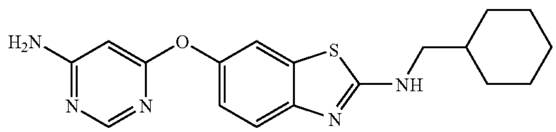 | 6-(6-aminopyrimidin-4-yloxy)-N-(cyclohexylmethyl)benzo[d]thiazol-2-amine |
| 9 | 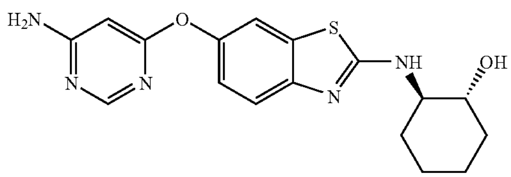 | (1R,2R)-2-(6-(6-aminopyrimidin-4-yloxy)benzo[d]thiazol-2-ylamino)cyclohexanol |
| 10 | 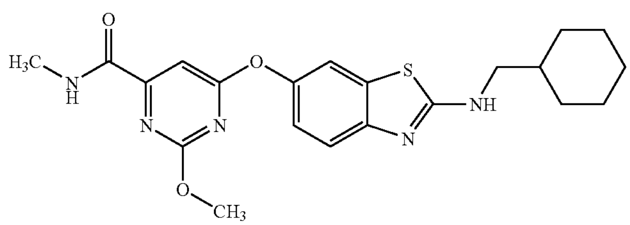 | 6-(2-(cyclohexylmethylamino)benzo[d]thiazol-6-yloxy)-2-methoxy-N-methylpyrimidine-4-carboxamide |
| 11 | 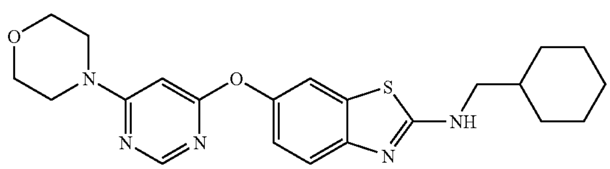 | N-(cyclohexylmethyl)-6-(6-morpholinopyrimidin-4-yloxy)benzo[d]thiazol-2-amine |
| 12 | 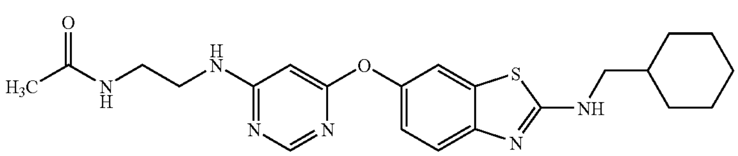 | N-(2-(6-(2-(cyclohexylmethylamino)benzo[d]thiazol-6-yloxy)pyrimidin-4-ylamino)ethyl)acetamide |
| 13 | 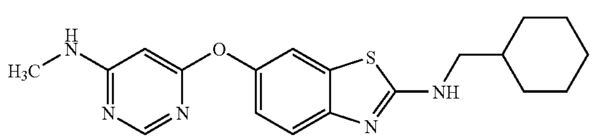 | N-(cyclohexylmethyl)-6-(6-(methylamino)pyrimidin-4-yloxy)benzo[d]thiazol-2-amine |
| 14 | 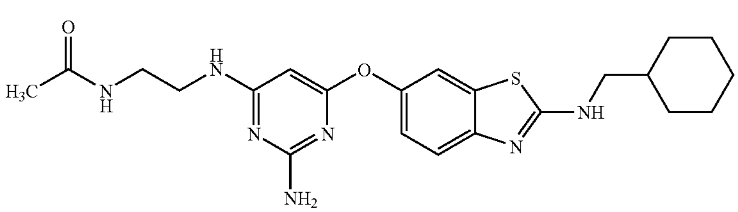 | N-(2-(2-amino-6-(2-(cyclohexylmethylamino)benzo[d]thiazol-6-yloxy)pyrimidin-4-ylamino)ethyl)acetamide |

TABLE 1-continued

| Cmpd # | Structure | Name |
|---|---|---|
| 15 | 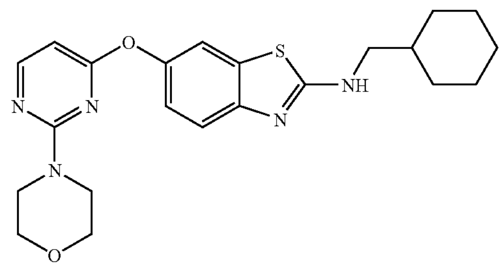 | N-(cyclohexylmethyl)-6-(2-morpholinopyrimidin-4-yloxy)benzo[d]thiazol-2-amine |
| 16 | 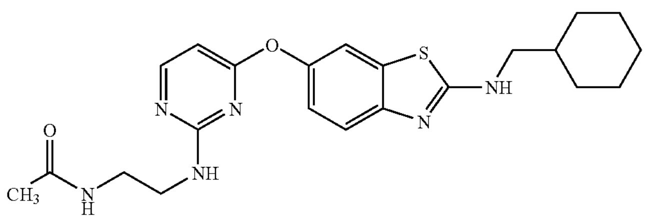 | N-(2-(4-(2-(cyclohexylmethylamino)benzo[d]thiazol-6-yloxy)pyrimidin-2-ylamino)ethyl)acetamide |
| 17 | 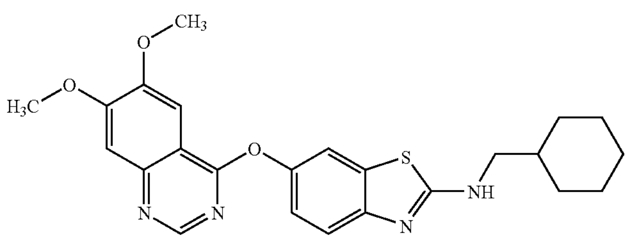 | N-(cyclohexylmethyl)-6-(6,7-dimethoxyquinazolin-4-yloxy)benzo[d]thiazol-2-amine |
| 18 | 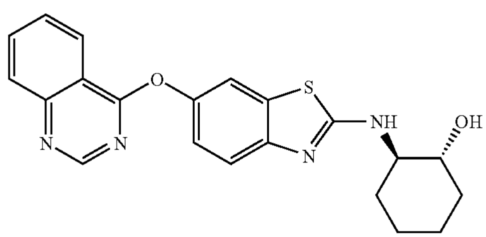 | (1R,2R)-2-(6-(quinazolin-4-yloxy)benzo[d]thiazol-2-ylamino)cyclohexanol |
| 19 | 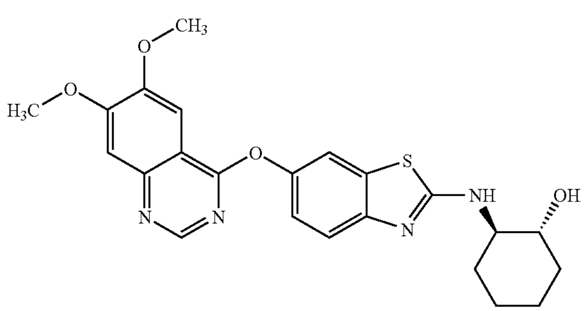 | (1R,2R)-2-(6-(6,7-dimethoxyquinazolin-4-yloxy)benzo[d]thiazol-2-ylamino)cyclohexanol |
| 20 | 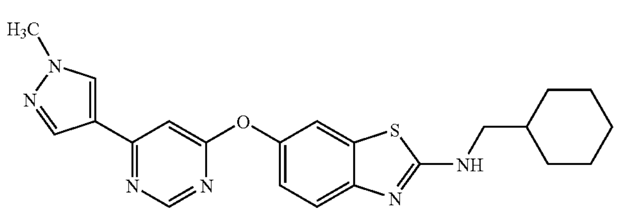 | N-(cyclohexylmethyl)-6-(6-(1-methyl-1H-pyrazol-4-yl)pyrimidin-4-yloxy)benzo[d]thiazol-2-amine |

TABLE 1-continued

| Cmpd # | Structure | Name |
|---|---|---|
| 21 | 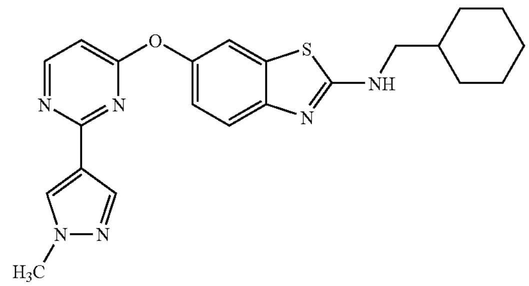 | N-(cyclohexylmethyl)-6-(2-(1-methyl-1H-pyrazol-4-yl)pyrimidin-4-yloxy)benzo[d]thiazol-2-amine |
| 22 | 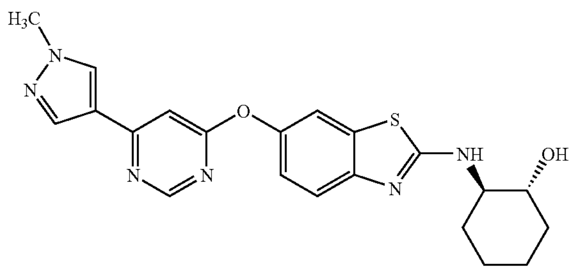 | (1R,2R)-2-(6-(6-(1-methyl-1H-pyrazol-4-yl)pyrimidin-4-yloxy)benzo[d]thiazol-2-ylamino)cyclohexanol |
| 23 | 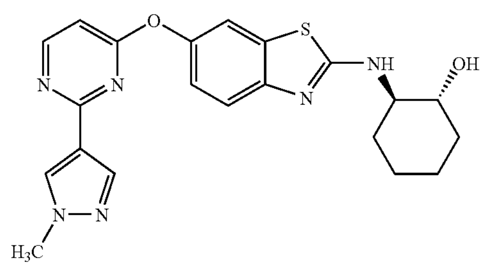 | (1R,2R)-2-(6-(2-(1-methyl-1H-pyrazol-4-yl)pyrimidin-4-yloxy)benzo[d]thiazol-2-ylamino)cyclohexanol |
| 24 | 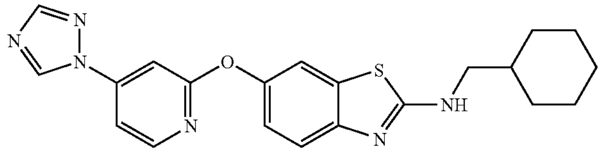 | 6-(4-(1H-1,2,4-triazol-1-yl)pyridin-2-yloxy)-N-(cyclohexylmethyl)benzo[d]thiazol-2-amine |
| 25 | 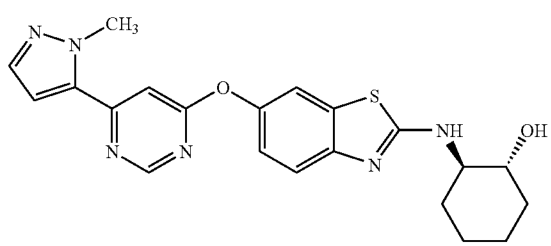 | (1R,2R)-2-(6-(6-(1-methyl-1H-pyrazol-5-yl)pyrimidin-4-yloxy)benzo[d]thiazol-2-ylamino)cyclohexanol |
| 26 | 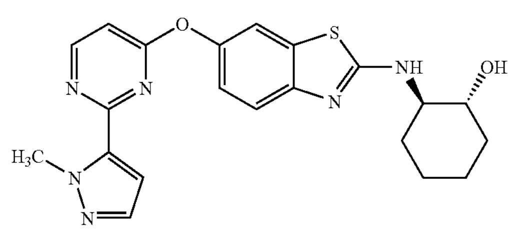 | (1R,2R)-2-(6-(2-(1-methyl-1H-pyrazol-5-yl)pyrimidin-4-yloxy)benzo[d]thiazol-2-ylamino)cyclohexanol |

TABLE 1-continued

| Cmpd # | Structure | Name |
|---|---|---|
| 27 | 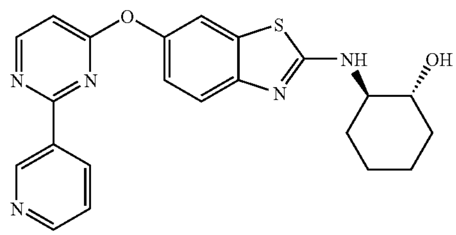 | (1R,2R)-2-(6-(2-(pyridin-3-yl)pyrimidin-4-yloxy)benzo[d]thiazol-2-ylamino)cyclohexanol |
| 28 | 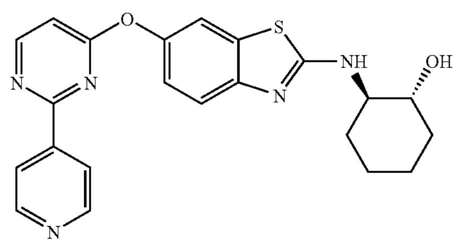 | (1R,2R)-2-(6-(2-(pyridin-4-yl)pyrimidin-4-yloxy)benzo[d]thiazol-2-ylamino)cyclohexanol |
| 29 | 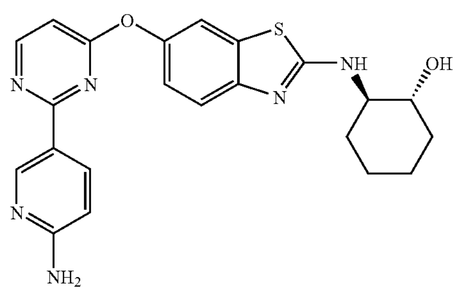 | (1R,2R)-2-(6-(2-(6-aminopyridin-3-yl)pyrimidin-4-yloxy)benzo[d]thiazol-2-ylamino)cyclohexanol |
| 30 | 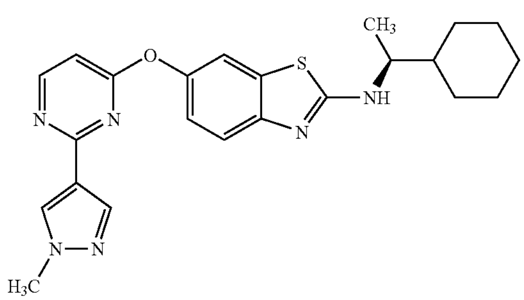 | (S)-N-(1-cyclohexylethyl)-6-(2-(1-methyl-1H-pyrazol-4-yl)pyrimidin-4-yloxy)benzo[d]thiazol-2-amine |
| 31 | 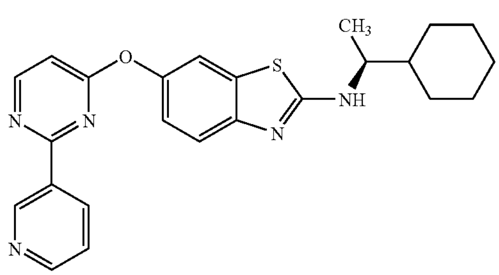 | (S)-N-(1-cyclohexylethyl)-6-(2-(pyridin-3-yl)pyrimidin-4-yloxy)benzo[d]thiazol-2-amine |

TABLE 1-continued

| Cmpd # | Structure | Name |
|---|---|---|
| 32 | 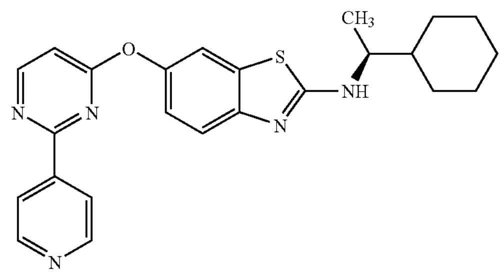 | (S)-N-(1-cyclohexylethyl)-6-(2-(pyridin-4-yl)pyrimidin-4-yloxy)benzo[d]thiazol-2-amine |
| 33 | 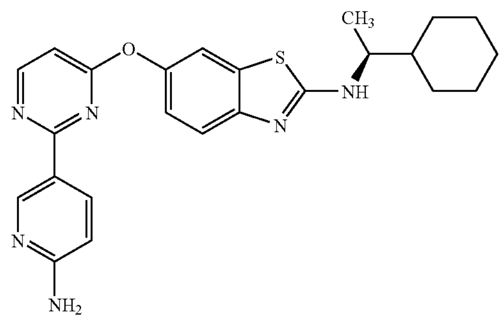 | (S)-6-(2-(6-aminopyridin-3-yl)pyrimidin-4-yloxy)-N-(1-cyclohexylethyl)benzo[d]thiazol-2-amine |
| 34 | 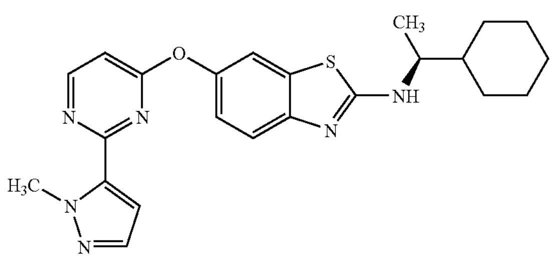 | (S)-N-(1-cyclohexylethyl)-6-(2-(1-methyl-1H-pyrazol-5-yl)pyrimidin-4-yloxy)benzo[d]thiazol-2-amine |
| 35 | 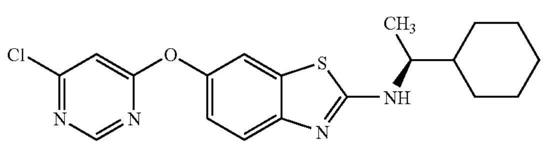 | (S)-6-(6-chloropyrimidin-4-yloxy)-N-(1-cyclohexylethyl)benzo[d]thiazol-2-amine |
| 36 | 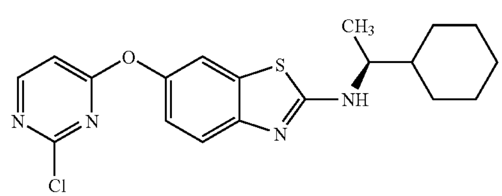 | (S)-6-(2-chloropyrimidin-4-yloxy)-N-(1-cyclohexylethyl)benzo[d]thiazol-2-amine |
| 37 | 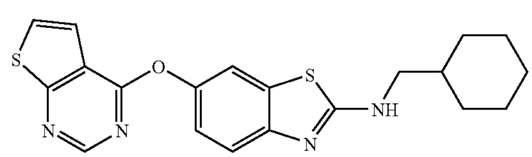 | N-(cyclohexylmethyl)-6-(thieno[2,3-d]pyrimidin-4-yloxy)benzo[d]thiazol-2-amine |
| 38 | 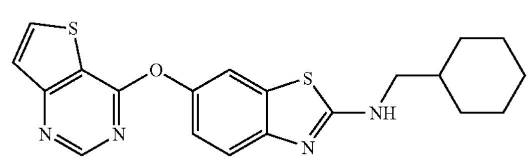 | N-(cyclohexylmethyl)-6-(thieno[3,2-d]pyrimidin-4-yloxy)benzo[d]thiazol-2-amine |

TABLE 1-continued

| Cmpd # | Structure | Name |
|---|---|---|
| 39 | 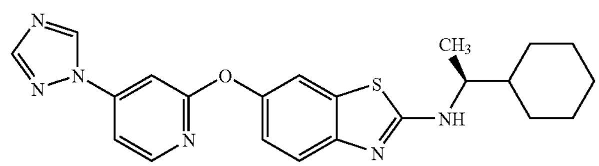 | (S)-6-(4-(1H-1,2,4-triazol-1-yl)pyridin-2-yloxy)-N-(1-cyclohexylethyl)benzo[d]thiazol-2-amine |
| 40 | 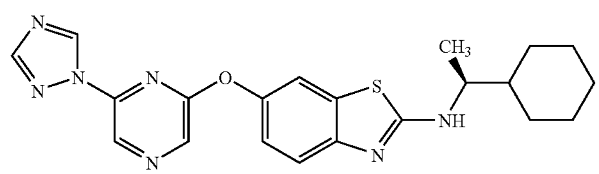 | (S)-6-(6-(1H-1,2,4-triazol-1-yl)pyrazin-2-yloxy)-N-(1-cyclohexylethyl)benzo[d]thiazol-2-amine |
| 41 | 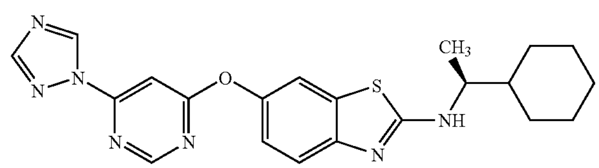 | (S)-6-(6-(1H-1,2,4-triazol-1-yl)pyrimidin-4-yloxy)-N-(1-cyclohexylethyl)benzo[d]thiazol-2-amine |
| 42 | 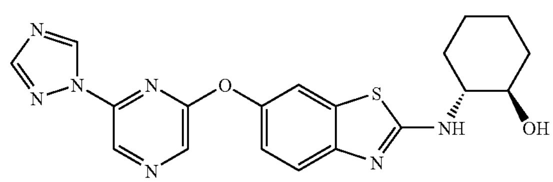 | (1R,2R)-2-(6-(6-(1H-1,2,4-triazol-1-yl)pyrazin-2-yloxy)benzo[d]thiazol-2-ylamino)cyclohexanol |
| 43 | 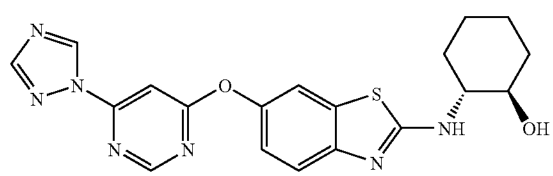 | (1R,2R)-2-(6-(6-(1H-1,2,4-triazol-1-yl)pyrimidin-4-yloxy)benzo[d]thiazol-2-ylamino)cyclohexanol |
| 44 | 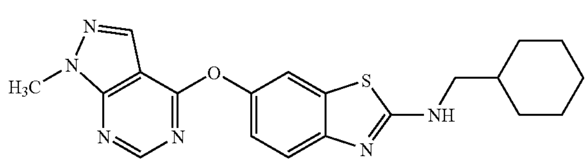 | N-(cyclohexylmethyl)-6-(1-methyl-1H-pyrazolo[3,4-d]pyrimidin-4-yloxy)benzo[d]thiazol-2-amine |
| 45 | 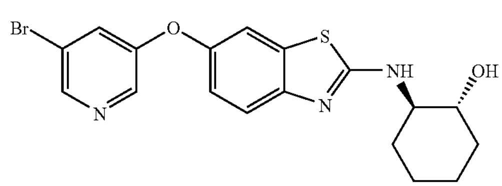 | (1R,2R)-2-(6-(5-bromopyridin-3-yloxy)benzo[d]thiazol-2-ylamino)cyclohexanol |
| 46 | 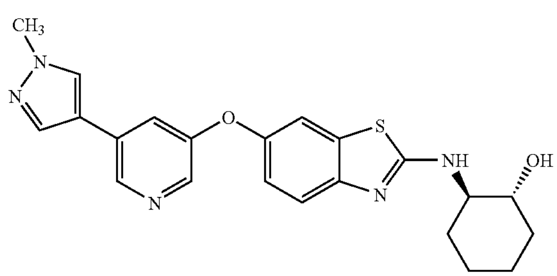 | (1R,2R)-2-(6-(5-(1-methyl-1H-pyrazol-4-yl)pyridin-3-yloxy)benzo[d]thiazol-2-ylamino)cyclohexanol |

TABLE 1-continued

| Cmpd # | Structure | Name |
|---|---|---|
| 47 | 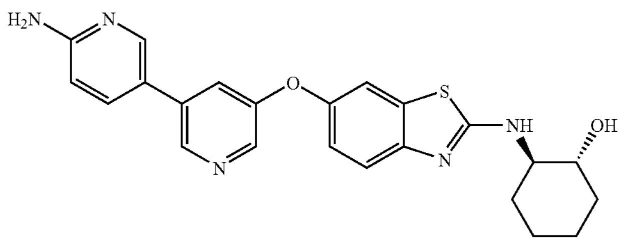 | (1R,2R)-2-(6-(6'-amino-3,3'-bipyridin-5-yloxy)benzo[d]thiazol-2-ylamino)cyclohexanol |
| 48 | 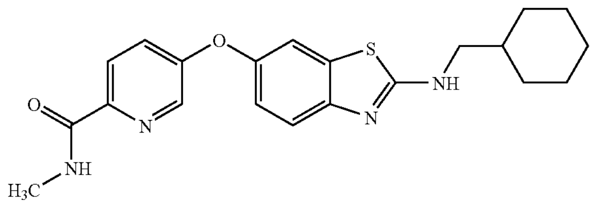 | 5-(2-(cyclohexylmethylamino)benzo[d]thiazol-6-yloxy)-N-methylpicolinamide |
| 49 | 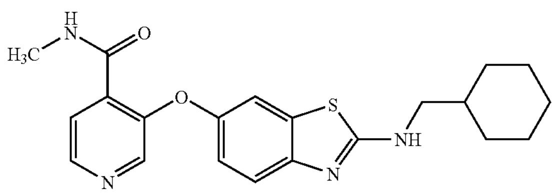 | 3-(2-(cyclohexylmethylamino)benzo[d]thiazol-6-yloxy)-N-methylisonicotinamide |
| 50 | 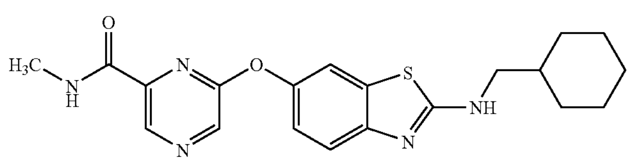 | 6-(2-(cyclohexylmethylamino)benzo[d]thiazol-6-yloxy)-N-methylpyrazine-2-carboxamide |
| 51 | 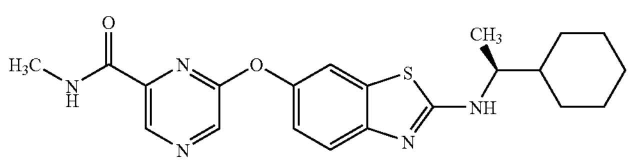 | (S)-6-(2-(1-cyclohexylethylamino)benzo[d]thiazol-6-yloxy)-N-methylpyrazine-2-carboxamide |
| 52 | 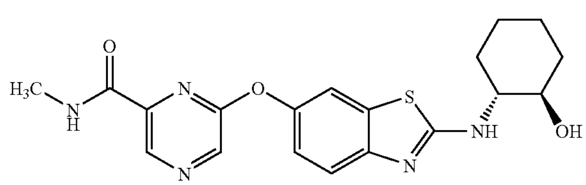 | 6-(2-((1R,2R)-2-hydroxycyclohexylamino)benzo[d]thiazol-6-yloxy)-N-methylpyrazine-2-carboxamide |
| 53 | 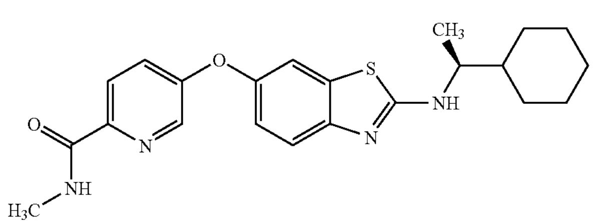 | (S)-5-(2-(1-cyclohexylethylamino)benzo[d]thiazol-6-yloxy)-N-methylpicolinamide |

TABLE 1-continued

| Cmpd # | Structure | Name |
|---|---|---|
| 54 | 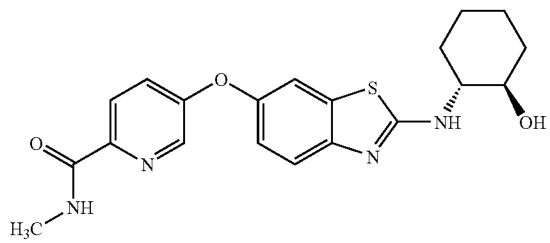 | 5-(2-(((1R,2R)-2-hydroxycyclohexylamino)benzo[d]thiazol-6-yloxy)-N-methylpicolinamide |
| 55 | 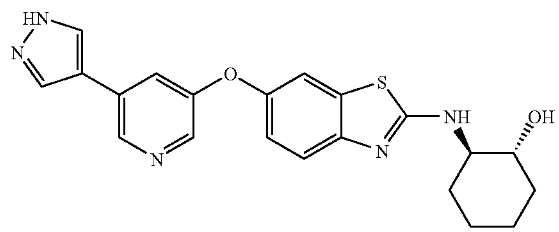 | (1R,2R)-2-(6-(5-(1H-pyrazol-4-yl)pyridin-3-yloxy)benzo[d]thiazol-2-ylamino)cyclohexanol |
| 56 | 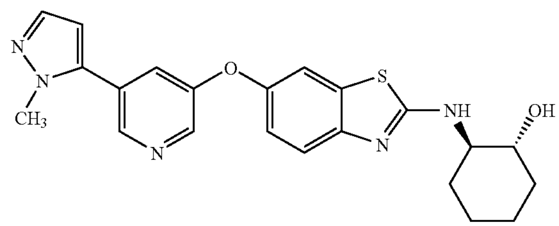 | (1R,2R)-2-(6-(5-(1-methyl-1H-pyrazol-5-yl)pyridin-3-yloxy)benzo[d]thiazol-2-ylamino)cyclohexanol |
| 57 | 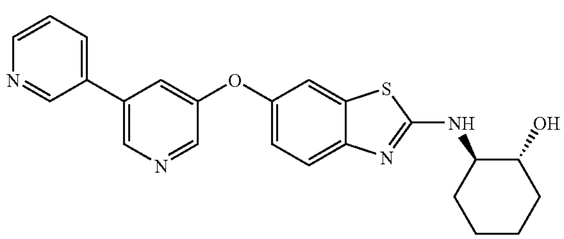 | (1R,2R)-2-(6-(3,3'-bipyridin-5-yloxy)benzo[d]thiazol-2-ylamino)cyclohexanol |
| 58 | 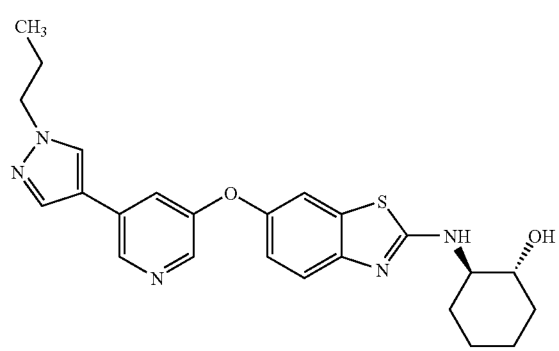 | (1R,2R)-2-(6-(5-(1-propyl-1H-pyrazol-4-yl)pyridin-3-yloxy)benzo[d]thiazol-2-ylamino)cyclohexanol |

TABLE 1-continued

| Cmpd # | Structure | Name |
|---|---|---|
| 59 | 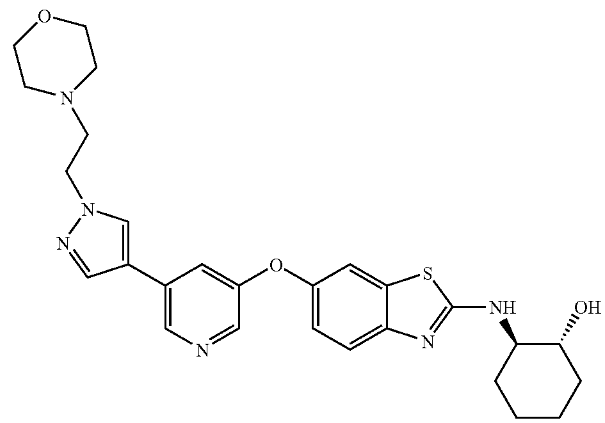 | (1R,2R)-2-(6-(5-(1-(2-morpholinoethyl)-1H-pyrazol-4-yl)pyridin-3-yloxy)benzo[d]thiazol-2-ylamino)cyclohexanol |
| 60 | 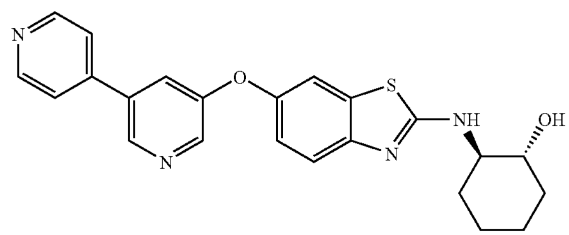 | (1R,2R)-2-(6-(3,4'-bipyridin-5-yloxy)benzo[d]thiazol-2-ylamino)cyclohexanol |
| 61 | 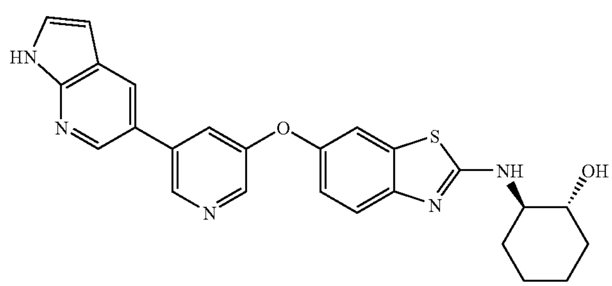 | (1R,2R)-2-(6-(5-(1H-pyrrolo[2,3-b]pyridin-5-yl)pyridin-3-yloxy)benzo[d]thiazol-2-ylamino)cyclohexanol |
| 62 | 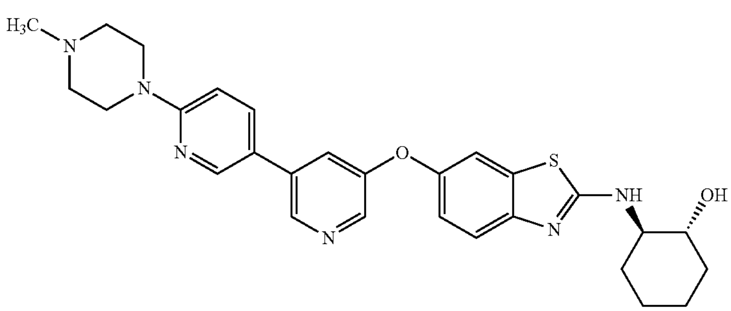 | (1R,2R)-2-(6-(6'-(4-methylpiperazin-1-yl)-3,3'-bipyridin-5-yloxy)benzo[d]thiazol-2-ylamino)cyclohexanol |
| 63 | 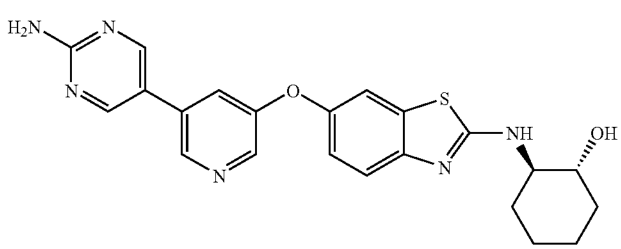 | (1R,2R)-2-(6-(5-(2-aminopyrimidin-5-yl)pyridin-3-yloxy)benzo[d]thiazol-2-ylamino)cyclohexanol |

TABLE 1-continued

| Cmpd # | Structure | Name |
| --- | --- | --- |
| 64 | 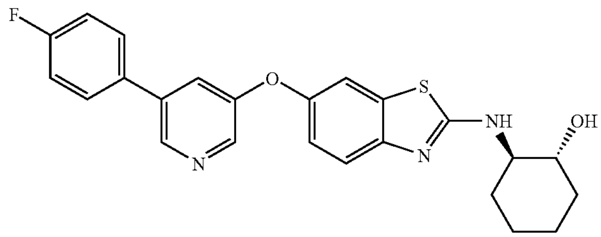 | (1R,2R)-2-(6-(5-(4-fluorophenyl)pyridin-3-yloxy)benzo[d]thiazol-2-ylamino)cyclohexanol |
| 65 | 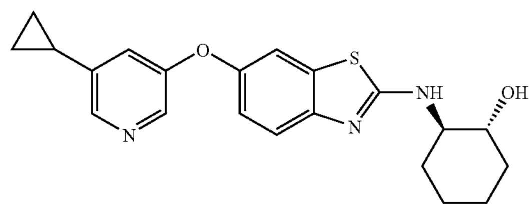 | (1R,2R)-2-(6-(5-cyclopropylpyridin-3-yloxy)benzo[d]thiazol-2-ylamino)cyclohexanol |
| 66 | 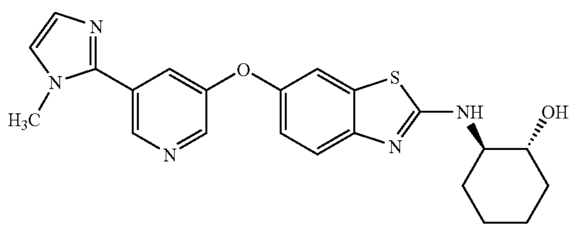 | (1R,2R)-2-(6-(5-(1-methyl-1H-imidazol-2-yl)pyridin-3-yloxy)benzo[d]thiazol-2-ylamino)cyclohexanol |
| 67 | 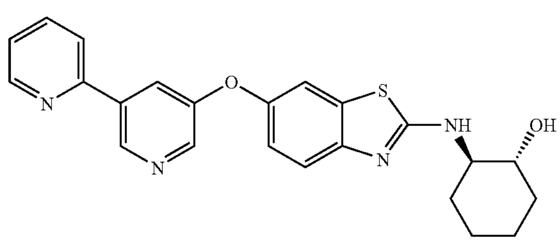 | (1R,2R)-2-(6-(2,3'-bipyridin-5'-yloxy)benzo[d]thiazol-2-ylamino)cyclohexanol |
| 68 | 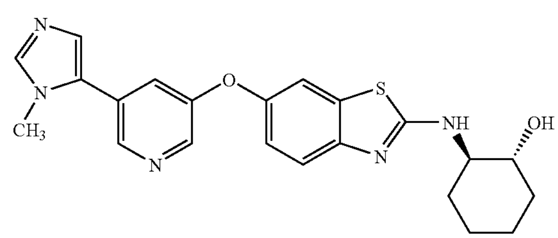 | (1R,2R)-2-(6-(5-(1-methyl-1H-imidazol-5-yl)pyridin-3-yloxy)benzo[d]thiazol-2-ylamino)cyclohexanol |
| 69 | 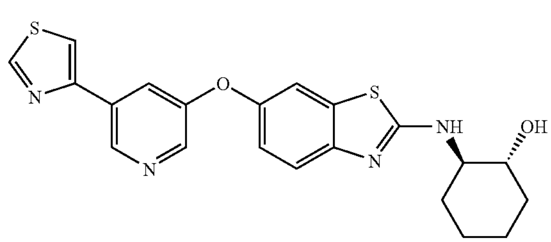 | (1R,2R)-2-(6-(5-(thiazol-4-yl)pyridin-3-yloxy)benzo[d]thiazol-2-ylamino)cyclohexanol |

TABLE 1-continued

| Cmpd # | Structure | Name |
|---|---|---|
| 70 | 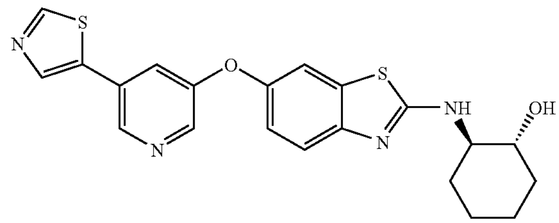 | (1R,2R)-2-(6-(5-(thiazol-5-yl) pyridin-3-yloxy)benzo[d] thiazol-2-ylamino)cyclohexanol |
| 71 | 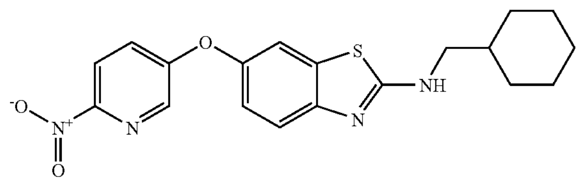 | N-(cyclohexylmethyl)-6-(6-nitropyridin-3-yloxy)benzo[d] thiazol-2-amine |
| 72 | 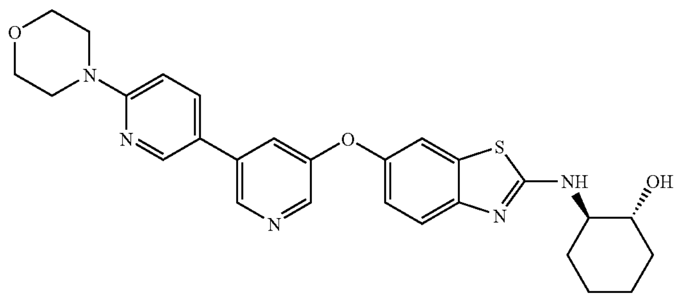 | (1R,2R)-2-(6-(6'-morpholino-3,3'-bipyridin-5-yloxy)benzo [d]thiazol-2-ylamino)cyclohexanol |
| 73 | 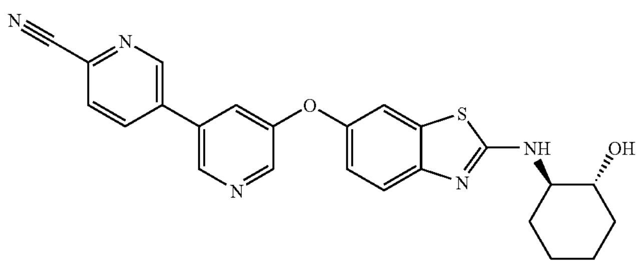 | 5'-(2-((1R,2R)-2-hydroxycyclohexylamino)benzo[d] thiazol-6-yloxy)-3,3'-bipyridine-6-carbonitrile |
| 74 | 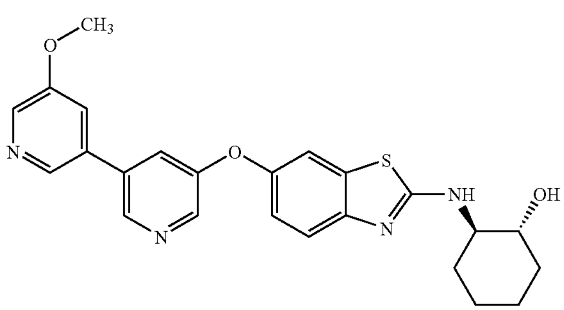 | (1R,2R)-2-(6-(5'-methoxy-3,3'-bipyridin-5-yloxy)benzo [d]thiazol-2-ylamino)cyclohexanol |
| 75 | 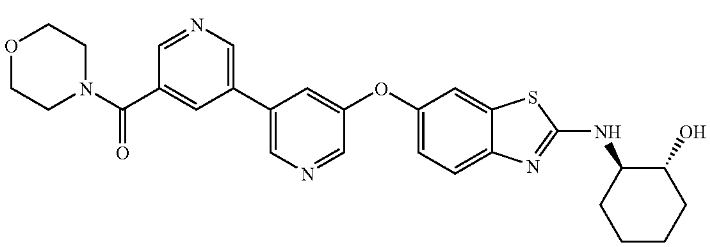 | (5'-(2-((1R,2R)-2-hydroxycyclohexylamino)benzo[d] thiazol-6-yloxy)-3,3'-bipyridin-5-yl)(morpholino)methanone |

TABLE 1-continued

| Cmpd # | Structure | Name |
|---|---|---|
| 76 | 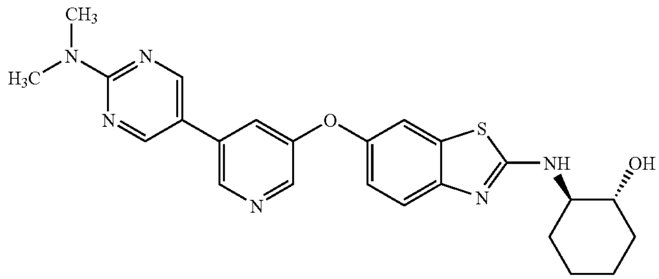 | (1R,2R)-2-(6-(5-(2-(dimethylamino)pyrimidin-5-yl)pyridin-3-yloxy)benzo[d]thiazol-2-ylamino)cyclohexanol |
| 77 | 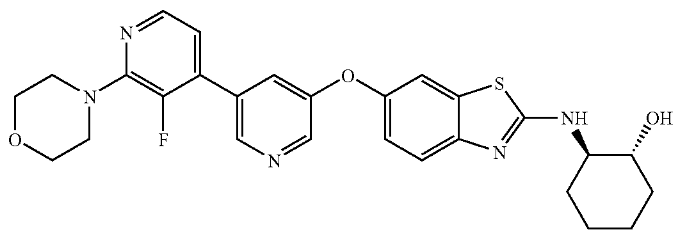 | (1R,2R)-2-(6-(3'-fluoro-2'-morpholino-3,4'-bipyridin-5-yloxy)benzo[d]thiazol-2-ylamino)cyclohexanol |
| 78 | 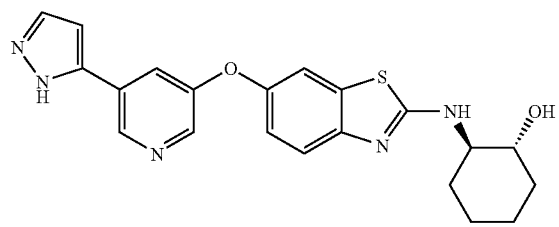 | (1R,2R)-2-(6-(5-(1H-pyrazol-5-yl)pyridin-3-yloxy)benzo[d]thiazol-2-ylamino)cyclohexanol |
| 79 | 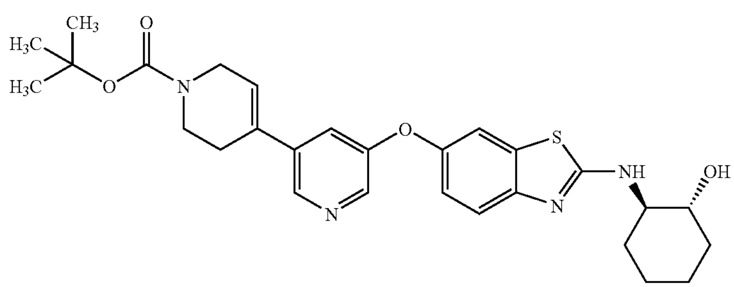 | tert-butyl 4-(5-(2-((1R,2R)-2-hydroxycyclohexylamino)benzo[d]thiazol-6-yloxy)pyridin-3-yl)-5,6-dihydropyridine-1(2H)-carboxylate |
| 80 | 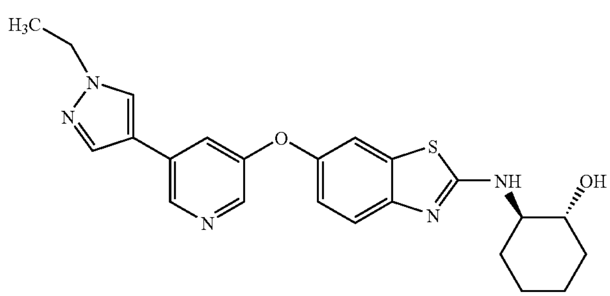 | (1R,2R)-2-(6-(5-(1-ethyl-1H-pyrazol-4-yl)pyridin-3-yloxy)benzo[d]thiazol-2-ylamino)cyclohexanol |

| Cmpd # | Structure | Name |
|---|---|---|
| 81 | 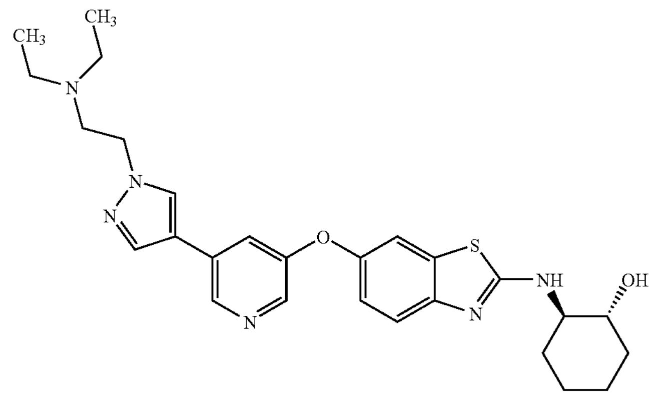 | (1R,2R)-2-(6-(5-(1-(2-diethylamino)ethyl)-1H-pyrazol-4-yl)pyridin-3-yloxy)benzo[d]thiazol-2-ylamino)cyclohexanol |
| 82 | 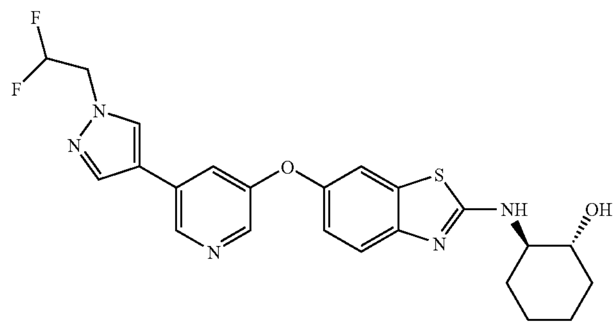 | (1R,2R)-2-(6-(5-(1-(2,2-difluoroethyl)-1H-pyrazol-4-yl)pyridin-3-yloxy)benzo[d]thiazol-2-ylamino)cyclohexanol |
| 83 | 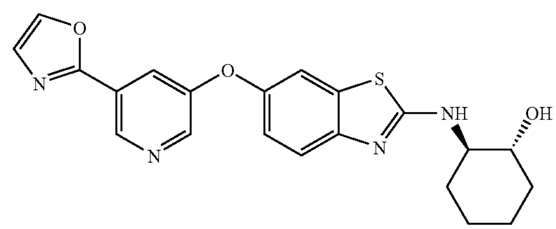 | (1R,2R)-2-(6-(5-(oxazol-2-yl)pyridin-3-yloxy)benzo[d]thiazol-2-ylamino)cyclohexanol |
| 84 | 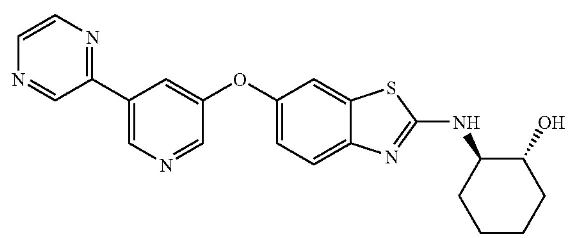 | (1R,2R)-2-(6-(5-(pyrazin-2-yl)pyridin-3-yloxy)benzo[d]thiazol-2-ylamino)cyclohexanol |
| 85 | 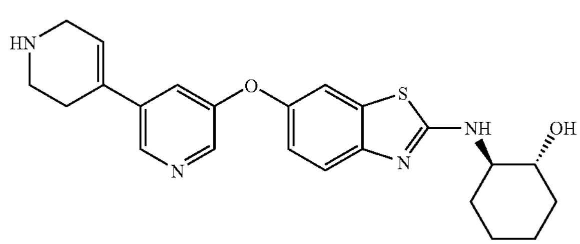 | (1R,2R)-2-(6-(5-(1,2,3,6-tetrahydropyridin-4-yl)pyridin-3-yloxy)benzo[d]thiazol-2-ylamino)cyclohexanol |
| 86 | 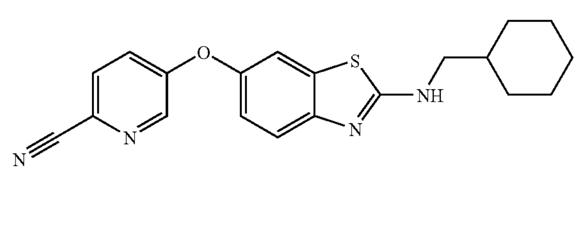 | 5-(2-(cyclohexylmethylamino)benzo[d]thiazol-6-yloxy)picolinonitrile |

TABLE 1-continued

| Cmpd # | Structure | Name |
|---|---|---|
| 87 | 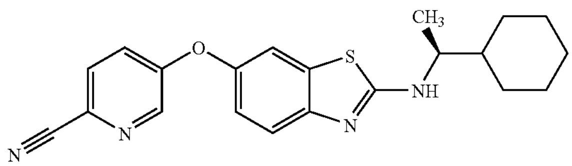 | (S)-5-(2-(1-cyclohexylethylamino)benzo[d]thiazol-6-yloxy)picolinonitrile |
| 88 | 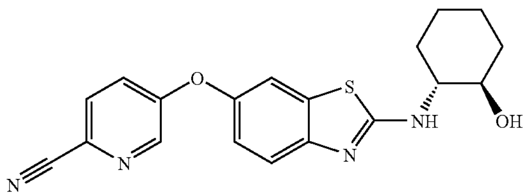 | 5-(2-((1R,2R)-2-hydroxycyclohexylamino)benzo[d]thiazol-6-yloxy)picolinonitrile |
| 89 | 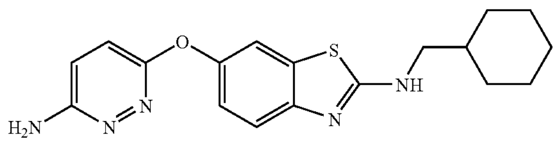 | 6-(6-aminopyridazin-3-yloxy)-N-(cyclohexylmethyl)benzo[d]thiazol-2-amine |
| 90 | 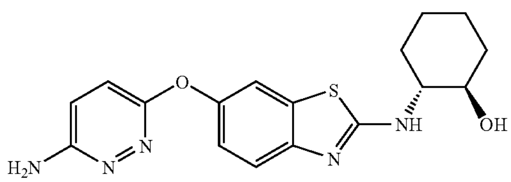 | (1R,2R)-2-(6-(6-aminopyridazin-3-yloxy)benzo[d]thiazol-2-ylamino)cyclohexanol |
| 91 | 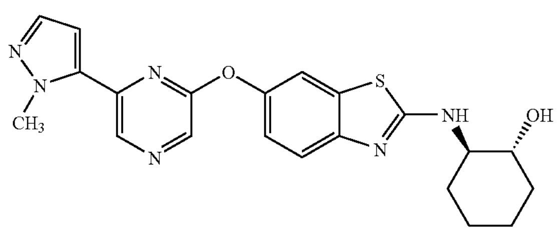 | (1R,2R)-2-(6-(6-(1-methyl-1H-pyrazol-5-yl)pyrazin-2-yloxy)benzo[d]thiazol-2-ylamino)cyclohexanol |
| 92 | 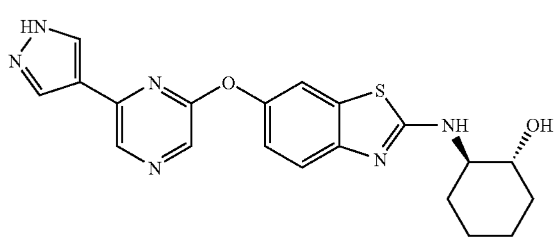 | (1R,2R)-2-(6-(6-(1H-pyrazol-4-yl)pyrazin-2-yloxy)benzo[d]thiazol-2-ylamino)cyclohexanol |
| 93 | 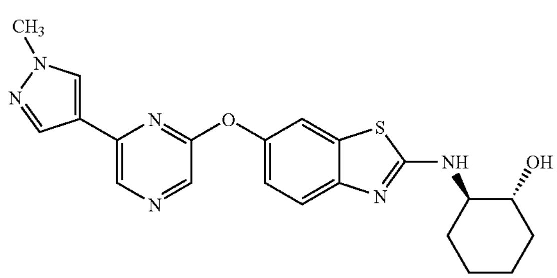 | (1R,2R)-2-(6-(6-(1-methyl-1H-pyrazol-4-yl)pyrazin-2-yloxy)benzo[d]thiazol-2-ylamino)cyclohexanol |

TABLE 1-continued

| Cmpd # | Structure | Name |
|---|---|---|
| 94 | 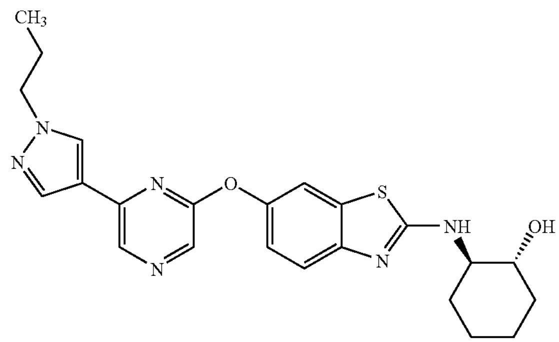 | (1R,2R)-2-(6-(6-(1-propyl-1H-pyrazol-4-yl)pyrazin-2-yloxy)benzo[d]thiazol-2-ylamino)cyclohexanol |
| 95 | 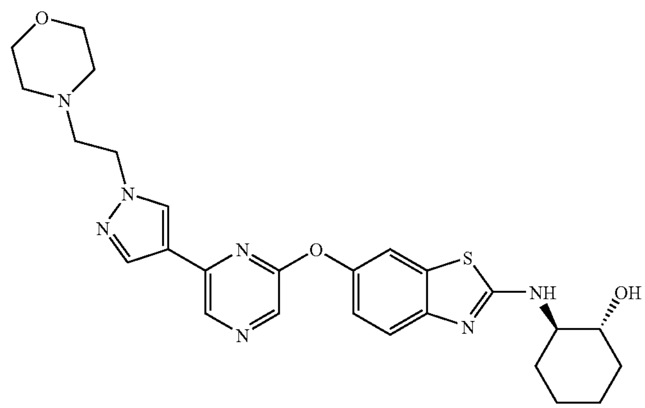 | (1R,2R)-2-(6-(6-(1-(2-morpholinoethyl)-1H-pyrazol-4-yl)pyrazin-2-yloxy)benzo[d]thiazol-2-ylamino)cyclohexanol |
| 96 | 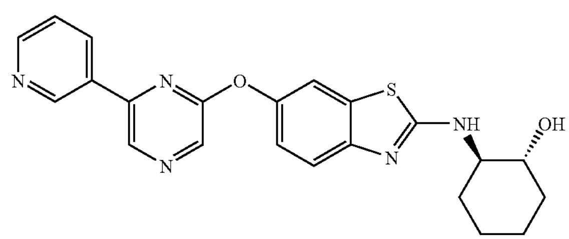 | (1R,2R)-2-(6-(6-(pyridin-3-yl)pyrazin-2-yloxy)benzo[d]thiazol-2-ylamino)cyclohexanol |
| 97 | 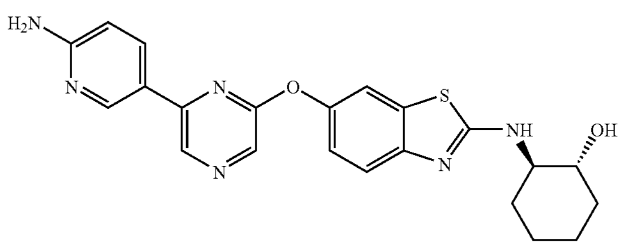 | (1R,2R)-2-(6-(6-(6-aminopyridin-3-yl)pyrazin-2-yloxy)benzo[d]thiazol-2-ylamino)cyclohexanol |
| 98 | 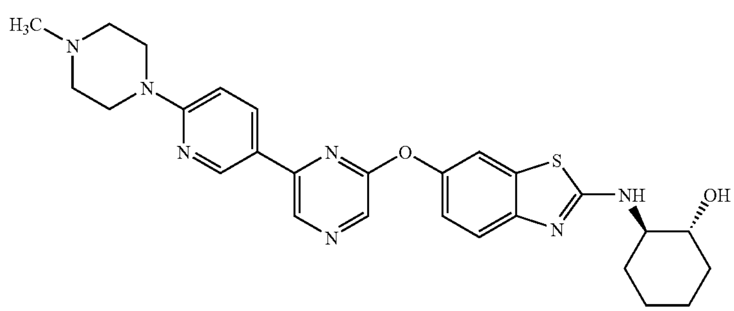 | (1R,2R)-2-(6-(6-(6-(4-methylpiperazin-1-yl)pyridin-3-yl)pyrazin-2-yloxy)benzo[d]thiazol-2-ylamino)cyclohexanol |

TABLE 1-continued

| Cmpd # | Structure | Name |
|---|---|---|
| 99 | 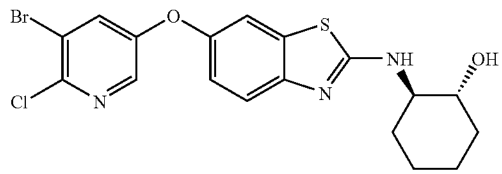 | (1R,2R)-2-(6-(5-bromo-6-chloropyridin-3-yloxy)benzo[d]thiazol-2-ylamino)cyclohexanol |
| 100 | 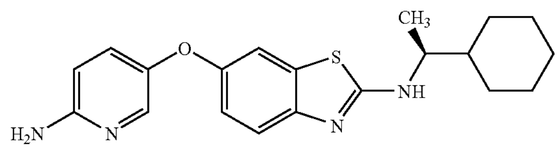 | (S)-6-(6-aminopyridin-3-yloxy)-N-(1-cyclohexylethyl)benzo[d]thiazol-2-amine |
| 101 | 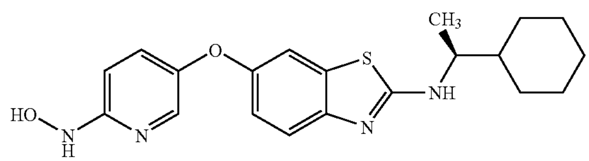 | (S)-N-(1-cyclohexylethyl)-6-(6-(hydroxyamino)pyridin-3-yloxy)benzo[d]thiazol-2-amine |
| 102 | 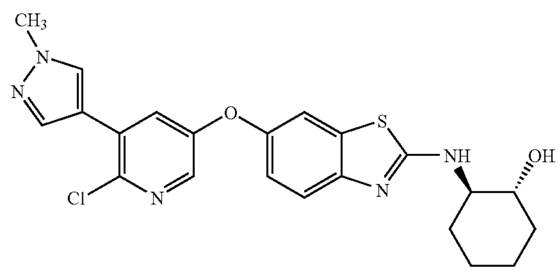 | (1R,2R)-2-(6-(6-chloro-5-(1-methyl-1H-pyrazol-4-yl)pyridin-3-yloxy)benzo[d]thiazol-2-ylamino)cyclohexanol |
| 103 | 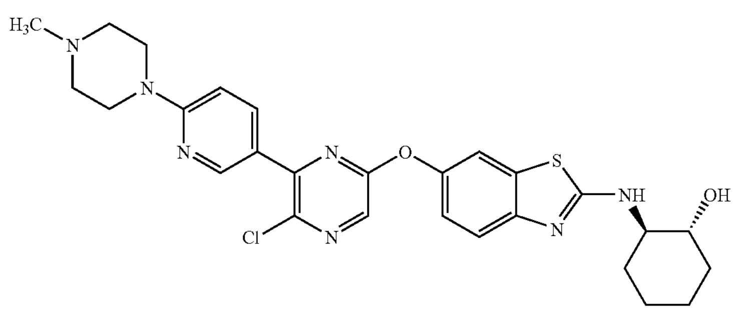 | (1R,2R)-2-(6-(2-chloro-6'-(4-methylpiperazin-1-yl)-3,3'-bipyridin-5-yloxy)benzo[d]thiazol-2-ylamino)cyclohexanol |
| 104 | 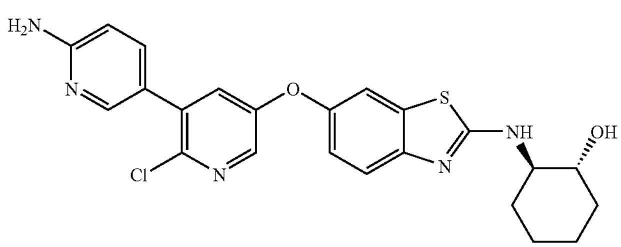 | (1R,2R)-2-(6-(6'-amino-2-chloro-3,3'-bipyridin-5-yloxy)benzo[d]thiazol-2-ylamino)cyclohexanol |
| 105 | 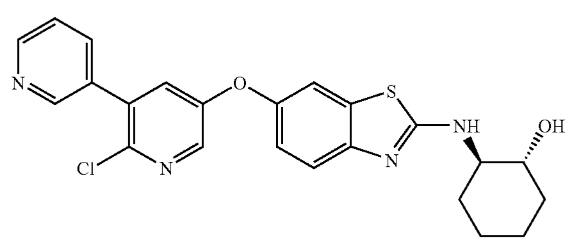 | (1R,2R)-2-(6-(2-chloro-3,3'-bipyridin-5-yloxy)benzo[d]thiazol-2-ylamino)cyclohexanol |

TABLE 1-continued

| Cmpd # | Structure | Name |
|---|---|---|
| 106 | 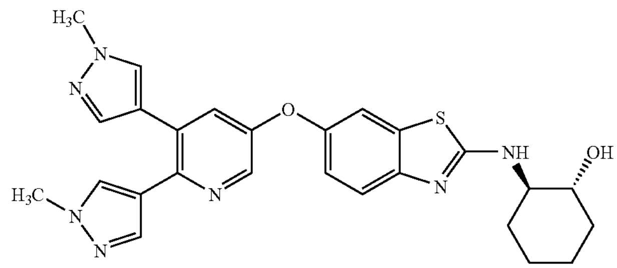 | (1R,2R)-2-(6-(5,6-bis(1-methyl-1H-pyrazol-4-yl)pyridin-3-yloxy)benzo[d]thiazol-2-ylamino)cyclohexanol |
| 107 | 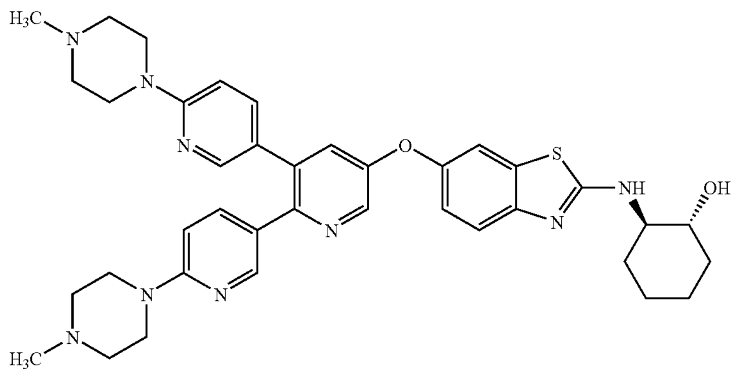 | (1R,2R)-2-(6-(5,6-bis(6-(4-methylpiperazin-1-yl)-pyridin-3-yl)pyridin-3-yloxy)benzo[d]thiazol-2-ylamino)cyclohexanol |
| 108 | 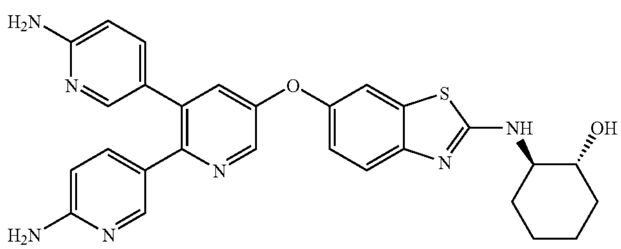 | (1R,2R)-2-(6-(5,6-bis(6-amino-pyridin-3-yl)pyridin-3-yloxy)benzo[d]thiazol-2-ylamino)cyclohexanol |
| 109 | 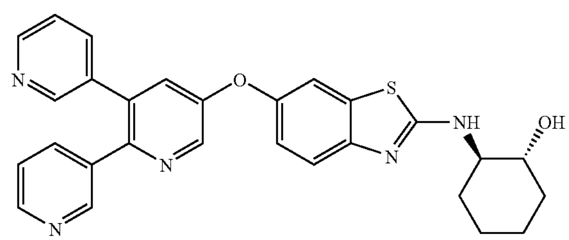 | (1R,2R)-2-(6-(5,6-bis(6-pyridin-3-yl)pyridin-3-yloxy)benzo[d]thiazol-2-ylamino)cyclohexanol |
| 110 | 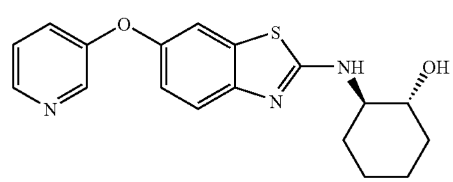 | (1R,2R)-2-(6-(pyridin-3-yloxy)benzo[d]thiazol-2-ylamino)cyclohexanol |

In some embodiments, provided is a pharmaceutical composition effective to inhibit CSF-1R activity in a human or animal subject when administered thereto, comprising a therapeutically effective amount of a compound of the invention including the compounds of Formulas (I), (II), (III), (IV), (V), (VI), or (VII), or an oxide, ester, prodrug, solvate, or pharmaceutically acceptable salts thereof and a pharmaceutically acceptable carrier.

It will also be apparent to those skilled in the art that the compounds of the invention, including the compounds of Formulas (I), (II), (III), (IV), (V), (VI), or (VII), or the pharmaceutically acceptable salts, esters, oxides, and prodrugs of any of them, may be subject to tautomerization and may therefore exist in various tautomeric forms.

Compounds of Formulas (I), (II), (III), (IV), (V), (VI), or (VII) as well as the pharmaceutically acceptable salts, esters, oxides, and prodrugs of any of them, may comprise asymmetrically substituted carbon atoms. Such asymmetrically substituted carbon atoms can result in the compounds existing in enantiomers, diastereomers, and other stereoisomeric forms that may be defined, in terms of absolute stereochemistry, such as in (R)- or (S)-forms. As a result, all such possible isomers, individual stereoisomers in their optically pure forms, mixtures thereof, racemic mixtures (or "racemates"), mixtures of diastereomers, as well as single diastereomers of the compounds are contemplated. The terms "S" and "R" configuration, as used herein, are as defined by the IUPAC 1974 RECOMMENDATIONS FOR SECTION E, FUNDAMENTAL STEREOCHEMISTRY, *Pure Appl. Chem.* 45:13-30 (1976).

Methods for Treating CSF-1R Mediated Diseases

There are three distinct mechanisms by which CSF-1R signaling is likely involved in tumor growth and metastasis. The first is that expression of CSF-ligand and receptor has been found in tumor cells originating in the female reproductive system (breast, ovarian, endometrium, cervical) (Scholl 1994; Kacinski 1997; Nagan 199; Kirma 2007) and the expression has been associated with breast cancer xenograft growth as well as poor prognosis in breast cancer patients. Two point mutations were seen in CSF-1R in about 10-20% of acute myelocytic leukemia, chronic myelocytic leukemia and myelodysplasia patients tested in one study, and one of the mutations was found to disrupt receptor turnover (Ridge 1990). However the incidence of the mutations could not be confirmed in later studies (Abu-Duhier 2003). Mutations were also found in some cases of hepatocellular cancer (Yang 2004) and idiopathic myelofibrosis (Abu-Duhier 2003).

Pigmented villonodular synovitis (PVNS) and Tenosynovial Giant cell tumors (TGCT) can occur as a result of a translocation that fuses the M-CSF gene to a collagen gene COL6A3 and results in overexpression of M-CSF (West 2006). A landscape effect is proposed to be responsible for the resulting tumor mass that consists of monocytic cells attracted by cells that express M-CSF. TGCTs are smaller tumors that can be relatively easily removed from fingers where they mostly occur. PVNS is more aggressive as it can recur in large joints and is not as easily controlled surgically.

The second mechanism is based on blocking signaling through M-CSF/CSF-1R at metastatic sites in bone which induces osteoclastogenesis, bone resorption and osteolytic bone lesions. Breast, kidney, and lung cancers are examples of cancers that have been found to metastasize to the bone and cause osteolytic bone disease resulting in skeletal complications. M-CSF released by tumor cells and stroma induces the differentiation of hematopoietic myeloid monocyte progenitors to mature osteoclasts in collaboration with the receptor activator of nuclear factor kappa-B ligand—RANKL. During this process, M-CSF acts as a permissive factor by giving the survival signal to osteoclasts (Tanaka 1993). Inhibition of CSF-1R kinase activity during osteoclast differentiation and maturation with a small molecule inhibitor is likely to prevent unbalanced activity of osteoclasts that cause osteolytic disease and the associated skeletal related events in metastatic disease. Whereas breast, lung cancer and multiple myeloma typically result in osteolytic lesions, metastasis to the bone in prostate cancer initially has an osteoblastic appearance in which increased bone forming activity results in 'woven bone' which is different from typical lamellar structure of normal bone. During disease progression bone lesions display a significant osteolytic component as well as high serum levels of bone resorption markers and suggests that anti-resorptive therapy may be useful. Bisphosphonates have been shown to inhibit the formation of osteolytic lesions and reduced the number of skeletal-related events only in men with hormone-refractory metastatic prostate cancer but at this point their effect on osteoblastic lesions is controversial and bisphosphonates have not been beneficial in preventing bone metastasis or hormone responsive prostate cancer to date. The effect of anti-resorptive agents in mixed osteolytic/osteoblastic prostate cancer is still being studied in the clinic (Choueiri 2006; Vessella 2006).

The third mechanism is based on the recent observation that tumor associated macrophages (TAM) found in solid tumors of the breast, prostate, ovarian and cervical cancers correlated with poor prognosis (Bingle 2002; Pollard 2004). Macrophages are recruited to the tumor by M-CSF and other chemokines. The macrophages can then contribute to tumor progression through the secretion of angiogenic factors, proteases and other growth factors and cytokines and may be blocked by inhibition of CSF-1R signaling. Recently it was shown by Zins et al (Zins 2007) that expression of siRNA of Tumor necrosis factor alpha (TNFα), M-CSF or the combination of both would reduce tumor growth in a mouse xenograft model between 34% and 50% after intratumoral injection of the respective siRNA into the xenograft. SiRNA targeting the TNFalpha secreted by the human SW620 cells reduced the mouse M-CSF and led to reduction of macrophages in the tumor. In addition treatment of MCF7 tumor xenografts with an antigen binding fragment directed against M-CSF antibody did result in 40% tumor growth inhibition, reversed the resistance to chemotherapeutics and improved survival of the mice when given in combination with chemotherapeutics (Paulus 2006).

TAMs are only one example of an emerging link between chronic inflammation and cancer. There is additional evidence for a link between inflammation and cancer as many chronic diseases are associated with an increased risk of cancer, cancers arise at sites of chronic inflammation, chemical mediators of inflammation are found in many cancers; deletion of the cellular or chemical mediators of inflammation inhibits development of experimental cancers and long-term use of anti-inflammatory agents reduce the risk of some cancers. A link to cancer exists for a number of inflammatory conditions among those *H. pylori* induced gastritis for gastric cancer, Schistosomiasis for bladder cancer, HHV8 for Kaposi's sarcoma, endometriosis for ovarian cancer and prostatitis for prostate cancer (Balkwill 2005). Macrophages are key Cells in chronic inflammation and respond differentially to their microenvironment. There are two types of macrophages that are considered extremes in a continuum of functional states: M1 macrophages are involved in Type 1 reactions. These reactions involve the activation by microbial products and consequent killing of pathogenic microorganisms that result in reactive oxygen intermediates. On the other end of the extreme are M2 macrophages involved in Type 2 reactions that promote cell proliferation, tune inflammation and adaptive immunity and promote tissue remodeling, angiogenesis and repair (Mantovani 2004). Chronic inflammation resulting in established neoplasia is usually associated with M2 macrophages. A pivotal cytokine that mediates inflammatory reactions is TNF-α that true to its name can stimulate anti-tumor immunity and hemorrhagic necrosis at high doses but has also recently been found to be expressed by tumor cells and acting as a tumor promoter (Zins 2007; Balkwill 2006). The specific role of macrophages with respect to the tumor still needs to be better understood including the potential spatial and temporal dependence on their function and the relevance to specific tumor types.

In another embodiment, a method for treating periodontitis, histiocytosis X, osteoporosis, Paget's disease of bone (PDB), bone loss due to cancer therapy, periprosthetic osteolysis, glucocorticoid-induced osteoporosis, rheumatoid arthritis, psiratic arthritis, osteoarthritis, inflammatory arthridies, and inflammation is provided.

Rabello 2006 has demonstrated that SNPs in the CSF1 gene exhibited a positive association with aggressive periodontitis: an inflammatory disease of the periodontal tissues that causes tooth loss due to resorption of the alveolar bone.

Histiocytosis X (also called Langerhans cell histiocytosis, LCH) is a proliferative disease of Langerhans dendritic cells that appear to differentiate into osteoclasts in bone and extraosseous LCH lesions. Langerhans cells are derived from circulating monocytes (Ginoux 2006). Increased levels of M-CSF that have been measured in sera and lesions where found to correlate with disease severity (da Costa 2005). The disease occurs primarily in a pediatric patient population and has to be treated with chemotherapy when the disease becomes systemic or is recurrent.

The pathophysiology of osteoporosis is mediated by loss of bone forming osteoblasts and increased osteoclast dependent bone resorption. Supporting data has been described by Cenci et al showing that an anti-M-CSF antibody injection preserves bone density and inhibits bone resorption in ovarectomized mice (Cenci 2000). Recently a potential link between postmenopausal bone loss due to estrogen deficiency was identified and found that the presence of TNF alpha producing T-cell affected bone metabolism (Roggia 2004). A possible mechanism could be the induction of M-CSF by TNF alpha in vivo. An important role for M-CSF in TNF-alpha-induced osteoclastogenesis was confirmed by the effect of an antibody directed against the M-CSF-inhibitor that blocked the TNF alpha induced osteolysis in mice and thereby making inhibitors of CSF-1R signaling potential targets for inflammatory arthritis (Kitaura 2005).

Paget's disease of bone (PDB) is the $2^{nd}$ most common bone metabolism disorder after osteoporosis in which focal abnormalities of increased bone turnover lead to complications such as bone pain, deformity, pathological fractures, and deafness. Mutations in four genes have been identified that regulate normal osteoclast function and predispose individuals to PDB and related disorders: insertion mutations in TNFRSF11A, which encodes receptor activator of nuclear factor (NF) kappaB (RANK)-a critical regulator of osteoclast function, inactivating mutations of TNFRSF11B which encodes osteoprotegerin (a decoy receptor for RANK ligand), mutations of the sequestosome 1 gene (SQSTM1), which encodes an important scaffold protein in the NFkappaB pathway and mutations in the valosin-containing protein (VCP) gene. This gene encodes VCP, which has a role in targeting the inhibitor of NFkappaB for degradation by the proteasome (Daroszewska, 2006). Targeted CSF-1R inhibitors provide an opportunity to block the deregulation of the RANKL signaling indirectly and add an additional treatment option to the currently used bisphosphonates.

Cancer therapy induced bone loss especially in breast and prostate cancer patients is an additional indication where a targeted CSF-1R inhibitor could prevent bone loss (Lester 2006).With the improved prognosis for early breast cancer the long-term consequences of the adjuvant therapies become more important as some of the therapies including chemotherapy, irradiation, aromatase inhibitors and ovary ablation affect bone metabolism by decreasing the bone mineral density, resulting in increased risk for osteoporosis and associated fractures (Lester 2006). The equivalent to adjuvant aromatase inhibitor therapy in breast cancer is androgen ablation therapy in prostate cancer which leads to loss of bone mineral density and significantly increases the risk of osteoporosis-related fractures (Stoch 2001).

Targeted inhibition of CSF-1R signaling is likely to be beneficial in other indications as well when targeted cell types include osteoclasts and macrophages e.g. treatment of specific complications in response to joint replacement as a consequence of rheumatoid arthritis. Implant failure due to periprosthetic bone loss and consequent loosing of protheses is a major complication of joint replacement and requires repeated surgery with high socioeconomic burdens for the individual patient and the health-care system. To date, there is no approved drug therapy to prevent or inhibit periprosthetic osteolysis (Drees 2007).

Glucocorticoid-induced osteoporosis (GIOP) is another indication in which a CSF-1R inhibitor could prevent bone loss after long-term glucocorticocosteroid use that is given as a result of various conditions among those chronic obstructive pulmonary disease, asthma and rheumatoid arthritis (Guzman-Clark 2007; Feldstein 2005).

Rheumatoid arthritis, psiratic arthritis and inflammatory arthridities are in itself potential indications for CSF-1R signaling inhibitors in that they consist of a macrophage component a to a varying degree bone destruction (Ritchlin 2003). Osteoarthritis and rheumatoid arthritis are inflammatory autoimmune disease caused by the accumulation of macrophages in the connective tissue and infiltration of macrophages into the synovial fluid, which is at least partially mediated by M-CSF. Campbell et al. (2000) demonstrated that M-CSF is produced by human-joint tissue cells (chondrocytes, synovial fibroblasts) in vitro and is found in synovial fluid of patients with rheumatoid arthritis, suggesting that it contributes to the synovial tissue proliferation and macrophage infiltration which is associated with the pathogenesis of the disease. Inhibition of CSF-1R signaling is likely to control the number of macrophages in the joint and alleviate the pain from the associated bone destruction. In order to minimize adverse affects and to further understand the impact of the CSF-1R signaling in these indications, one method is to specifically inhibit CSF-1R without targeting a myriad other kinases, such as Raf kinase.

Recent literature reports correlate increased circulating M-CSF with poor prognosis and atherosclerotic progression in chronic coronary artery disease (Saitoh 2000; Ikonomidis 2005); M-CSF influences the atherosclerotic process by aiding the formation of foam cells (macrophages with ingested oxidized LDL) that express CSF-1R and represent the initial plaque (Murayama 1999).

Expression and signaling of M-CSF and CSF-1R is found in activated microglia. Microglia, which are resident macrophages of the central nervous system, can be activated by various insults, including infection and traumatic injury. M-CSF is considered a key regulator of inflammatory responses in the brain and M-CSF levels increase in HIV-1 encephalitis, Alzheimer's disease (AD) and brain tumors. Microgliosis as a consequence of autocrine signaling by M-CSF/CSF-1R results in induction of inflammatory cytokines and nitric oxides being released as demonstrated by e.g. using an experimental neuronal damage model (Hao 2002; Murphy 1998). Microglia that have increased expression of CSF-1R are found to surround plaques in AD and in the amyloid precursor protein V717F transgenic mouse model of AD (Murphy 2000). On the other hand op/op mice with fewer microglia in the brain resulted in fibrilar deposition of Aβ and neuronal loss compared to normal control suggesting that microglia do have a neuroprotective function in the development of AD lacking in the op/op mice (Kaku 2003).

In other aspects, provided is a method for treating CSF-1R related disorders in a human or animal subject in need of such treatment comprising administering to said subject an amount of a compound of Formula (I), (II), (III), (IV), (V), (VI), or (VII) effective to reduce or prevent tumor growth in the subject.

In other aspects, provided is a method for treating CSF-1R related disorders in a human or animal subject in need of such treatment comprising administering to said subject an amount of a compound of Formula (I), (II), (III), (IV), (V), (VI), or (VII) effective to reduce or prevent osteoclastogenesis, bone resorption and/or bone lesions in the subject.

In yet other aspects, provided is a method for treating CSF-1R related disorders in a human or animal subject in need of such treatment comprising administering to said subject an amount of a compound of Formula (I), (II), (III), (IV), (V), (VI), or (VII) effective to treat the disorder in the subject in combination with at least one additional agent for the treatment of tumor growth and/or metastasis, osteoclastogenesis, bone resorption and/or bone lesions. In a more particular embodiment the additional agent is a bisphosphonate.

In yet other aspects, provided is a compound of Formula (I), (II), (III), (IV), (V), (VI), or (VII) capable of selectively or preferentially inhibiting CSF-1R. In one embodiment the selective inhibitors of CSF-1R are capable of inhibiting CSF-1R at greater than about 5-fold, or about 10 fold, or about 20 fold, or about 30 fold, or about 50 fold, or about 100 fold, or about 250 fold, or about 500 fold, or about 750 fold, or about 1,000 fold, or about 2,000 fold the inhibitory activity (with respect to $IC_{50}$ values, for example) in Raf kinase.

In other aspects provided is a method of inhibiting CSF-1R comprising contacting a cell with a CSF-1R inhibitor of Formula ((I), (II), (III), (IV), (V), (VI), or (VII).

In one aspect, the inhibitory effect of CSF-1R inhibitory compounds on Raf is determined using the following biotinylated assay. The Raf kinase activity is measured by providing ATP, a recombinant kinase inactive MEK substrate and assaying the transfer of phosphate moiety to the MEK residue. Recombinant full length MEK with an inactivating K97R ATP binding site mutation (rendering kinase inactive) is expressed in $E.$ $coli$ and labelled with biotin post purification. The MEK cDNA is subcloned with an N-terminal $(His)_6$ tag and expressed in $E.$ $coli$ and the recombinant MEK substrate is purified from $E.$ $coli$ lysate by nickel affinity chromatography followed by anion exchange. The final MEK substrate preparation is biotinylated (Pierce EZ-Link Sulfo-NHS-LC-Biotin) and concentrated to about 11.25 μM. Recombinant Raf (including c-Raf and mutant B-Raf isoforms) is obtained by purification from sf9 insect cells infected with the corresponding human Raf recombinant expression vectors. The Recombinant Raf isoforms are purified via a Glu antibody interaction or by Metal Ion Chromatography.

For each assay, the compound is serially diluted, for instance, starting at 25 μM with 3-fold dilutions, in DMSO and then mixed with various Raf isoforms (about 0.50 nM each). The kinase inactive biotin-MEK substrate (50 nM) is added in reaction buffer plus ATP (1 μM). The reaction buffer contains 30 mM Tris-HCl$_2$ pH 7.5, 10 mM MgCl$_2$, 2 mM DTT, 4 mM EDTA,' 25 mM beta-glycerophosphate, 5 mM MnCl$_2$, and 0.01% BSA/PBS. Reactions are subsequently incubated for about 2 hours at room temperature and stopped by the addition of 0.5 M EDTA. Stopped reaction mixture is transferred to a neutradavin-coated plate and incubated for about 1 hour. Phosphorylated product is measured with the DELFIA time-resolved fluorescence system, using a rabbit anti-p-MEK (Cell Signaling) as the primary antibody and europium labeled anti-rabbit as the secondary antibody. Time resolved fluorescence can be read on a Wallac 1232 DELFIA fluorometer. The concentration of the compound for 50% inhibition ($IC_{50}$) is calculated by non-linear regression using XL Fit data analysis software.

In yet other aspects, provided is a method for treating CSF-1R related disorders in a human or animal subject in need of such treatment comprising administering to said subject an amount of a compound of Formula (I), (II), (III), (IV), (V), (VI), or (VII) effective to reduce or prevent tumor growth in the subject in combination with at least one additional agent for the treatment of cancer. In a more particular embodiment the additional agent is a bisphosphonate.

A number of suitable anticancer agents to be used as combination therapeutics are contemplated for use. Examples of the additional anticancer agents include, but are not limited to, agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons [e.g. IFN-α, etc.] and interleukins [e.g. IL-2, etc.], etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other examples of chemotherapeutic compounds and anticancer therapies suitable for coadministration with the disclosed compounds of Formula (I), (II), (III), (IV), (V), (VI), or (VII) are known to those skilled in the art.

In some embodiments, additional anticancer agents to be used in combination with the compounds comprise agents that induce or stimulate apoptosis. Agents that induce apoptosis include, but are not limited to, radiation (e.g., ω); kinase inhibitors (e.g., Epidermal Growth Factor Receptor [EGFR] kinase inhibitor, Vascular Endothelial Growth Factor Receptor [VEGFR] kinase inhibitor, Fibroblast Growth Factor Receptor [FGFR] kinase inhibitor, Platelet-derived Growth Factor Receptor [PDGFR] I kinase inhibitor, and Bcr-Abl kinase inhibitors such as STI-571, Gleevec, and Glivec]); antisense molecules; antibodies [e.g., Herceptin and Rituxan]; anti-estrogens [e.g., raloxifene and tamoxifen]; anti-androgens [e.g., flutamide, bicalutamide, finasteride, aminoglutethamide, ketoconazole, and corticosteroids]; cyclooxygenase 2 (COX-2) inhibitors [e.g., Celecoxib, meloxicam, NS-398, and non-steroidal antiinflammatory drugs (NSAIDs)]; and cancer chemotherapeutic drugs [e.g., irinotecan (Camptosar), CPT-11, fludarabine (Fludara), dacarbazine (DTIC), dexamethasone, mitoxantrone, Mylotarg, VP-16, cisplatinum, 5-FU, Doxrubicin, Taxotere or taxol; cellular signaling molecules; ceramides and cytokines; and staurosprine, and the like.

The compounds of the disclosed embodiments presented herein are useful in vitro or in vivo in inhibiting the growth of cancer cells. Such cancers include myelocytic leukemia, idiopathic myelofibrosis, breast cancer, cervical cancer, ovarian cancer, endometrial cancer, prostate cancer, hepatocellular cancer, multiple myeloma, lung cancer, renal cancer, and bone cancer. In some aspects the cancers are sarcomas such as pigmented villonodular synovitis (PVNS) and tenosynovial giant cell tumors (TGCT). The compounds may be used alone or in compositions together with a pharmaceutically acceptable carrier or excipient.

In other aspects, provided are pharmaceutical compositions comprising at least one compound of Formula (I), (II), (III), (IV), (V), (VI), or (VII) together with a pharmaceutically acceptable carrier suitable for administration to a human or animal subject, either alone or together with other anticancer agents.

In other aspects, provided are methods of manufacture of compounds of Formula (I), (II), (III), (IV), (V), (VI), or (VII) as described herein.

Other aspects provide pharmaceutical compositions comprising compounds of Formula (I), (II), (III), (IV), (V), (VI), or (VII) as described herein, wherein said compound preferentially inhibits CSF-1R over Raf kinase. More particularly said compound inhibits Raf kinase at greater than about 1 µM.

Other aspects further comprise an additional agent. More particularly, said additional agent is a bisphosphonate.

Other aspects provide compounds of Formula (I), (II), (III), (IV), (V), (VI), or (VII) effective to inhibit CSF-1R activity in a human or animal subject when administered thereto. More particularly, said compound exhibits an $IC_{50}$ value with respect to CSF-1R inhibition of less than about 1 µM. More particularly, said compound exhibits an $IC_{50}$ value with respect to Raf inhibition of greater than about 1 µM.

Another embodiment provides a method of inhibiting CSF-1R, wherein said compound selectively inhibits CSF-1R.

The compounds of the embodiments are useful in vitro or in vivo in inhibiting the growth of cancer cells. The compounds may be used alone or in compositions together with a pharmaceutically acceptable carrier or excipient.

Administration and Pharmaceutical Composition

In general, the compounds of the embodiments will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day. All of these factors are within the skill of the attending clinician.

Effective amounts of the compounds generally include any amount sufficient to detectably inhibit CSF-1R activity by any of the assays described herein, by other CSF-1R kinase activity assays known to those having ordinary skill in the art or by detecting an inhibition or alleviation of symptoms of cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

A therapeutically effective dose generally can be a total daily dose administered to a host in single or divided doses may be in amounts, for example, of from about 0.001 to about 1000 mg/kg body weight daily and from about 1.0 to about 30 mg/kg body weight daily. Dosage unit compositions may contain such amounts of submultiples thereof to make up the daily dose.

The choice of formulation depends on various factors such as the mode of drug administration and bioavailability of the drug substance. The drug can be administered as pharmaceutical compositions by any one of the following routes: oral, systemic (e.g., transdermal, intranasal or by suppository), or parenteral (e.g., intramuscular, intravenous or subcutaneous) administration. One manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another manner for administration is inhalation such as for delivering a therapeutic agent directly to the respiratory tract (see U.S. Pat. No. 5,607,915).

Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Liquid and semisolid excipients can be selected from glycerol, propylene glycol, water, ethanol and various oils, including those of petroleum, animal, vegetable or synthetic origin, e.g., peanut oil, soybean oil, mineral oil, sesame oil, etc. In some embodiments liquid carriers, particularly for injectable solutions, include water, saline, aqueous dextrose, and glycols. Other suitable pharmaceutically acceptable excipients are described in "Remington's Pharmaceutical Sciences," Mack Pub. Co., New Jersey (1991).

As used herein, the term "pharmaceutically acceptable salts" refers to the nontoxic acid or alkaline earth metal salts of the compounds of Formulas (I), (II), (III), (IV), (V), (VI), or (VII). These salts can be prepared in situ during the final isolation and purification of the compounds of Formulas (I), (II), (III), (IV), (V), (VI), or (VII), or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with agents such as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of Formulas (I), (II), (III), (IV), (V), (VI), or (VII), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically, acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the embodiments. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

It will be apparent to those skilled in the art that the compounds of Formulas (I), (II), (III), (IV), (V), (VI), or (VII) or the pharmaceutically acceptable salts, esters, oxides, and prodrugs of any of them, may be processed in vivo through metabolism in a human or animal body or cell to produce metabolites. The term "metabolite" as used herein refers to the formula of any derivative produced in a subject after administration of a parent compound. The derivatives may be produced from the parent compound by various biochemical transformations in the subject such as, for example, oxidation, reduction, hydrolysis, or conjugation and include, for example, oxides and demethylated derivatives.' The metabolites of a compound of the embodiments may be identified using routine techniques known in the art. See, e.g., Bertolini, G. et al., *J. Med. Chem.* 40:2011-2016 (1997); Shan, D. et al., *J. Pharm. Sci.* 86(7):765-767; Bagshawe K., *Drug Dev. Res.* 34:220-230 (1995); Bodor, N., *Advances in Drug Res.* 13:224-331 (1984); Bundgaard, H.; *Design of Prodrugs* (Elsevier Press 1985); and Larsen, I. K., *Design and Application of Prodrugs, Drug Design and Development* (Krogsgaard-Larsen et al., eds., Harwood Academic Publishers, 1991). It should be understood that individual chemical compounds that are metabolites of the compounds of Formulas (I), (II), (III), (IV), (V), (VI), or (VII) or the pharmaceutically acceptable salts, esters, oxides and prodrugs of any of them, are included within the embodiments provided herein.

The compounds of the preferred embodiments may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intrathecal, intramuscular, infrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the embodiments can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like. Examples of lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq. (1976).

Compressed gases may be used to disperse a compound of the embodiments in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from about 10 to about 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of about 400 nm) in the presence of a surface modifier and then dispersed in a liquid medium to give a pharmaceutical formulation that exhibits remarkably high bioavailability.

Combination Therapies

While the compounds of the embodiments can be administered as the sole active pharmaceutical agent, they can also be used in combination with one or more other agents used in the treatment of cancer. The compounds of the embodiments are also useful in combination with known therapeutic agents and anti-cancer agents, and combinations of the presently disclosed compounds with other anti-cancer or chemotherapeutic agents are within the scope of the embodiments. Examples of such agents can be found in *Cancer Principles and Practice of Oncology*, V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The compounds of the embodiments are also useful when co-administered with radiation therapy.

Therefore, in one embodiment, the compounds are also used in combination with known anticancer agents including, for example, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

Estrogen receptor modulators are compounds that can interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethyl-propanoate, 4,4'-dihydroxybenzophenone-2,4-dinitrophenyl-hydrazone, and SH646.

Androgen receptor modulators are compounds which can interfere with or inhibit the binding of androgens to an androgen receptor. Representative examples of androgen receptor modulators include finasteride and other 5α-reductase inhibitors, nilutamide, flutamide, bicalutamide, liarozole, and abiraterone acetate. Retinoid receptor modulators are compounds which interfere or inhibit the binding of retinoids to a retinoid receptor. Examples of retinoid receptor modulators include bexarotene, tretinoin, 13-cis-retinoic acid, 9-cis-retinoic acid, α-difluoromethylornithine, LX23-7553, trans-N-(4'-hydroxyphenyl)retinamide, and N4-carboxyphenyl retinamide.

Cytotoxic and/or cytostatic agents are compounds which can cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors. Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mutdiamine-platinum(II)bis[diamine(chloro) platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032). A representative example of a hypoxia activatable compound is tirapazamine. Proteasome inhibitors include, but are not limited to, lactacystin and bortezomib. Examples of microtubule inhibitors/microtubule-stabilizing agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. Representative examples of topoisomerase inhibitors include topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-k]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13

(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroOxy-3,5-dimethoxyphenyl]-5,5a,6,8,8a,9-hexahydrofuro(3',4':6,7)naphtho(2,3-d)-1,3-dioxol-6-one, 2,3-(methylene-dioxy)-5-methyl-7-hydroxy-8-methoxy-benzo[c]-phenanthridinium, 6,9-bis[(2-amino-ethyl)amino]benzo[g]isoquinoline-5,10-dione, 5-(3-aminopropylamino)-7,10-dihydroxy-2-(2-hydroxyethylaminomethyl)-6H-pyrazolo[4,5,1'-de]acridin-6-one, N-[1-[2(diethylamino)-ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna. Examples of inhibitors of mitotic kinesins, such as the human mitotic kinesin KSP, are described in PCT Publications WO 01/30768 and WO 01/98278, WO 03/050,064 (Jun. 19, 2003), WO 03/050,122 (Jun. 19, 2003), WO 03/049,527 (Jun. 19, 2003), WO 03/049,679 (Jun. 19, 2003), WO 03/049,678 (Jun. 19, 2003) and WO 03/39460 (May 15, 2003) and pending PCT Appl. Nos. US03/06403 (filed Mar. 4, 2003), US03/15861 (filed May 19, 2003), US03/15810 (filed May 19, 2003), US03/18482 (filed Jun. 12, 2003) and US03/18694 (filed Jun. 12, 2003). In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Inhibitors of kinases involved in mitotic progression include, but are not limited to, inhibitors of aurora kinase, inhibitors of Polo-like kinases (PLK) (e.g., inhibitors of PLK-1), inhibitors of bub-1 and inhibitors of bub-1R. Antiproliferative agents include antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-glycero-B-L-manno-heptopyranosyl] adenine, aplidine, ecteinascidin, troxacitabine, 4-[2-amino-4-oxo4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1-diazatetracyclo (7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone. Examples of monoclonal antibody targeted therapeutic agents include those therapeutic agents which have cytotoxic agents or radioisotopes attached to a cancer cell specific or target cell specific monoclonal antibody. Examples include, for example, Bexxar. HMG-CoA reductase inhibitors are inhibitors of 3-hydroxy-3-methylglutaryl-CoA reductase. Compounds which have inhibitory activity for HMG-CoA reductase can be readily identified by using assays well-known in the art such as those described or cited in U.S. Pat. No. 4,231,938 and WO 84/02131. Examples of HMG-CoA reductase inhibitors that may be used include, but are not limited to, lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. In an embodiment, the HMG-CoA reductase inhibitor is selected from lovastatin or simvastatin.

Prenyl-protein transferase inhibitors are compounds which inhibit any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2(1H)-quinolinone, (−)-6-[amino(4-chlorophenyl)(1-methyl-1H-imidazol-5-yl) methyl]-4-(3-chlorophenyl)-1-methyl-2(1H)-quinolinone, (+)-6-[amino(4-chlorophenyl)(1-methyl-1H-imidazol-5-yl) methyl]-4-(3-chlorophenyl)-1-methyl-2(1H)-quinolinone, 5(S)-n-butyl-1-(2,3-dimethylphenyl)-4-[1-(4-cyanobenzyl)-5-imnidazolylmethyl-2-piperazinone, (S)-1-(3-chlorophenyl)-4-[1-(4-cyanobenzyl)-5-imidazolylmethyl]-542-(ethanesulfonyl)methyl)-2-piperazinone, 5(S)-n-butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{-[4-hydroxymethyl-4-(4-chloropyridin-2-ylmethyl)-piperidine-1-ylmethyl]-2-methylimidazol-1-ylmethyl}benzonitrile, 4-{-5-[4-hydroxymethyl-4-(3-chlorobenzyl)-piperidine-1-ylmethyl]-2-methylimidazol-1-ylmethyl}-benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2'] bipyridin-5'-ylmethyl]-3H-imidazol-4-yl-methyl}benzonitrile, 4-{3-[4-(2-oxo-2H-[1,2']bipyridin-5'-ylmethyl]-3H-imidazol-4-yl-methyl}benzonitrile, 4-[3-(2-oxo-1-phenyl-1,2-dihydropyridin-4-ylmethyl)-3H-imidazol-4-ylmethyl}benzonitrile, 18,19-dihydro-19-oxo-5H,17H-6, 10:12,16-dimetheno-1H-imidazo[4,3-c][1,11,4]dioxaazacyclo-nonadecine-9-carbonitrile, (*)-19,20-dihydro-19-oxo-5H-18,21-ethano-12,14-etheno-6,10-metheno-22H-benzo[d]imidazo[4,3-k]-[1,6,9,12]oxatriaza-cyclooctadecine-9-carbonitrile, 19,20-dihydro-19-oxo-5H, 17H-18,21-ethano-6,10:12,16-dimetheno-22H-imidazo[3,4-h][1,8,11,14]oxatriazacycloeicosine-9-carbonitrile, and (.+-.)-19,20-dihydro-3-methyl-19-oxo-5H-18,21-ethano-12, 14-etheno-6,10-metheno-22H-benzo[d]imidazo[4,3-k][1,6, 9,12]oxa-triazacyclooctadecine-9-carbonitrile. Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0

604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer* 35(9):1394-1401 (1999).

Angiogenesis inhibitors refers to compounds that can inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-.alpha., interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS 89:7384 (1992); *JNCI* 69:475 (1982); *Arch. Opthalmol.* 108:573 (1990); *Anat. Rec.*, (238):68 (1994); *FEBS Letters* 372:83 (1995); *Clin, Orthop.* 313:76 (1995); *J. Mol. Endocrinol.* 16:107 (1996); *Jpn. J. Pharmacol.* 75:105 (1997); *Cancer Res.* 57:1625 (1997); *Cell* 93:705 (1998); *Intl. J. Mol. Med.* 2:715 (1998); *J. Biol. Chem.* 274:9116 (1999)), steroidal anti-inflammatories (such as corticosteroids, mineralocorticoids, dexamethasone, prednisone, prednisolone, methylpred, betamethasone), carboxyamidotriazole, combretastatin A4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, 17:963-968 (October 1999); Kim et al., *Nature*, 362:841-844 (1993); WO 00/44777; and WO 00/61186). Other therapeutic agents that modulate or inhibit angiogenesis and may also be used in combination with the compounds of the embodiments include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002). The embodiments also encompass combinations of the compounds of the embodiments with NSAIDs which are selective COX-2 inhibitors (generally defined as those which possess a specificity for inhibiting COX-2 over COX-1 of at least about 100 fold as measured by the ratio of $IC_{50}$ for COX-2 over $IC_{50}$ for COX-1 evaluated by cell or microsomal assays). Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference. Representative inhibitors of COX-2 that are useful in the methods of the embodiments include 3-phenyl-4-(4-(methylsulfonyl)phenyl)-2-(5H)-furanone; and 5-chloro-3-(4-methylsulfonyl)phenyl-2-(2-methyl-5-pyridinyl)pyridine. Compounds which are described as specific inhibitors of COX-2 and are therefore useful in the embodiments, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, U.S. Pat. No. 5,932,598, issued Aug. 3, 1999, U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998. Other examples of angiogenesis inhibitors include, but are not limited to, endostatin, ukrain, ranpirnase, IM862,5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

Agents that interfere with cell cycle checkpoints are compounds that can inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

Inhibitors of cell proliferation and survival signaling pathway can be pharmaceutical agents that can inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of cytokine receptors, inhibitors of MET, inhibitors of PI3K (for example LY294002), serine/threonine kinases (including but not limited to inhibitors of Akt such as described in WO 02/083064, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779). Such agents include small molecule inhibitor compounds and antibody antagonists.

Apoptosis inducing agents include activators of TNF receptor family members (including the TRAIL receptors).

In certain embodiments, representative agents useful in combination with the compounds of the embodiments for the treatment of cancer include, for example, irinotecan, topotecan, gemcitabine, 5-fluorouracil, leucovorin carboplatin, cisplatin, taxanes, tezacitabine, cyclophosphamide, vinca alkaloids, imatinib (Gleevec), anthracyclines, rituximab, trastuzumab, as well as other cancer chemotherapeutic agents.

The above compounds to be employed in combination with the compounds of the embodiments can be used in therapeutic amounts as indicated in the *Physicians' Desk Reference* (PDR) 47th Edition (1993), which is incorporated herein by reference, or such therapeutically useful amounts as would be known to one of ordinary skill in the art.

The compounds of the embodiments and the other anticancer agents can be administered at the recommended maximum clinical dosage or at lower doses. Dosage levels of the active compounds in the compositions of the embodiments may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

General Synthetic Methods

The compounds disclosed herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds disclosed herein may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of the embodiments, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4th Edition), and Larock's *Comprehensive Organic Transformations* (VCH Publishers Inc., 1989).

The various starting materials, intermediates, and compounds of the embodiments may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Compounds of the embodiments may generally be prepared using a number of methods familiar to one of skill in the art, and may generally be made in accordance with the following reaction Schemes 1 and 2, which are described in detail in the Examples below.

General Schemes:

Schemes 1 and 2 illustrate general methods for the preparation of intermediates and compounds of the invention. These compounds are prepared from starting materials that are known in the art or are commercially available.

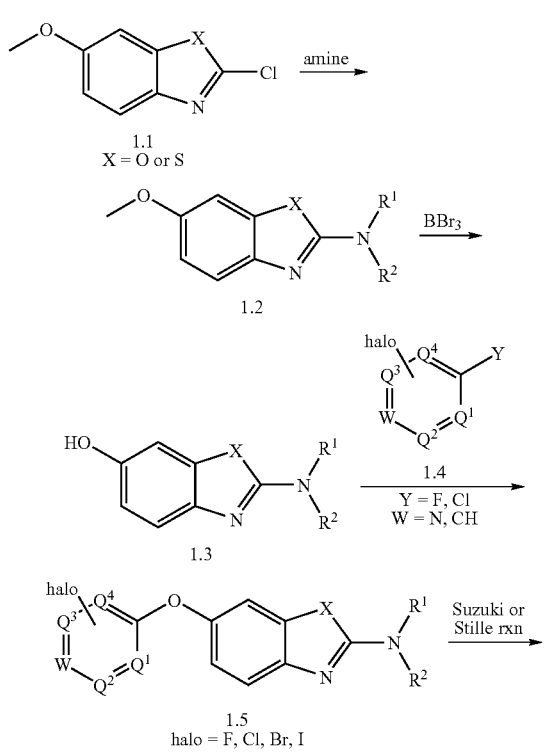

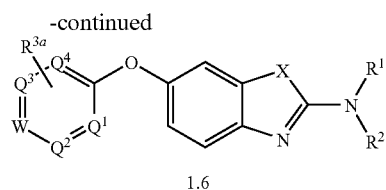

1.6

In Scheme 1, benzoxazoles or benzothiazoles of formula 1.1, where for illustrative purposes the oxygen protecting group is a methyl group, is reacted with a substituted amine $HNR^1R^2$ to provided intermediates 1.2. Treatment of 1.2 with a de-methylation reagent such as, for example, $BBr_3$ provides phenols of formula 1.3. Subsequent treatment of intermediates of formula 1.3 with a halo heteroaryl group of formula 1.4 at temperatures generally ranging from, but not limited to, room temperature to 130° C. in the presence of a base such as, for example, potassium or cesium carbonate provides compounds for formula 1.5. Further treatment with boronic acids or stannanes under Suzuki or Stille coupling conditions that are known in the art provides compounds of formula 1.6.

Scheme 2

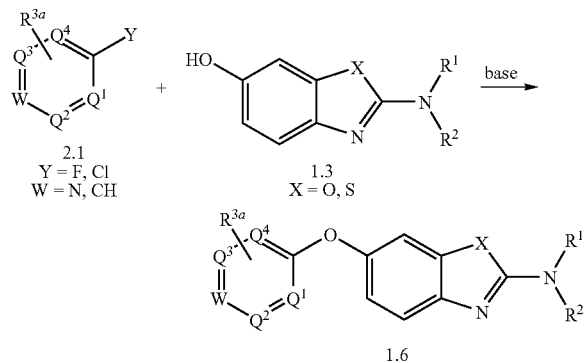

In Scheme 2 benzoxazoles or benzothiazoles of formula 1.6 can be prepared starting with halo-heteroaryls of formula 2.1 such as halo-pyrimidines, halo-pyrazines, or halo-pyridine, that is reacted with a phenol intermediate of formula 1.3 in the presence of a base such as, for example, potassium or cesium carbonate in a solvent such as, for example, dimethyl formamide, acetonitrile or dioxane under suitable ether forming conditions.

EXAMPLES

Referring to the examples that follow, compounds of the embodiments were synthesized using the methods described herein, or other methods, which are known in the art.

The compounds and/or intermediates were characterized by high performance liquid chromatography (HPLC) using a Waters Millenium chromatography system with a 2695 Separation Module (Milford, Mass.). The analytical columns were reversed phase Phenomenex Luna C18-5μ, 4.6×50 min, from Alltech (Deerfield, Ill.). A gradient elution was used (flow 2.5 mL/min), typically starting with 5% acetonitrile/95% water and progressing to 100% acetonitrile over a period of 10 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.).

In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LCMS instruments: a Waters System (Alliance HT HPLC and a Micromass ZQ mass spectrometer; Column: Eclipse XDB-C18, 2.1×50 mm; gradient: 5-95% (or 35-95%, or 65-95% or 95-95%) acetonitrile in water with 0.05% TFA over a 4 min period; flow rate 0.8 mL/min; molecular weight range 200-1500; cone Voltage 20 V; column temperature 40° C.) or a Hewlett Packard System (Series 1100 HPLC; Column: Eclipse XDB-C18, 2.1×50 mm; gradient: 5-95% acetonitrile in water with 0.05 TFA over a 4 min period; flow rate 0.8 mL/min; molecular weight range 150-850; cone Voltage 50 V; column temperature 30° C.). All masses were reported as those of the protonated parent ions.

GCMS analysis is performed on a Hewlett Packard instrument (HP6890 Series gas chromatograph with a Mass Selective Detector 5973; injector volume: 1 μL; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.). The spectral reference was either TMS or the known chemical shift of the solvent. Some compound samples were run at elevated temperatures (e.g., 75° C.) to promote increased sample solubility.

The purity of some of the compounds is assessed by elemental analysis (Desert Analytics, Tucson, Ariz.).

Melting points are determined on a Laboratory Devices MeI-Temp apparatus (Holliston, Mass.).

Preparative separations are carried out using a Flash 40 chromatography system and KP-Sil, 60A (Biotage, Charlottesville, Va.), or by flash column chromatography using silica gel (230-400 mesh) packing material, or by HPLC using a Waters 2767 Sample Manager, C-18 reversed phase column, 30×50 mm, flow 75 mL/min. Typical solvents employed for the Flash 40 Biotage system and flash column chromatography are dichloromethane, methanol, ethyl acetate, hexane, acetone, aqueous ammonia (or ammonium hydroxide), and triethyl amine. Typical solvents employed for the reverse phase HPLC are varying concentrations of acetonitrile and water with 0.1% trifluoroacetic acid.

The examples below as well as throughout the application, the following abbreviations have the following meanings. If not defined, the terms have their generally accepted meanings.

Abbreviations

ACN Acetonitrile
BINAP 2,2'-bis(diphenylphosphino)-1,1'-binapthyl
DCM Dichloromethane
DIEA diisopropylethylamine
DIPEA N,N-diisopropylethylamine
DME 1,2-dimethoxyethane
DMF N,N-dimethylformamide
DMSO dimethyl sulfoxide
DPPF 1,1'-bis(diphenylphosphino)ferrocene
eq equivalent
EtOAc ethyl acetate
EtOH ethanol
HATU 2-(7-aza-1H-benzotriazole-1-yl)-1,1,3,3-tetramethyluronium hexafluorophosphate HPLC high performance liquid chromatography
MCPBA meta-chloroperoxybenzoic acid
MeOH methanol
NBS N-bromosuccinimide
NMP N-methyl-2-pyrrolidone
Rt rentention time
THF tetrahydrofuran Example 1

2-(cyclohexylmethylamino)benzo[d]thiazol-6-ol

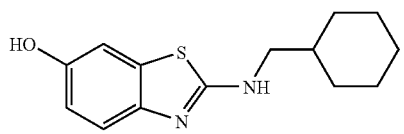

Step 1.

To a solution of 2-chloro-6-methoxybenzo[d]thiazole (900 mg, 4.5 mmol) in 4.5 mL of NMP was added cyclohexylmethanamine (865 mg, 7.65 mmol) and DIPEA (1.57 mL, 9.0 mmol). The reaction solution was stirred at 105-110° C. for 66 hours. The reaction was diluted with EtOAc (250 mL) and washed with saturated NaHCO$_3$ (2×60 mL), water (3×60 mL), saturated NaCl (60 mL), dried with sodium sulfate, filtered and concentrated in vacuo to give N-(cyclohexylmethyl)-6-methoxybenzo[d]thiazol-2-amine as a solid (1.18 grams). ES/MS m/z 277.1 (MH$^+$).

Step 2.

To a solution of N-(cyclohexylmethyl)-6-methoxybenzo[d]thiazol-2-amine (1.40 g, 5.05 mmol) in 12 mL of DCM was added 1 M boron tribromide in DCM (10.6 mL, 10.6 mmol) slowly over about 3 min at 0° C. The reaction solution was stirred at 0° C. for 20 min and at room temperature for additional 2 hours. The reaction mixture was concentrated under reduced pressure. The residue was dissolved in EtOAc (200 mL) and water (50 mL) and the mixture was stirred at room temperature for 10 min. To the mixture was carefully added excess of solid NaHCO$_3$ until basic and stirring was continued for 1 hour. The mixture was phase separated and the aqueous layer was extracted with EtOAc (100 mL). The combined organic layers were washed with water (30 mL), saturated NaCl solution (25 mL) and dried over sodium sulfate. This mixture was filter through a plug of silica gel and concentrated under reduced pressure to give the title compound as a solid (1.32 grams). ES/MS m/z 263.1 (MH$^+$).

Example 2

(S)-2-(1-cyclohexylethylamino)benzo[d]thiazol-6-ol

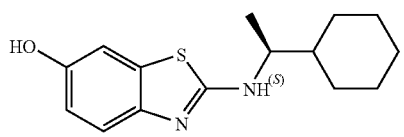

Step 1.

To a solution of 2-chloro-6-methoxybenzo[d]thiazole (2.0 g, 10 mmol) in 10 mL of NMP was added (S)-1-cyclohexylethanamine (2.3 g, 18 mmol) and DIPEA (3.5 mL, mmol). The reaction solution was stirred at 110° C. for 96 hours. The reaction was diluted with EtOAc (170 mL) and washed with saturated NaHCO$_3$ (60 mL), 5% NaHCO$_3$ solution (60 mL), water (60 mL), saturated NaCl (60 mL), dried over sodium sulfate, filtered and concentrated in vacuo to give (S)—N-(1-cyclohexylethyl)-6-methoxybenzo[d]thiazol-2-amine as crude solid (3.39 grams). ES/MS m/z 291.1 (MH$^+$).

Step 2.

To a solution of (S)—N-(1-cyclohexylethyl)-6-methoxybenzo[d]thiazol-2-amine (3.39 g, 10 mmol) in 30 mL of DCM was added 1 M boron tribromide in DCM (20 mL, 20 mmol) slowly at 0° C. The reaction solution was stirred at 0° C. for 20 min and then at room temperature for 2 hours. The reaction mixture was concentrated in vacuo and the residue was dissolved in EtOAc (400 mL) and water (90 mL) and stirred at room temperature for 10 min. To the mixture was added excess solid NaHCO$_3$ until basic. Stirring was continued at room temperature for 1 hour. The separated aqueous layer was extracted with EtOAc (100 mL). The combined organic layers were washed water (50 mL), saturated NaCl solution (50 mL), dried over sodium sulfate, filtered and concentrated under reduced pressure. Purification by silica gel column chromatography with EtOAc/hexanes (3/7) provided the title compound as a solid (2.0 grams). ES/MS m/z 277.1 (MH$^+$).

Example 3

2-((1R,2R)-2-hydroxycyclohexylamino)benzo[d]thiazol-6-ol

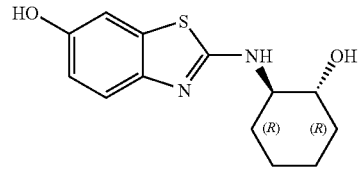

Step 1.

To an ice bath cooled solution of amine (1R,2R)-(−)-2-benzyloxycyclohexylamine (20 g, 97.4 mmol) in dry MeOH (390 mL) was added 4.0 M HCl solution in dioxane (49 mL, 195 mmol) slowly via syringe. The ice bath was removed and resulting solution was sparged with N$_2$ for 10 min. 10% Pd/C (3 g, 28 mmol) was added to the solution and the reaction was purged with H$_2$ and maintained under a H$_2$ atmosphere. After 4 h, an additional 10 mL of 4.0 M HCl solution in dioxane was added and the reaction was maintained under a H$_2$ atmosphere overnight. Upon completion (followed by LCMS), the reaction was filtered through a thin, tightly packed pad of Celite and the collected solids were washed successively with MeOH and EtOAc. The combined organic filtrates were concentrated under reduced pressure to provide (1R,2R)-2-aminocyclohexanol hydrochloride as a pale-colored solid, (13.8 g, 91 mmol, 93%). LCMS m/z 116.0 (MH$^+$), Rt=0.37 min.

Step 2.

To a solution of 2-chloro-6-methoxybenzo[d]thiazole (1.0 g, 5 mmol) in 5.5 mL of NMP was added (1R,2R)-2-aminocyclohexanol hydrochloride (910 mg, 6 mmol) and DIPEA (2.44 mL, 14 mmol). The reaction solution was stirred at 115°

C. for 96 hours. The crude reaction solution was purified by preparative HPLC to give purified fractions that was combined and neutralized with solid NaHCO₃. The resulting solution was extracted with EtOAc (2×300 mL). The combined organic layers were washed with water (60 mL) and brine (60 mL), then dried over Na₂SO₄ and evaporated in vacuo to give (1R,2R)-2-(6-methoxybenzo[d]thiazol-2-ylamino)cyclohexanol (1.06 g, 3.81 mmol) as an ivory solid. ES/MS m/z 279.1 (MH⁺).

Step 3.

To a solution of (1R,2R)-2-(6-methoxybenzo[d]thiazol-2-ylamino)cyclohexanol (1.06 g, 3.81 mmol) in 16 mL of DCM was added 1 M boron tribromide in DCM (8 mL, 8 mmol) slowly at 0° C. The reaction solution was stirred at room temperature for 2 hours. After removal of all solvent in vacuo, the mixture was quenched with water (30 mL) and diluted NaHCO₃ solution, and extraction with EtOAc (3×100 mL). The combined organic extracts were dried over Na₂SO₄ and subsequent removal of EtOAc in vacuo yielded the desired product (1.16 g) as a pink solid. The residue was purified by flash column chromatography to give the title compound (1.0 g, 3.78 mmol) as a brown solid. ES/MS m/z 265.1 (H⁺).

Example 4

3-chloro-N-methylpyridine-4-carboxamide

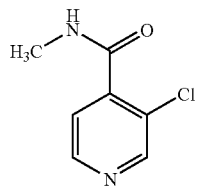

Step 1.

To a suspension of 3-chloroisonicotinic acid (750 mg, 4.76 mmol, 1.0 eq) in 25 mL of toluene was added thionyl chloride (3.0 mL, 41.6 mmol, 8.7 eq) at room temperature. The reaction mixture was stirred at 100° C. for 3 hours. The mixture was concentrated under reduced pressure, dissolved in 25 mL of toluene and concentrated again to give crude 3-chloroisonicotinoyl chloride hydrochloride salt, which was used in the next step without further purification.

Step 2.

To a suspension of crude 3-chloroisonicotinoyl chloride hydrochloride in 25 mL of THF was added methylamine solution (2M in THF, 20 mL, 40 mmol, 8.4 eq) at 0° C. The reaction mixture was stirred at room temperature for 1 hour and concentrated under reduced pressure. The crude material was dissolved in EtOAc (75 mL) and water/brine/saturated sodium bicarbonate solution (1/1/1, 75 mL) and phase separated. The aqueous layer was extracted with EtOAc. The combined organic layers were washed with water/brine/saturated sodium bicarbonate solution (1/1/1, 25 mL) and brine (25 mL) and dried over sodium sulfate. Removal of the solvent under reduced pressure afforded the title compound as an off-white solid (321 mg, 39.7%), which was used without further purification. ES/MS m/z 171.0, (MH⁺), Rt=0.65 min.

Example 5

5-chloro-N-methylpyridine-2-carboxamide

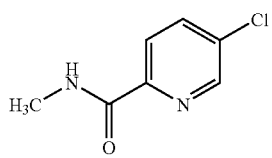

5-Chloropicolinic acid was converted to the title compound by a similar procedure as described in Example 4. Yield: 754 mg, 69.5%. ES/MS m/z 171.0, (MH⁺), Rt=1.92 min.

Example 6

6-chloro-N-methylpyrazine-2-carboxamide

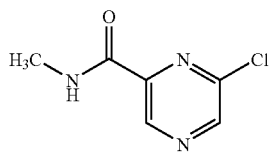

5-Chloropyrazine-2-carboxylic acid was converted to the title compound by a similar procedure as described in Example 4. Yield: 315 mg, 58.1%. ES/MS m/z 172.0, (MH⁺), Rt=1.50 min.

Example 7

2-chloro-6-(1H-1,2,4-triazol-1-yl)pyrazine

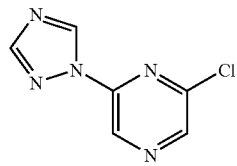

To a solution of 1,2,4-triazole (276 mg, 4.0 mmol, 2.0 eq) in 1.5 mL of DMF was added carefully sodium hydride (60 wt. %. in mineral oil, 120 mg, 3.0 mmol, 3.0 eq) (caution: intensive gas development). The reaction mixture was stirred at room temperature for 45 min. 2,6-Dichloropyrazine (298 mg, 2.0 mmol, 1.0 eq) in 0.5 mL of DMF was added and the reaction mixture was heated at 95° C. for 60 min. The mixture was allowed to cool to room temperature and diluted with EtOAc (15 mL) and water (15 mL). The separated organic layer was concentrated under reduced pressure to afford crude material containing the title compound. The crude material was suspended in NMP (2 mL) and directly used in coupling reactions with phenols. ES/MS m/z 182.0, (MH⁺), Rt=1.68 min.

Example 8

4-chloro-6-(1H-1,2,4-triazol-1-yl)pyrimidine

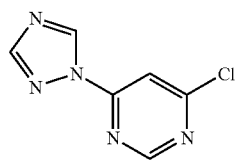

4,6-Dichloropyrimidine was converted to the title compound by a similar procedure as described in Example 7. ES/MS m/z 182.0, (MH$^+$), Rt=1.65 min.

Example 9

6-(6-aminopyridazin-3-yloxy)-N-(cyclohexylmethyl)benzo[d]thiazol-2-amine (89)

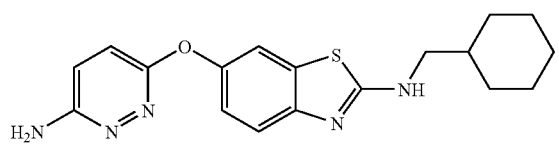

A solution of 2-(cyclohexylmethylamino)benzo[d]thiazol-6-ol (30 mg, 0.114 mmol; see Example 1 above), cesium carbonate (120 mg, 0.368 mmol), and 6-chloropyridazin-3-amine (22.2 mg, 0.171 mmol) in 0.7 mL of DMF was heated at 120° C. for 4 days. The crude reaction mixture was filtered, purified by preparative HPLC and lyophilized to give the title compound as its TFA salt (3 mg). ES/MS m/z 356.0 (MH$^+$), Rt=2.07 min.

Example 10

(S)-5-(2-(1-cyclohexylethylamino)benzo[d] thiazol-6-yloxy)picolinonitrile (87)

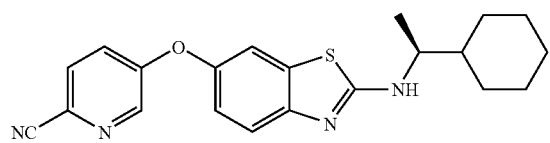

To a reaction mixture of (S)-2-(1-cyclohexylethylamino)benzo[d]thiazol-6-ol (15 mg, 0.057 mmol; see Example 2 above) and cesium carbonate (47 mg, 0.143 mmol) in 0.6 mL of NMP was added 5-chloropicolinonitrile (15.8 mg, 0.114 mmol). The reaction mixture was stirred at 85° C. for 22 hours or until completion by LC. The crude reaction mixture was filtered, purified by preparative HPLC and lyophilized to give the title compound as its TFA salt (16 mg). ES/MS m/z 379.0, (MH$^+$), Rt=2.86 min.

Example 11

(S)—N-(1-cyclohexylethyl)-6-(6-nitropyridin-3-yloxy)benzo[d]thiazol-2-amine

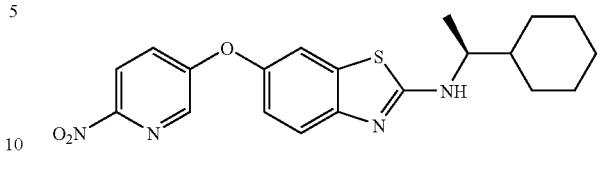

To a reaction mixture of (S)-2-(1-cyclohexylethylamino)benzo[d]thiazol-6-ol (25 mg, 0.095 mmol; see Example 2 above) and cesium carbonate (78 mg, 0.239 mmol) in 0.6 mL of NMP was added 5-chloro-2-nitropyridine (22.7 mg, 0.143 mmol). The reaction mixture was stirred at 85° C. for 16 hours. The crude reaction mixture was filtered, purified by preparative HPLC and lyophilized to give the title compound as its TFA salt (13 mg). ES/MS m/z 398.9 (MH$^+$), Rt=2.86 min.

Example 12

(S)-6-(6-aminopyridin-3-yloxy)-N-(1-cyclohexylethyl)benzo[d]thiazol-2-amine (100) and (S)—N-(1-cyclohexylethyl)-6-(6-(hydroxyamino)pyridin-3-yloxy)benzo[d]thiazol-2-amine (101)

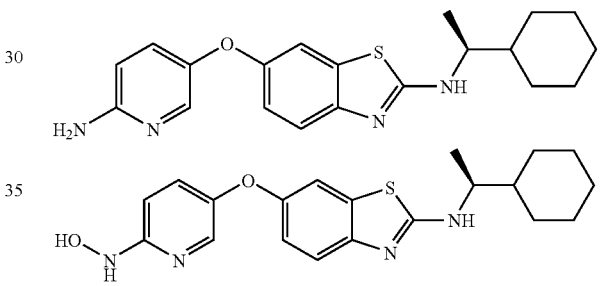

To a solution of (S)—N-(1-cyclohexylethyl)-6-(6-nitropyridin-3-yloxy)benzo[d]thiazol-2-amine (13 mg, 0.033 mmol) in MeOH (1 mL) was added palladium on activated carbon (10 wt. %, ~25 mg). The reaction mixture was stirred vigorously under hydrogen atmosphere (balloon) for 24 hours. The crude reaction mixture was filtered, purified by preparative HPLC and lyophilized to give the title compounds as TFA salts. 100: ES/MS m/z 369.1 (MH$^+$), Rt=2.16 min; 101: ES/MS m/z 385.1 (MH$^+$), Rt=2.18 min.

Example 13

5-(2-((1R,2R)-2-hydroxycyclohexylamino)benzo[d]thiazol-6-yloxy)-N-methylpicolinamide (54)

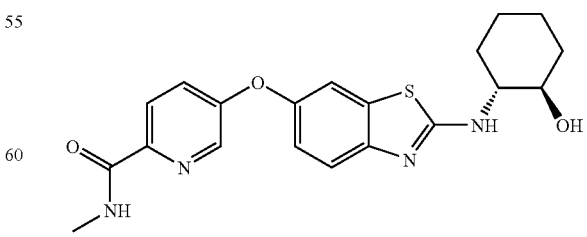

To a reaction mixture of 2-((1R,2R)-2-hydroxycyclohexylamino)benzo[d]thiazol-6-ol (15 mg, 0.057 mmol; see Example 3 above) and cesium carbonate (46 mg, 0.142 mmol) in 0.6 mL of NMP was added 5-chloro-N-methylpyridine-2-carboxamide (14.5 mg, 0.085 mmol; see Example 5 above). The reaction mixture was stirred at 110° C. for 16 hours or until done by LC. The crude reaction mixture was filtered, purified by preparative HPLC and lyophilized to give the title compound as its TFA salt (5.0 mg). ES/MS m/z 398.9, (MH+), Rt=2.01 min.

Example 14

(S)-6-(2-(1-cyclohexylethylamino)benzo[d]thiazol-6-yloxy)-N-methylpyrazine-2-carboxamide (51)

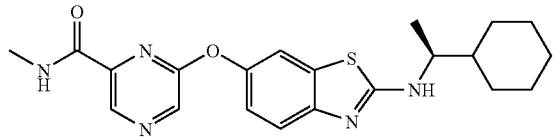

To a reaction mixture of (S)-2-(1-cyclohexylethylamino)benzo[d]thiazol-6-ol (15 mg, 0.057 mmol; see Example 2 above) and cesium carbonate (47 mg, 0.143 mmol) in 0.5 mL of NMP was added 6-chloro-N-methylpyrazine-2-carboxamide (19.6 mg, 0.114 mmol; see Example 6 above). The reaction mixture was stirred at 85° C. for 3 hours or until done by LC. The crude reaction mixture was filtered, purified by preparative HPLC and lyophilized to give the title compound as its TFA salt (12 mg). ES/MS m/z 412.0, (MH+), Rt=2.50 min.

Example 15

3-(2-(cyclohexylmethylamino)benzo[d]thiazol-6-yloxy)-N-methylisonicotinamide (49)

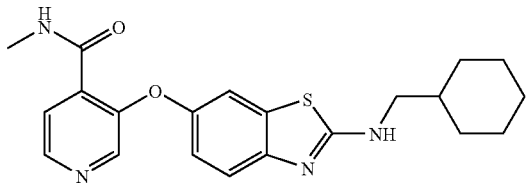

To a reaction mixture of 2-(cyclohexylmethylamino)benzo[d]thiazol-6-ol (30 mg, 0.114 mmol; see Example 1 above) and cesium carbonate (120 mg, 0.368 mmol) in 0.7 mL of DMF was added 3-chloro-N-methylpyridine-4-carboxamide (21.5 mg, 0.126 mmol; see Example 4 above). The reaction mixture was stirred at 85° C. for 16 hours or until done by LC. The crude reaction mixture was filtered, purified by preparative HPLC and lyophilized to give the title compound as its TFA salt (9.0 mg). ES/MS m/z 397.0 (MH+), Rt=2.16 min.

Example 16

N-(cyclohexylmethyl)-6-(1-methyl-1H-pyrazolo[3,4-d]pyrimidin-4-yloxy)benzo[d]thiazol-2-amine (44)

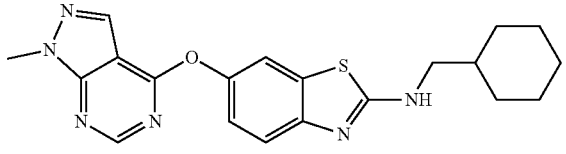

To a reaction mixture of 2-(cyclohexylmethylamino)benzo[d]thiazol-6-ol (19 mg, 0.072 mmol; see Example 1 above) and cesium carbonate (60 mg, 0.184 mmol) in 0.5 mL of NMP was added 4-chloro-1-methyl-1H-pyrazolo[3,4-d]pyrimidine (18.2 mg, 0.108 mmol). The reaction mixture was stirred at 110° C. for 2 hours or until done by LC. The crude reaction mixture was filtered, purified by preparative HPLC and lyophilized to give the title compound as its TFA salt (16.0 mg). ES/MS m/z 395.0 (MH+), Rt=2.40 min.

Example 17

(1R,2R)-2-(6-(6-(1H-1,2,4-triazol-1-yl)pyrimidin-4-yloxy)benzo[d]thiazol-2-ylamino)cyclohexanol (43)

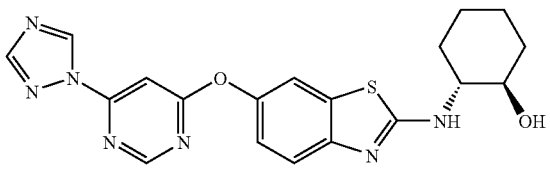

To a reaction mixture of 24(1R,2R)-2-hydroxycyclohexylamino)benzo[d]thiazol-6-ol (20 mg, 0.076 mmol; see Example 3 above) and cesium carbonate (60 mg, 0.183 mmol) in 0.6 mL of NMP was added a suspension of crude 4-chloro-6-(1H-1,2,4-triazol-1-yl)pyrimidine (0.25 mL; see Example 8 above). The reaction mixture was stirred at 110° C. for 3 hours or until done by LC. The crude reaction mixture was filtered, purified by preparative HPLC and lyophilized to give the title compound as its TFA salt (6.0 mg). ES/MS m/z 410.0, (MH+), Rt=1.83 min.

Example 18

(S)-6-(6-(1H-1,2,4-triazol-1-yl)pyrazin-2-yloxy)-N-(1-cyclobexylethyl)benzo[d]thiazol-2-amine (40)

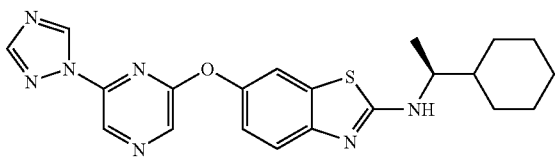

To a reaction mixture of (S)-2-(1-cyclohexylethylamino)benzo[d]thiazol-6-ol (20 mg, 0.076 mmol; see Example 2 above) and cesium carbonate (60 mg, 0.183 mmol) in 0.8 mL of NMP was added a suspension of crude 2-chloro-6-(1H-1,2,4-triazol-1-yl)pyrazine in NMP (0.25 mL; see Example 7 above). The reaction mixture was stirred at 110° C. for 3 hours or until done by LC. The crude reaction mixture was filtered, purified by preparative HPLC and lyophilized to give the title compound as its TFA salt (6.3 mg). ES/MS m/z 422.1, (MH+), Rt=2.62 min.

Example 19

(1R,2R)-2-(6-(5-bromopyridin-3-yloxy)benzo[d]thiazol-2-ylamino)cyclohexanol (45)

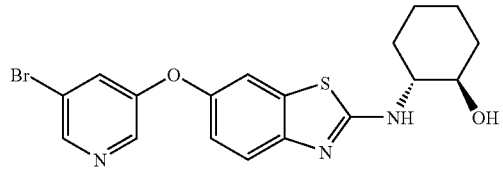

To a reaction mixture of 2-((1R,2R)-2-hydroxycyclohexylamino)benzo[d]thiazol-6-ol (30 mg, 0.113 mmol; see Example 3 above) in 0.5 mL of NMP was added cesium carbonate (78 mg, 0.238 mmol) and stirred for 3-5 min at room temperature. To this mixture was added 3-bromo-5-fluoropyridine (40 mg, 0.226 mmol). The reaction mixture was stirred at 110° C. for 18 hours or until done by LC. The crude reaction mixture was filtered, purified by preparative HPLC and lyophilized to give the title compound as its TFA salt (31.0 mg). ES/MS m/z 419.9/421.9 (MH$^+$), Rt=2.27 min.

Example 20

6-(4-chloropyridin-3-yloxy)-N-(cyclohexylmethyl)benzo[d]thiazol-2-amine (1)

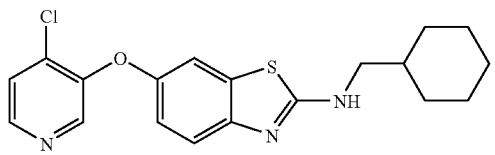

To a reaction mixture of 2-(cyclohexylmethylamino)benzo[d]thiazol-6-ol (18 mg, 0.068 mmol; see Example 1 above) in 0.4 mL of NMP was added cesium carbonate (56 mg, 0.171 mmol) and stirred for 1-3 min at room temperature. To this mixture was added 4-chloro-3-fluoropyridine (17.8 mg, 0.136 mmol). The reaction mixture was heated at 90° C. for 24 hours or until done by LC. The crude reaction mixture was filtered, purified by preparative HPLC and lyophilized to give the title compound as its TFA salt (2.5 mg). ES/MS m/z 374.1 (MH$^+$), Rt=2.41 min.

Example 21

(S)-6-(2-chloropyrimidin-4-yloxy)-N-(1-cyclohexylethyl)benzo[d]thiazol-2-amine (36)

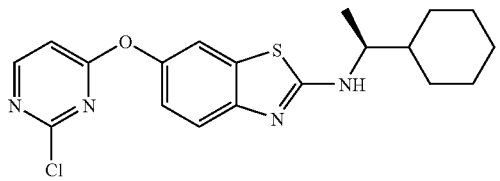

To a reaction mixture of (S)-2-(1-cyclohexylethylamino)benzo[d]thiazol-6-ol (135 mg, 0.487 mmol; see Example 2 above) in 1.8 mL of NMP was added cesium carbonate (397 mg, 1.22 mmol) and stirred for 3-5 min at room temperature. To this mixture was added 2,4-dichloropyrimidine (145 mg, 0.974 mmol). The reaction mixture was stirred at 55-60° C. for 18 hours or until done by LC. The crude reaction mixture was filtered, purified by preparative HPLC and lyophilized to give the title compound as its TFA salt (155 mg). ES/MS m/z 389.1, (MH$^+$), Rt=2.76 min.

Example 22

6-(6-chloropyrimidin-4-yloxy)-N-(cyclohexylmethyl)benzo[d]thiazol-2-amine (2)

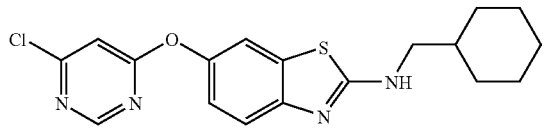

To a reaction mixture of 2-(cyclohexylmethylamino)benzo[d]thiazol-6-ol (18 mg, 0.068 mmol; see Example 1 above) in 0.4 mL of NMP was added cesium carbonate (56 mg, 0.171 mmol) and stirred for 1-3 min at room temperature. To this mixture was added 4,6-dichloropyrimidine (20.3 mg, 0.136 mmol). The reaction mixture was stirred at 90° C. for 3 hours or until done by LC. The crude reaction mixture was filtered, purified by preparative HPLC and lyophilized to give the title compound as its TFA salt (5.3 mg). ES/MS m/z 375.1 (MH$^+$), Rt=2.78 min.

Example 23

(1R,2R)-2-(6-(quinazolin-4-yloxy)benzo[d]thiazol-2-ylamino)cyclohexanol (18)

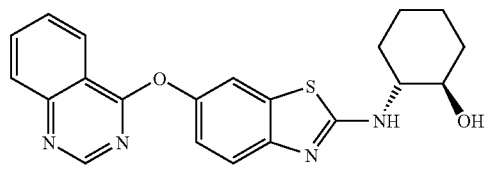

To a reaction mixture of 2-(((1R,2R)-2-hydroxycyclohexylamino)benzo[d]thiazol-6-ol (15.1 mg, 0.057 mmol; see Example 3 above) in 0.4 mL of NMP was added cesium carbonate (47 mg, 0.143 mmol) and stirred for 1-3 min at room temperature. To this mixture was added 4-chloroquinazoline (18.8 mg, 0.114 mmol). The reaction mixture was stirred at room temperature for 5 hours or until done by LC. The crude reaction mixture was filtered, purified by preparative HPLC, freebased, concentrated under reduced pressure and lyophilized to give the title compound (7.4 mg) as a solid. ES/MS m/z 393.2 (MHS, Rt=2.10 min.

Examples 24-27

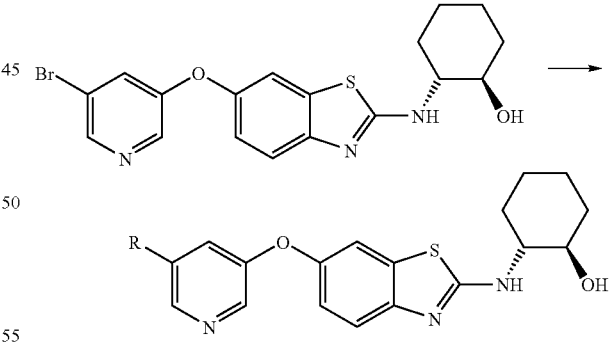

Example 24

(1R,2R)-2-(6-(5-(1-methyl-1H-pyrazol-4-yl)pyridin-3-yloxy)benzo[d]thiazol-2-ylamino)cyclohexanol (46)

To a reaction mixture of (1R,2R)-2-(6-(5-bromopyridin-3-yloxy)benzo[d]thiazol-2-ylamino)cyclohexanol (12 mg, 0.0286 mmol, see Example 19 above) in 0.6 mL of DME was added 1-methyl-4-(4,4,5,5-tetramethyl-1,3,2-dioxaborolan- 2-yl)-1H-pyrazole (24 mg, 0.114 mmol), Pd(dppf)$_2$Cl$_2$ (7.2 mg, 0.0086 mmol) and 2M Na$_2$CO$_3$ (0.15 mL, 0.30 mmol). The reaction solution was stirred at 100-105° C. for 2 hours or until done by LC. The crude reaction mixture was concentrated to solid re-dissolved in 0.8 mL DMF, filtered, purified on preparative HPLC and lyophilized to give the title compound as TFA salt (4.9 mg). ES/MS m/z 422.1 (MH$^+$), Rt=1.83 min.

Example 25 tert-butyl-4-(5-(24(1R,2R)-2-hydroxycyclohexylamino)benzo[d]thiazol-6-yloxy)pyridin-3-yl)-5,6-dihydropyridine-1(2H)-carboxylate (79)

To a reaction mixture of (1R,2R)-2-(6-(5-bromopyridin-3-yloxy)benzo[d]thiazol-2-ylamino)cyclohexanol (12.5 mg, 0.030 mmol, see Example 19 above) in 0.5 mL of NMP was added tert-butyl 4-(4,4,5,5-tetramethyl-1,3,2-dioxaborolan-2-yl)-5,6-dihydropyridine-1(2H)-carboxylate (37 mg, 0.120 mmol), Pd(dppf)$_2$Cl$_2$ (7.5 mg, 0.009 mmol) and 2M Na$_2$CO$_3$ (0.10 mL, 0.20 mmol). The reaction solution was stirred at 105-110° C. for 2 hours or until done by LC. The crude reaction mixture was filtered, purified on preparative HPLC and lyophilized to give the title compound as TFA salt (10.2 mg). ES/MS m/z 523.2 (MH$^+$), Rt=2.41 min.

Example 26

(1R,2R)-2-(6-(5-(1-(2,2-difluoroethyl)-1H-pyrazol-4-yl)pyridin-3-yloxy)benzo[d]thiazol-2-ylamino)cyclohexanol (82)

To a reaction mixture of 4-(4,4,5,5-tetramethyl-1,3,2-dioxaborolan-2-yl)-1H-pyrazole (210 mg, 1.08 mmol) in 2.0 mL of NMP was added cesium carbonate (672 mg, 2.06 mmol). The reaction mixture was stirred for 5 min and then 1,1-difluoro-2-iodoethane (197 mg, 1.03 mmol) was added and stirred at room temperature for 40 hours. From the above crude reaction mixture, 0.8 mL (0.432 mol) was removed and used. (The remaining 1.2 mL was stored in freezer). To the 0.8 mL reaction mixture above was added (1R,2R)-2-(6-(5-bromopyridin-3-yloxy)benzo[d]thiazol-2-ylamino)cyclohexanol (15.0 mg, 0.0357 mmol, see Example 19 above), Pd(dppf)$_2$Cl$_2$ (8.8 mg, 0.0107 mmol) and 2 M Na$_2$CO$_3$ (0.108 mL, 0.216 mmol). The reaction solution was stirred at 105-110° C. for 90 min or until done by LC. The crude reaction mixture was filtered, purified on preparative HPLC and lyophilized to give the title compound as TFA salt (3.3 mg). ES/MS m/z 472.1 (MH$^+$), Rt=2.03 min.

Example 27

(1R,2R)-2-(6-(2,3'-bipyridin-5-yloxy)benzo[d]thiazol-2-ylamino)cyclohexanol (67)

To a reaction mixture of (1R,2R)-2-(6-(5-bromopyridin-3-yloxy)benzo[d]thiazol-2-ylamino)cyclohexanol (12.5 mg, 0.030 mmol, see Example 19 above) in 0.5 mL of DMF was added lithium chloride (19 mg, 0.45 mmol), Pd(dppf)$_2$Cl$_2$ (7.5 mg, 0.009 mmol) and then 2-(tributylstannyl)pyridine (44 mg, 0.12 mmol). The reaction was stirred at 110° C. for 4 hours or until done by LC. The crude reaction mixture was filtered, purified on preparative HPLC and lyophilized to give the title compound as TFA salt (2.4 mg). ES/MS m/z 419.1 (MH$^+$), Rt=2.00 min.

Examples 28-30

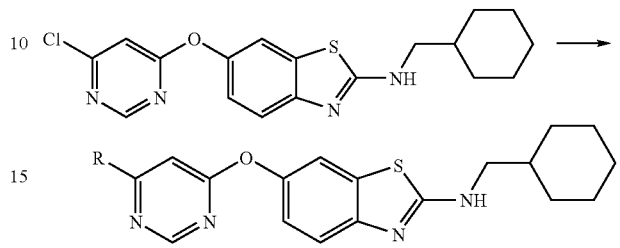

Example 28

N-(cyclohexylmethyl)-6-(6-(1-methyl-1H-pyrazol-4-yl)pyrimidin-4-yloxy)benzo[d]thiazol-2-amine (20)

To a reaction mixture of 6-(6-chloropyrimidin-4-yloxy)-N-(cyclohexylmethyl)benzo[d]thiazol-2-amine (15 mg, 0.040 mmol, see Example 22 above) in 0.6 mL of DME was added 1-methyl-4-(4,4,5,5-tetramethyl-1,3,2-dioxaborolan-2-yl)-1H-pyrazole (42 mg, 0.20 mmol), Pd(dppf)$_2$Cl$_2$ (6.6 mg, 0.008 mmol) and 2M Na$_2$CO$_3$ (0.18 mL, 0.36 mmol). The reaction solution was stirred at 100-105° C. for 90 min or until done by LC. The crude reaction mixture was concentrated to solid re-dissolved in 0.8 mL DMF, filtered, purified on preparative HPLC and lyophilized to give title compound as TFA salt (6.7 mg). ES/MS m/z 421.2 (MH$^+$), Rt=2.46 min.

Example 29

N-(cyclohexylmethyl)-6-(6-morpholinopyrimidin-4-yloxy)benzo[d]thiazol-2-amine (11)

To the reaction mixture of 6-(6-chloropyrimidin-4-yloxy)-N-(cyclohexylmethyl)benzo[d]thiazol-2-amine (15 mg, 0.040 mmol, see Example 22 above) in 0.4 mL of NMP was added DIPEA (0.0175 mL, 0.10 mmol) and morpholine (28.0 mg, 0.32 mmol). The reaction solution was stirred at 105-110° C. for 5 hours or until done by LC. The crude reaction was filtered, purified on preparative HPLC and lyophilized to give title compound as TFA salt (5.7 mg). ES/MS m/z 426.2 (MH$^+$), Rt=2.46 min.

Example 30

Synthesis of N-(cyclohexylmethyl)-6-(6-(methylamino)pyrimidin-4-yloxy)benzo[d]thiazol-2-amine (13)

To a reaction mixture of 6-(6-chloropyrimidin-4-yloxy)-N(cyclohexylmethyl)benzo[d]thiazol-2-amine (15 mg, 0.040 mmol, see Example 22 above) in 0.4 mL of NMP was added DIPEA (0.0175 mL, 0.10 mmol) and methanamine 40% solution in water (0.2 mL, 2.58 mmol). The reaction solution was sealed in a glass tube and stirred at 105° C. for 20 hours or until done by LC. The crude reaction was concentrated, filtered, purified on preparative HPLC and lyophilized to give title compound as TFA salt (5.6 mg). ES/MS m/z 370.2 (MH+), Rt=2.20 min.

Example 31

(1R,2R)-2-(6-(5-(1,2,3,6-tetrahydropyridin-4-yl) pyridin-3-yloxy)benzo[d]thiazol-2-ylamino)cyclohexanol (85)

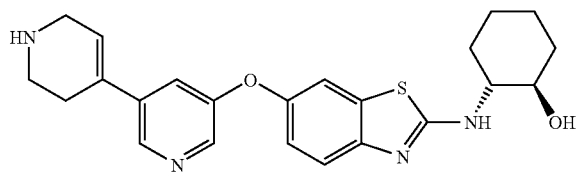

To a solid tert-butyl 4-(5-(2-(((1R,2R)-2-hydroxycyclohexylamino)benzo[d]thiazol-6-yloxy)pyridin-3-yl)-5,6-dihydropyridine-1(2H)-carboxylate (7.2 mg, 0.0138 mmol, see Example 25 above) was added 4M HCl in Dioxane (1 mL, 4.0 mmol). The reaction mixture was stirred at room temperature for 1 hour. The crude reaction mixture was concentrated to a solid and lyophilized to give title compound as HCl salt (4.8 mg). ES/MS m/z 423.2 (MH+), Rt=1.72 min.

Example 32

6-(2-(Cyclohexylmethylamino)benzo[d] thiazol-6-yloxy)-2-methoxy-n-methylpyrimidine-4-carboxamide (10)

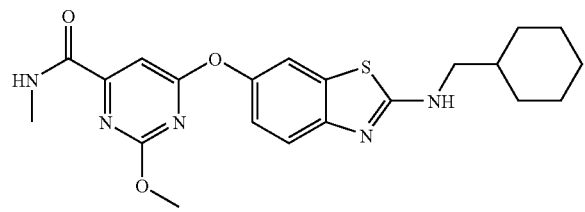

Step 1.
To the reaction mixture of 2-(cyclohexylmethylamino) benzo[d]thiazol-6-ol (18.0 mg, 0.068 mmol; see Example 1 above) in 0.4 mL of NMP was added cesium carbonate (56 mg, 0.171 mmol) and stirred for 1-3 min at room temperature. To this mixture was added methyl 2,6-dichloropyrimidine-4-carboxylate (28 mg, 0.136 mmol). The reaction mixture was stirred at 60° C. for 2 hours or until done by LC. The crude reaction mixture was filtered, purified by preparative HPLC and lyophilized to give methyl 2-chloro-6-(2-(cyclohexylmethylamino)benzo[d]thiazol-6-yloxy)pyrimidine-4-carboxylate as its TFA salt (7.0 mg). ES/MS m/z 433.1 (MH+), Rt=2.51 min.
Step 2.
To a reaction mixture of methyl 2-chloro-6-(2-(cyclohexylmethylamino)benzo[d]thiazol-6-yloxy)pyrimidine-4-carboxylate (94 mg, 0.217 mmol, see Step 1 above) in 3.0 mL of THF and 0.75 mL of MeOH was added 1M aqueous solution of lithium hydroxide (0.651 mL, 0.651 mmol). The reaction mixture was stirred at room temperature for 1 hours or until done by LC. The crude reaction mixture was acidified with 1M HCl, concentrated to a solid, dissolved in 2.0 mL DMF, filtered, purified by preparative HPLC and lyophilized to give 6-(2-(cyclohexylmethylamino)benzo[d]thiazol-6-yloxy)-2-methoxypyrimidine-4-carboxylic acid as its TFA salt (14.0 mg). ES/MS m/z 415.1 (MH+), Rt=2.46 min.
Step 3.
To a reaction mixture of 6-(2-(cyclohexylmethylamino) benzo[d]thiazol-6-yloxy)-2-methoxypyrimidine-4-carboxylic acid (10 mg, 0.024 mmol, see Step 2 above) in 0.6 mL of NMP add DIPEA (0.033 mL, 0.192 mmol), HATU (18.3 mg, 0.048 mmol) and stir for 2-3 min. To this mixture add methanamine hydrochloride (6.4 mg, 0.096 mmol) and stir at room temperature for 5 hours or until done by LC. The crude reaction mixture was filtered, purified by preparative HPLC and lyophilized to give the title compound 6-(2-(cyclohexylmethylamino)benzo[d]thiazol-6-yloxy)-2-methoxy-N-methylpyrimidine-4-carboxamide as its TFA salt (3.4 mg). ES/MS m/z 428.1 (MH+), Rt=2.56 min.

Example 33

(1R,2R)-2-(6-(5-bromo-6-chloropyridin-3-yloxy) benzo[d]thiazol-2-ylamino)cyclohexanol (99)

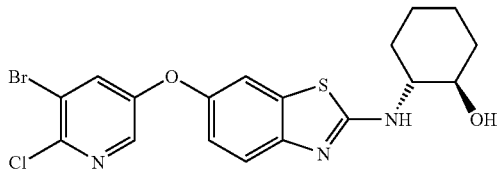

To a reaction mixture of 2-((1R,2R)-2-hydroxycyclohexylamino)benzo[d]thiazol-6-ol (140 mg, 0.53 mmol; see Example 3 above) in 1.8 mL of NMP was added cesium carbonate (380 mg, 1.166 mmol) and stirred for 3-5 minutes at room temperature. To this mixture was added 3-bromo-2-chloro-5-fluoropyridine (223 mg, 1.06 mmol). The reaction mixture was stirred at 50-55° C. for 24 hours or until done by LC. The crude reaction mixture was filtered, purified by preparative HPLC and lyophilized to give the title compound as its TFA salt (122.0 mg). ES/MS m/z 454.0/456.0 (MH+), Rt=2.64 min.

Example 34

(1R,2R)-2-(6-(6-chloro-5-(1-methyl-1H-pyrazol-4-yl)pyridin-3-yloxy)benzo[d]thiazol-2-ylamino)cyclohexanol (102)

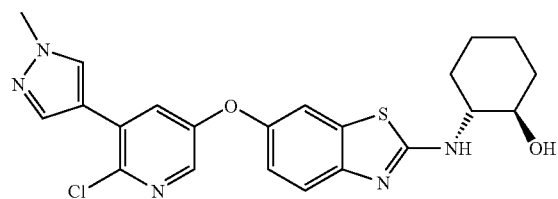

To a reaction mixture of (1R,2R)-2-(6-(5-bromo-6-chloropyridin-3-yloxy)benzo[d]thiazol-2-ylamino)cyclohexanol (26.0 mg, 0.0573 mmol) in 0.6 mL of DME was added 1-methyl-4-(4,4,5,5-tetramethyl-1,3,2-dioxaborolan-2-yl)-1H- pyrazole (19.1 mg, 0.0917 mmol), Pd(dppf)₂Cl₂ (11.7 mg, 0.0143 mmol) and 2M Na₂CO₃ (0.17 mL, 0.34 mmol). The reaction solution was stirred at 105-110° C. for 75 minutes or until done by LC. The crude reaction mixture was concentrated to solid re-dissolved in 0.8 mL NMP, filtered, purified on prep HPLC and lyophilized to give the title compound as TFA salt (5.9 mg). ES/MS m/z 456.1 (MH⁺), Rt=2.30 min.

Example 35

Synthesis of (1R,2R)-2-(6-(pyridin-3-yloxy)benzo[d]thiazol-2-ylamino)cyclohexanol (110)

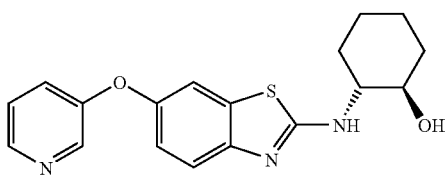

To the solid (1R,2R)-2-(6-(5-bromopyridin-3-yloxy)benzo[d]thiazol-2-ylamino)cyclohexanol (18 mg, 0.043 mmol) under argon was added Palladium 10 wt. % on activated carbon (9.0 mg), ethanol (1.2 mL), and DIPEA (0.023 mL, 0.1129 mmol). To the reaction vessel was added a hydrogen filled balloon and was evacuated then refilled with hydrogen five times. The reaction mixture under hydrogen was stirred at room temperature for 4 hours or until done by LC. The crude reaction mixture was flushed with argon and filtered with an in-line filter and flushed with ethanol. The filtrate was concentrated to a solid which was re-dissolved in 0.8 mL DMF, purified on prep HPLC and lyophilized to give the title compound as TFA salt (7.2 mg). ES/MS m/z 342.1 (MH⁺), Rt=1.73 min.

Example 36

2-chloro-4-(1H-1,2,4-triazol-1-yl)pyridine

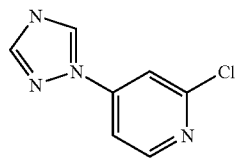

Sodium hydride (60 wt. %. in mineral oil, 400 mg, 10.0 mmol, 5.0 eq) was carefully suspended in 5 mL of DMA (caution: intensive gas development). To the mixture was added carefully 1,2,4-triazole (691 mg, 10.0 mmol, 5.0 eq) and the mixture was stirred at room temperature for 30 min. 2,4-Dichloropyridine (300 mg, 2.0 mmol, 1.0 eq) was added in portions and the reaction mixture was heated at 100° C. for 3.5 hours. The mixture was allowed to cool to room temperature and diluted with saturated NaCl solution (25 mL) and EtOAc (15 mL). The separated aqueous layer was extracted with EtOAc (3×25 mL) and the combined organic layers were washed with saturated NaCl solution (25 mL), dried over sodium sulfate and concentrated under reduced pressure. Purification by silica column chromatography with EtOAc/hexanes (3/1) provided 2-chloro-4-(1H-1,2,4-triazol-1-yl)pyridine as a white solid. Yield: 290 mg. ES/MS m/z 181.1 (MH⁺).

Example 37

6-(4-(1H-1,2,4-triazol-1-yl)pyridin-2-yloxy)-N-(cyclohexylmethyl)benzo[d]thiazol-2-amine (24)

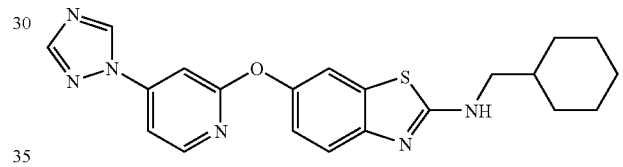

To a reaction mixture of 2-(cyclohexylmethylamino)benzo[d]thiazol-6-ol (20 mg, 0.076 mmol; see Example 1 above) and cesium carbonate (62.1 mg, 0.905 mmol) in 0.5 mL of NMP was added 2-chloro-4-(1H-1,2,4-triazol-1-yl)pyridine (34.4 mg, 0.191 mmol). The reaction mixture was stirred at 110° C. for about 16 hours. The crude reaction mixture was filtered, purified by preparative HPLC and lyophilized to give the title compound as its TFA salt (16.0 mg). ES/MS m/z 407.1 (MH⁺), Rt=2.48 min.

The compounds in the following Table 2 were made according to procedures similar to those described in the Examples above as indicated in the Method column.

TABLE 2

| No. | Structure | Name | (M + H)+, Rt (min.) | Method |
|---|---|---|---|---|
| 3 | ![structure] | 6-(2-(cyclohexylmethylamino)benzo[d]thiazol-6-yloxy)pyrimidine-2,4-diamine | 371.2, 1.84 | Ex. 19 |

TABLE 2-continued

| No. | Structure | Name | (M + H)+, Rt (min.) | Method |
|---|---|---|---|---|
| 4 | 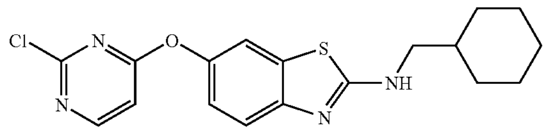 | 6-(2-chloropyrimidin-4-yloxy)-N-(cyclohexylmethyl)benzo[d]thiazol-2-amine | 375.1, 2.68 | Ex. 21 |
| 5 | 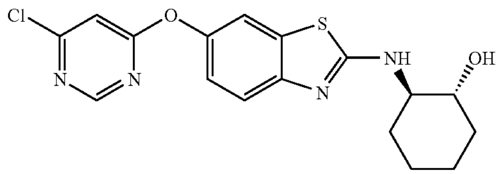 | (1R,2R)-2-(6-(6-chloropyrimidin-4-yloxy)benzo[d]thiazol-2-ylamino)cyclohexanol | 377.1, 2.08 | Ex. 22 |
| 6 | 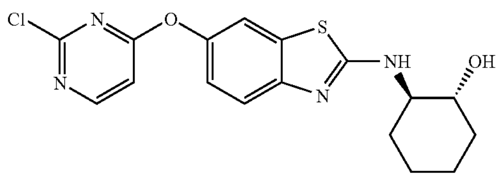 | (1R,2R)-2-(6-(2-chloropyrimidin-4-yloxy)benzo[d]thiazol-2-ylamino)cyclohexanol | 377.1, 2.01 | Ex. 21 |
| 7 | 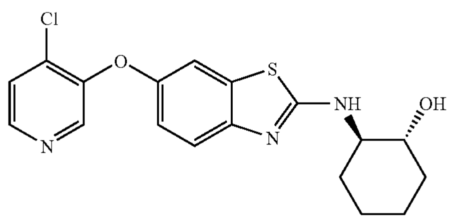 | (1R,2R)-2-(6-(4-chloropyridin-3-yloxy)benzo[d]thiazol-2-ylamino)cyclohexanol | 376.1, 2.02 | Ex. 20 |
| 8 | 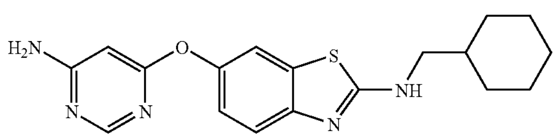 | 6-(6-aminopyrimidin-4-yloxy)-N-(cyclohexylmethyl)benzo[d]thiazol-2-amine | 356.1, 2.12 | Ex. 19 |
| 9 | 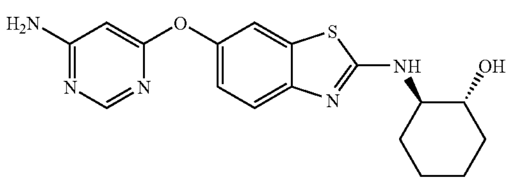 | (1R,2R)-2-(6-(6-aminopyrimidin-4-yloxy)benzo[d]thiazol-2-ylamino)cyclohexanol | 358.1, 1.68 | Ex. 19 |
| 12 | 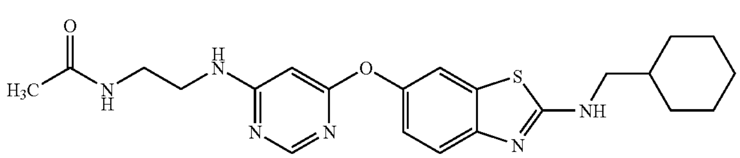 | N-(2-(6-(2-(cyclohexylmethylamino)benzo[d]thiazol-6-yloxy)pyrimidin-4-ylamino)ethyl)acetamide | 441.1, 2.10 | Ex. 29 |
| 14 | 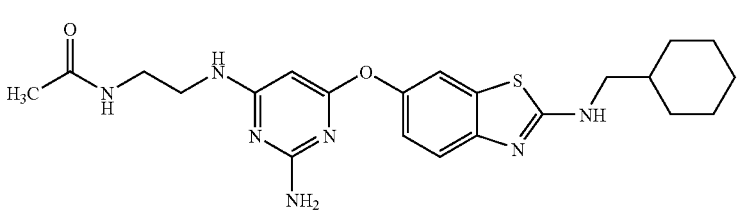 | N-(2-(2-amino-6-(2-(cyclohexylmethylamino)benzo[d]thiazol-6-yloxy)pyrimidin-4-ylamino)ethyl)acetamide | 456.2, 2.09 | Ex. 29 |

TABLE 2-continued

| No. | Structure | Name | (M + H)+, Rt (min.) | Method |
|---|---|---|---|---|
| 15 | 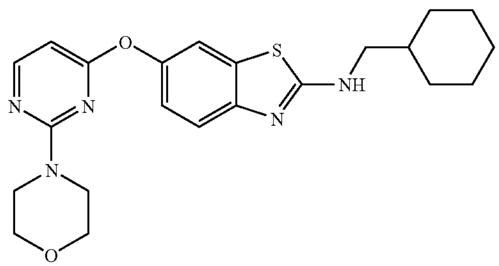 | N-(cyclohexylmethyl)-6-(2-morpholinopyrimidin-4-yloxy)benzo[d]thiazol-2-amine | 426.2, 2.35 | Ex. 29 |
| 16 | 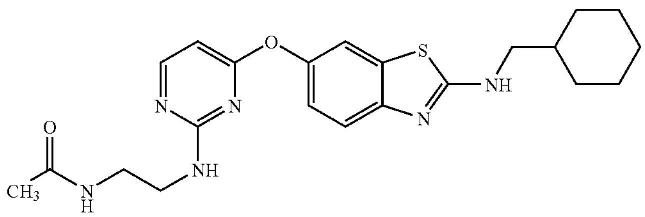 | N-(2-(4-(2-(cyclohexylmethylamino)benzo[d]thiazol-6-yloxy)pyrimidin-2-ylamino)ethyl)acetamide | 441.2, 2.11 | Ex. 29 |
| 17 | 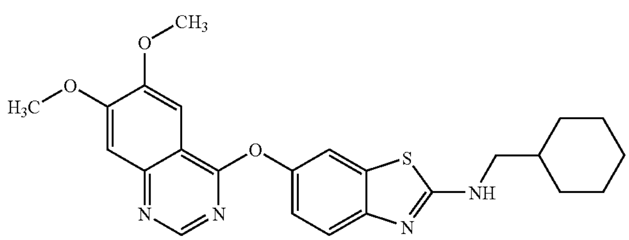 | N-(cyclohexylmethyl)-6-(6,7-dimethoxyquinazolin-4-yloxy)benzo[d]thiazol-2-amine | 451.2, 2.48 | Ex. 23 |
| 19 | 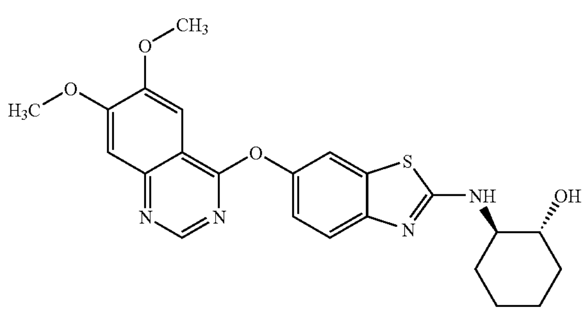 | (1R,2R)-2-(6-(6,7-dimethoxyquinazolin-4-yloxy)benzo[d]thiazol-2-ylamino)cyclohexanol | 453.2, 2.05 | Ex. 23 |
| 21 | 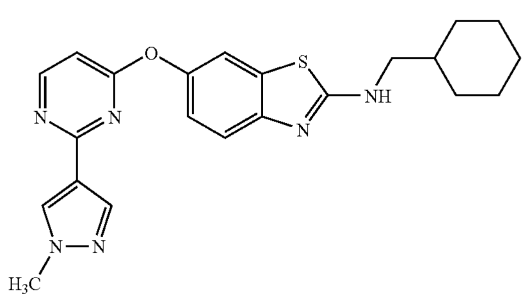 | N-(cyclohexylmethyl)-6-(2-(1-methyl-1H-pyrazol-4-yl)pyrimidin-4-yloxy)benzo[d]thiazol-2-amine | 421.2, 2.45 | Ex. 28 |

TABLE 2-continued

| No. | Structure | Name | (M + H)+, Rt (min.) | Method |
|---|---|---|---|---|
| 22 | 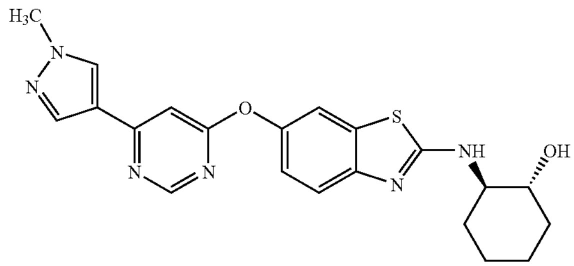 | (1R,2R)-2-(6-(6-(1-methyl-1H-pyrazol-4-yl)pyrimidin-4-yloxy)benzo[d]thiazol-2-ylamino)cyclohexanol | 423.2, 1.99 | Ex. 28 |
| 23 | 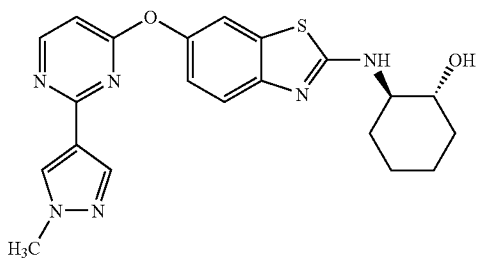 | (1R,2R)-2-(6-(2-(1-methyl-1H-pyrazol-4-yl)pyrimidin-4-yloxy)benzo[d]thiazol-2-ylamino)cyclohexanol | 423.2, 2.00 | Ex. 28 |
| 25 | 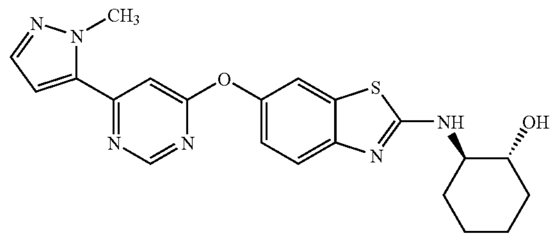 | (1R,2R)-2-(6-(6-(1-methyl-1H-pyrazol-5-yl)pyrimidin-4-yloxy)benzo[d]thiazol-2-ylamino)cyclohexanol | 423.2, 2.13 | Ex. 28 |
| 26 | 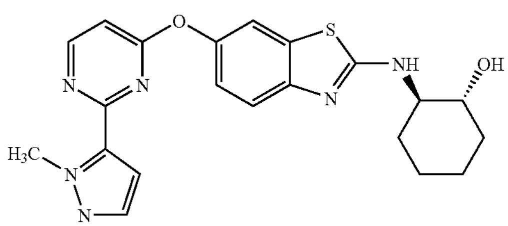 | (1R,2R)-2-(6-(2-(1-methyl-1H-pyrazol-5-yl)pyrimidin-4-yloxy)benzo[d]thiazol-2-ylamino)cyclohexanol | 423.2, 2.16 | Ex. 28 |
| 27 | 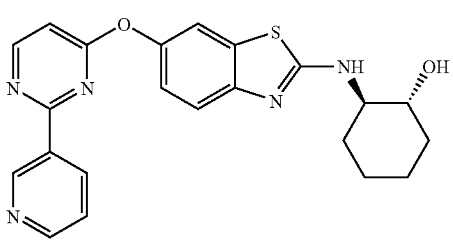 | (1R,2R)-2-(6-(2-(pyridin-3-yl)pyrimidin-4-yloxy)benzo[d]thiazol-2-ylamino)cyclohexanol | 420.1, 1.89 | Ex. 28 |
| 28 | 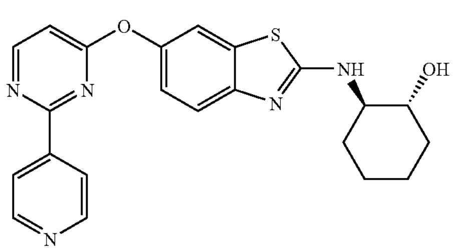 | (1R,2R)-2-(6-(2-(pyridin-4-yl)pyrimidin-4-yloxy)benzo[d]thiazol-2-ylamino)cyclohexanol | 420.1, 1.88 | Ex. 28 |

TABLE 2-continued

| No. | Structure | Name | (M + H)+, Rt (min.) | Method |
|---|---|---|---|---|
| 29 | 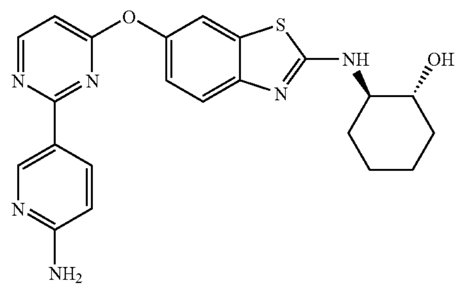 | (1R,2R)-2-(6-(2-(6-aminopyridin-3-yl)pyrimidin-4-yloxy)benzo[d]thiazol-2-ylamino)cyclohexanol | 435.1, 1.91 | Ex. 28 |
| 30 | 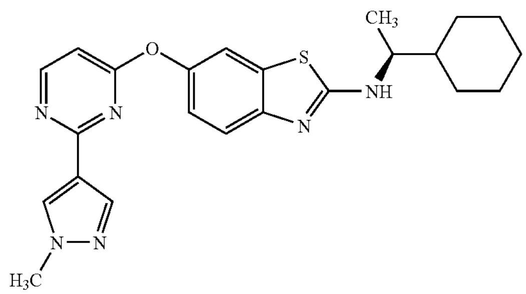 | (S)-N-(1-cyclohexylethyl)-6-(2-(1-methyl-1H-pyrazol-4-yl)pyrimidin-4-yloxy)benzo[d]thiazol-2-amine | 435.2, 2.55 | Ex. 28 |
| 31 | 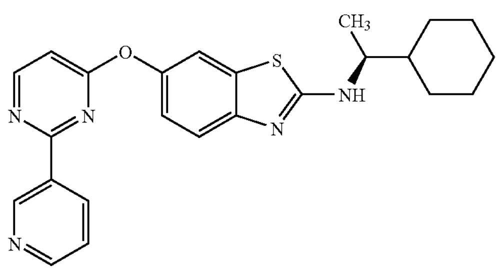 | (S)-N-(1-cyclohexylethyl)-6-(2-(pyridin-3-yl)pyrimidin-4-yloxy)benzo[d]thiazol-2-amine | 432.2, 2.41 | Ex. 28 |
| 32 | 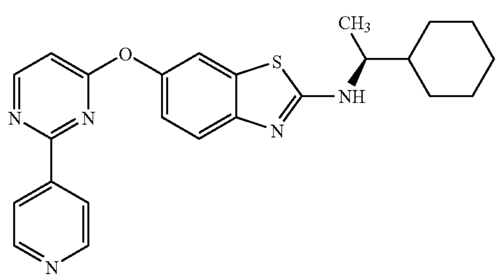 | (S)-N-(1-cyclohexylethyl)-6-(2-(pyridin-4-yl)pyrimidin-4-yloxy)benzo[d]thiazol-2-amine | 432.1, 2.34 | Ex. 28 |
| 33 | 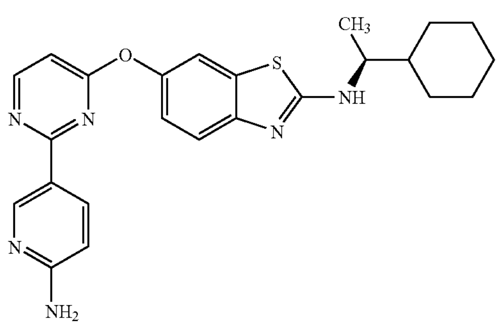 | (S)-6-(2-(6-aminopyridin-3-yl)pyrimidin-4-yloxy)-N-(1-cyclohexylethyl)benzo[d]thiazol-2-amine | 447.1, 2.36 | Ex. 28 |

TABLE 2-continued

| No. | Structure | Name | (M + H)+, Rt (min.) | Method |
|---|---|---|---|---|
| 34 | 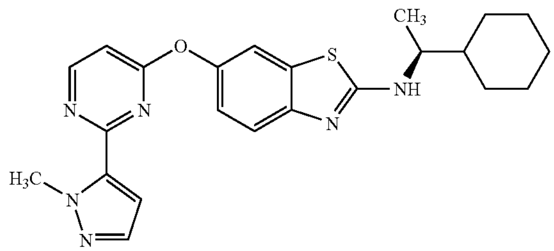 | (S)-N-(1-cyclohexylethyl)-6-(2-(1-methyl-1H-pyrazol-5-yl)pyrimidin-4-yloxy)benzo[d]thiazol-2-amine | 435.2, 2.77 | Ex. 28 |
| 35 | 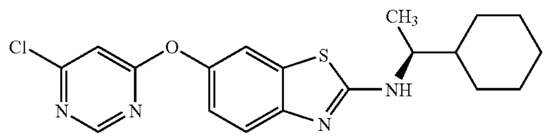 | (S)-6-(6-chloropyrimidin-4-yloxy)-N-(1-cyclohexylethyl)benzo[d]thiazol-2-amine | 389.1, 2.83 | Ex. 21 |
| 37 | 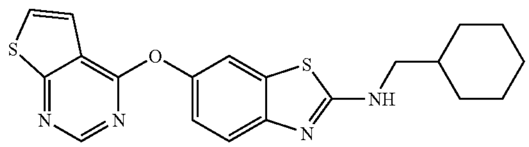 | N-(cyclohexylmethyl)-6-(thieno[2,3-d]pyrimidin-4-yloxy)benzo[d]thiazol-2-amine | 397.1, 2.85 | Ex. 16 |
| 38 | 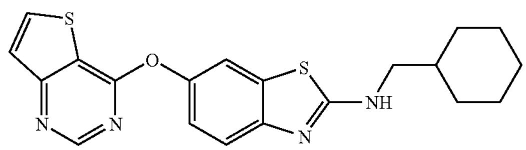 | N-(cyclohexylmethyl)-6-(thieno[3,2-d]pyrimidin-4-yloxy)benzo[d]thiazol-2-amine | 397.1, 2.66 | Ex. 16 |
| 39 | 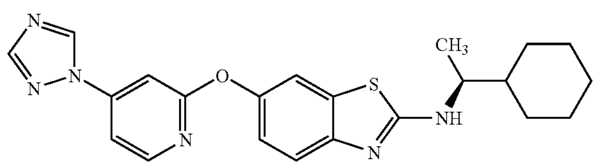 | (S)-6-(4-(1H-1,2,4-triazol-1-yl)pyridin-2-yloxy)-N-(1-cyclohexylethyl)benzo[d]thiazol-2-amine | 421.1, 2.55 | Ex. 37 |
| 41 | 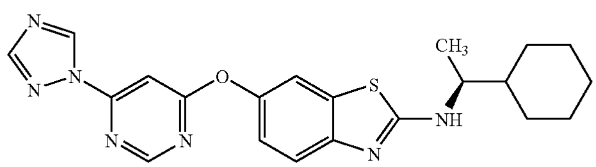 | (S)-6-(6-(1H-1,2,4-triazol-1-yl)pyrimidin-4-yloxy)-N-(1-cyclohexylethyl)benzo[d]thiazol-2-amine | 422.1, 2.64 | Ex. 17 |
| 42 | 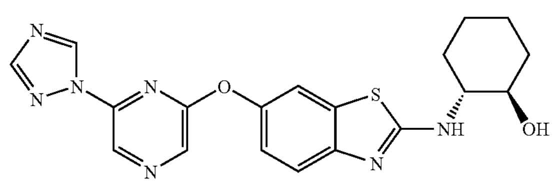 | (1R,2R)-2-(6-(6-(1H-1,2,4-triazol-1-yl)pyrazin-2-yloxy)benzo[d]thiazol-2-ylamino)cyclohexanol | 410.0, 1.85 | Ex. 18 |
| 47 | 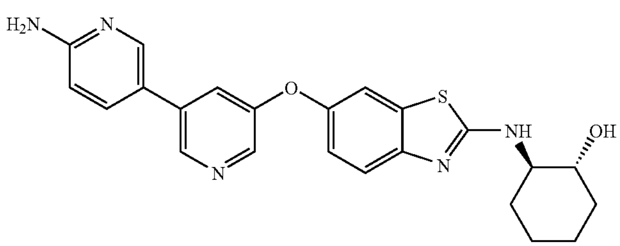 | (1R,2R)-2-(6-(6'-amino-3,3'-bipyridin-5-yloxy)benzo[d]thiazol-2-ylamino)cyclohexanol | 434.0, 1.75 | Ex. 24 |

TABLE 2-continued

| No. | Structure | Name | (M + H)+, Rt (min.) | Method |
|---|---|---|---|---|
| 48 | 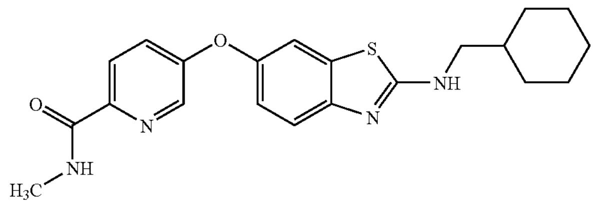 | 5-(2-(cyclohexylmethylamino)benzo[d]thiazol-6-yloxy)-N-methylpicolinamide | 397.1, 2.59 | Ex. 13 |
| 50 | 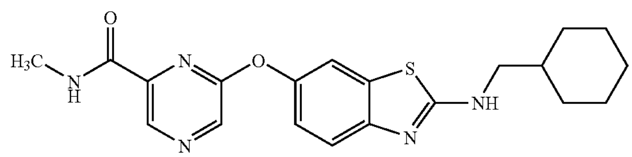 | 6-(2-(cyclohexylmethylamino)benzo[d]thiazol-6-yloxy)-N-methylpyrazine-2-carboxamide | 398.1, 2.40 | Ex. 14 |
| 52 | 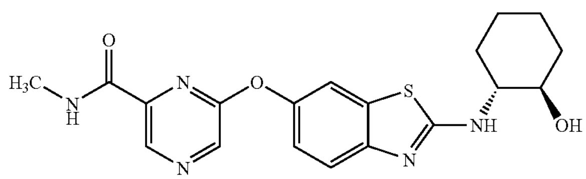 | 6-(2-((1R,2R)-2-hydroxycyclohexylamino)benzo[d]thiazol-6-yloxy)-N-methylpyrazine-2-carboxamide | 400.0, 1.90 | Ex. 14 |
| 53 | 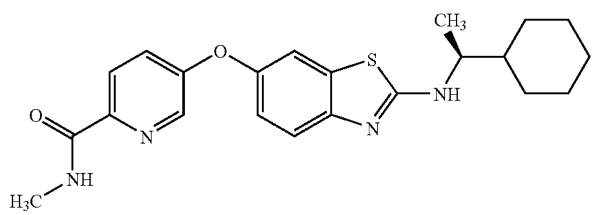 | (S)-5-(2-(1-cyclohexylethylamino)benzo[d]thiazol-6-yloxy)-N-methylpicolinamide | 411.0, 2.61 | Ex. 13 |
| 55 | 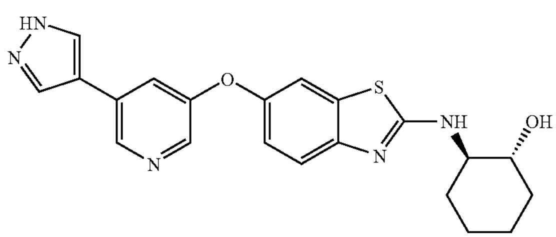 | (1R,2R)-2-(6-(5-(1H-pyrazol-4-yl)pyridin-3-yloxy)benzo[d]thiazo-2-ylamino)cyclohexanol | 408.1, 1.80 | Ex. 25 |
| 56 | 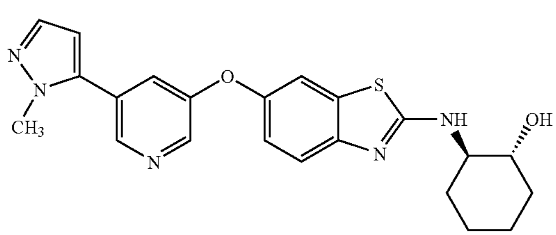 | (1R,2R)-2-(6-(5-(1-methyl-1H-pyrazol-5-yl)pyridin-3-yloxy)benzo[d]thiazol-2-ylamino)cyclohexanol | 422.1, 2.05 | Ex. 25 |
| 57 | 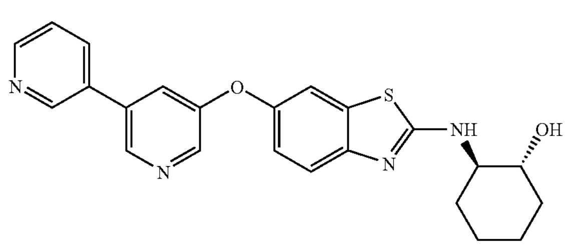 | (1R,2R)-2-(6-(3,3'-bipyridin-5-yloxy)benzo[d]thiazol-2-ylamino)cyclohexanol | 419.1, 1.82 | Ex. 25 |

TABLE 2-continued

| No. | Structure | Name | (M + H)+, Rt (min.) | Method |
|---|---|---|---|---|
| 58 | 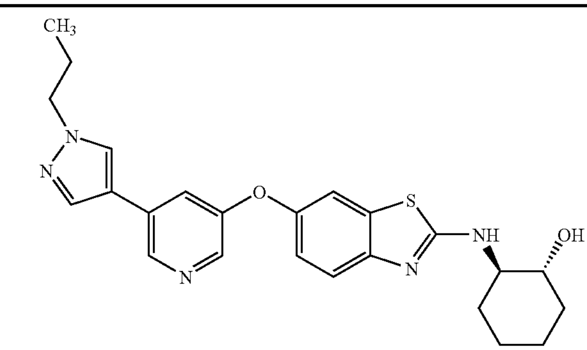 | (1R,2R)-2-(6-(5-(1-propyl-1H-pyrazol-4-yl)pyridin-3-yloxy)benzo[d]thiazol-2-ylamino)cyclohexanol | 450.1, 2.10 | Ex. 25 |
| 59 | 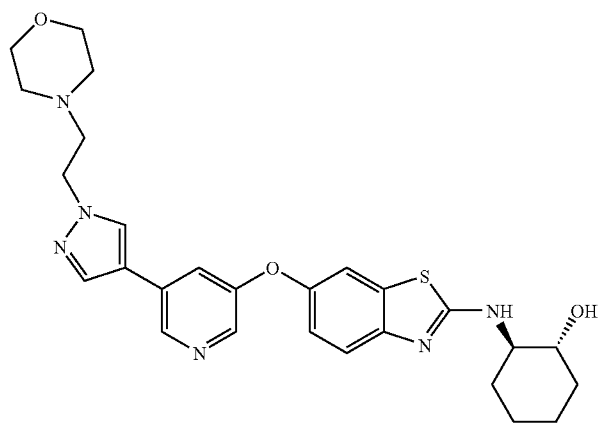 | (1R,2R)-2-(6-(5-(1-(2-morpholinoethyl)-1H-pyrazol-4-yl)pyridin-3-yloxy)benzo[d]thiazol-2-ylamino)cyclohexanol | 521.1, 1.75 | Ex. 25 |
| 60 | 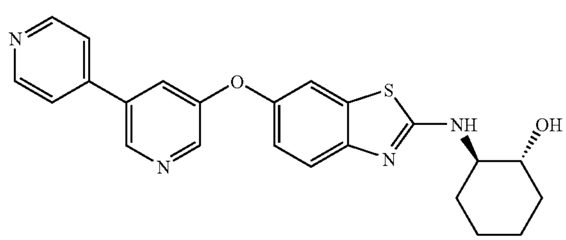 | (1R,2R)-2-(6-(3,4'-bipyridin-5-yloxy)benzo[d]thiazol-2-ylamino)cyclohexanol | 419.0, 1.78 | Ex. 25 |
| 61 | 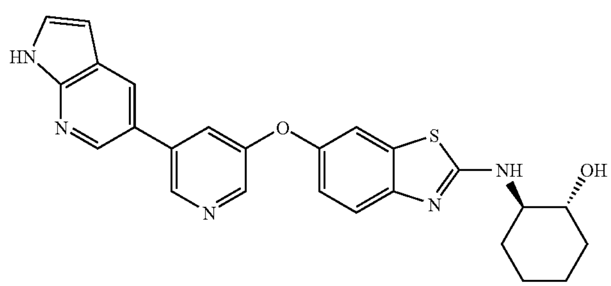 | (1R,2R)-2-(6-(5-(1H-pyrrolo[2,3-b]pyridin-5-yl)pyridin-3-yloxy)benzo[d]thiazol-2-ylamino)cyclohexanol | 458.1, 1.95 | Ex. 25 |
| 62 | 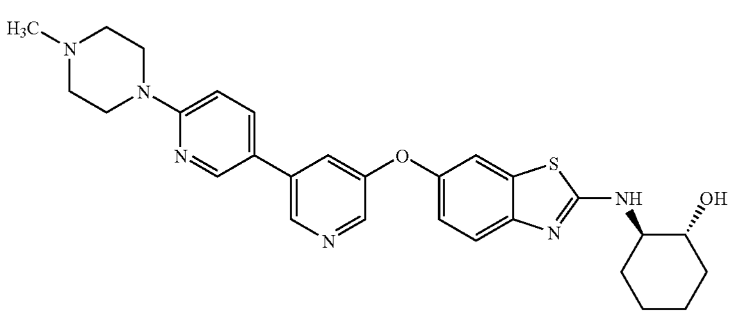 | (1R,2R)-2-(6-(6'-(4-methylpiperazin-1-yl)-3,3'-bipyridin-5-yloxy)benzo[d]thiazol-2-ylamino)cyclohexanol | 517.1, 1.77 | Ex. 25 |

TABLE 2-continued

| No. | Structure | Name | (M + H)+, Rt (min.) | Method |
|---|---|---|---|---|
| 63 | 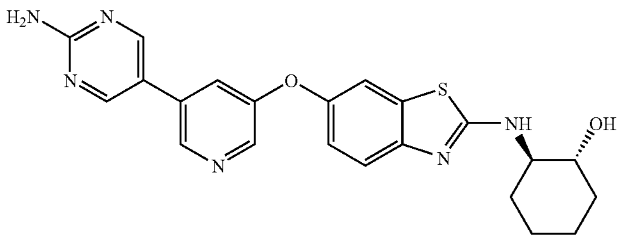 | (1R,2R)-2-(6-(5-(2-aminopyrimidin-5-yl)pyridin-3-yloxy)benzo[d]thiazol-2-ylamino)cyclohexanol | 435.1, 1.80 | Ex. 25 |
| 64 | 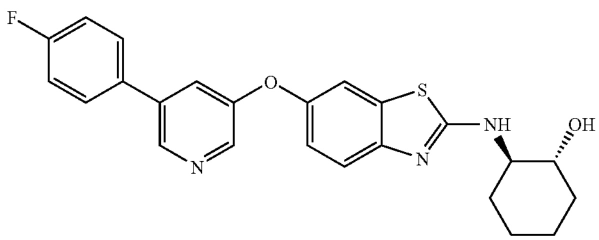 | (1R,2R)-2-(6-(5-(4-fluorophenyl)pyridin-3-yloxy)benzo[d]thiazol-2-ylamino)cyclohexanol | 436.1, 2.34 | Ex. 25 |
| 65 | 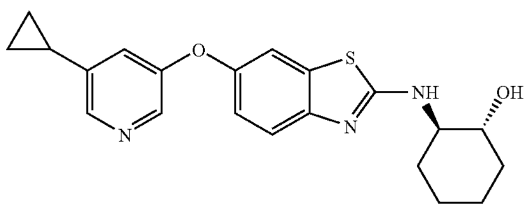 | (1R,2R)-2-(6-(5-cyclopropylpyridin-3-yloxy)benzo[d]thiazol-2-ylamino)cyclohexanol | 382.1, 1.95 | Ex. 25 |
| 66 | 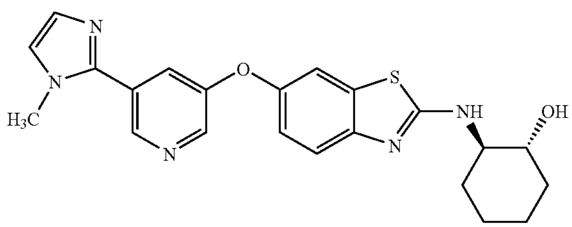 | (1R,2R)-2-(6-(5-(1-methyl-1H-imidazol-2-yl)pyridin-3-yloxy)benzo[d]thiazol-2-ylamino)cyclohexanol | 422.1, 1.81 | Ex. 27 |
| 68 | 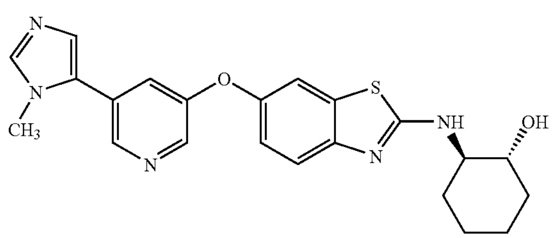 | (1R,2R)-2-(6-(5-(1-methyl-1H-imidazol-5-yl)pyridin-3-yloxy)benzo[d]thiazol-2-ylamino)cyclohexanol | 422.1, 1.81 | Ex. 27 |
| 69 | 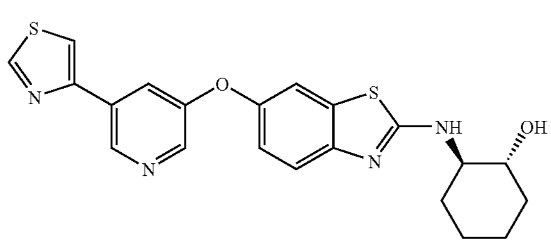 | (1R,2R)-2-(6-(5-(thiazol-4-yl)pyridin-3-yloxy)benzo[d]thiazol-2-ylamino)cyclohexanol | 425.0, 2.02 | Ex. 27 |

TABLE 2-continued

| No. | Structure | Name | (M + H)+, Rt (min.) | Method |
|---|---|---|---|---|
| 70 | 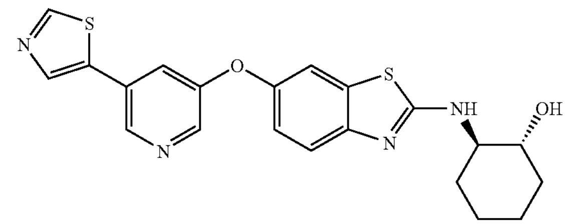 | (1R,2R)-2-(6-(5-(thiazol-5-yl)pyridin-3-yloxy)benzo[d]thiazol-2-ylamino)cyclohexanol | 425.0, 2.07 | Ex. 27 |
| 71 | 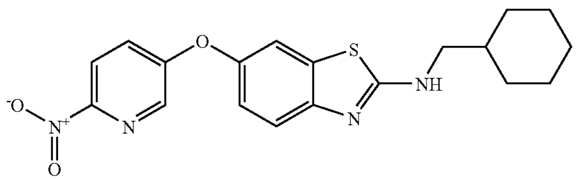 | N-(cyclohexylmethyl)-6-(6-nitropyridin-3-yloxy)benzo[d]thiazol-2-amine | 385.0, 2.92 | 11 |
| 72 | 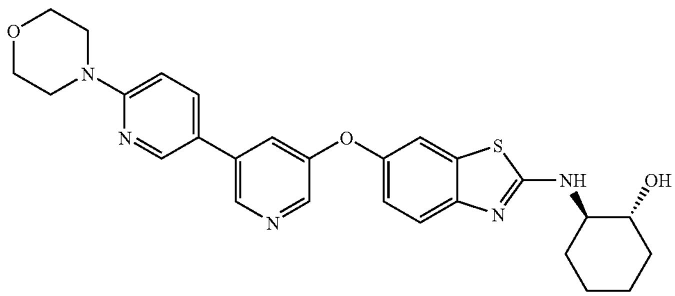 | (1R,2R)-2-(6-(6'-morpholino-3,3'-bipyridin-5-yloxy)benzo[d]thiazol-2-ylamino)cyclohexanol | 504.1, 1.90 | Ex. 25 |
| 73 | 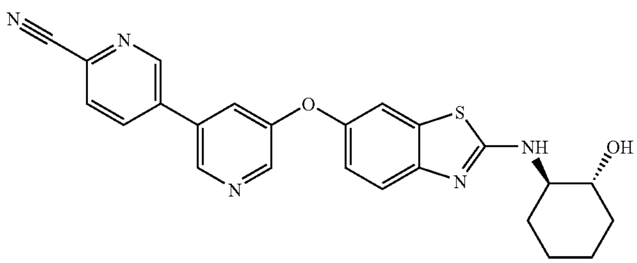 | 5'-(2-((1R,2R)-2-hydroxycyclohexylamino)benzo[d]thiazol-6-yloxy)-3,3'-bipyridine-6-carbonitrile | 444.1, 2.19 | Ex. 25 |
| 74 | 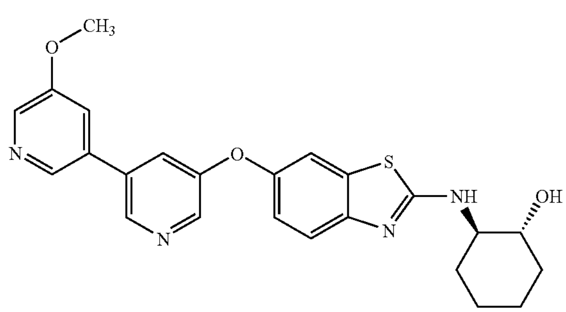 | (1R,2R)-2-(6-(5'-methoxy-3,3'-bipyridin-5-yloxy)benzo[d]thiazol-2-ylamino)cyclohexanol | 449.1, 1.93 | Ex. 25 |
| 75 | 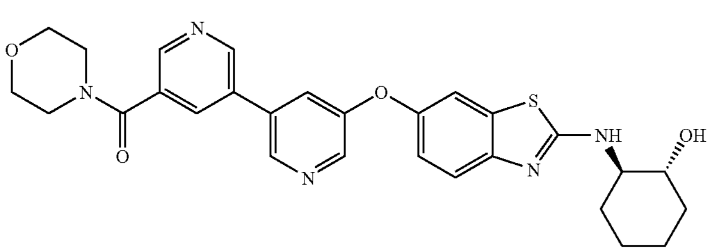 | (5'-(2-((1R,2R)-2-hydroxycyclohexylamino)benzo[d]thiazol-6-yloxy)-3,3'-bipyridin-5-yl)(morpholino)methanone | 532.1, 1.94 | Ex. 25 |

TABLE 2-continued

| No. | Structure | Name | (M + H)+, Rt (min.) | Method |
|---|---|---|---|---|
| 76 | 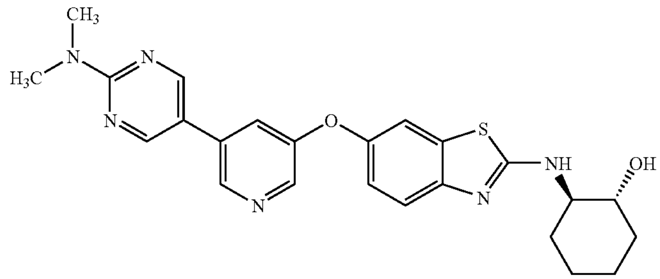 | (1R,2R)-2-(6-(5-(2-(dimethylamino)pyrimidin-5-yl)pyridin-3-yloxy)benzo[d]thiazol-2-ylamino)cyclohexanol | 463.1, 2.08 | Ex. 25 |
| 77 | 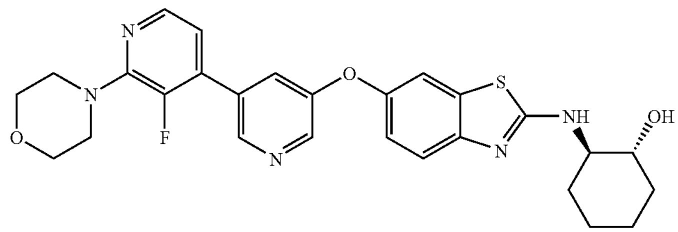 | (1R,2R)-2-(6-(3'-fluoro-2'-morpholino-3,4'-bipyridin-5-yloxy)benzo[d]thiazol-2-yl amino hexanol | 522.1, 2.28 | Ex. 25 |
| 78 | 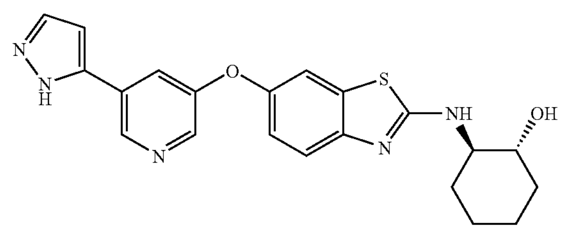 | (1R,2R)-2-(6-(5-(1H-pyrazol-5-yl)pyridin-3-yloxy)benzo[d]thiazol-2-ylamino)cyclohexanol | 408.1, 1.90 | Ex. 25 |
| 80 | 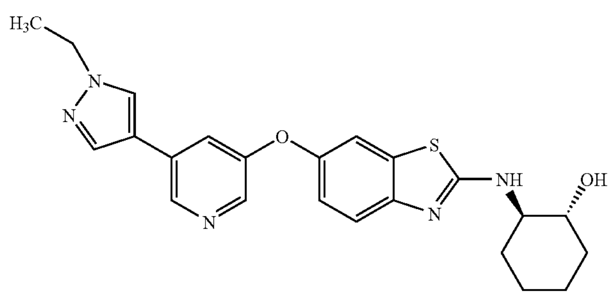 | (1R,2R)-2-(6-(5-(1-ethyl-1H-pyrazol-4-yl)pyridin-3-yloxy)benzo[d]thiazol-2-ylamino)cyclohexanol | 436.1, 1.98 | Ex. 26 |
| 81 | 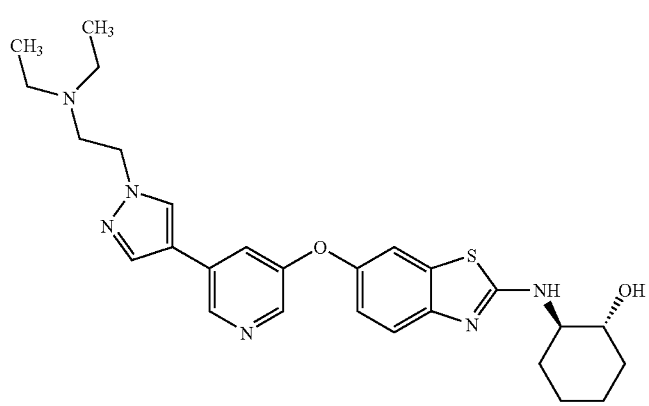 | (1R,2R)-2-(6-(5-(1-(2-(diethylamino)ethyl)-1H-pyrazol-4-yl)pyridin-3-yloxy)benzo[d]thiazol-2-ylamino)cyclohexanol | 507.2, 1.83 | Ex. 26 |

TABLE 2-continued

| No. | Structure | Name | (M + H)+, Rt (min.) | Method |
|---|---|---|---|---|
| 83 | 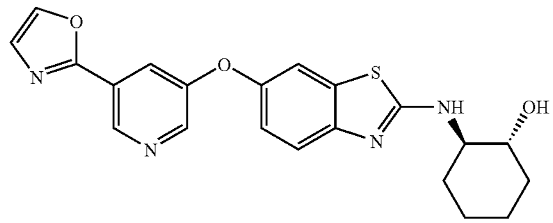 | (1R,2R)-2-(6-(5-(oxazol-2-yl)pyridin-3-yloxy)benzo[d]thiazol-2-ylamino)cyclohexanol | 409.1, 2.13 | Ex. 27 |
| 84 | 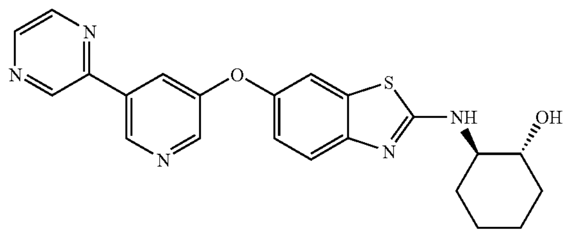 | (1R,2R)-2-(6-(5-(pyrazin-2-yl)pyridin-3-yloxy)benzo[d]thiazol-2-ylamnino)cyclohexanol | 420.1, 2.02 | Ex. 27 |
| 86 | 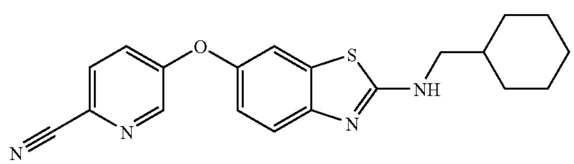 | 5-(2-(cyclohexylmethylamino)benzo[d]thiazol-6-yloxy)picolinonitrile | 365.0, 2.77 | Ex. 10 |
| 88 | 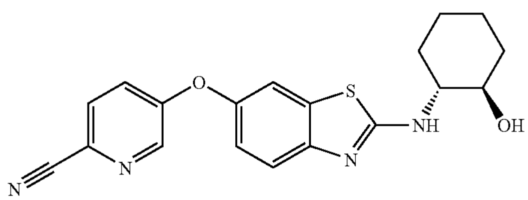 | 5-(2-((1R,2R)-2-hydroxycyclohexylamino)benzo[d]thiazol-6-yloxy)picolinonitrile | 366.9, 2.14 | Ex. 10 |
| 90 | 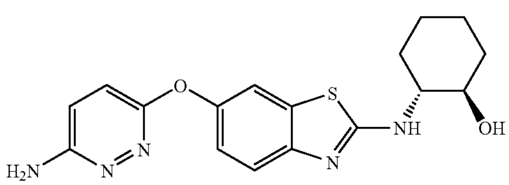 | (1R,2R)-2-(6-(6-aminopyridazin-3-yloxy)benzo[d]thiazol-2-ylamino)cyclohexanol | 358.0, 1.66 | Ex. 9 |
| 91 | 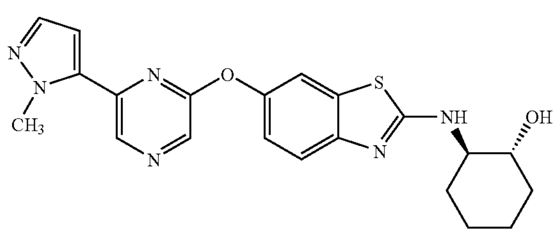 | (1R,2R)-2-(6-(6-(1-methyl-1H-pyrazol-5-yl)pyrazin-2-yloxy)benzo[d]thiazol-2-ylamino)cyclohexanol | 423.1, 2.20 | Ex. 25 |
| 92 | 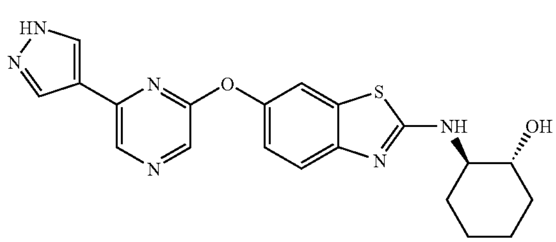 | (1R,2R)-2-(6-(6-(1H-pyrazol-4-yl)pyrazin-2-yloxy)benzo[d]thiazol-2-ylamino)cyclohexanol | 409.1, 2.04 | Ex. 25 |

TABLE 2-continued

| No. | Structure | Name | (M + H)+, Rt (min.) | Method |
|---|---|---|---|---|
| 93 | 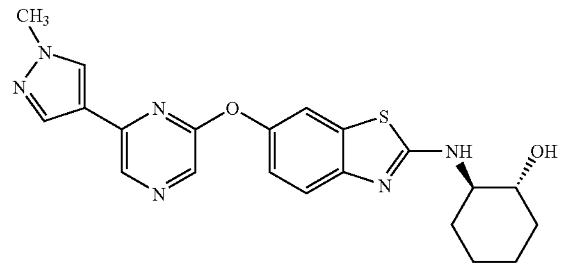 | (1R,2R)-2-(6-(6-(1-methyl-1H-pyrazol-4-yl)pyrazin-2-yloxy)benzo[d]thiazol-2-ylamino)cyclohexanol | 423.1, 2.12 | Ex. 25 |
| 94 | 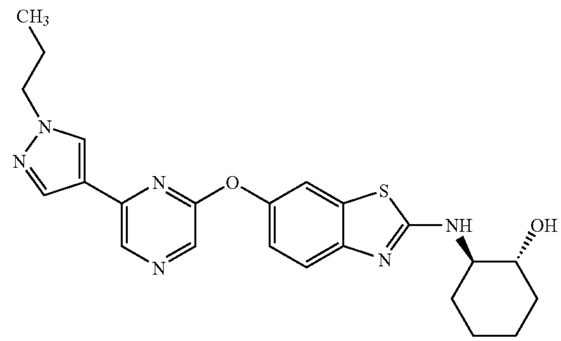 | (1R,2R)-2-(6-(6-(1-propyl-1H-pyrazol-4-yl)pyrazin-2-yloxy)benzo[d]thiazol-2-ylamino)cyclohexanol | 451.2, 2.33 | Ex. 25 |
| 95 | 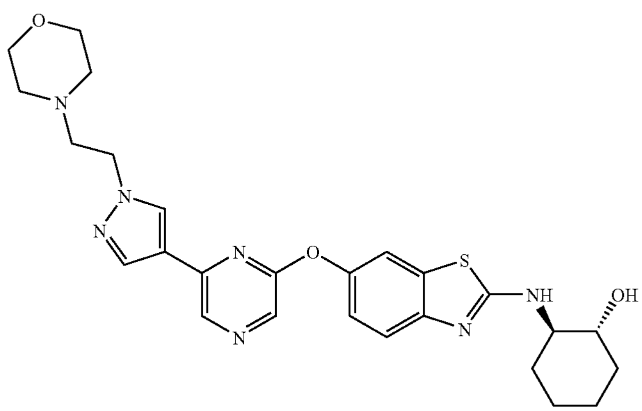 | (1R,2R)-2-(6-(6-(1-(2-morpholinoethyl)-1H-pyrazol-4-yl)pyrazin-2-yloxy)benzo[d]thiazol-2-ylamino)cyclohexanol | 522.2, 1.93 | Ex. 25 |
| 96 | 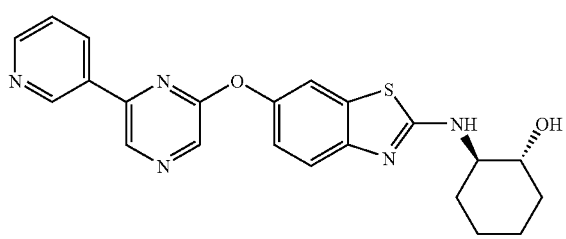 | (1R,2R)-2-(6-(6-(pyridin-3-yl)pyrazin-2-yloxy)benzo[d]thiazol-2-ylamino)cyclohexanol | 420.1, 1.90 | Ex. 25 |
| 97 | 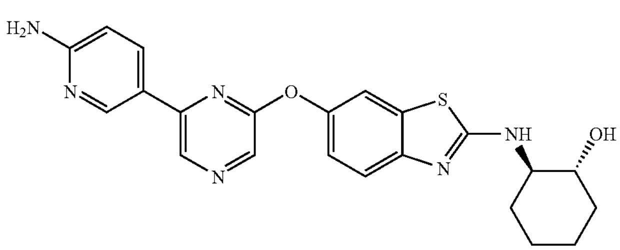 | (1R,2R)-2-(6-(6-(6-aminopyridin-3-yl)pyrazin-2-yloxy)benzo[d]thiazol-2-ylamino)cyclohexanol | 435.1, 1.94 | Ex. 25 |

TABLE 2-continued

| No. | Structure | Name | (M + H)+, Rt (min.) | Method |
|---|---|---|---|---|
| 98 | 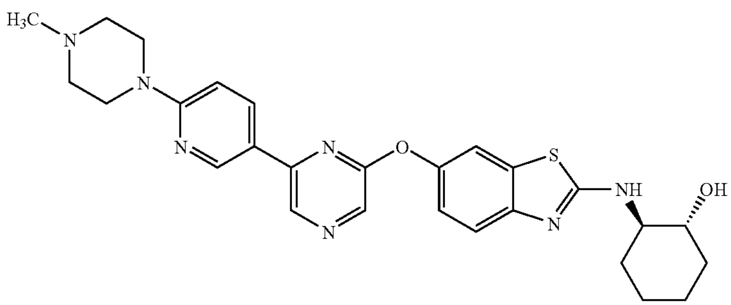 | (1R,2R)-2-(6-(6-(6-(4-methylpiperazin-1-yl)pyridin-3-yl)pyrazin-2-yloxy)benzo[d]thiazol-2-ylamino)cyclohexanol | 518.2, 1.99 | Ex. 25 |
| 103 | 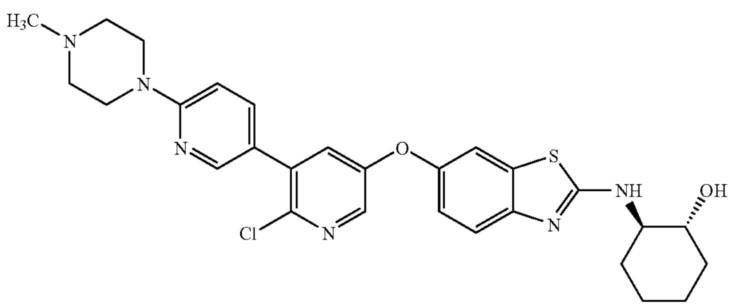 | (1R,2R)-2-(6-(2-chloro-6'-(4-methylpiperazin-1-yl)-3,3'-bipyridin-5-yloxy)benzo[d]thiazol-2-ylamino)cyclohexanol | 551.2, 2.05 | Ex. 34 |
| 104 | 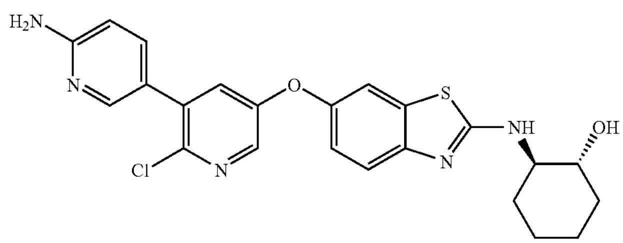 | (1R,2R)-2-(6-(6'-amino-2-chloro-3,3'-bipyridin-5-yloxy)benzo[d]thiazol-2-ylamino)cyclohexanol | 468.1, 2.00 | Ex. 34 |
| 105 | 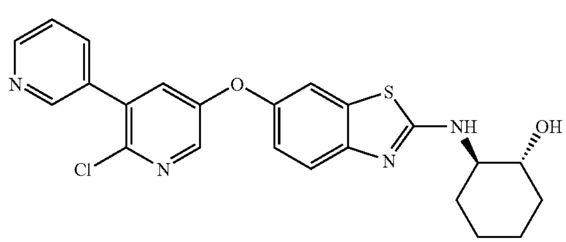 | (1R,2R)-2-(6-(2-chloro-3,3'-bipyridin-5-yloxy)benzo[d]thiazol-2-ylamino)cyclohexanol | 453.1, 2.00 | Ex. 34 |
| 106 | 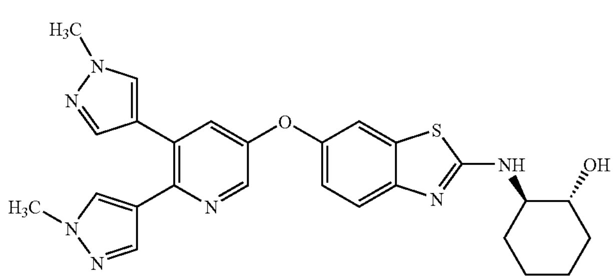 | (1R,2R)-2-(6-(5,6-bis(1-methyl-1H-pyrazol-4-yl)pyridin-3-yloxy)benzo[d]thiazol-2-ylamino)cyclohexanol | 502.2, 1.95 | Ex. 34 |

TABLE 2-continued

| No. | Structure | Name | (M + H)+, Rt (min.) | Method |
|---|---|---|---|---|
| 107 | 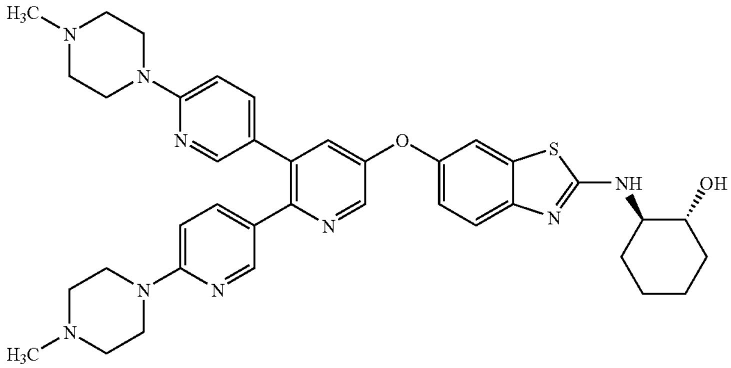 | (1R,2R)-2-(6-(5,6-bis(6-(4-methylpiperazin-1-yl)-pyridin-3-yl)pyridin-3-yloxy)benzo[d]thiazol-2-ylamino)cyclohexanol | 692.4, 1.87 | Ex. 34 |
| 108 | 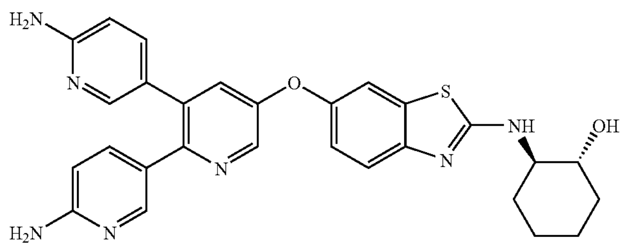 | (1R,2R)-2-(6-(5,6-bis(6-amino-pyridin-3-yl)pyridin-3-yloxy)benzo[d]thiazol-2-ylamino)cyclohexanol | 526.2, 1.81 | Ex. 34 |
| 109 | 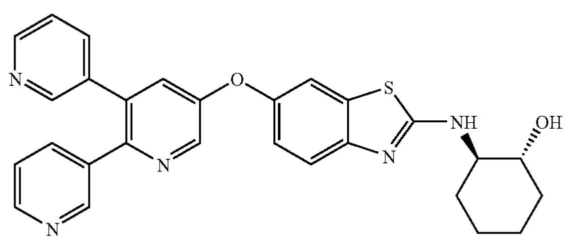 | (1R,2R)-2-(6-(5,6-bis(pyridin-3-yl)pyridin-3-yloxy)benzo[d]thiazol-2-ylamino)cyclohexanol | 496.1, 1.83 | Ex. 34 |

BIOLOGICAL EXAMPLES

Biological Example 1

In Vitro Kinase Assays for Colony Stimulating Factor-1 Receptor (CSF-1R)

The kinase activity of various protein tyrosine kinases can be measured by providing ATP and a suitable peptide or protein tyrosine-containing substrate, and assaying the transfer of phosphate moiety to the tyrosine residue. Recombinant protein corresponding to the cytoplasmic domain of the human CSF-1R was purchased from Invitrogen Corporation, Carlsbad, Calif. U.S.A. (#PV3249). For each assay, test compounds were serially diluted, starting at 25 µM with 3 fold dilutions, in DMSO in 384 well plates then mixed with an appropriate kinase reaction buffer consisting of 50 mM Hepes, 5 mM $MgCl_2$, 10 mM $MnCl_2$, 0.1% BSA, pH 7.5, 1.0 mM dithiothreitol, 0.01% Tween 80 plus 1 µM ATP. Kinase protein and an appropriate biotinylated peptide substrate at 50 nM were added to give a final volume of 20 µL, reactions were incubated for 2 hours at room temperature and stopped by the addition of 10 µL of 45 mM EDTA, 50 mM Hepes pH 7.5. Added to the stopped reaction mix was 30 µL of PT66 Alphascreen beads (Perkin Elmer, Boston, Mass., U.S.A.). The reaction was incubated overnight and read on the Envision (Perkin Elmer). Phosphorylated peptide product was measured with the AlphaScreen system (Perkin Elmer) using acceptor beads coated with anti-phosphotyrosine antibody PT66 and donor beads coated with streptavidin that emit a fluorescent signal at the 520-620 nM emission wave length if in close proximity. The concentration of each compound for 50% inhibition ($IC_{50}$) was calculated by non-linear regression using XL Fit data analysis software.

CSF-1R kinase was assayed in 50 mM Hepes pH 7.0, 5 mM $MgCl_2$, 10 mM $MnCl_2$, 1 mM DTT, 1 mg/mL BSA, 1.0 µM ATP, and 0.05 µM biotin-GGGGRPRAATF-$NH_2$ (SEQ ID NO:1) peptide substrate. CSF-1R kinase was added at final concentration of 4 nM.

Biological Example 2

In Vitro Inhibition of CSF-1R Receptor Tyrosine Phosphorylation

To test the inhibition of CSF-1R receptor tyrosine phosphorylation, HEK293H purchased from Invitrogen Cat. #11631017 cells transfected with the full-length human CSF-1R receptor cloned in house into mammalian episomal transfection vector were incubated for 1 h with serial dilutions of compounds starting at 10 µM with 3 fold dilutions and then stimulated for 8 min with 50 ng/mL MCSF. After the supernatant was removed, the cells were lysed on ice with lysis buffer (150 mM NaCl, 20 mM Tris, pH 7.5, 1 mM EDTA, 1 mM EGTA, 1% Triton X-100 and NaF, protease and phosphatase inhibitors) and then shaken for 15-20 min at 4° C. The lysate was then transferred to total CSF-1R antibody coated 96-well plates that had already been blocked with 3% Blocker A from Mesoscale discovery (MSD) for 2 hours and washed afterwards. Lysates were incubated overnight at 4° C. and the plates were then washed 4× with MSD Tris Wash Buffer. The SULFO-TAG anti-pTyr antibody from MSD was diluted to 20 nM final in 1% Blocker A (MSD) solution and added to the washed plates and incubated for 1.5-2 h before addition of read buffer (MSD). The plates were read on the Sector 6000 instrument (MSD). Raw data was imported in Abase and $EC_{50}$s calculated with XL-fit data analysis software.

Biological Example 3

CSF-1R Inhibitors in MNFS-60 PWPd Model

Five million MNFS-60 cells were implanted in HBSS/matrigel solution s.q. in the right flank. Approximately 3 weeks following tumor cell injection tumors were measured and selected mice were randomized (n=3 except for the vehicle group, where n=6) into groups based on their tumor size.

Compounds that inhibited M-CSF mediated proliferation in MNFS-60 cells and phosphorylation of CSF-1R with $EC_{50}$s<100 nM were tested in the MNFS-60 syngeneic tumor model ($5 \times 10^6$ where implanted subcutaneously in matrigel and grown 3-4 weeks until they reached approximately 150 mm$^2$). A single 100 mg/kg dose of representative compounds listed in Table 1 was administered to MNFS-60 tumored animals; plasma and tumor samples were harvested at various time points after dosing starting at 1 h up to 24 h.

Several of the compounds disclosed herein were shown to inhibit Tyr723 phosphorylation of CSF-1R in tumor lysates at ≧50% compared to vehicle control 4 hrs after dosing as determined by Western Blot.

Compounds disclosed herein can be tested in a rapid onset severe arthritis mouse model (Terato, K. et al., *Journal of Immunology* 148:2103-2108; 1992) with treatment starting on day three after injection of the anti-collagen antibody cocktail followed by LPS stimulation. Throughout the 12 days of treatment with CSF-1R inhibitors, the extent of swelling in the paws and bone resorption severity can be scored.

Biological Example 4

Inhibition of Raf Kinase Signaling in an In Vitro Biochemical Assay

The inhibitory effect of compounds on Raf was determined using the following biotinylated assay. The Raf kinase activity was measured by providing ATP, a recombinant kinase inactive MEK substrate and assaying the transfer of phosphate moiety to the MEK residue. Recombinant full length MEK with an inactivating K97R ATP binding site mutation (rendering kinase inactive) was expressed in *E. coli* and labelled with biotin post purification. The MEK cDNA was subcloned with an N-terminal (His)$_6$ tag and expressed in *E. coli* and the recombinant MEK substrate was purified from *E. coli* lysate by nickel affinity chromatography followed by anion exchange. The final MEK substrate preparation was biotinylated (Pierce EZ-Link Sulfo-NHS-LC-Biotin) and concentrated to 11.25 μM. Recombinant Raf (including c-Raf and mutant B-Raf isoforms) was obtained by purification from sf9 insect cells infected with the corresponding human Raf recombinant expression vectors. The recombinant Raf isoforms were purified via a Glu antibody interaction or by Metal Ion Chromatography.

For each assay, the compound was serially diluted, starting at 25 μM with 3-fold dilutions, in DMSO and then mixed with various Raf isoforms (0.50 nM each). The kinase inactive biotin-MEK substrate (50 nM) was added in reaction buffer plus ATP (1 μM). The reaction buffer contained 30 mM Tris-HCL$_2$ pH 7.5, 10 mM MgCl$_2$, 2 mM DTT, 4 mM EDTA, 25 mM beta-glycerophosphate, 5 mM MnCl$_2$, and 0.01% BSA/PBS. Reactions were subsequently incubated for 2 hours at room temperature and stopped by the addition of 0.5 M EDTA. Stopped reaction mixture was transferred to a neutradavin-coated plate (Pierce) and incubated for 1 hour. Phosphorylated product was measured with the DELFIA time-resolved fluorescence system (Wallac), using a rabbit anti-p-MEK (Cell Signaling) as the primary antibody and europium labeled anti-rabbit as the secondary antibody. Time resolved fluorescence can be read on a Wallac 1232 DELFIA fluorometer. The concentration of the compound for 50% inhibition ($IC_{50}$) was calculated by non-linear regression using XL Fit data analysis software.

Biological Example 5

Inhibition of cKIT and PDGFRb Kinase Signaling in an In Vitro Biochemical Assay

The IC50 values for the inhibition of RTKs were determined in the alphascreen format measuring the inhibition by compound of phosphate transfer to a substrate by the respective enzyme. Briefly, the respective RTK domain purchased as human recombinant protein (cKIT Upstate #14-559, PDGFRb Invitrogen #P3082) were incubated with serial dilutions of compound in the presence of substrate and ATP concentrations within 3 times the Km of the enzyme.

The kinase domain of cKIT was assayed in 50 mM Hepes, pH=7.5, 5 mM MgCl2, 10 mM MnCl2, 1 mM DTT, 0.1% BSA with 0.06 uM biotinylated peptide substrate (GGLFD-DPSYVNVQNL-NH2) and 15 uM ATP (ATP KM apparent=15 uM). The kinase domain of PDGFRβ was assayed in 50 mM Hepes, pH=7.5, 20 mM MgCl2, 1 mM DTT, 0.1% BSA with 0.1 uM biotinylated peptide substrate (GGLFD-DPSYVNVQNL-NH2) and 10 uM ATP (ATP KM apparent=25 uM). Reactions were incubated at room temperature for 3 to 4 hr and stopped with buffer (20 mM EDTA, 0.01% Tween-20 for both PDGFRb and cKIT). Alphascreen PY20 beads were added to the stopped cKIT reactions and PY20 Ab/Protein A Alphascreen beads were added to the PDGFRβ stopped reactions. Both reactions were incubated overnight and read on the Alphascreen reader. The concentration of compound for 50% inhibition ($IC_{50}$) was calculated employing non-linear regression using XL-Fit data analysis software. As a control compound, staurosporine is run in every assay and a Z'>0.5 is required to validate results.

Biological Example 6

Cell Viability Assay in MCSF Dependent MNFS60 Cells

Cell viability was assessed by Cell Titer Glo, Promega. MNFS60 (murine AML cells) were seeded in TC treated 96-well plates at a density of 5,000 cells per well in RPMI-1640, 10% FBS, and 1% Penicillin Streptomycin prior to addition of compound. Test compounds were serially diluted (3 fold) in DMSO to 500× the final concentration. For each concentration of test compound, 2 μl (500×) aliquots of compound or 100% DMSO (control) were diluted in 500 μl of culture medium that contained 2× final concentration of growth factor MCSF for 2× concentration and then diluted 1× on the cells. Final concentration of MCSF is 10 ng/mL. Cells were incubated for 72 hrs at 37° C., 5% $CO_2$. After the incubation 100 μl Cell Titer Glo is added to each well to determine viable cells. The assay was performed according to the manufacturer's instruction (Promega Corporation, Madison, Wis. USA). Each experimental condition was performed in triplicate. Raw data was imported in Abase and $EC_{50}$s calculated with XL-fit data analysis software: Relative light units of wells that contained cells without MCSF in the media and as a consequence didn't grow were defined as 100% inhibited.

Biological Example 7

Tumor Induced Osteolysis Model

Tumor-induced osteolysis (TIO) models have been shown to recapitulate gross bone destruction seen in cancer patients with osteolytic tumor metastasis and have been reported extensively in both the bisphosphonate literature and in conjunction with the testing of novel anti-osteolytic agents. Results from these studies correlate well with human clinical activity (Kim S-J et al., 2005, Canc. Res., 65(9): 3707; Corey, E et al., 2003, Clin. Canc. Res., 9:295; Alvarez, E. et al., 2003, Clin. Canc. Res., 9: 5705). The procedure includes injection of tumor cells directly into the proximal tibia. Once the cells are established, they proliferate and secrete factors that potentiate osteoclast activity, resulting in trabecular and cortical bone resorption. Animals are treated with anti-resorptive agents following tumor cell implantation and bone destruction is measured in a number of ways at the end of the study.

The tumor cell lines utilized in this protocol are of human origin and represent tumor lines that have been previously modified such that they now express the enzyme Luciferase in order to track tumor cells in the animal using the Xenogen system. The strength of the light signal also gives an indication of approximately how many tumor cells are located at a particular site.

Mice are injected subcutaneously with either 2.5 mg/kg flunixin meglumine 30 minutes prior to cell inoculation to provide post-procedural analgesia. The mice are then anesthetized by isoflurane inhalation (ketamine/xylazine injection may be used if isoflurane is not available). Anesthetized animals are placed in the supine position and following tumor cell aspiration into a 50 or 100 μl micro-syringe fitted with a 26- or 27-gauge needle, the needle will be inserted through the cortex of the anterior tuberosity of the right tibia with a rotating "drill-like" movement to minimize the chance for cortical fracture. Successful passage of the needle through the cortex and into the marrow is indicated by loss of resistance against the forward movement of the needle. Once the bone cortex is traversed, 10-20 μl of cell suspension (6×10^5 MDA-MB-231Luc breast carcinoma or 3×10^5 PC-3MLuc prostate carcinoma cells) will be injected into the tibia bone marrow. Animals will be observed to ensure uneventful recovery (warming pad or lamp) until they have recovered from anesthesia.

Progression of tumor growth in the bone can be divided into five stages (Stages 0-4). The stages are defined as follows and can be monitored by comparison to the uninjected (left) leg of the mouse:

Stage 0: normal, no sign of any change in the bone.
Stage 1: Equivocal or minimal lesion; cortex/architecture normal.
Stage 2: Definite lesion; minimal cortex/architecture disruption.
Stage 3: Large lesion; cortex/architecture disruption.
Stage 4: Gross destruction; no preservation of architecture, "late stage". Animals reaching this stage will be taken off the study and euthanized.

Photon imaging of the legs are used to assess the tumor growth at the injection and remote sites during study using the Xenogen system to quantitate tumor cells in the tibia and confirm lack of leakage into other areas. Radiograms of the legs are taken up to once a week through the end of the study using Faxitron X-ray Unit to assess cortical bone destruction at the injection site. While using more invasive cell lines such as the PC-3M-Luc, we monitor bone damage one to two weeks after injection and weekly thereafter. For cell lines that form lesions at a slower rate, such as the MDA-MB-231 Luc, which does not manifest bone damage until 4-5 weeks post-implantation, first radiographic images are taken approximately 4 weeks after animals have been intratibially implanted with cells to establish baseline controls and then once a week to measure bone damage starting at a time point when lesions begin to develop based on model development pilot studies. For example, in mice injected with MDA-MB-231Luc, an image would be taken approximately 4 weeks post-implantation, with weekly images thereafter.

Animals may be dosed with small molecules, monoclonal antibodies, or proteins once or twice daily, by any standard routes.

The endpoint of this study is the time point at which the majority of untreated (negative control) animals have reached late stage disease (Stage 4) and have been euthanized. At that point, the remaining animals in the study are euthanized, regardless of the stage of their tumors. Studies last approximately 5-10 weeks depending on the cell line. After the final x-ray is taken, blood is drawn from the animals by cardiac puncture (for assaying serum bone markers; see below). Endpoint x-ray images are then distributed to 5 volunteers who score each image according to the scoring system detailed above. Scores for each mouse are averaged and expressed as mean osteolytic score or percent of animals with severe osteolysis (animals with scores greater than 2).

Biological Example 8

Mouse Trap5b Assay (IDS Inc., Fountain Hills, Ariz.)

This assay is a solid phase immunofixed enzyme activity assay for the determination of osteoclast-derived tartrate-resistant acid phosphatase 5b in mouse serum samples. Trap5b is expressed by bone resorbing osteoclasts and secreted into the circulation. Thus, serum Trap5b is considered to be a useful marker of osteoclast activity, number and bone resorption.

The mouse Trap5b assay uses a polyclonal antibody prepared using recombinant mouse Trap5b as antigen. In the test, the antibody is incubated in anti-rabbit IgG-coated microtiter wells. After washing, standard, controls and diluted serum samples are incubated in the wells, and bound Trap5b activity is determined with a chromogenic substrate to develop color. The reaction is stopped and the absorbance of the reaction mixture read in a microtiter plate reader at 405 nm. Color intensity is directly proportional to the amount and activity of Trap5b present in the sample. By plotting the mean absorbance for each standard on the ordinate against concentration on the abscissa, values for unknown samples can be read from the standard curve and expressed in U/L Trap5b. Analytical sensitivity of the assay is 0.1 U/L and inter- and intra-assay variation are below 10%.

While a number of the embodiments of the invention and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

Table 3 shows the percent inhibition activities of the representative compounds of the invention when tested when tested at about 1 μM in the indicated assay as described in the Biological Examples. It is contemplated that compounds having 0% inhibition at 1 μM will exhibit inhibitory activities at a higher concentration. An "N/D" means that the compound was not tested in the particular assay.

TABLE 3

| Cmpd | CSF1RK 1 | CKIT | PDGF RK BETA | CPEC50 MNFS60MCSF | PCSF1R |
|---|---|---|---|---|---|
| 1 | 100 | 66 | 34 | 22 | N/D |
| 2 | 78 | 11 | 6 | N/D | N/D |
| 3 | 19 | 23 | 0 | N/D | N/D |
| 4 | 73 | 23 | 0 | N/D | N/D |
| 5 | 41 | 25 | 0 | N/D | N/D |
| 6 | 18 | 19 | 0 | N/D | N/D |
| 7 | 100 | 25 | 11 | 42 | N/D |
| 8 | 100 | 75 | 46 | 30 | N/D |
| 9 | 97 | 13 | 2 | 15 | N/D |
| 10 | 96 | 16 | 5 | 27 | N/D |
| 11 | 68 | 19 | 13 | N/D | N/D |
| 12 | 80 | 13 | 37 | N/D | N/D |
| 13 | 98 | 42 | 30 | 18 | N/D |
| 14 | 26 | 23 | 0 | N/D | N/D |
| 15 | 94 | 26 | 16 | N/D | N/D |
| 16 | 89 | 22 | 35 | N/D | N/D |
| 17 | 100 | 99 | 98 | 100 | N/D |
| 18 | 100 | 22 | 11 | 38 | N/D |
| 19 | 100 | 34 | 30 | 100 | N/D |
| 20 | 100 | 99 | 82 | 96 | N/D |
| 21 | 100 | 100 | 92 | 100 | N/D |
| 22 | 100 | 29 | 11 | 100 | N/D |
| 23 | 100 | 19 | 7 | 100 | N/D |
| 24 | 44 | 7 | 9 | 0 | N/D |
| 25 | 69 | 22 | 0 | 14 | N/D |
| 26 | 100 | 24 | 20 | 19 | N/D |
| 27 | 100 | 20 | 8 | 54 | 78 |
| 28 | 100 | 18 | 25 | 67 | 88 |
| 29 | 100 | 13 | 11 | 76 | N/D |
| 30 | 100 | 24 | 21 | 100 | N/D |
| 31 | 100 | 29 | 6 | 58 | 59 |
| 32 | 100 | 30 | 14 | 58 | 70 |
| 33 | 100 | 32 | 22 | 78 | N/D |
| 34 | 100 | 21 | 6 | 19 | N/D |
| 35 | 79 | 20 | 2 | N/D | N/D |
| 36 | 59 | 19 | 0 | N/D | N/D |
| 37 | 100 | 75 | 39 | 0 | N/D |
| 38 | 100 | 99 | 83 | N/D | N/D |
| 39 | 27 | 33 | 0 | N/D | N/D |
| 40 | 68 | 32 | 17 | N/D | N/D |
| 41 | 99 | 28 | 0 | 0 | N/D |
| 42 | 51 | 9 | 10 | N/D | N/D |
| 43 | 57 | 15 | 14 | N/D | N/D |
| 44 | 99 | 14 | 19 | 0 | N/D |
| 45 | 100 | 60 | 5 | 96 | 93 |
| 46 | 100 | 60 | 12 | 100 | N/D |
| 47 | 100 | 63 | 1 | 100 | N/D |
| 48 | 96 | 22 | 8 | 0 | N/D |
| 49 | 95 | 32 | 6 | N/D | N/D |
| 50 | 98 | 32 | 11 | N/D | N/D |
| 51 | 97 | 32 | 14 | 3 | N/D |
| 52 | 78 | 33 | 12 | N/D | N/D |
| 53 | 98 | 12 | 13 | 13 | N/D |
| 54 | 87 | 56 | 13 | N/D | N/D |
| 55 | 100 | 84 | 19 | N/D | N/D |
| 56 | 100 | 43 | 10 | 93 | 96 |
| 57 | 100 | 45 | 0 | 96 | 96 |
| 58 | 100 | 86 | 7 | N/D | N/D |
| 59 | 100 | 78 | 16 | N/D | N/D |
| 60 | 100 | 52 | 3 | 97 | 95 |
| 61 | 100 | 84 | 8 | N/D | N/D |
| 62 | 100 | 77 | 26 | N/D | N/D |
| 63 | 100 | 35 | 14 | 61 | 80 |
| 64 | 100 | 54 | 8 | 100 | 95 |
| 65 | 100 | 73 | 8 | N/D | N/D |
| 66 | 100 | 40 | 9 | 90 | 96 |
| 67 | 100 | 94 | 36 | N/D | N/D |
| 68 | 100 | 33 | 21 | 85 | 93 |
| 69 | 100 | 97 | 31 | N/D | N/D |
| 70 | 100 | 64 | 13 | 100 | N/D |
| 71 | 25 | 11 | 1 | N/D | N/D |
| 72 | 100 | 76 | 10 | N/D | N/D |
| 73 | 99 | 44 | 3 | 23 | N/D |
| 74 | 100 | 59 | 1 | 100 | N/D |
| 75 | 100 | 28 | 5 | 33 | N/D |
| 76 | 100 | 24 | 0 | 54 | N/D |
| 77 | 100 | 83 | 6 | N/D | N/D |
| 78 | 100 | 88 | 9 | N/D | N/D |
| 79 | 100 | 48 | 9 | 93 | 93 |
| 80 | 100 | 66 | 0 | 100 | N/D |
| 81 | 100 | 56 | 0 | 100 | N/D |
| 82 | 100 | 82 | 0 | N/D | N/D |
| 83 | 100 | 86 | 98 | N/D | N/D |
| 84 | 100 | 99 | 100 | 100 | N/D |
| 85 | 96 | 13 | 2 | 13 | N/D |
| 86 | 39 | 19 | 1 | N/D | N/D |
| 87 | 32 | 16 | 0 | N/D | N/D |
| 88 | 32 | 15 | 0 | N/D | N/D |
| 89 | 75 | 46 | 9 | N/D | N/D |
| 90 | 28 | 33 | 87 | N/D | N/D |
| 91 | 95 | 21 | 14 | N/D | N/D |
| 92 | 100 | 27 | 23 | 70 | 93 |
| 93 | 100 | 18 | 22 | 82 | 95 |
| 94 | 100 | 13 | 9 | 80 | 95 |
| 95 | 100 | 18 | 8 | 47 | N/D |
| 96 | 100 | 23 | 9 | 32 | N/D |
| 97 | 100 | 24 | 19 | 62 | 91 |
| 98 | 100 | 15 | 12 | 100 | 98 |
| 99 | 83 | 27 | 21 | N/D | N/D |
| 100 | 100 | 90 | 31 | N/D | N/D |
| 101 | 100 | 74 | 31 | 58 | N/D |
| 102 | 86 | 11 | 7 | N/D | N/D |
| 103 | 100 | 14 | 9 | 35 | N/D |
| 104 | 86 | 15 | 15 | N/D | N/D |
| 105 | 43 | 9 | 9 | N/D | N/D |
| 106 | 81 | 13 | 18 | N/D | N/D |
| 107 | 100 | 16 | 26 | 100 | 86 |
| 108 | 93 | 10 | 23 | N/D | N/D |
| 109 | 48 | 11 | 16 | N/D | N/D |
| 110 | 100 | 10 | 14 | 54 | N/D |

The following references are cited in the specification.

Sherr, C. J., et al., *The c-fms proto-oncogene product is related to the receptor for the mononuclear phagocyte growth factor, CSF* 1. Cell, 1985. 41(3): p. 665-676.

Roussel, M. F., et al., *Transforming potential of the c-fms proto-oncogene* (CSF-1 receptor). 1987. 325(6104): p. 549-552.

Lee, P. S., et al., *The Cbl protooncoprotein stimulates CSF-1 receptor multiubiquitination and endocytosis, and attenuates macrophage proliferation*. Embo J, 1999. 18(13): p. 3616-28.

Inaba, T., et al., *Expression of M-CSF receptor encoded by c-fms on smooth muscle cells derived from arteriosclerotic lesion*. J Biol Chem, 1992. 267(8): p. 5693-9.

Baker, A. H., et al., *Expression of the colony-stimulating factor 1 receptor in B lymphocytes*. Oncogene, 1993. 8(2): p. 371-8.

Sawada, M., et al., *Activation and proliferation of the isolated microglia by colony stimulating factor-1 and possible involvement of protein kinase C*. Brain Res, 1990. 509(1): p. 119-24.

Stanley, E. R., et al., *Biology and action of colony—stimulating factor-1*. Mol Reprod Dev, 1997. 46(1): p. 4-10.

Bourette, R. P. and L. R. Rohrschneider, *Early events in M-CSF receptor signaling*. Growth Factors, 2000. 17(3): p. 155-66.

Pollard, J. W., *Role of colony-stimulating factor-1 in reproduction and development*. Mol Reprod Dev, 1997. 46(1): p. 54-60; discussion 60-1.

Dai, X. M., et al., *Targeted disruption of the mouse colony-stimulating factor 1 receptor gene results in osteopetrosis, mononuclear phagocyte deficiency, increased primitive progenitor cell frequencies, and reproductive defects*. Blood, 2002. 99(1): p. 111-20.

Scholl, S. M., et al., *Anti-colony-stimulating factor-1 antibody staining in primary breast adenocarcinomas correlates with marked inflammatory cell infiltrates and prognosis*. J Natl Cancer Inst, 1994. 86(2): p. 120-6.

Kacinski, B. M., *CSF-1 and its receptor in breast carcinomas and neoplasms of the female reproductive tract*. Mol Reprod Dev, 1997. 46(1): p. 71-4.

Ngan, H. Y., et al., *Proto-oncogenes and p53 protein expression in normal cervical stratified squamous epithelium and cervical intra-epithelial neoplasia*. Eur J Cancer, 1999. 35(10): p. 1546-50.

Kirma, N., et al., *Elevated expression of the oncogene c-fms and its ligand, the macrophage colony-stimulating factor-1, in cervical cancer and the role of transforming growth factor-beta1 in inducing c-fms expression*. Cancer Res, 2007. 67(5): p. 1918-26.

Ridge, S. A., et al., *FMS mutations in myelodysplastic, leukemic, and normal subjects*. Proc Natl Acad Sci USA, 1990. 87(4): p. 1377-80.

Abu-Duhier, F. M., et al., *Mutational analysis of class III receptor tyrosine kinases (C-KIT, C-FMS, FLT3) in idiopathic myelofibrosis*. Br J Haematol, 2003. 120(3): p. 464-70.

Yang, D. H., et al., *The relationship between point mutation and abnormal expression of c-fms oncogene in hepatocellular carcinoma*. Hepatobiliary Pancreat Dis Int, 2004. 3(1): p. 86-9.

West, R. B., et al., *A landscape effect in tenosynovial giant-cell tumor from activation of CSF1 expression by a translocation in a minority of tumor cells*. Proc Natl Acad Sci USA, 2006. 103(3): p. 690-5.

Tanaka, S., et al., *Macrophage colony-stimulating factor is indispensable for both proliferation and differentiation of osteoclast progenitors*. J Clin Invest, 1993. 91(1): p. 257-63.

Choueiri, M. B., et al., *The central role of osteoblasts in the metastasis of prostate cancer*. Cancer Metastasis Rev, 2006. 25(4): p. 601-9.

Vessella, R. L. and E. Corey, *Targeting factors involved in bone remodeling as treatment strategies in prostate cancer bone metastasis*. Clin Cancer Res, 2006. 12(20 Pt 2): p. 6285s-6290s.

Bingle, L., N. J. Brown, and C. E. Lewis, *The role of tumour-associated macrophages in tumour progression: implications for new anticancer therapies*. J Pathol, 2002. 196(3): p. 254-65.

Pollard, J. W., *Tumour-educated macrophages promote tumour progression and metastasis*. Nat Rev Cancer, 2004. 4(1): p. 71-8.

Zins, K., et al., *Colon Cancer Cell-Derived Tumor Necrosis Factor-{alpha} Mediates the Tumor Growth-Promoting Response in Macrophages by Up-regulating the Colony-Stimulating Factor-1 Pathway*10.1158/0008-5472.CAN-06-2295. Cancer Res, 2007. 67(3): p. 1038-1045.

Paulus, P., et al., *Colony-Stimulating Factor-1 Antibody Reverses Chemoresistance in Human MCF-7 Breast Cancer Xenografts*10.1158/0008-5472.CAN-05-3 523. Cancer Res, 2006. 66(8): p. 4349-4356.

Balkwill, F., K. A. Charles, and A. Mantovani, *Smoldering and polarized inflammation in the initiation and promotion of malignant disease*. Cancer Cell, 2005. 7(3): p. 211-7.

Mantovani, A., et al., *The chemokine system in diverse forms of macrophage activation and polarization*. Trends Immunol, 2004. 25(12): p. 677-86.

Balkwill, F., *TNF-alpha in promotion and progression of cancer*. Cancer Metastasis Rev, 2006. 25(3): p. 409-16.

Cohen, M. S., et al., *Structural bioinformatics-based design of selective, irreversible kinase inhibitors*. Science, 2005. 308(5726): p. 1318-21.

Rabello, D., et al., *CSF1 gene associated with aggressive periodontitis in the Japanese population*. Biochem Biophys Res Commun, 2006. 347(3): p. 791-6.

da Costa, C. E., et al., *Presence of osteoclast-like multinucleated giant cells in the bone and nonostotic lesions of Langerhans cell histiocytosis*. J Exp Med, 2005. 201(5): p. 687-93.

Cenci, S., et al., *M-CSF neutralization and egr-1 deficiency prevent ovariectomy-induced bone loss*. J Clin Invest, 2000. 105(9): p. 1279-87.

Roggia, C., et al., *Role of TNF-alpha producing T-cells in bone loss induced by estrogen deficiency*. Minerva Med, 2004. 95(2): p. 125-32.

Kitaura, H., et al., *M-CSF mediates TNF-induced inflammatory osteolysis*. J Clin Invest, 2005. 115(12): p. 3418-27.

Daroszewska, A. and S. H. Ralston, *Mechanisms of disease: genetics of Paget's disease of bone and related disorders*. Nat Clin Pract Rheumatol, 2006. 2(5): p. 270-7.

Lester, J. E., et al., *Current management of treatment-induced bone loss in women with breast cancer treated in the United Kingdom*. Br J Cancer, 2006. 94(1): p. 30-5.

Lester, J., et al., *The causes and treatment of bone loss associated with carcinoma of the breast*. Cancer Treat Rev, 2005. 31(2): p. 115-42.

Stoch, S. A., et al., *Bone loss in men with prostate cancer treated with gonadotropin-releasing hormone agonists*. J Clin Endocrinol Metab, 2001. 86(6): p. 2787-91.

Drees, P., et al., *Mechanisms of disease: Molecular insights into aseptic loosening of orthopedic implants*. Nat Clin Pract Rheumatol, 2007. 3(3): p. 165-71.

Guzman-Clark, J. R., et al., *Barriers in the management of glucocorticoid-induced osteoporosis*. Arthritis Rheum, 2007. 57(1): p. 140-6.

Feldstein, A. C., et al., *Practice patterns in patients at risk for glucocorticoid-induced osteoporosis*. Osteoporos Int, 2005. 16(12): p. 2168-74.

Ritchlin, C. T., et al., *Mechanisms of TNF-alpha-and RANKL-mediated osteoclastogenesis and bone resorption in psoriatic arthritis*. J Clin Invest, 2003. 111(6): p. 821-31.

Campbell, I. K., et al., *The colony-stimulating factors and collagen-induced arthritis: exacerbation of disease by M-CSF and G-CSF and requirement for endogenous M-CSF*. J Leukoc Biol, 2000. 68(1): p. 144-50.

Saitoh, T., et al., *Clinical significance of increased plasma concentration of macrophage colony-stimulating factor in patients with angina pectoris*. J Am Coll Cardiol, 2000. 35(3): p. 655-65.

Ikonomidis, I., et al., *Increased circulating C-reactive protein and macrophage-colony stimulating factor are complementary predictors of long-term outcome in patients with chronic coronary artery disease*. Eur Heart J, 2005. 26(16): p. 1618-24.

Murayama, T., et al., *Intraperitoneal administration of anti-c-fms monoclonal antibody prevents initial events of atherogenesis but does not reduce the size of advanced lesions in apolipoprotein E-deficient mice*. Circulation, 1999. 99(13): p. 1740-6.

Hao, A. J., S. T. Dheen, and E. A. Ling, *Expression of macrophage colony-stimulating factor and its receptor in microglia activation is linked to teratogen-induced neuronal damage*. Neuroscience, 2002. 112(4): p. 889-900.

Murphy, G. M., Jr., L. Yang, and B. Cordell, *Macrophage colony-stimulating factor augments beta-amyloid-induced interleukin-1, interleukin-6, and nitric oxide production by microglial cells*. J Biol Chem, 1998. 273(33): p. 20967-71.

Murphy, G. M., Jr., et al., *Expression of macrophage colony-stimulating factor receptor is increased in the AbetaPP (V717F) transgenic mouse model of Alzheimer's disease*. Am J Pathol, 2000. 157(3): p. 895-904.

Kaku, M., et al., *Amyloid beta protein deposition and neuron loss in osteopetrotic (op/op) mice*. Brain Res Brain Res Protoc, 2003. 12(2): p. 104-8.

What is claimed is:

1. A compound that is of the Formula (I):

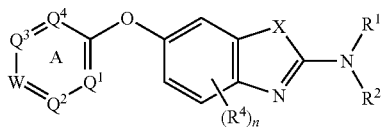

(I)

or a pharmaceutically acceptable salt thereof, wherein:
X is O or S;
A is a six-member ring where W is C—$R^3$ or N, each of $Q^1$, $Q^2$, $Q^3$ and $Q^4$ is independently C—$R^3$ or N, provided that at least one of $Q^1$, $Q^2$, $Q^3$ and $Q^4$ is N and at most three of $Q^1$, $Q^2$, $Q^3$, $Q^4$ and W are N;
$R^1$ is L-$R^{1b}$ wherein L is a covalent bond, alkylene, or substituted alkylene, and $R^{1b}$ is

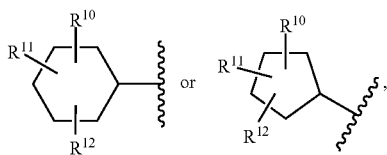

wherein $R^{10}$, $R^{11}$, and $R^{12}$ are independently selected from the group consisting of hydrogen, halo, hydroxy, alkyl, substituted alkyl, alkoxy, substituted alkoxy, amino, substituted amino, cycloalkyl, substituted cycloalkyl, heterocyclyl, substituted heterocyclyl, aryl, substituted aryl, heteroaryl, and substituted heteroaryl; or $R^{11}$ is taken together with $R^{12}$ to form a group selected from the group consisting of aryl, substituted aryl, heterocyclyl, substituted heterocyclyl, heteroaryl, and substituted heteroaryl;
$R^2$ is H or methyl;
each $R^3$ is independently hydrogen or $R^{3a}$, where each $R^{3a}$ is independently selected from the group consisting of halo, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclic, substituted heterocyclic, amino, substituted amino, acyl, acylamino, alkoxy, substituted alkoxy, carboxyl, carboxyl ester, substituted sulfonyl, aminosulfonyl, and aminocarbonyl; or two $R^{3a}$ groups on two adjoining carbon atoms are taken together with the carbon atoms bound thereto to form a group selected from aryl, substituted aryl, heterocyclic, substituted heterocyclic, heteroaryl, or substituted heteroaryl;
each $R^4$ is independently alkyl, substituted alkyl, alkoxy, substituted alkoxy, amino, substituted amino, or halo; and
n is 0, 1, or 2.

2. A compound of claim 1 that is of the Formula (II):

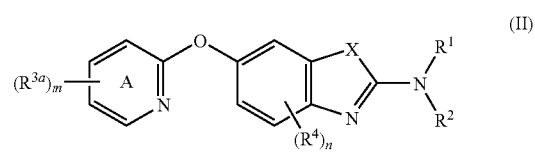

(II)

or a pharmaceutically acceptable salt thereof, wherein:
X is O or S;
each $R^{3a}$ is independently selected from the group consisting of halo, nitro, hydroxyamino, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclic, substituted heterocyclic, amino, substituted amino, acyl, acylamino, alkoxy, substituted alkoxy, carboxyl, carboxyl ester, substituted sulfonyl, aminosulfonyl, and aminocarbonyl; or two $R^{3a}$ groups on two adjoining carbon atoms are taken together with the carbon atoms bound thereto to form a group selected from aryl, substituted aryl, heterocyclic, substituted heterocyclic, heteroaryl, or substituted heteroaryl;
each $R^4$ is independently alkyl, substituted alkyl, alkoxy, substituted alkoxy, amino, substituted amino, or halo;
m is 0, 1, 2, or 3, and
n is 0, 1, or 2.

3. A compound of claim 1 that is of the Formula (III):

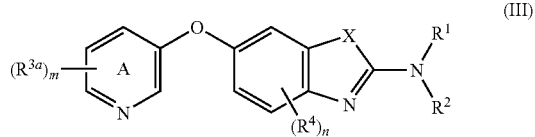

(III)

or a pharmaceutically acceptable salt thereof, wherein:
X is O or S;
each $R^{3a}$ is independently selected from the group consisting of halo, nitro, hydroxyamino, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclic, substituted heterocyclic, amino, substituted amino, acyl, acylamino, alkoxy, substituted alkoxy, carboxyl, carboxyl ester, substituted sulfonyl, aminosulfonyl, and aminocarbonyl; or two $R^{3a}$ groups on two adjoining carbon atoms are taken together with the carbon atoms bound thereto to form a group selected from aryl, substituted aryl, heterocyclic, substituted heterocyclic, heteroaryl, or substituted heteroaryl;

each $R^4$ is independently alkyl, substituted alkyl, alkoxy, substituted alkoxy, amino, substituted amino, or halo;

m is 0, 1, 2, or 3, and n is 0, 1, or 2.

4. A compound of claim 1 that is of the Formula (IV):

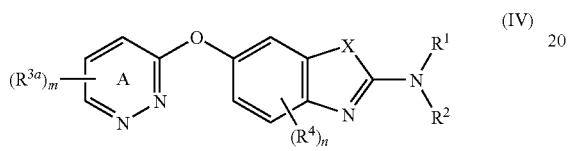

(IV)

or a pharmaceutically acceptable salt thereof, wherein:

X is O or S;

each $R^{3a}$ is independently selected from the group consisting of hydrogen, halo, nitro, hydroxyamino, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclic, substituted heterocyclic, amino, substituted amino, acyl, acylamino, alkoxy, substituted alkoxy, carboxyl, carboxyl ester, substituted sulfonyl, aminosulfonyl, and aminocarbonyl; or two $R^{3a}$ groups on two adjoining carbon atoms are taken together with the carbon atoms bound thereto to form a group selected from aryl, substituted aryl, heterocyclic, substituted heterocyclic, heteroaryl, or substituted heteroaryl;

each $R^4$ is independently alkyl, substituted alkyl, alkoxy, substituted alkoxy, amino, substituted amino, or halo;

m is 0, 1, 2, or 3, and n is 0, 1, or 2.

5. A compound of claim 1 that is of the Formula (V):

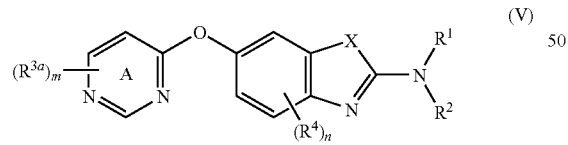

(V)

or a pharmaceutically acceptable salt thereof, wherein:

X is O or S;

each $R^{3a}$ is independently selected from the group consisting of hydrogen, halo, nitro, hydroxyamino, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclic, substituted heterocyclic, amino, substituted amino, acyl, acylamino, alkoxy, substituted alkoxy, carboxyl, carboxyl ester, substituted sulfonyl, aminosulfonyl, and aminocarbonyl; or two $R^{3a}$ groups on two adjoining carbon atoms are taken together with the carbon atoms bound thereto to form a group selected from aryl, substituted aryl, heterocyclic, substituted heterocyclic, heteroaryl, or substituted heteroaryl;

each $R^4$ is independently alkyl, substituted alkyl, alkoxy, substituted alkoxy, amino, substituted amino, or halo;

m is 0, 1, 2, or 3, and n is 0, 1, or 2.

6. A compound of claim 1 that is of the Formula (VI):

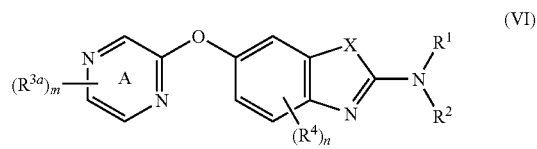

(VI)

or a pharmaceutically acceptable salt thereof, wherein:

X is O or S;

each $R^{3a}$ is hydrogen or $R^{3a}$, where each $R^{3a}$ is independently selected from the group consisting of halo, nitro, hydroxyamino, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclic, substituted heterocyclic, amino, substituted amino, acyl, acylamino, alkoxy, substituted alkoxy, carboxyl, carboxyl ester, substituted sulfonyl, aminosulfonyl, and aminocarbonyl; or two $R^{3a}$ groups on two adjoining carbon atoms are taken together with the carbon atoms bound thereto to form a group selected from aryl, substituted aryl, heterocyclic, substituted heterocyclic, heteroaryl, or substituted heteroaryl;

each $R^4$ is independently alkyl, substituted alkyl, alkoxy, substituted alkoxy, amino, substituted amino, or halo;

m is 0, 1, 2, or 3, and n is 0, 1, or 2.

7. A compound of claim 1 that is of the Formula (VII):

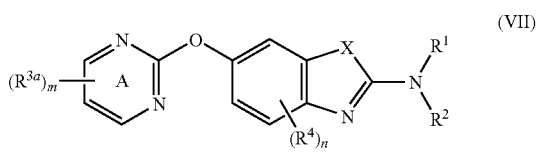

(VII)

or a pharmaceutically acceptable salt thereof, wherein:

X is O or S;

each $R^{3a}$ is independently selected from the group consisting of halo, nitro, hydroxyamino, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclic, substituted heterocyclic, amino, substituted amino, acyl, acylamino, alkoxy, substituted alkoxy, carboxyl, carboxyl ester, substituted sulfonyl, aminosulfonyl, and aminocarbonyl; or two $R^{3a}$ groups on two adjoining carbon atoms are taken together with the carbon atoms bound thereto to form a group selected from aryl, substituted aryl, heterocyclic, substituted heterocyclic, heteroaryl, or substituted heteroaryl;

each $R^4$ is independently alkyl, substituted alkyl, alkoxy, substituted alkoxy, amino, substituted amino, or halo;

m is 0, 1, 2, or 3, and n is 0, 1, or 2.

8. A compound of any one of claims 1 to 7, wherein X is S.

9. A compound of any one of claims 1 to 7, wherein $R^2$ is H.

10. A compound of any one of claims 1 to 7, wherein each $R^{3a}$ group is independently selected from the group consisting of F, Cl, Br, —$NH_2$, —NHOH, —$NO_2$, —CN, —$CF_3$,

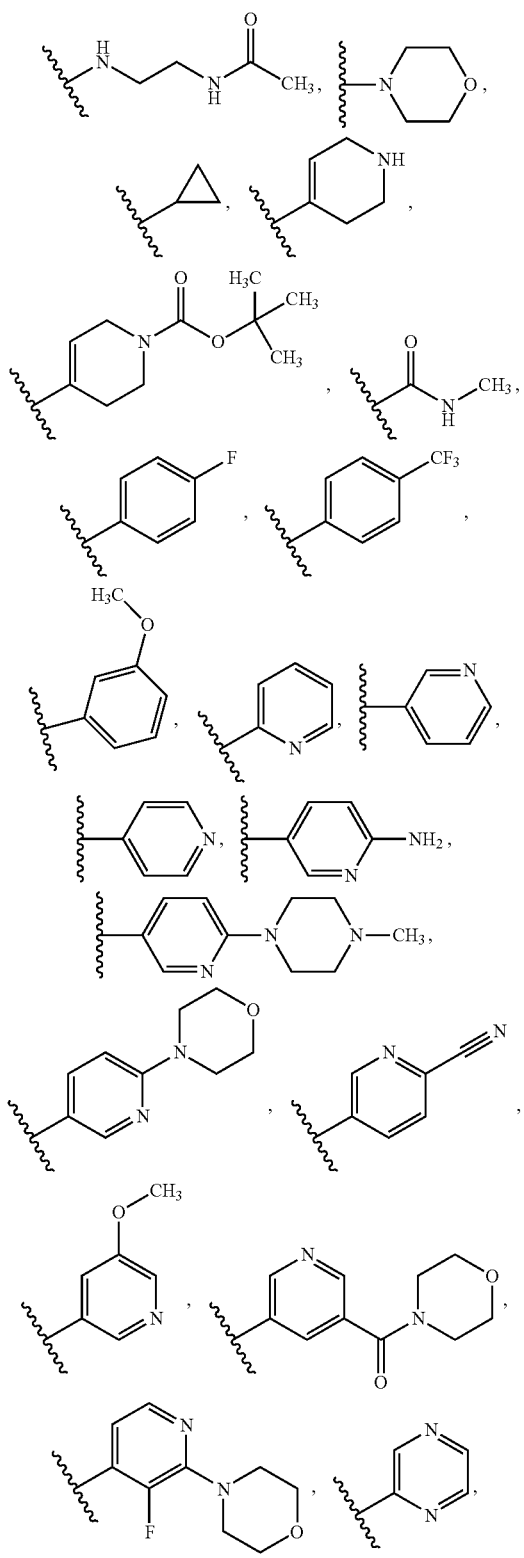

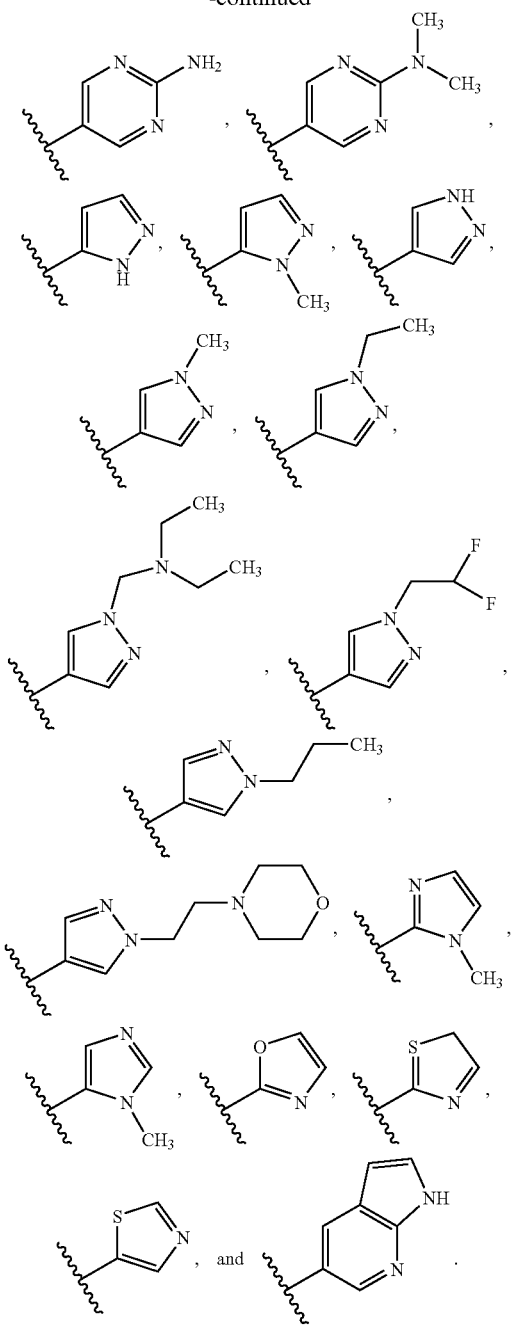

11. A compound of claim 1, wherein L is a covalent bond.

12. A compound of claim 1, wherein L is alkylene substituted with 0, 1, 2, or 3 substituents independently selected from alkyl, substituted alkyl, hydroxy, alkoxy, haloalkoxy, aminocarbonyl, carboxyl ester, and carboxyl.

13. A compound of claim 12, wherein L is methylene optionally substituted with a substituent selected from the group consisting of alkyl, substituted alkyl, hydroxy, alkoxy, haloalkoxy, aminocarbonyl, carboxyl ester, and carboxyl.

14. A compound of claim 13, wherein L is —$CH_2$— or —$CH(CH_3)$—.

15. A compound of claim 1, wherein $R^{10}$, $R^{11}$, and $R^{12}$ are independently selected from the group consisting of hydrogen, halo, hydroxyl, alkyl, substituted alkyl, and alkoxy.

16. A compound of claim 1, wherein at least one of $R^{10}$, $R^{11}$, and $R^{12}$ is hydroxy.

17. A compound of claim 1, wherein $R^{11}$ is taken together with $R^{12}$ to form aryl or substituted aryl.

18. A compound of claim 1, wherein $R^{1b}$ is

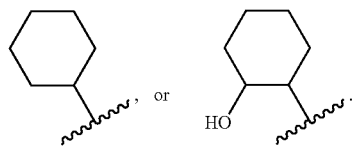

19. A compound of claim 1, wherein $R^{1b}$ is

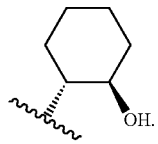

20. A compound of claim 1, wherein $R^{1b}$ is

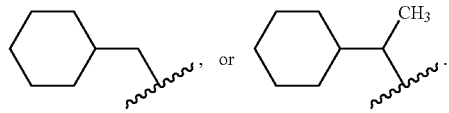

21. A compound of claim 1, wherein $R^{1b}$ is

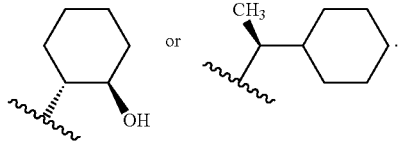

22. A compound of any one of claims 1 to 7, wherein two $R^{3a}$ groups on two adjoining carbon atoms are taken together with the carbon atoms bound thereto to form a benzene, thiophene, or pyrazole ring, wherein said benzene, thiophene, or pyrazole ring is substituted with 0, 1, 2, or 3 substituents independently selected from halo, hydroxy, alkyl, and alkoxy.

23. A compound of claim 2, wherein A is

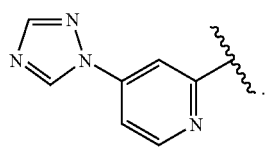

24. A compound of claim 3, wherein A is selected from the group consisting of

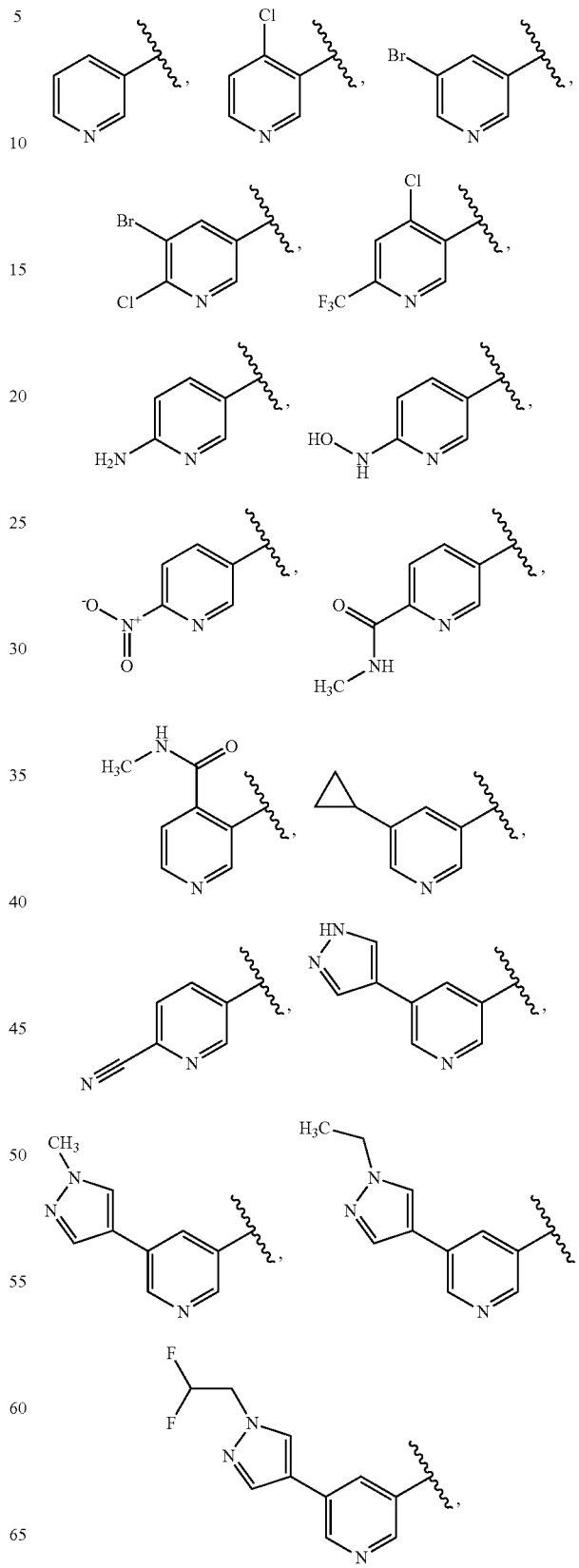

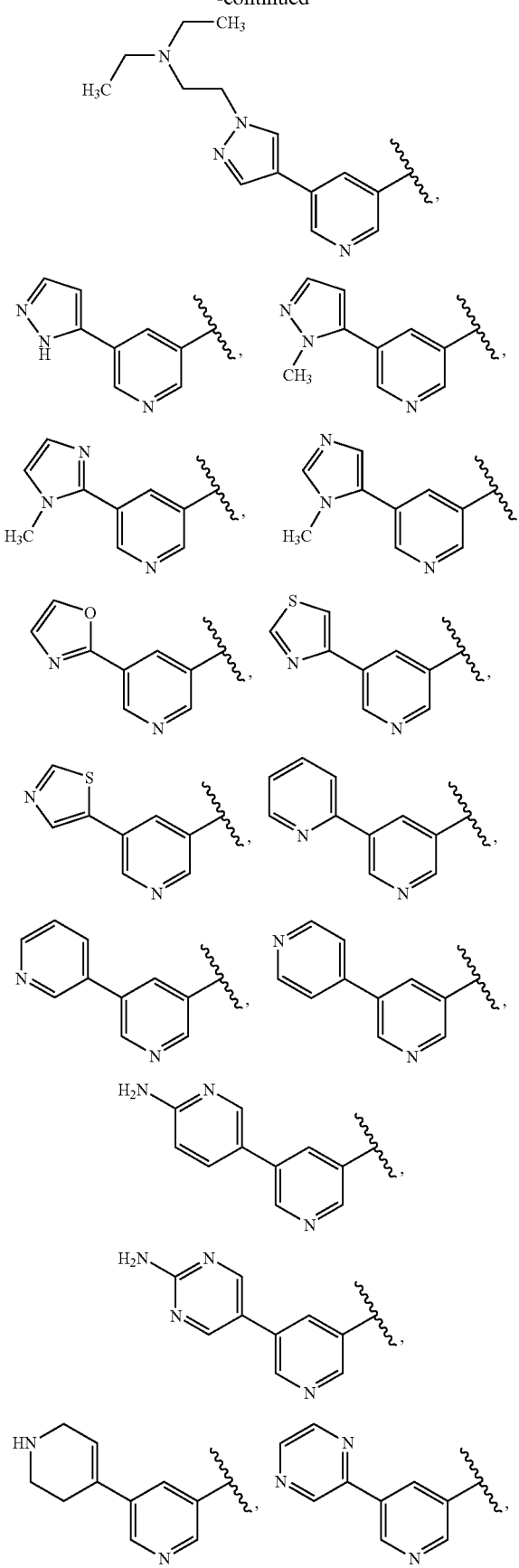
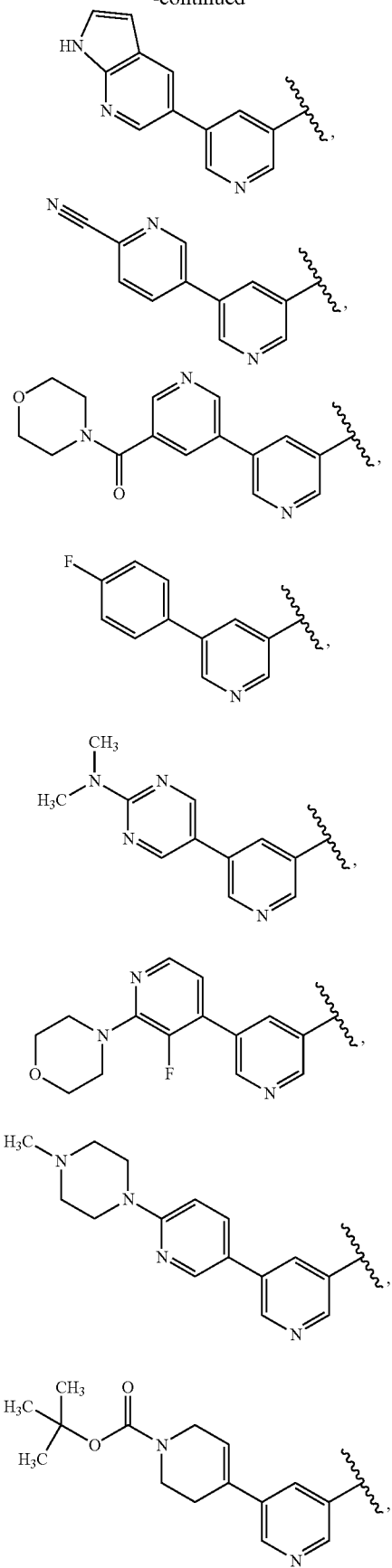

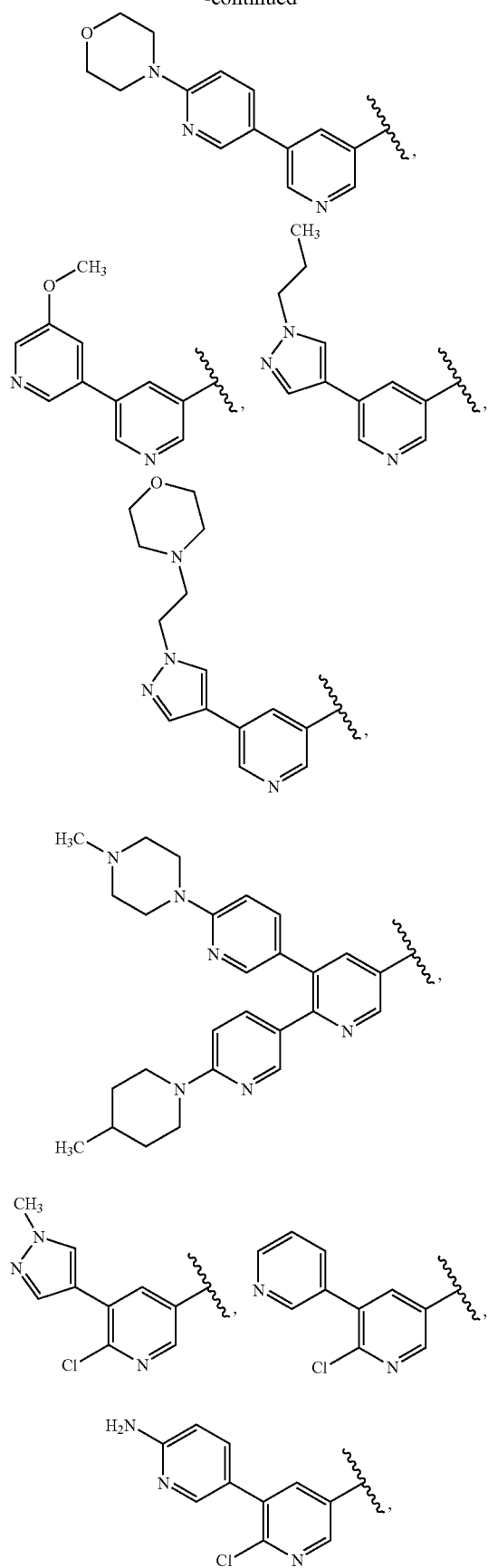
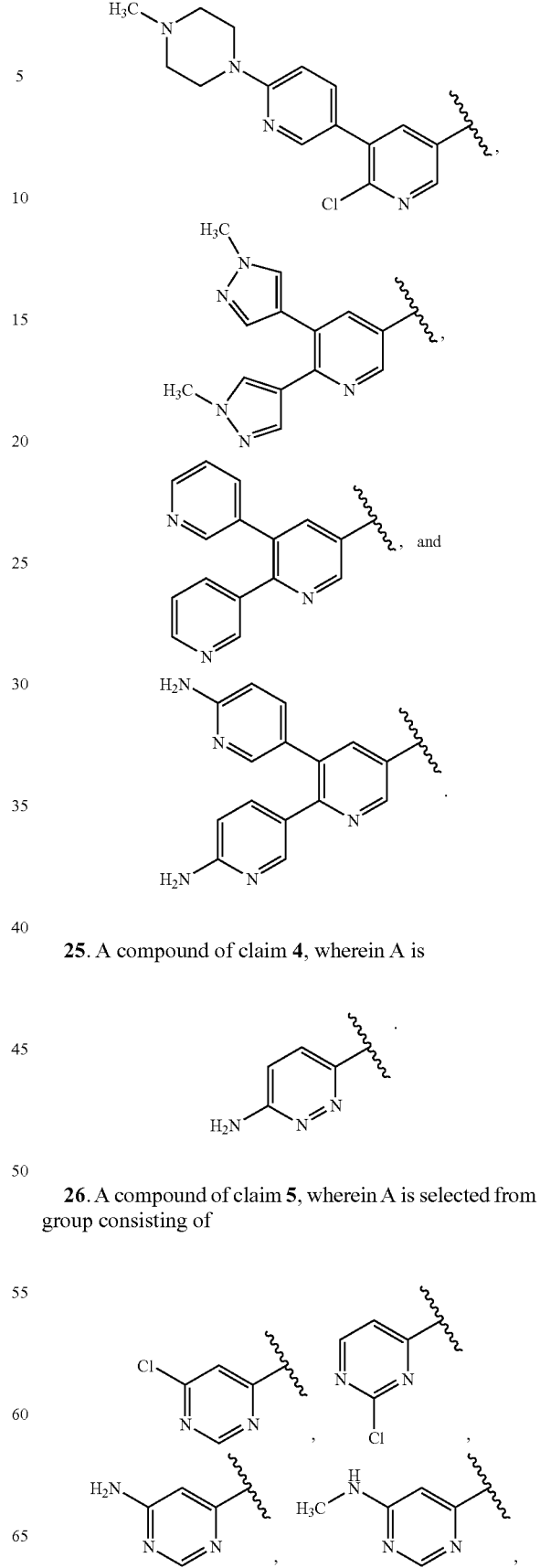
25. A compound of claim 4, wherein A is
26. A compound of claim 5, wherein A is selected from the group consisting of

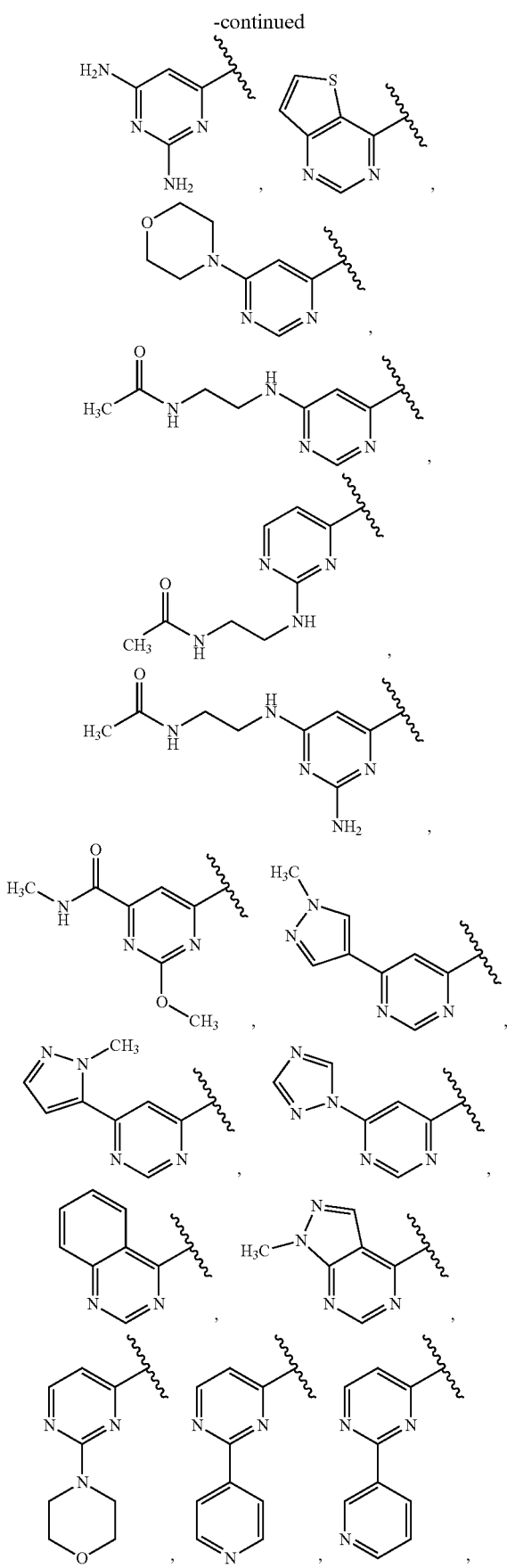
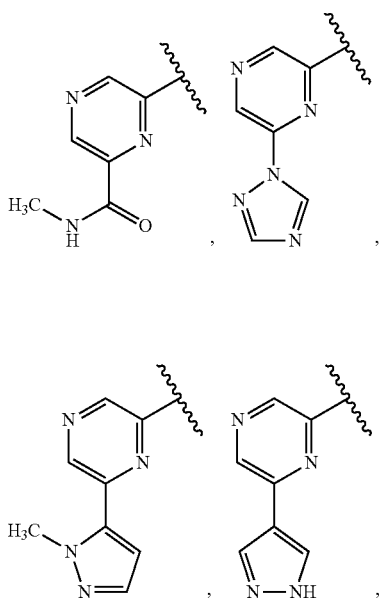
27. A compound of claim 6, wherein A is selected from the group consisting of 153
-continued

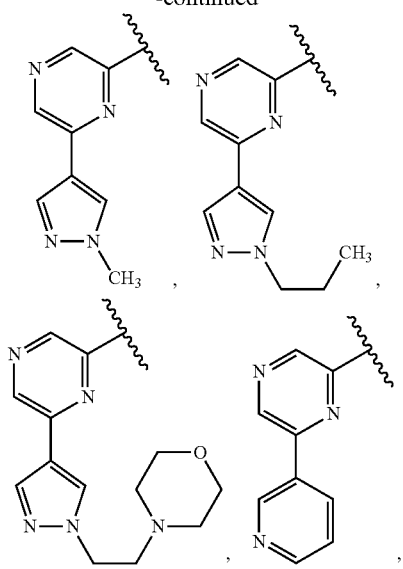

154
-continued

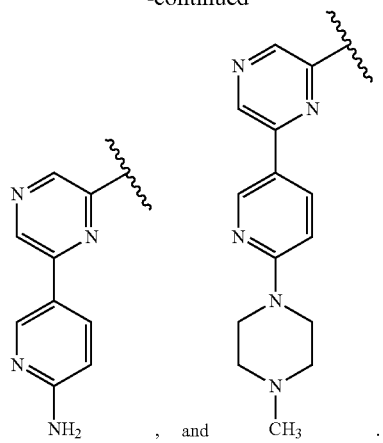

28. A compound of claim 1 or a pharmaceutically acceptable salt thereof, wherein the compound is selected from the following list of compounds:

| Cmpd | Structure | Name |
|---|---|---|
| 1 | 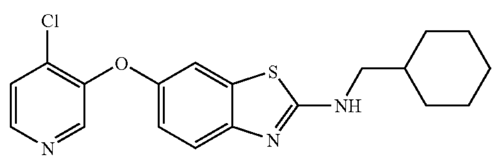 | 6-(4-chloropyridin-3-yloxy)-N-(cyclohexylmethyl)benzo[d]thiazol-2-amine |
| 2 | 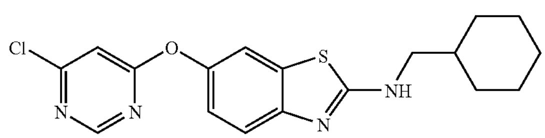 | 6-(6-chloropyrimidin-4-yloxy)-N-(cyclohexylmethyl)benzo[d]thiazol-2-amine |
| 3 | 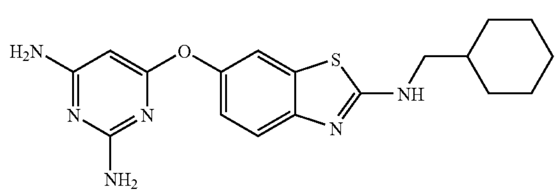 | 6-(2-(cyclohexylmethylamino)benzo[d]thiazol-6-yloxy)pyrimidine-2,4-diamine |
| 4 | 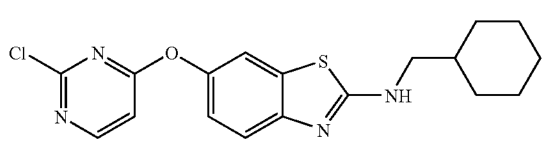 | 6-(2-chloropyrimidin-4-yloxy)-N-(cyclohexylmethyl)benzo[d]thiazol-2-amine |
| 5 | 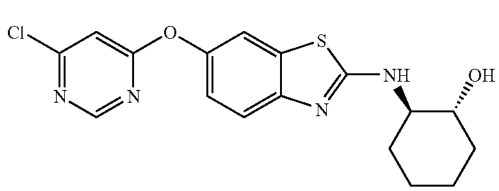 | (1R,2R)-2-(6-(6-chloropyrimidin-4-yloxy)benzo[d]thiazol-2-ylamino)cyclohexanol |

-continued

| Cmpd | Structure | Name |
|---|---|---|
| 6 | 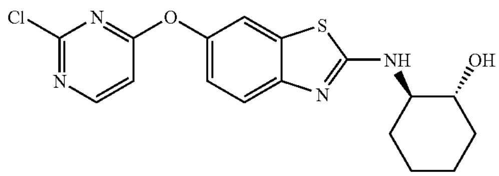 | (1R,2R)-2-(6-(2-chloropyrimidin-4-yloxy)benzo[d]thiazol-2-ylamino)cyclohexanol |
| 7 | 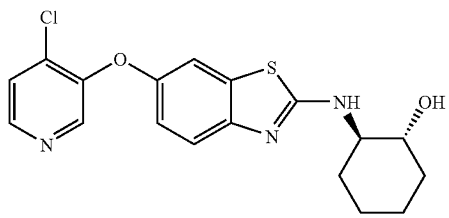 | (1R,2R)-2-(6-(4-chloropyrimidin-3-yloxy)benzo[d]thiazol-2-ylamino)cyclohexanol |
| 8 | 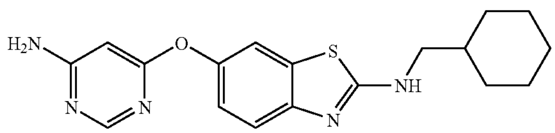 | 6-(6-aminopyrimidin-4-yloxy)-N-(cyclohexylmethyl)benzo[d]thiazol-2-amine |
| 9 | 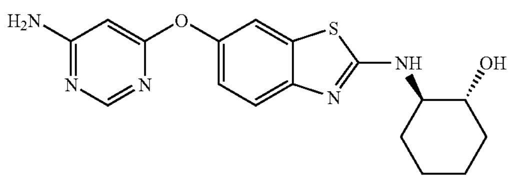 | (1R,2R)-2-(6-(6-aminopyrimidin-4-yloxy)benzo[d]thiazol-2-ylamino)cyclohexanol |
| 10 | 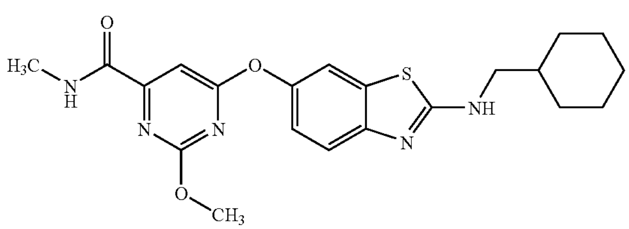 | 6-(2-(cyclohexylmethylamino)benzo[d]thiazol-6-yloxy)-2-methoxy-N-methyl-pyrimidin-4-carboxamide |
| 11 | 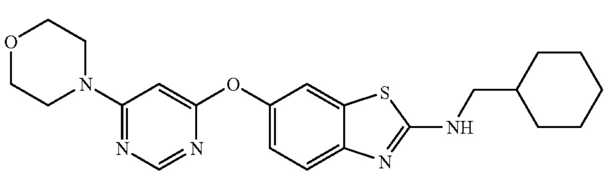 | N-(cyclohexylmethyl)-6-(6-morpholinopyrimidin-4-yloxy)benzo[d]thiazol-2-amine |
| 12 | 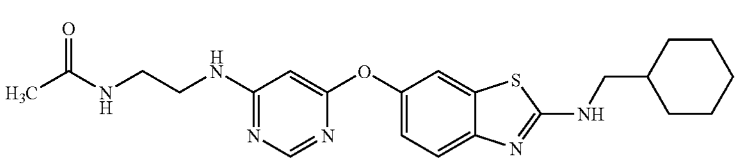 | N-(2-(6-(2-(cyclohexylmethyl-amino)benzo[d]thiazol-6-yloxy)pyrimidin-4-ylamino)ethyl)acetamide |
| 13 | 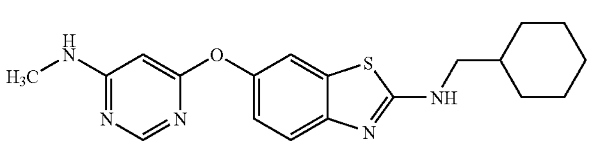 | N-(cyclohexylmethyl)-6-(6-(methylamino)pyrimidin-4-yloxy)benzo[d]thiazol-2-amine |

-continued

| Cmpd | Structure | Name |
|---|---|---|
| 14 | 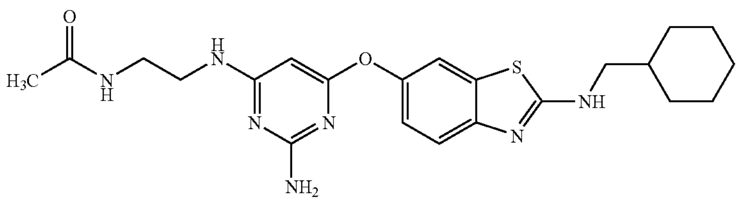 | N-(2-(2-amino-6-(2-(cyclohexylmethylamino)benzo[d]thiazol-6-yloxy)pyrimidin-4-ylamino)ethyl)acetamide |
| 15 | 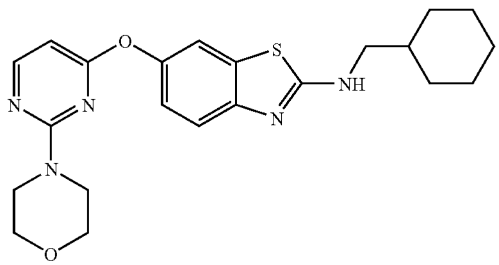 | N-(cyclohexylmethyl)-6-(2-morpholinopyrimidin-4-yloxy)benzo[d]thiazol-2-amine |
| 16 | 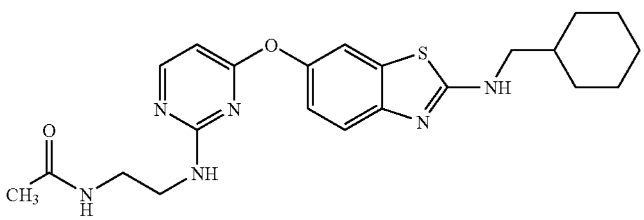 | N-(2-(4-(2-(cyclohexylmethylamino)benzo[d]thiazol-6-yloxy)pyrimidin-2-ylamino)ethyl)acetamide |
| 17 | 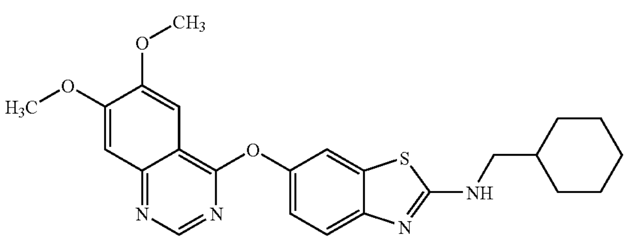 | N-(cyclohexylmethyl)-6-(6,7-dimethoxyquinazolin-4-yloxy)benzo[d]thiazol-2-amine |
| 18 | 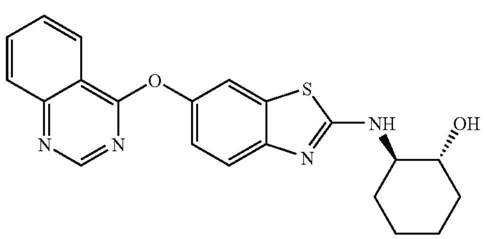 | (1R,2R)-2-(6-(quinazolin-4-yloxy)benzo[d]thiazol-2-ylamino)cyclohexanol |
| 19 | 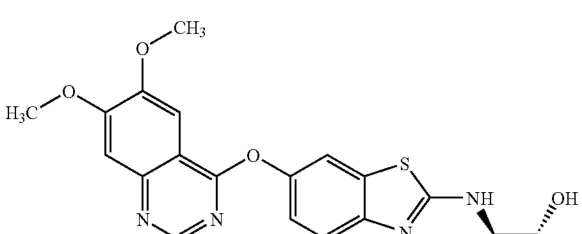 | (1R,2R)-2-(6-(6,7-dimethoxy-quinazolin-4-yloxy)benzo[d]thiazol-2-ylamino)cyclohexanol |

-continued

| Cmpd | Structure | Name |
|---|---|---|
| 20 | 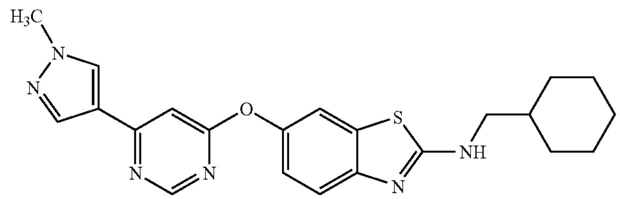 | N-(cyclohexylmethyl)-6-(6-(1-methyl-1H-pyrazol-4-yl)pyrimidin-4-yloxy)benzo[d]thiazol-2-amine |
| 21 | 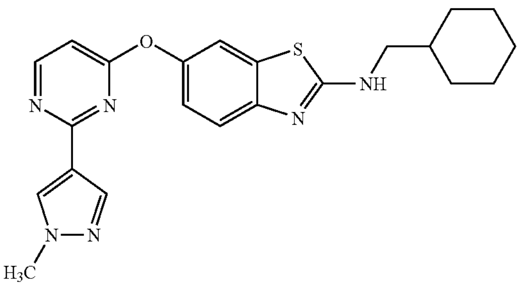 | N-(cyclohexylmethyl)-6-(2-(1-methyl-1H-pyrazol-4-yl)pyrimidin-4-yloxy)benzo[d]thiazol-2-amine |
| 22 | 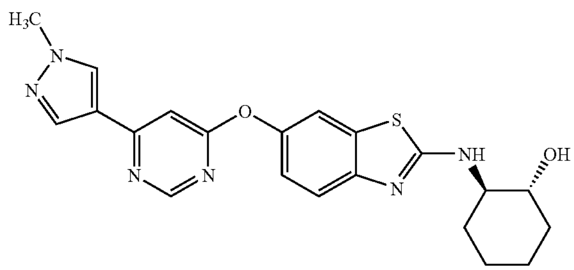 | (1R,2R)-2-(6-(6-(1-methyl-1H-pyrazol-4-yl)pyrimidin-4-yloxy)benzo[d]thiazol-2-ylamino)cyclohexanol |
| 23 | 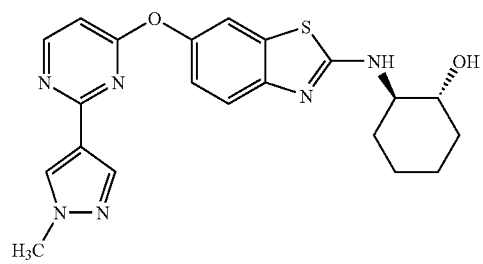 | (1R,2R)-2-(6-(2-(1-methyl-1H-pyrazol-4-yl)pyrimidin-4-yloxy)benzo[d]thiazol-2-ylamino)cyclohexanol |
| 24 | 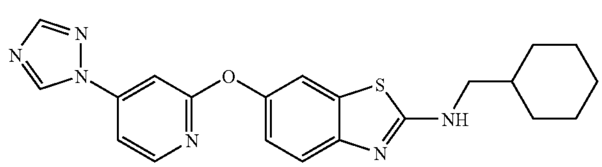 | 6-(4-(1H-1,2,4-triazol-1-yl)pyridin-2-yloxy)-N-(cyclohexylmethyl)benzo[d]thiazol-2-amine |
| 25 | 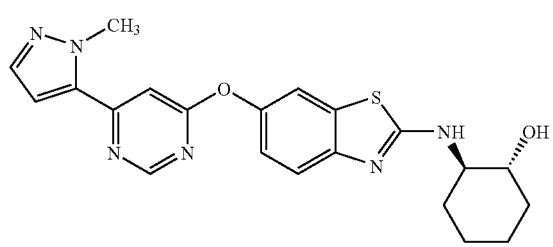 | (1R,2R)-2-(6-(6-(1-methyl-1H-pyrazol-5-yl)pyrimidin-4-yloxy)benzo[d]thiazol-2-ylamino)cyclohexanol |

-continued

| Cmpd | Structure | Name |
|---|---|---|
| 26 | 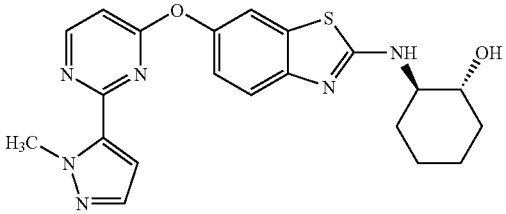 | (1R,2R)-2-(6-(2-(1-methyl-1H-pyrazol-5-yl)pyrimidin-4-yloxy)benzo[d]thiazol-2-ylamino)cyclohexanol |
| 27 | 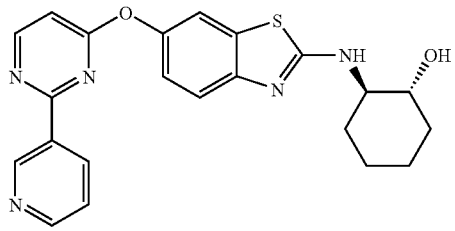 | (1R,2R)-2-(6-(2-(pyridin-3-yl)pyrimidin-4-yloxy)benzo[d]thiazol-2-ylamino)cyclohexanol |
| 28 | 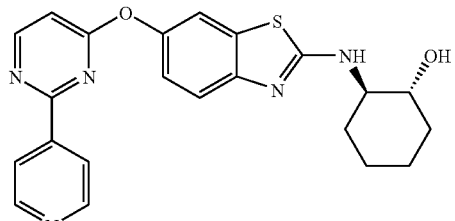 | (1R,2R)-2-(6-(2-(pyridin-4-yl)pyrimidin-4-yloxy)benzo[d]thiazol-2-ylamino)cyclohexanol |
| 29 | 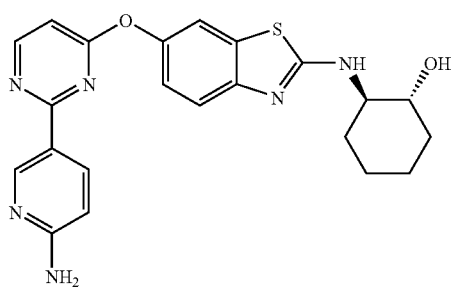 | (1R,2R)-2-(6-(2-(6-aminopyridin-3-yl)pyrimidin-4-yloxy)benzo[d]thiazol-2-ylamino)cyclohexanol |
| 30 | 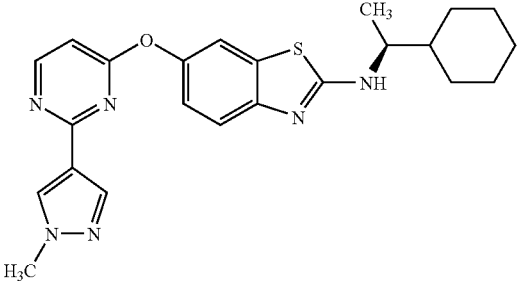 | (S)-N-(1-cyclohexylethyl)-6-(2-(1-methyl-1H-pyrazol-4-yl)pyrimidin-4-yloxy)benzo[d]thiazol-2-amine |
| 31 | 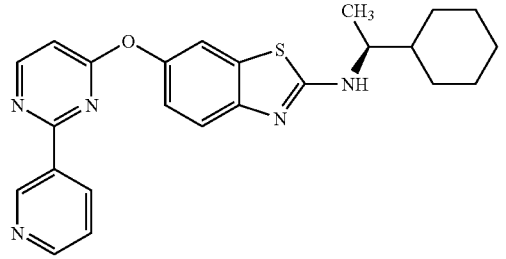 | (S)-N-(1-cyclohexylethyl)-6-(2-(pyridin-3-yl)pyrimidin-4-yloxy)benzo[d]thiazol-2-amine |

-continued

| Cmpd | Structure | Name |
|---|---|---|
| 32 | 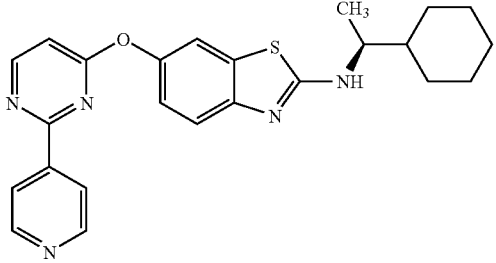 | (S)-N-(1-cyclohexylethyl)-6-(2-(pyridin-4-yl)pyrimidin-4-yloxy)benzo[d]thiazol-2-amine |
| 33 | 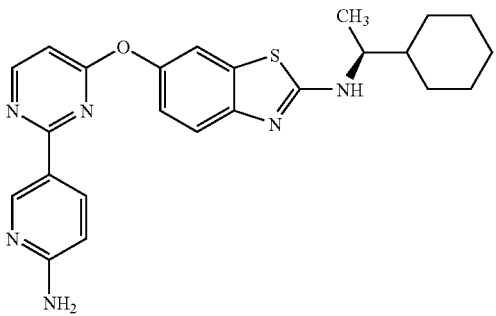 | (S)-6-(2-(6-aminopyridin-3-yl)pyrimidin-4-yloxy)-N-(1-cyclohexylethyl)benzo[d]thiazol-2-amine |
| 34 | 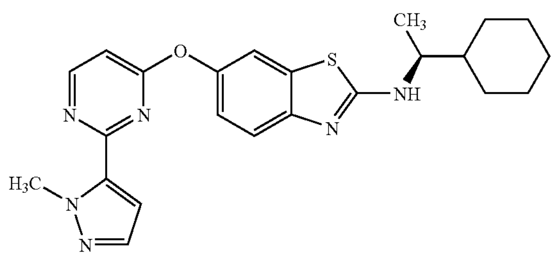 | (S)-N-(1-cyclohexylethyl)-6-(2-(1-methyl-1H-pyrazol-5-yl)pyrimidin-4-yloxy)benzo[d]thiazol-2-amine |
| 35 | 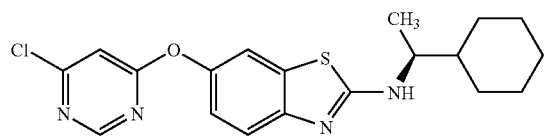 | (S)-6-(6-chloropyrimidin-4-yloxy)-N-(1-cyclohexylethyl)benzo[d]thiazol-2-amine |
| 36 | 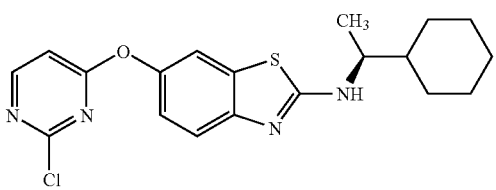 | (S)-6-(2-chloropyrimidin-4-yloxy)-N-(1-cyclohexylethyl)benzo[d]thiazol-2-amine |
| 37 | 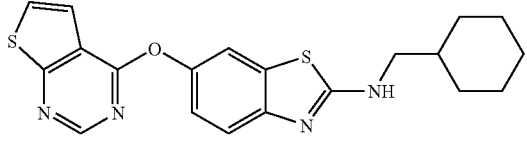 | N-(cyclohexylmethyl)-6-(thieno[2,3-d]pyrimidin-4-yloxy)benzo[d]thiazol-2-amine |
| 38 | 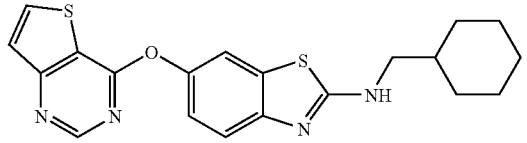 | N-(cyclohexylmethyl)-6-(thieno[3,2-d]pyrimidin-4-yloxy)benzo[d]thiazol-2-amine |

-continued

| Cmpd | Structure | Name |
|---|---|---|
| 39 | 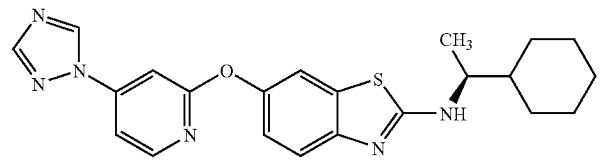 | (S)-6-(4-(1H-1,2,4-triazol-1-yl)pyridin-2-yloxy)-N-(1-cyclohexylethyl)benzo[d]thiazol-2-amine |
| 40 | 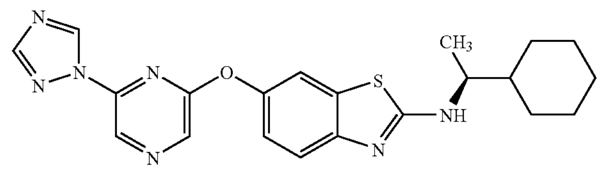 | (S)-6-(6-(1H-1,2,4-triazol-1-yl)pyrazin-2-yloxy)-N-(1-cyclohexylethyl)benzo[d]thiazol-2-amine |
| 41 | 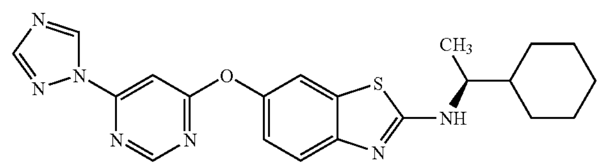 | (S)-6-(6-(1H-1,2,4-triazol-1-yl)pyrimidin-4-yloxy)-N-(1-cyclohexylethyl)benzo[d]thiazol-2-amine |
| 42 | 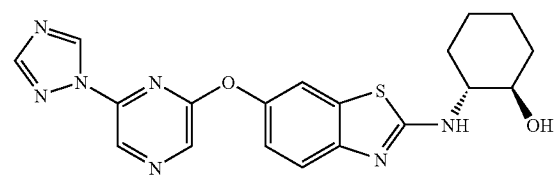 | (1R,2R)-2-(6-(6-(1H-1,2,4-triazol-1-yl)pyrazin-2-yloxy)benzo[d]thiazol-2-ylamino)cyclohexanol |
| 43 | 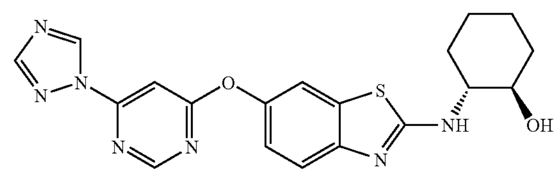 | (1R,2R)-2-(6-(6-(1H-1,2,4-triazol-1-yl)pyrimidin-4-yloxy)benzo[d]thiazol-2-ylamino)cyclohexanol |
| 44 | 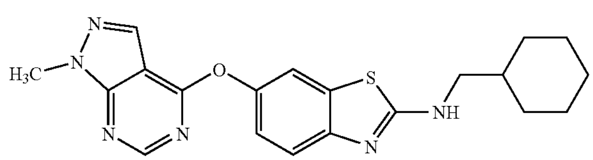 | N-(cyclohexylmethyl)-6-(1-methyl-1H-pyrazolo[3,4-d]pyrimidin-4-yloxy)benzo[d]thiazol-2-amine |
| 45 | 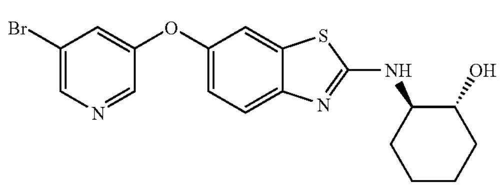 | (1R,2R)-2-(6-(5-bromo-pyrimidin-3-yloxy)benzo[d]thiazol-2-ylamino)cyclohexanol |
| 46 | 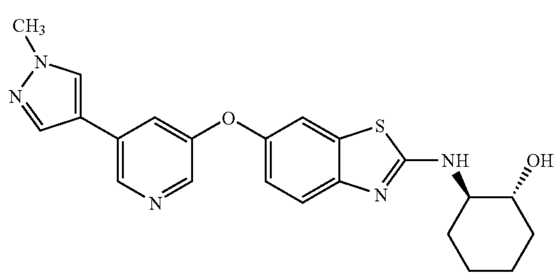 | (1R,2R)-2-(6-(5-(1-methyl-1H-pyrazol-4-yl)pyridin-3-yloxy)benzo[d]thiazol-2-ylamino)cyclohexanol |

| Cmpd | Structure | Name |
|---|---|---|
| 47 | 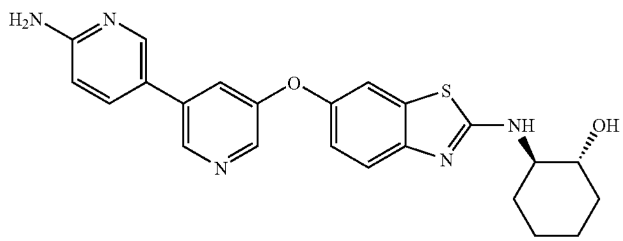 | (1R,2R)-2-(6-(6'-amino-3,3'-bipyridin-5-yloxy)benzo[d]thiazol-2-ylamino)cyclohexanol |
| 48 | 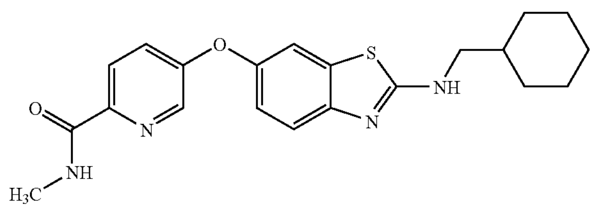 | 5-(2-(cyclohexylmethylamino)benzo[d]thiazol-6-yloxy)-N-methylpicolinamide |
| 49 | 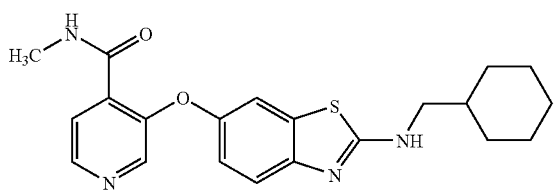 | 3-(2-(cyclohexylmethylamino)benzo[d]thiazol-6-yloxy)-N-methylisonicotinamide |
| 50 | 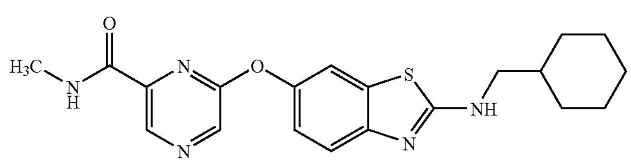 | 6-(2-(cyclohexylmethylamino)benzo[d]thiazol-6-yloxy)-N-methylpyrazine-2-carboxamide |
| 51 | 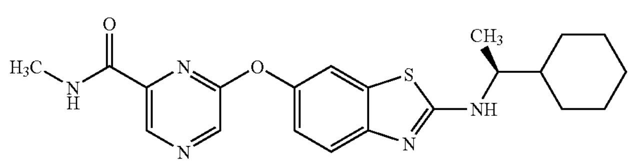 | (S)-6-(2-(1-cyclohexylethylamino)benzo[d]thiazol-6-yloxy)-N-methylpyrazine-2-carboxamide |
| 52 | 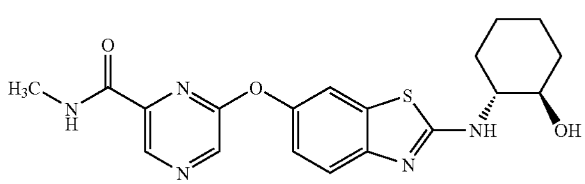 | 6-(2-((1R,2R)-2-hydroxycyclohexylamino)benzo[d]thiazol-6-yloxy)-N-methylpyrazine-2-carboxamide |
| 53 | 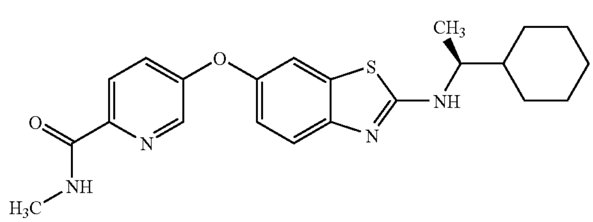 | (S)-5-(2-(1-cyclohexylethylamino)benzo[d]thiazol-6-yloxy)-N-methylpicolinamide |

-continued

| Cmpd | Structure | Name |
|---|---|---|
| 54 | 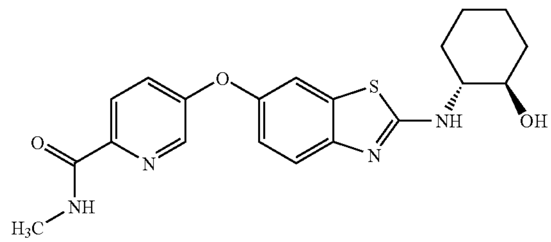 | 5-(2-((1R,2R)-2-hydroxycyclohexyl-amino)benzo[d]thiazol-6-yloxy)-N-methylpicolinamide |
| 55 | 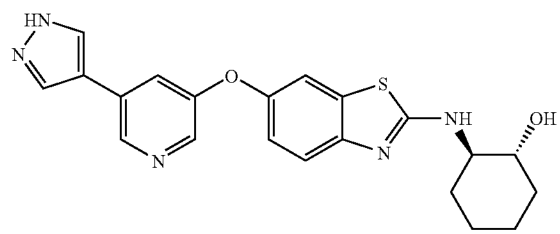 | (1R,2R)-2-(6-(5-(1H-pyrazol-4-yl)pyridin-3-yloxy)benzo[d]thiazol-2-ylamino)cyclohexanol |
| 56 | 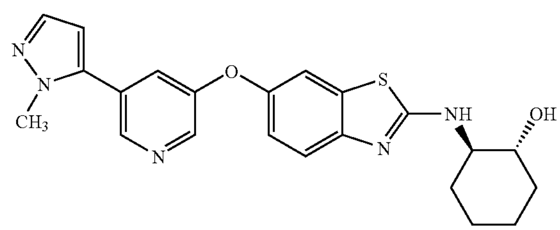 | (1R,2R)-2-(6-(5-(1-methyl-1H-pyrazol-5-yl)pyridin-3-yloxy)benzo[d]thiazol-2-ylamino)cyclohexanol |
| 57 | 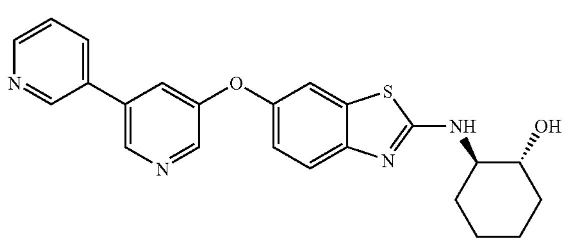 | (1R,2R)-2-(6-(3,3'-bipyridin-5-yloxy)benzo[d]thiazol-2-ylamino)cyclohexanol |
| 58 | 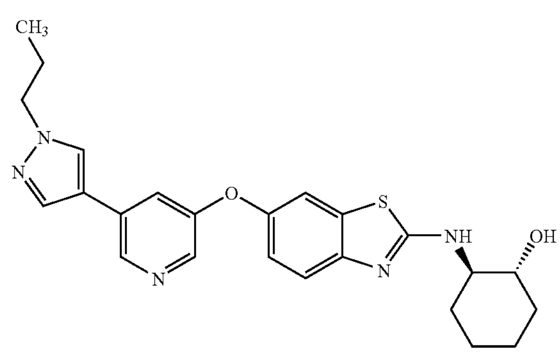 | (1R,2R)-2-(6-(5-(1-propyl-1H-pyrazol-4-yl)pyridin-3-yloxy)benzo[d]thiazol-2-ylamino)cyclohexanol |

| Cmpd | Structure | Name |
|---|---|---|
| 59 | 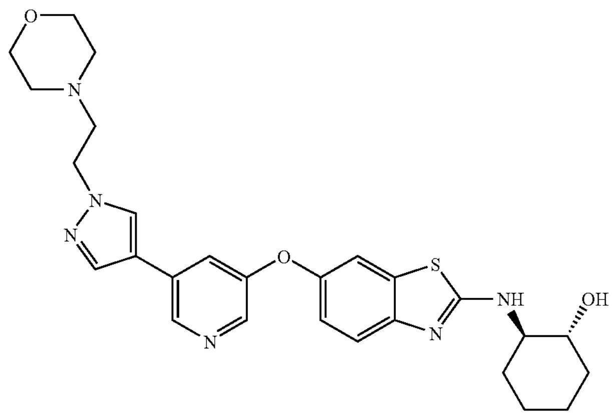 | (1R,2R)-2-(6-(5-(1-(2-morpholino-ethyl)-1H-pyrazol-4-yl)pyridin-3-yloxy)benzo[d]thiazol-2-ylamino)cyclohexanol |
| 60 | 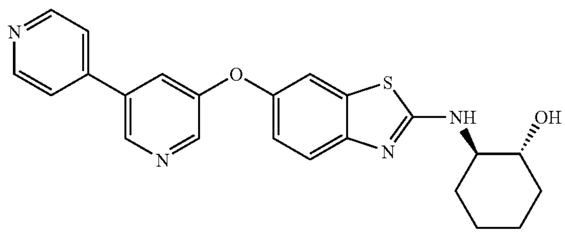 | (1R,2R)-2-(6-(3,4'-bipyridin-5-yloxy)benzo[d]thiazol-2-ylamino)cyclohexanol |
| 61 | 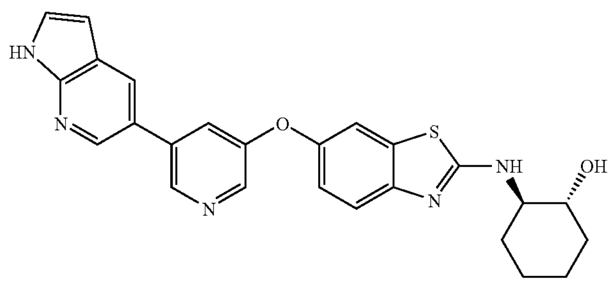 | (1R,2R)-2-(6-(5-(1H-pyrrolo[2,3-b]pyridin-5-yl)pyridin-3-yloxy)benzo[d]thiazol-2-ylamino)cyclohexanol |
| 62 | 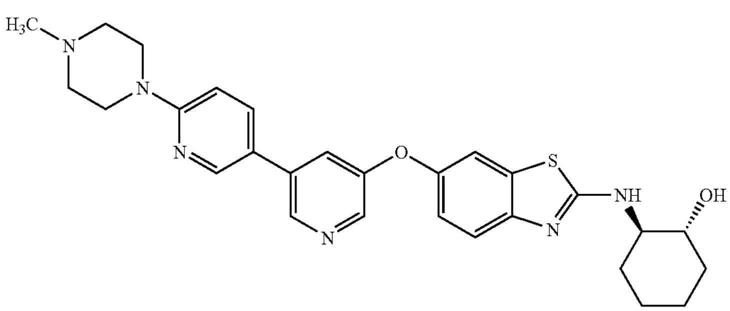 | (1R,2R)-2-(6-(6'-(4-methyl piperazin-1-yl)-3,3'-bipyridin-5-yloxy)benzo[d]thiazol-2-ylamino)cyclohexanol |
| 63 | 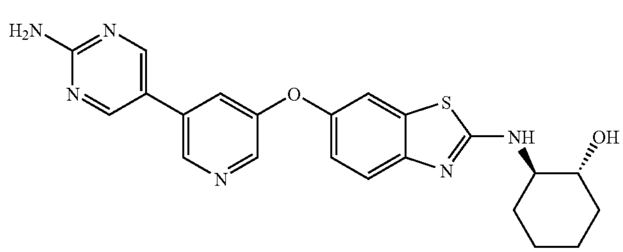 | (1R,2R)-2-(6-(5-(2-amino-pyrimidin-5-yl)pyridin-3-yloxy)benzo[d]thiazol-2-ylamino)cyclohexanol |

-continued

| Cmpd | Structure | Name |
| --- | --- | --- |
| 64 | 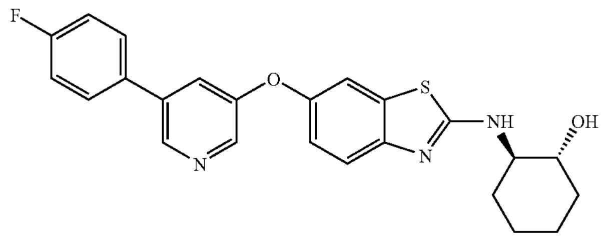 | (1R,2R)-2-(6-(5-(4-fluorophenyl)pyridin-3-yloxy)benzo[d]thiazol-2-ylamino)cyclohexanol |
| 65 | 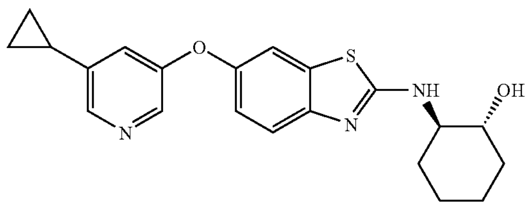 | (1R,2R)-2-(6-(5-cyclopropyl-pyridin-3-yloxy)benzo[d]thiazol-2-ylamino)cyclohexanol |
| 66 | 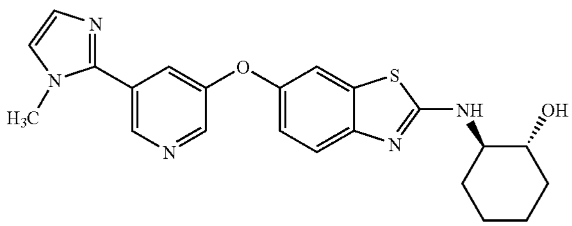 | (1R,2R)-2-(6-(5-(1-methyl-1H-imidazol-2-yl)pyridin-3-yloxy)benzo[d]thiazol-2-yl amino)cyclohexanol |
| 67 | 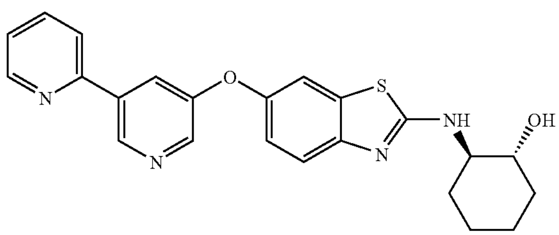 | (1R,2R)-2-(6-(2,3'-bipyridin-5'-yloxy)benzo[d]thiazol-2-ylamino)cyclohexanol |
| 68 | 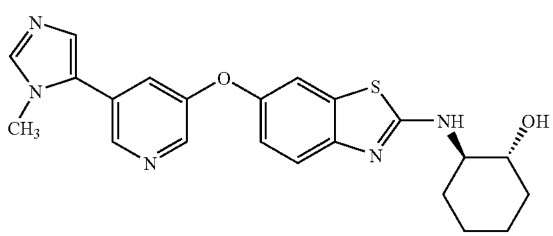 | (1R,2R)-2-(6-(5-(1-methyl-1H-imidazol-5-yl)pyridin-3-yloxy)benzo[d]thiazol-2-yl amino)cyclohexanol |
| 69 | 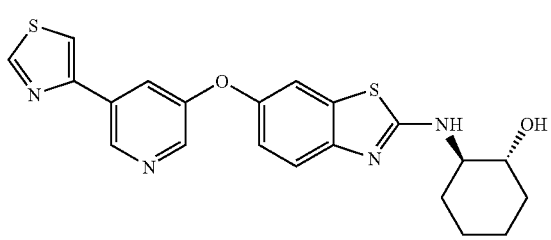 | (1R,2R)-2-(6-(5-(thiazol-4-yl)pyridin-3-yloxy)benzo[d]thiazol-2-ylamino)cyclohexanol |

| Cmpd | Structure | Name |
|---|---|---|
| 70 | 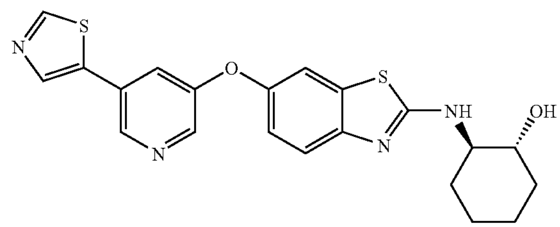 | (1R,2R)-2-(6-(5-(thiazol-5-yl)pyridin-3-yloxy)benzo[d]thiazol-2-ylamino)cyclohexanol |
| 71 | 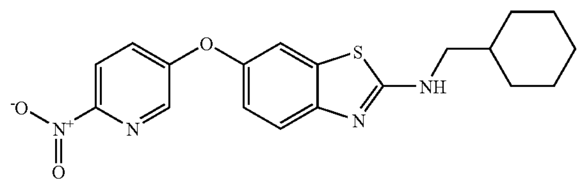 | N-(cyclohexylmethyl)-6-(6-nitropyridin-3-yloxy)benzo[d]thiazol-2-amine |
| 72 | 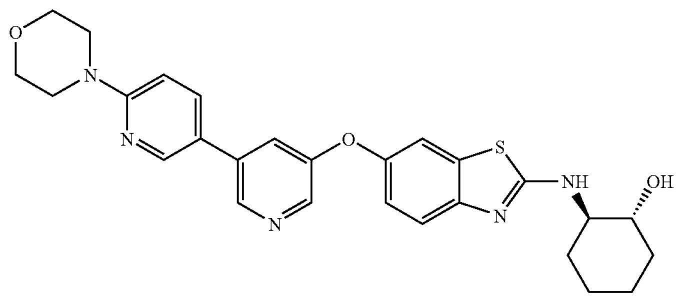 | (1R,2R)-2-(6-(6'-morpholino-3,3'-bipyridin-5-yloxy)benzo[d]thiazol-2-ylamino)cyclohexanol |
| 73 | 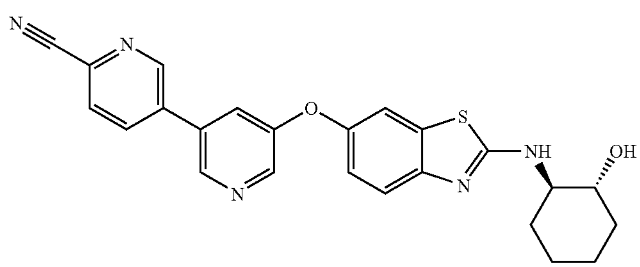 | 5'-(2-((1R,2R)-2-hydroxycyclohexylamino)benzo[d]6-yloxy)-3,3'-bipyridine-6-carbonitrile |
| 74 | 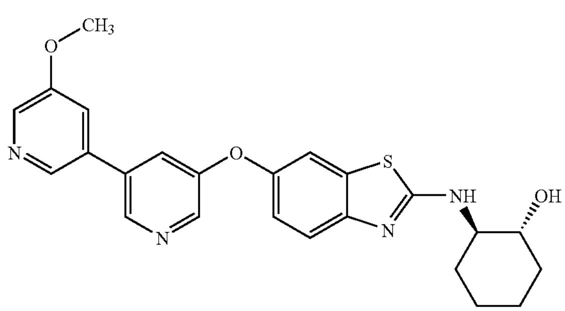 | (1R,2R)-2-(6-(5'-methoxy-3,3'-bipyridin-5-yloxy)benzo[d]thiazol-2-ylamino)cyclohexanol |
| 75 | 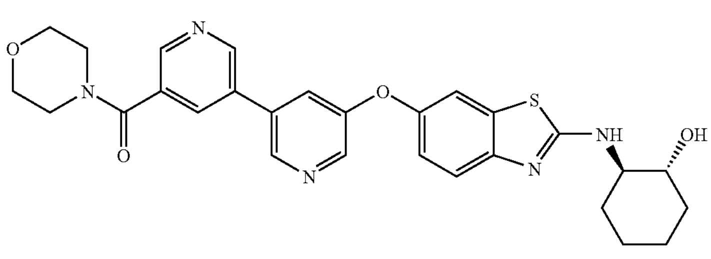 | (5'-(2-((1R,2R)-2-hydroxycyclohexylamino)benzo[d]thiazol-6-yloxy)-3,3'-bipyridin-5-yl)(morpholino)methanone |

-continued

| Cmpd | Structure | Name |
|---|---|---|
| 76 | 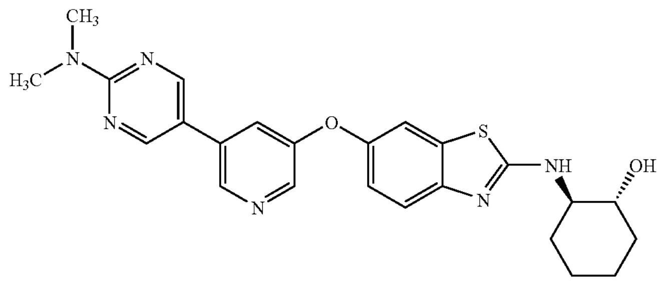 | (1R,2R)-2-(6-(5-(2-(dimethylamino)pyrimidin-5-yl)pyridin-3-yloxy)benzo[d]thiazol-2-ylamino)cyclohexanol |
| 77 | 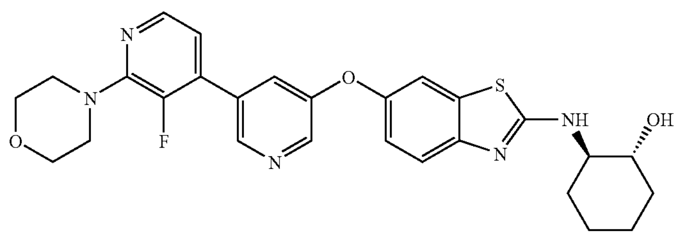 | (1R,2R)-2-(6-(3'-fluoro-2'-morpholino-3,4'-bipyridin-5-yloxy)benzo[d]thiazol-2-yl amino)cyclohexanol |
| 78 | 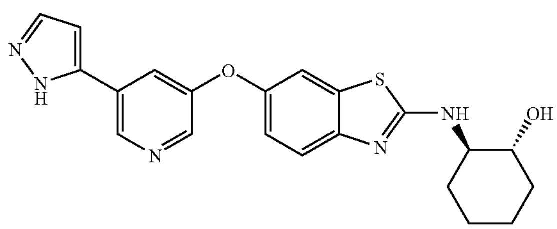 | (1R,2R)-2-(6-(5-(1H-pyrazol-5-yl)pyridin-3-yloxy)benzo[d]thiazol-2-ylamino)cyclohexanol |
| 79 | 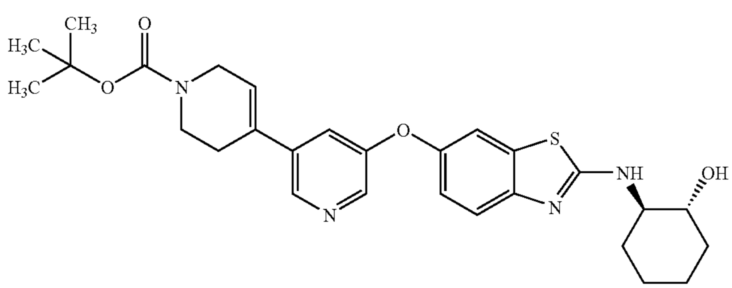 | 4-(5-(2-((1R,2R)-2-hydroxycyclohexylamino)benzo[d]thiazol-6-yloxy)pyridin-3-yl)-5,6-dihydropyridine-1(2H)-carboxylate |
| 80 | 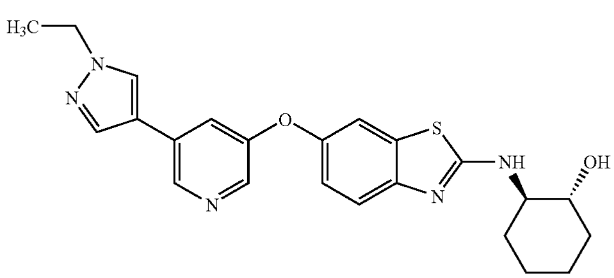 | (1R,2R)-2-(6-(5-(1-ethyl-1H-pyrazol-4-yl)pyridin-3-yloxy)benzo[d]thiazol-2-ylamino)cyclohexanol |

-continued

| Cmpd | Structure | Name |
|---|---|---|
| 81 | 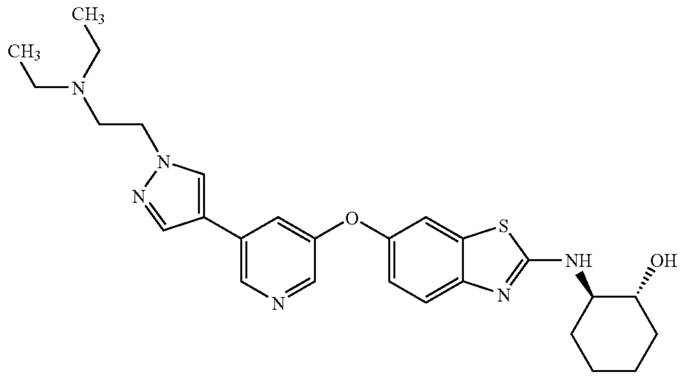 | (1R,2R)-2-(6-(5-(1-(2-(diethylamino)ethyl)-1H-pyrazol-4-yl)pyridin-3-yloxy)benzo[d]thiazol-2-ylamino)cyclohexanol |
| 82 | 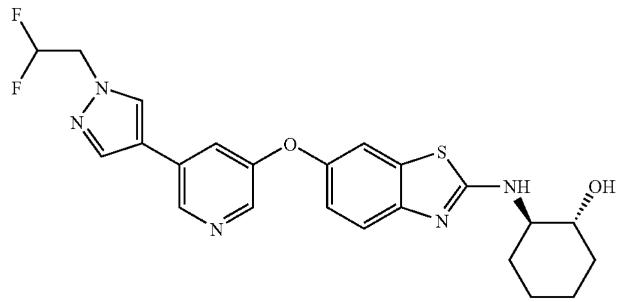 | (1R,2R)-2-(6-(5-(1-(2,2-difluoroethyl)-1H-pyrazol-4-yl)pyridin-3-yloxy)benzo[d]thiazol-2-ylamino)cyclohexanol |
| 83 | 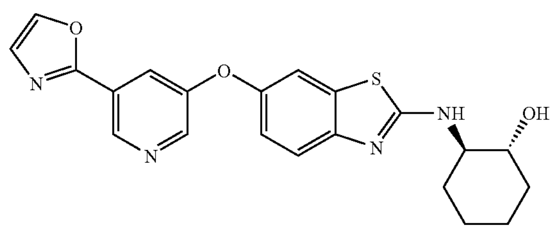 | (1R,2R)-2-(6-(5-(oxazol-2-yl)pyridin-3-yloxy)benzo[d]thiazol-2-ylamino)cyclohexanol |
| 84 | 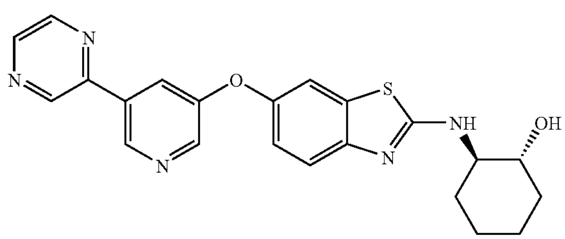 | (1R,2R)-2-(6-(5-(pyrazin-2-yl)pyridin-3-yloxy)benzo[d]thiazol-2-ylamino)cyclohexanol |
| 85 | 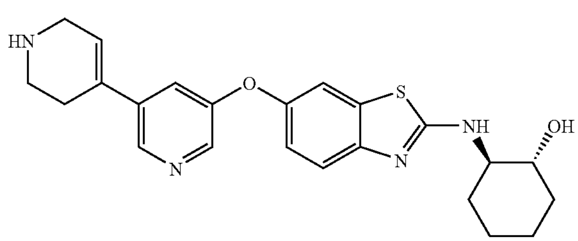 | (1R,2R)-2-(6-(5-(1,2,3,6-tetrahydropyridin-4-yl)pyridin-3-yloxy)benzo[d]thiazol-2-ylamino)cyclohexanol |
| 86 | 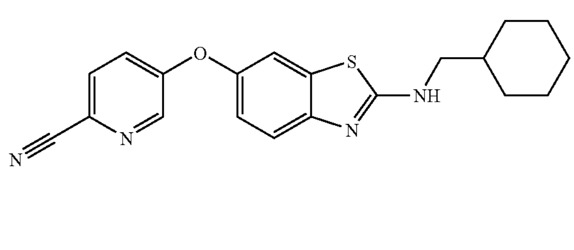 | 5-(2-(cyclohexylmethylamino)benzo[d]thiazol-6-yloxy)picolinonitrile |

| Cmpd | Structure | Name |
|---|---|---|
| 87 | 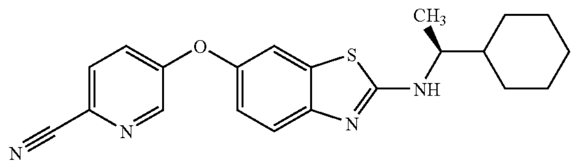 | (S)-5-(2-(1-cyclohexylethyl amino)benzo[d]thiazol-6-yloxy) picolinonitrile |
| 88 | 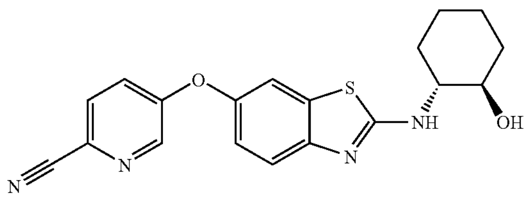 | 5-(2-((1R,2R)-2-hydroxy-cyclohexylamino)benzo[d] thiazol-6-yloxy)picolinonitrile |
| 89 | 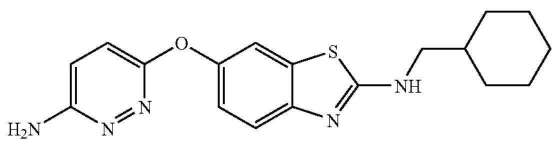 | 6-(6-aminopyridazin-3-yloxy)-N-(cyclohexylmethyl)benzo [d]thiazol-2-amine |
| 90 | 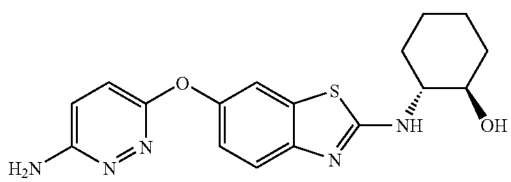 | (1R,2R)-2-(6-(6-aminopyridazin-3-yloxy)benzo[d]thiazol-2-ylamino)cyclohexanol |
| 91 | 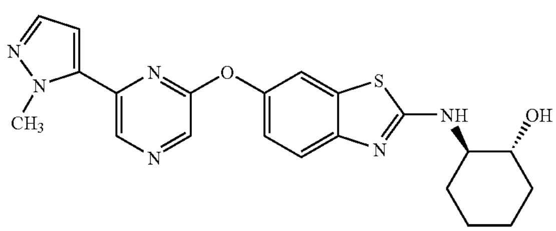 | (1R,2R)-2-(6-(6-(1-methyl-1H-pyrazol-5-yl)pyrazin-2-yloxy)benzo[d]thiazol-2-ylamino)cyclohexanol |
| 92 | 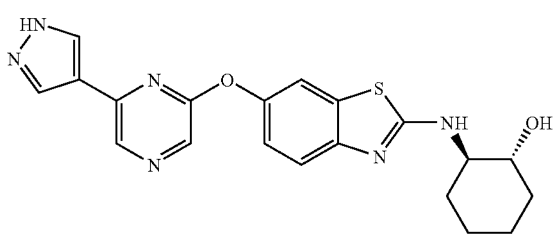 | (1R,2R)-2-(6-(6-(1H-pyrazol-4-yl)pyrazin-2-yloxy)benzo [d]thiazol-2-ylamino) cyclohexanol |
| 93 | 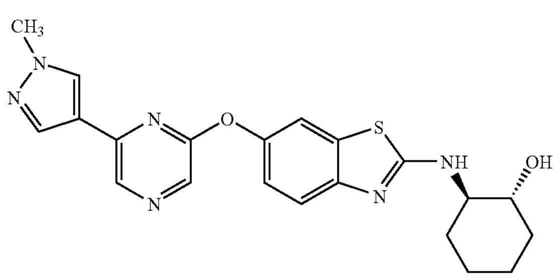 | (1R,2R)-2-(6-(6-(1-methyl-1H-pyrazol-4-yl)pyrazin-2-yloxy)benzo[d]thiazol-2-ylamino)cyclohexanol |

| Cmpd | Structure | Name |
|---|---|---|
| 94 | 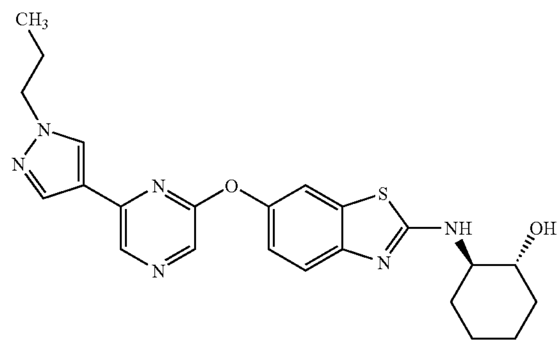 | (1R,2R)-2-(6-(6-(1-propyl-1H-pyrazol-4-yl)pyrazin-2-yloxy)benzo[d]thiazol-2-ylamino)cyclohexanol |
| 95 | 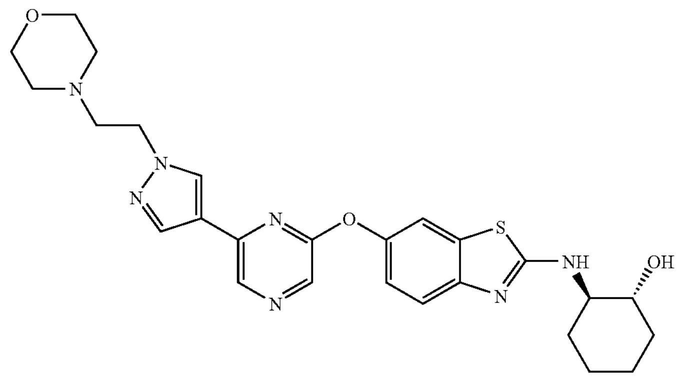 | (1R,2R)-2-(6-(6-(1-(2-morpholino-ethyl)-1H-pyrazol-4-yl)pyrazin-2-yloxy)benzo[d]thiazol-2-ylamino)cyclohexanol |
| 96 | 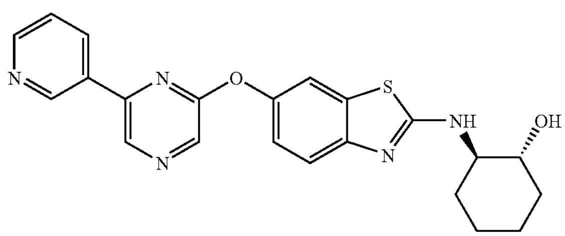 | (1R,2R)-2-(6-(6-(pyridin-3-yl)pyrazin-2-yloxy)benzo[d]thiazol-2-ylamino)cyclohexanol |
| 97 | 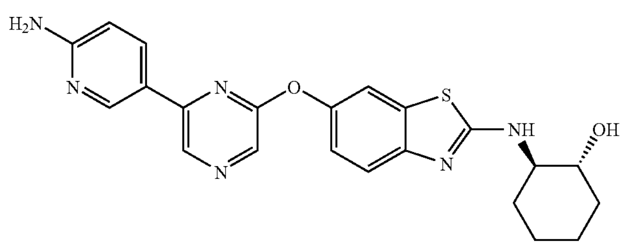 | (1R,2R)-2-(6-(6-(6-amino-pyridin-3-yl)pyrazin-2-yloxy)benzo[d]thiazol-2-ylamino)cyclohexanol |
| 98 | 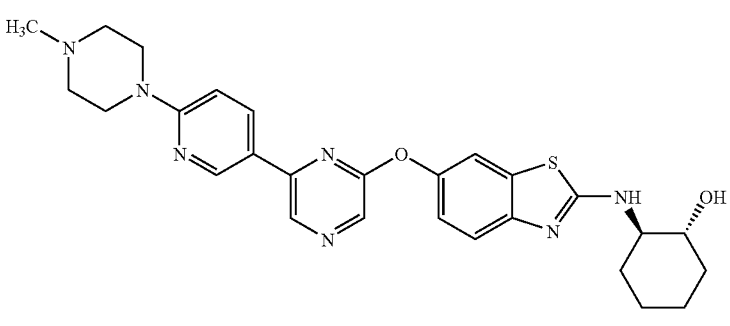 | (1R,2R)-2-(6-(6-(6-(4-methylpiperazin-1-yl)pyridin-3-yl)pyrazin-2-yloxy)benzo[d]thiazol-2-ylamino)cyclohexanol |

-continued

| Cmpd | Structure | Name |
|---|---|---|
| 99 | 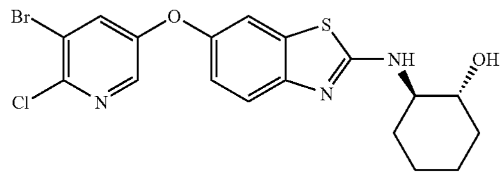 | (1R,2R)-2-(6-(5-bromo-6-chloropyridin-3-yloxy)benzo[d]thiazol-2-ylamino)cyclohexanol |
| 100 | 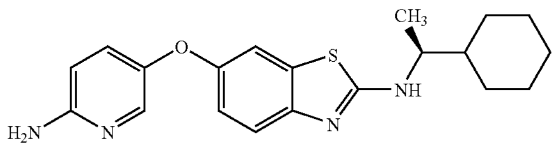 | (S)-6-(6-aminopyridin-3-yloxy)-N-(1-cyclohexylethyl)benzo[d]thiazol-2-amine |
| 101 | 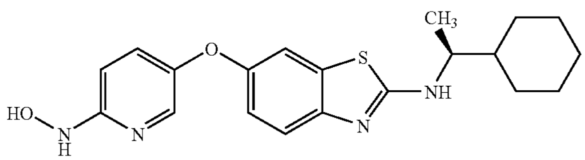 | (S)-N-(1-cyclohexylethyl)-6-(6-(hydroxyamino)pyridin-3-yloxy)benzo[d]thiazol-2-amine |
| 102 | 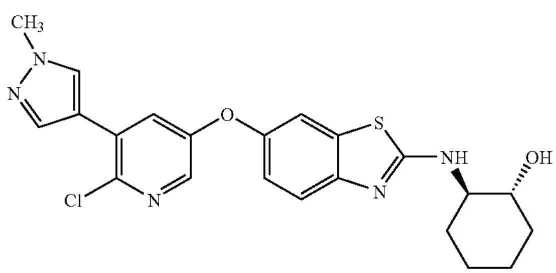 | (1R,2R)-2-(6-(6-chloro-5-(1-methyl-1H-pyrazol-4-yl)pyridin-3-yloxy)benzo[d]thiazol-2-ylamino)cyclohexanol |
| 103 | 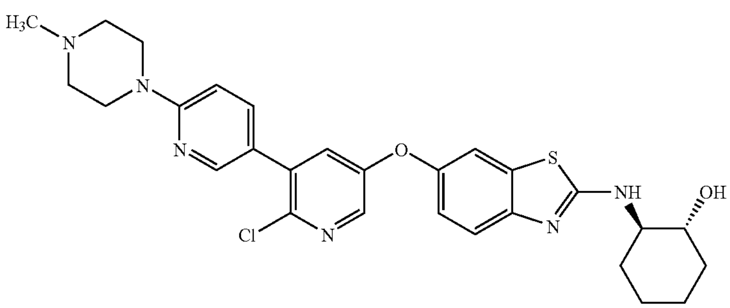 | (1R,2R)-2-(6-(2-chloro-6'-(4-methylpiperazin-1-yl)-3,3'-bipyridin-5-yloxy)benzo[d]thiazol-2-ylamino)cyclohexanol |
| 104 | 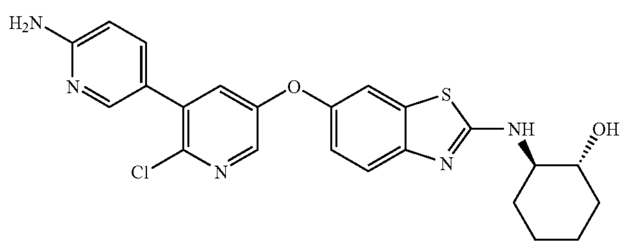 | (1R,2R)-2-(6-(6'-amino-2-chloro-3,3'-bipyridin-5-yloxy)benzo[d]thiazol-2-ylamino)cyclohexanol |
| 105 | 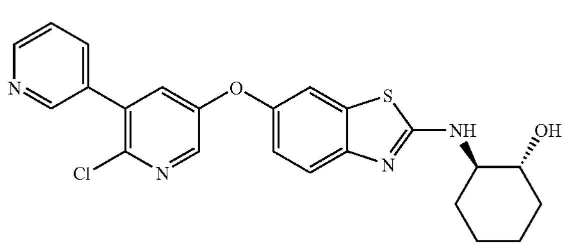 | (1R,2R)-2-(6-(2-chloro-3,3'-bipyridin-5-yloxy)benzo[d]thiazol-2-ylamino)cyclohexanol |

| Cmpd | Structure | Name |
|---|---|---|
| 106 | 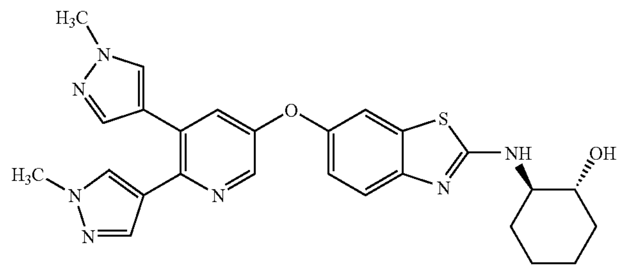 | (1R,2R)-2-(6-(5,6-bis(1-methyl-1H-pyrazol-4-yl)pyridin-3-yloxy)benzo[d]thiazol-2-ylamino)cyclohexanol |
| 107 | 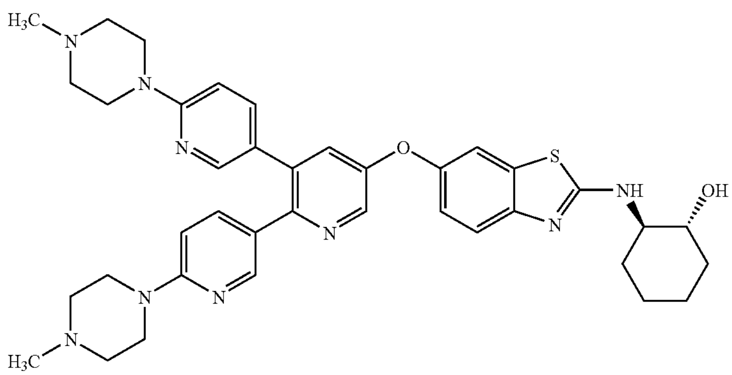 | (1R,2R)-2-(6-(5,6-bis(6-(4-methylpiperazin-1-yl)-pyridin-3-yl)pyridin-3-yloxy)benzo[d]thiazol-2-ylamino)cyclohexanol |
| 108 | 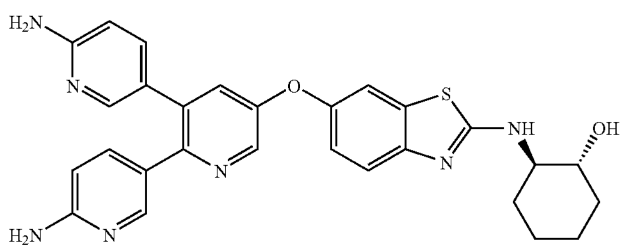 | (1R,2R)-2-(6-(5,6-bis(6-amino-pyridin-3-yl)pyridin-3-yloxy)benzo[d]thiazol-2-ylamino)cyclohexanol |
| 109 | 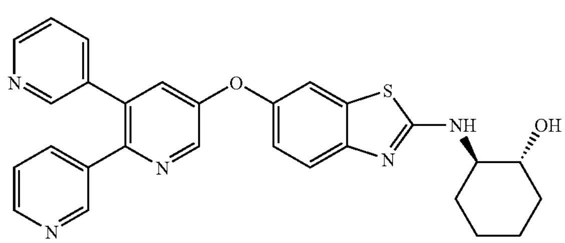 | (1R,2R)-2-(6-(5,6-bis(pyridin-3-yl)pyridin-3-yloxy)benzo[d]thiazol-2-ylamino)cyclohexanol |
| 110 | 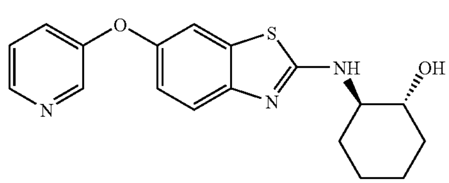 | (1R,2R)-2-(6-(pyridin-3-yloxy)benzo[d]thiazol-2-ylamino)cyclohexanol. |

29. A pharmaceutical composition effective to inhibit CSF-1R activity in a human or animal subject when administered thereto, comprising a therapeutically effective amount of a compound of any one of claims 1 to 7 and a pharmaceutically acceptable carrier.

30. A composition of claim 29, wherein said compound exhibits an $IC_{50}$ value with respect to CSF-1R inhibition of less than 1 µm.

31. A composition of claim 30, further comprising an additional agent.

32. A composition of claim 31, wherein said additional agent is a bisphosphonate.

33. A compound of any one of claims 1 to 7, wherein said compound preferentially inhibits CSF-1R over Raf kinase.

34. A compound of claim 33, wherein said compound inhibits CSF-1R at greater than about 5-fold the activity with respect to $IC_{50}$ values than in Raf kinase.

35. A method of inhibiting or ameliorating a CSF-1R mediated disorder in a human or animal subject, comprising administering to the human or animal subject a composition comprising an amount of a compound of any one of claims 1 to 7 effective to inhibit CSF-1R activity in the human or animal subject wherein said CSF-1R mediated disorder is selected from the group consisting of osteoporosis, arthritis, atherosclerosis, chronic glomerular nephritis, and histiocytosis.

36. A method of claim 35, wherein said compound selectively inhibits CSF-1R.

37. A method of claim 35, wherein the CSF-1R mediated disorder is rheumatoid arthritis.

38. A method of claim 35, wherein the composition further comprises at least one additional agent for treating the CSF-1R mediated disorder.

39. A method of inhibiting CSF-1R comprising contacting a cell with a compound of any one of claims 1 to 7.

* * * * *